US012543493B2

(12) United States Patent
Kim et al.

(10) Patent No.: US 12,543,493 B2
(45) Date of Patent: Feb. 3, 2026

(54) ORGANIC LIGHT-EMITTING DEVICE

(71) Applicant: SFC CO., LTD., Chungcheongbuk-do (KR)

(72) Inventors: Kyeong-hyeon Kim, Chungcheongbuk-do (KR); Se-jin Lee, Chungcheongbuk-do (KR); Si-in Kim, Chungcheongbuk-do (KR); Seok-bae Park, Chungcheongbuk-do (KR); Hee-dae Kim, Chungcheongbuk-do (KR); Yeong-tae Choi, Chungcheongbuk-do (KR); Seung-soo Lee, Chungcheongbuk-do (KR); Ji-yung Kim, Chungcheongbuk-do (KR); Kyung-tae Kim, Chungcheongbuk-do (KR); Myeong-jun Kim, Chungcheongbuk-do (KR); Tae-gyun Lee, Chungcheongbuk-do (KR); Joon-ho Kim, Chungcheongbuk-do (KR)

(73) Assignee: SFC CO., LTD., Chungcheongbuk-do (KR)

( * ) Notice: Subject to any disclaimer, the term of this patent is extended or adjusted under 35 U.S.C. 154(b) by 396 days.

(21) Appl. No.: 18/280,745

(22) PCT Filed: Mar. 8, 2022

(86) PCT No.: PCT/KR2022/003273

§ 371 (c)(1),
(2) Date: Sep. 7, 2023

(87) PCT Pub. No.: WO2022/191583

PCT Pub. Date: Sep. 15, 2022

(65) Prior Publication Data

US 2024/0196736 A1 Jun. 13, 2024

(30) Foreign Application Priority Data

Mar. 8, 2021 (KR) ........................ 10-2021-0030257

(51) Int. Cl.

| | |
|---|---|
| ***H10K 85/60*** | (2023.01) |
| ***C07D 307/79*** | (2006.01) |
| ***C07D 307/91*** | (2006.01) |
| ***C07D 333/54*** | (2006.01) |
| ***C07D 409/04*** | (2006.01) |
| ***C07F 5/02*** | (2006.01) |
| ***C09K 11/06*** | (2006.01) |
| ***H10K 50/12*** | (2023.01) |

(52) U.S. Cl.

CPC ......... *H10K 85/615* (2023.02); *C07D 307/79* (2013.01); *C07D 307/91* (2013.01); *C07D 333/54* (2013.01); *C07D 409/04* (2013.01); *C07F 5/027* (2013.01); *C09K 11/06* (2013.01); *H10K 85/626* (2023.02); *H10K 85/6574* (2023.02); *H10K 85/6576* (2023.02); *H10K 85/658* (2023.02); *C09K 2211/1018* (2013.01); *H10K 50/12* (2023.02)

(58) Field of Classification Search

CPC .. C07D 307/79; C07D 307/91; C07D 333/54; C07D 409/04; C07F 5/027; C09K 11/06; C09K 2211/1018; H10K 85/626; H10K 85/6574; H10K 85/6576; H10K 85/658; H10K 50/12; H10K 50/11; H10K 85/636; H10K 85/657; H10K 85/30; H10K 85/361; H10K 85/654; H10K 85/655; H10K 85/6572; H10K 85/615

See application file for complete search history.

(56) References Cited

U.S. PATENT DOCUMENTS

| | | | | |
|---|---|---|---|---|
| 8,426,036 B2 * | 4/2013 | Nishimura | C09K 11/06 | 252/301.16 |
| 8,647,754 B2 * | 2/2014 | Mizuki | C09B 3/78 | 313/506 |
| 10,916,724 B2 * | 2/2021 | Lee | C07D 251/24 | |
| 2009/0079334 A1 * | 3/2009 | Kim | H10K 85/655 | 556/415 |

(Continued)

FOREIGN PATENT DOCUMENTS

| | | |
|---|---|---|
| JP | 2005-47868 A | 2/2005 |
| JP | 2020-198280 A | 12/2020 |
| KR | 10-2053569 B1 | 12/2019 |
| KR | 10-2020-0024136 A | 3/2020 |
| KR | 10-2020-0047400 A | 5/2020 |

(Continued)

OTHER PUBLICATIONS

International Search Report from corresponding PCT Application No. PCT/KR2022/003273, Dated Jun. 22, 2022.

(Continued)

*Primary Examiner* — Victor A Mandala

(74) *Attorney, Agent, or Firm* — Harness, Dickey & Pierce, P.L.C.

(57) ABSTRACT

The present invention relates to an organic light-emitting device employing, as a host of a light emission layer, an anthracene derivative compound having a characteristic structure by introduction of a benzofuran structure into the anthracene backbone, and as a dopant of the light emission layer, a polycyclic compound having a characteristic structure. The organic light-emitting device according to the present invention is an organic light-emitting device with significantly improved external quantum efficiency and can be advantageously utilized not only for lighting devices but also for various display devices, such as flat, flexible, and wearable displays.

10 Claims, No Drawings

(56) References Cited

U.S. PATENT DOCUMENTS

| | | | | |
|---|---|---|---|---|
| 2016/0020405 | A1* | 1/2016 | Ito | H10K 85/6572 252/500 |
| 2016/0204355 | A1* | 7/2016 | Kim | C07C 211/54 257/40 |
| 2016/0308137 | A1* | 10/2016 | Park | C09K 11/025 |
| 2018/0123055 | A1* | 5/2018 | Park | C07D 495/04 |
| 2019/0330152 | A1* | 10/2019 | Yang | C07C 211/54 |
| 2020/0028097 | A1* | 1/2020 | Lee | C07D 495/04 |
| 2020/0395553 | A1* | 12/2020 | Park | H10K 85/322 |
| 2021/0036233 | A1* | 2/2021 | Joo | H10K 85/615 |
| 2021/0296589 | A1* | 9/2021 | Song | C07F 5/027 |

FOREIGN PATENT DOCUMENTS

| | | | |
|---|---|---|---|
| KR | 10-2020-0066208 | A | 6/2020 |
| KR | 10-2176164 | B1 | 11/2020 |
| KR | 10-2020-0145674 | A | 12/2020 |
| WO | 2008/143229 | A1 | 11/2008 |
| WO | 2020/085829 | A1 | 4/2020 |
| WO | WO-2021-021840 | A1 | 2/2021 |

OTHER PUBLICATIONS

Extended European Search Report from corresponding European Patent Application No. 22767479.3, dated Apr. 2, 2025.

Notification of Provision of Information about Patent Applications from corresponding Korean Patent Application No. 10-2022-0029195, dated Apr. 18, 2025.

* cited by examiner

ORGANIC LIGHT-EMITTING DEVICE

CROSS-REFERENCE TO RELATED APPLICATIONS

This application is a national phase application of PCT Application No. PCT/KR2022/003273, filed on 8 Mar. 2022, which claims the benefit and priority to Korean Patent Application No. 10-2021-0030257, filed on 8 Mar. 2021. The entire disclosures of the applications identified in this paragraph are incorporated herein by references.

TECHNICAL FIELD

The present invention relates to a highly efficient organic light emitting device that includes a light emitting layer employing, as a host, an anthracene derivative with a specific structure in which a benzofuran structure is introduced to the anthracene skeleton and, as a dopant, a polycyclic compound with a specific structure, achieving significantly improved external quantum efficiency.

BACKGROUND ART

Organic light emitting devices are self-luminous devices in which electrons injected from an electron injecting electrode (cathode) recombine with holes injected from a hole injecting electrode (anode) in a light emitting layer to form excitons, which emit light while releasing energy. Such organic light emitting devices have the advantages of low driving voltage, high luminance, large viewing angle, and short response time and can be applied to full-color light emitting flat panel displays. Due to these advantages, organic light emitting devices have received attention as next-generation light sources.

The above characteristics of organic light emitting devices are achieved by structural optimization of organic layers of the devices and are supported by stable and efficient materials for the organic layers, such as hole injecting materials, hole transport materials, light emitting materials, electron transport materials, electron injecting materials, and electron blocking materials. However, more research still needs to be done to develop structurally optimized structures of organic layers for organic light emitting devices and stable and efficient materials for organic layers of organic light emitting devices.

Particularly, for maximum efficiency in a light emitting layer, an appropriate combination of energy band gaps of a host and a dopant is required such that holes and electrons migrate to the dopant through stable electrochemical paths to form excitons.

DETAILED DESCRIPTION OF THE INVENTION

Problems to be Solved by the Invention

Accordingly, the present invention is intended to provide a highly efficient organic light emitting device that includes a light emitting layer employing specific host and dopant materials, achieving significantly improved luminous efficiency.

Means for Solving the Problems

One aspect of the present invention provides an organic light emitting device including a first electrode, a second electrode opposite to the first electrode, and a light emitting layer interposed between the first and second electrodes wherein the light emitting layer includes, as a host, an anthracene derivative represented by Formula A:

[Formula A]

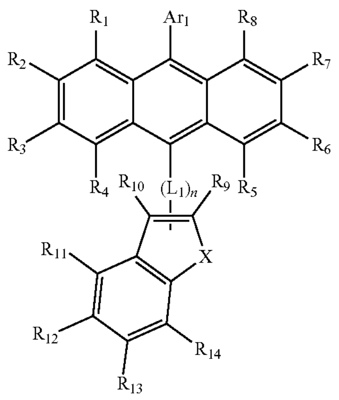

and, as a dopant, a compound represented by one of Formulas D-1 to D-8:

[Formula D-1]

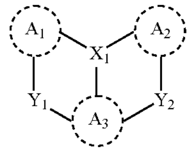

[Formula D-2]

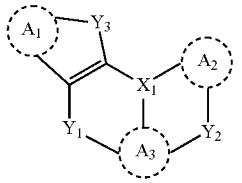

[Formula D-3]

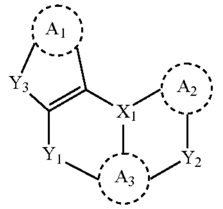

[Formula D-4]

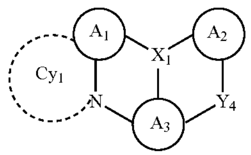

[Formula D-5]

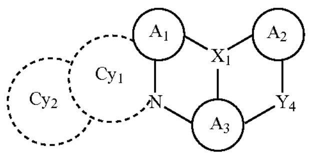

-continued

[Formula D-6]

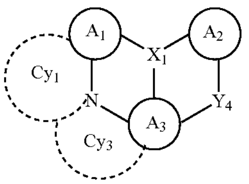

[Formula D-7]

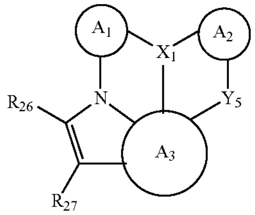

[Formula D-8]

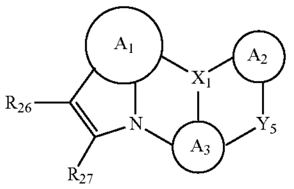

The specific structures of Formulas A and D-1 to D-8, definitions of the substituents in Formulas A and D-1 to D-8, and specific compounds that can be represented by Formulas A and D-1 to D-8 are described below.

Effects of the Invention

The organic light emitting device of the present invention includes a light emitting layer employing, as a host, an anthracene derivative with a specific structure in which a benzofuran structure is introduced to the anthracene skeleton and, as a dopant, a polycyclic compound with a specific structure. The use of the host and dopant ensures significantly improved external quantum efficiency and high efficiency of the device. Due to these advantages, the organic light emitting device of the present invention can find useful industrial applications in not only lighting systems but also a variety of displays, including flat panel displays, flexible displays, and wearable displays.

BEST MODE FOR CARRYING OUT THE INVENTION

The present invention will now be described in more detail.

One aspect of the present invention is directed to an organic light emitting device including a first electrode, a second electrode opposite to the first electrode, and one or more organic layers interposed between the first and second electrodes wherein one of the organic layers, preferably a light emitting layer includes, as a host, a compound represented by Formula A:

[Formula A]

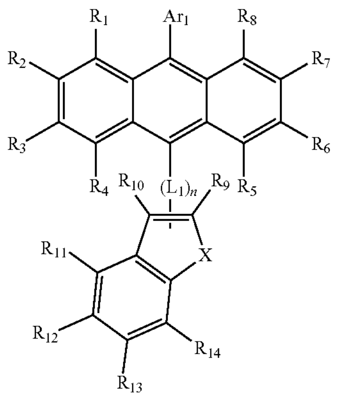

wherein $Ar_1$ is selected from substituted or unsubstituted $C_6$-$C_{50}$ aryl, substituted or unsubstituted $C_2$-$C_{50}$ heteroaryl, and substituted or unsubstituted $C_3$-$C_{50}$ mixed aliphatic-aromatic cyclic groups, $R_1$ to $R_{14}$ are the same as or different from each other and are each independently selected from hydrogen, deuterium, substituted or unsubstituted $C_1$-$C_{30}$ alkyl, substituted or unsubstituted $C_6$-$C_{50}$ aryl, substituted or unsubstituted $C_2$-$C_{30}$ alkenyl, substituted or unsubstituted $C_2$-$C_{30}$ alkynyl, substituted or unsubstituted $C_3$-$C_{30}$ cycloalkyl, substituted or unsubstituted $C_3$-$C_{30}$ cycloalkenyl, substituted or unsubstituted $C_2$-$C_{50}$ heteroaryl, substituted or unsubstituted $C_2$-$C_{30}$ heterocycloalkyl, substituted or unsubstituted $C_1$-$C_{30}$ alkoxy, substituted or unsubstituted $C_6$-$C_{50}$ aryloxy, substituted or unsubstituted $C_1$-$C_{30}$ alkylthioxy, substituted or unsubstituted $C_6$-$C_{50}$ arylthioxy, substituted or unsubstituted amine, substituted or unsubstituted silyl, substituted or unsubstituted germanium, substituted or unsubstituted $C_3$-$C_{50}$ mixed aliphatic-aromatic cyclic groups, cyano, and halogen, with the proviso that either one of $R_9$ and $R_{10}$ is optionally bonded to the linker $L_1$, X is an oxygen (O) or sulfur (S) atom, $L_1$ is a single bond or is selected from substituted or unsubstituted $C_6$-$C_{50}$ arylene and substituted or unsubstituted $C_2$-$C_{50}$ heteroarylene, and n is an integer from 1 to 3, provided that when n is 2 or more, the linkers $L_1$ are the same as or different from each other, and as a dopant, a compound represented by one of Formulas D-1 to D-8:

[Formula D-1]

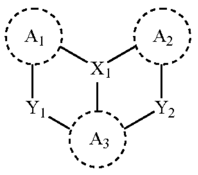

wherein $X_1$ is selected from B, P═O, and P═S, $Y_1$ and $Y_2$ are each independently selected from $NR_{21}$, $CR_{22}R_{23}$, O, S, Se, and $SiR_{24}R_{25}$, $A_1$ to $A_3$ are each independently selected from substituted or unsubstituted $C_6$-$C_{50}$ aromatic hydrocarbon rings, substituted or unsubstituted $C_2$-$C_{50}$ aromatic heterocyclic rings, substituted or unsubstituted $C_3$-$C_{30}$ aliphatic rings, and substituted or unsubstituted $C_3$-$C_{30}$ mixed aliphatic-aromatic rings, and $R_{21}$ to $R_{25}$ are the same as or different from each other and are each independently selected from hydrogen, deuterium, substituted or unsubstituted $C_1$-$C_{30}$ alkyl, substituted or unsubstituted $C_2$-$C_{30}$ alkenyl, substituted or unsubstituted $C_2$-$C_{30}$ alkynyl, substituted or unsubstituted $C_6$-$C_{50}$ aryl, substituted or unsubstituted $C_3$-$C_{30}$ cycloalkyl, substituted or unsubstituted $C_3$-$C_{30}$ heterocycloalkyl, substituted or unsubstituted $C_2$-$C_{50}$ heteroaryl, substituted or unsubstituted $C_1$-$C_{30}$ alkoxy, substituted or unsubstituted $C_6$-$C_{30}$ aryloxy, substituted or unsubstituted $C_1$-$C_{30}$ alkylthioxy, substituted or unsubstituted $C_6$-$C_{30}$ arylthioxy, substituted or unsubstituted amine, substituted or unsubstituted silyl, substituted or unsubstituted $C_3$-$C_{20}$ mixed aliphatic-aromatic cyclic groups, nitro, cyano, and halogen, with the proviso that each of $R_{21}$ to $R_{25}$ is optionally bonded to one or more of the rings $A_1$ to $A_3$ to form an alicyclic or aromatic monocyclic or polycyclic ring or a mixed aliphatic-aromatic ring, the substituents of each of the rings $A_1$ to $A_3$ are optionally linked to each other to form an alicyclic or aromatic monocyclic or polycyclic ring or a mixed aliphatic-aromatic ring, $R_{22}$ and $R_{23}$ are optionally linked to each other to form an alicyclic or aromatic monocyclic or polycyclic ring or a mixed aliphatic-aromatic ring, and $R_{24}$ and $R_{25}$ are optionally linked to each other to form an alicyclic or aromatic monocyclic or polycyclic ring or a mixed aliphatic-aromatic ring,

[Formula D-2]

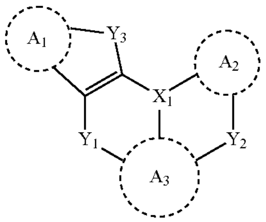

wherein $Y_3$ is selected from $NR_{21}$, $CR_{22}R_{23}$, O, S, Se, and $SiR_{24}R_{25}$ and $X_1$, $Y_1$, $Y_2$, $A_1$ to $A_3$, and $R_{21}$ to $R_{25}$ are as defined in Formula D-1,

[Formula D-3]

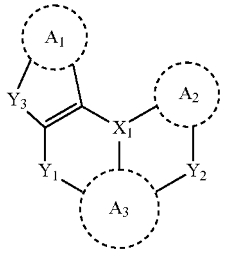

wherein $Y_3$ is as defined in Formula D-2 and $X_1$, $Y_1$, $Y_2$, $A_1$ to $A_3$, and $R_{21}$ to $R_{25}$ are as defined in Formula D-1,

[Formula D-4]

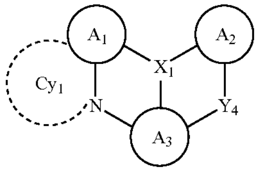

wherein $Y_4$ is selected from $NR_{21}$, $CR_{22}R_{23}$, O, S, Se, and $SiR_{24}R_{25}$, $X_1$, $A_1$ to $A_3$, and $R_{21}$ to $R_{25}$ are as defined in Formula D-1, and $Cy_1$ represents a ring formed by a substituted or unsubstituted $C_2$-$C_5$ alkylene group with the adjacent nitrogen (N) atom, the aromatic carbon atom in the ring $A_1$ to which the nitrogen (N) atom is bonded, and the aromatic carbon atom in the ring $A_1$ to which $Cy_1$ is to be bonded,

[Formula D-5]

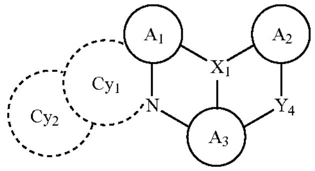

wherein $Y_4$ is selected from $NR_{21}$, $CR_{22}R_{23}$, O, S, Se, and $SiR_{24}R_{25}$, and $X_1$, $A_1$ to $A_3$, and $R_{21}$ to $R_{25}$ are as defined in Formula D-1, $Cy_1$ is as defined in Formula D-4, $Cy_2$ represents a saturated hydrocarbon ring attached to $Cy_1$ and formed by a substituted or unsubstituted $C_2$-$C_5$ alkylene group with carbon atoms in $Cy_1$,

[Formula D-6]

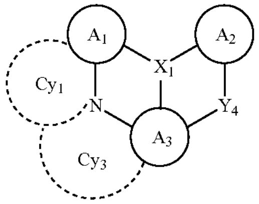

wherein $Y_4$ is selected from $NR_{21}$, $CR_{22}R_{23}$, O, S, Se, and $SiR_{24}R_{25}$, $X_1$, $A_1$ to $A_3$, and $R_{21}$ to $R_{25}$ are as defined in Formula D-1, $Cy_1$ is as defined in Formula D-4, and $Cy_3$ represents a ring formed by a substituted or unsubstituted $C_1$-$C_4$ alkylene group with the aromatic carbon atom in the ring $A_3$ to which $Cy_3$ is to be bonded, the nitrogen (N) atom, the aromatic carbon atom in the ring $A_3$ to which the nitrogen atom is bonded, and the carbon atom in $Cy_1$ to which the nitrogen atom is bonded,

[Formula D-7]

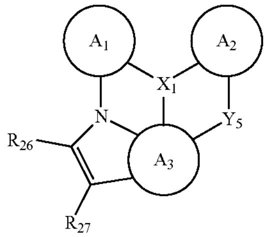

wherein $Y_5$ is selected from $NR_{21}$, $CR_{22}R_{23}$, O, S, Se, and $SiR_{24}R_{25}$ and $X_1$, $A_1$ to $A_3$, and $R_{21}$ to $R_{27}$ are as defined in Formula D-1, and

[Formula D-8]

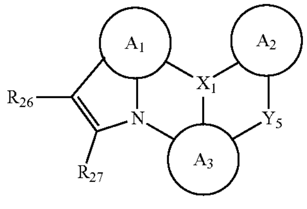

wherein $Y_5$ is as defined in Formula D-7 and $X_1$, $A_1$ to $A_3$, and $R_{21}$ to $R_{27}$ are as defined in Formula D-1.

As used herein, the term "substituted" in the definitions of $Ar_1$, $R_1$ to $R_{14}$, and $L_1$ in Formula A and $Y_1$ to $Y_5$, $A_1$ to $A_3$, $Cy_1$ to $Cy_3$, $R_{26}$, and $R_{27}$ in Formulas D-1 to D-8 indicates substitution with one or more substituents selected from deuterium, cyano, halogen, hydroxyl, nitro, $C_1$-$C_{24}$ alkyl, $C_1$-$C_{24}$ haloalkyl, $C_3$-$C_{30}$ cycloalkyl, $C_2$-$C_{24}$ alkenyl, $C_2$-$C_{24}$ alkynyl, $C_1$-$C_{24}$ heteroalkyl, $C_6$-$C_{30}$ aryl, $C_7$-$C_{30}$ arylalkyl, $C_7$-$C_{30}$ alkylaryl, $C_2$-$C_{30}$ heteroaryl, $C_2$-$C_{30}$ heteroarylalkyl, $C_1$-$C_{24}$ alkoxy, $C_6$-$C_{30}$ aryloxy, $C_1$-$C_{24}$ amine, $C_1$-$C_{24}$ silyl, $C_3$-$C_{30}$ mixed aliphatic-aromatic cyclic groups, boron, aluminum, phosphoryl, hydroxyl, selenium, tellurium, nitro, and halogen. One or more hydrogen atoms in each of the substituents are optionally replaced by deuterium atoms.

In the "substituted or unsubstituted $C_1$-$C_{30}$ alkyl", "substituted or unsubstituted $C_6$-$C_{50}$ aryl", etc., the number of carbon atoms in the alkyl or aryl group indicates the number of carbon atoms constituting the unsubstituted alkyl or aryl moiety without considering the number of carbon atoms in the substituent(s). For example, a phenyl group substituted with a butyl group at the para-position corresponds to a $C_6$ aryl group substituted with a $C_4$ butyl group.

As used herein, the expression "bonded to an adjacent group to form a ring" means that the corresponding group combines with an adjacent group to form a substituted or unsubstituted alicyclic or aromatic ring and the term "adjacent substituent" may mean a substituent on an atom directly attached to an atom substituted with the corresponding substituent, a substituent disposed sterically closest to the corresponding substituent or another substituent on an atom substituted with the corresponding substituent. For example, two substituents substituted at the ortho position of a benzene ring or two substituents on the same carbon in an aliphatic ring may be considered "adjacent" to each other.

In the present invention, the alkyl groups may be straight or branched. Specific examples of the alkyl groups include, but are not limited to, methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 2-methylpentyl, 4-methylhexyl, and 5-methylhexyl groups.

The alkenyl group is intended to include straight and branched ones and may be optionally substituted with one or more other substituents. The alkenyl group may be specifically a vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, stilbenyl or styrenyl group but is not limited thereto.

The alkynyl group is intended to include straight and branched ones and may be optionally substituted with one or more other substituents. The alkynyl group may be, for example, ethynyl or 2-propynyl but is not limited thereto.

The cycloalkenyl group is a non-aromatic cyclic unsaturated hydrocarbon group having one or more carbon-carbon double bonds. The cycloalkenyl group may be, for example, cyclopropenyl, cyclobutenyl, cyclopentenyl, cyclohexenyl, cycloheptenyl, 1,3-cyclohexadienyl, 1,4-cyclohexadienyl, 2,4-cycloheptadienyl or 1,5-cyclooctadienyl but is not limited thereto.

The aromatic hydrocarbon rings or aryl groups may be monocyclic or polycyclic ones. Examples of the monocyclic aryl groups include, but are not limited to, phenyl, biphenyl, terphenyl, and stilbenyl groups. Examples of the polycyclic aryl groups include naphthyl, anthracenyl, phenanthrenyl, pyrenyl, perylenyl, tetracenyl, chrysenyl, fluorenyl, acenaphathcenyl, triphenylene, and fluoranthrene groups but the scope of the present invention is not limited thereto.

The aromatic heterocyclic rings or heteroaryl groups refer to aromatic groups containing one or more heteroatoms. Examples of the aromatic heterocyclic rings or heteroaryl groups include, but are not limited to, thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phthalazinyl, pyridopyrimidinyl, pyridopyrazinyl, pyrazinopyrazinyl, isoquinoline, indole, carbazole, benzoxazole, benzimidazole, benzothiazole, benzocarbazole, benzothiophene, dibenzothiophene, benzofuranyl, dibenzofuranyl, phenanthroline, thiazolyl, isoxazolyl, oxadiazolyl, thiadiazolyl, benzothiazolyl, and phenothiazinyl groups.

The aliphatic hydrocarbon rings or cycloalkyl groups refer to non-aromatic rings consisting only of carbon and hydrogen atoms. The aliphatic hydrocarbon ring is intended to include monocyclic and polycyclic ones and may be optionally substituted with one or more other substituents. As used herein, the term "polycyclic" means that the aliphatic hydrocarbon ring may be directly attached or fused to one or more other cyclic groups. The other cyclic groups may be aliphatic hydrocarbon rings and other examples thereof include aliphatic heterocyclic, aryl, and heteroaryl groups. Specific examples of the aliphatic hydrocarbon rings include, but are not limited to, cycloalkyl groups such as cyclopropyl, cyclobutyl, cyclopentyl, adamantyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, and cyclooctyl, cycloalkanes such as cyclohexane and cyclopentane, and cycloalkenes such as cyclohexene and cyclobutene.

The aliphatic heterocyclic rings or heterocycloalkyl groups refer to aliphatic rings containing one or more heteroatoms such as O, S, Se, N, and Si. The aliphatic heterocyclic ring is intended to include monocyclic or polycyclic ones and may be optionally substituted with one or more other substituents. As used herein, the term "polycyclic" means that the aliphatic heterocyclic ring such as heterocycloalkyl, heterocycloalkane or heterocycloalkene may be directly attached or fused to one or more other cyclic groups. The other cyclic groups may be aliphatic heterocyclic rings and other examples thereof include aliphatic hydrocarbon rings, aryl groups, and heteroaryl groups.

The mixed aliphatic-aromatic cyclic groups refer to structures in which at least one aliphatic ring and at least one aromatic ring are linked or fused together and which are overall non-aromatic. The mixed aliphatic-aromatic polycyclic rings may contain one or more heteroatoms selected from N, O, P, and S other than carbon atoms (C).

The alkoxy group may be specifically a methoxy, ethoxy, propoxy, isobutyloxy, sec-butyloxy, pentyloxy, iso-amyloxy or hexyloxy group but is not limited thereto.

The silyl group is intended to include —$SiH_3$, alkylsilyl, arylsilyl, alkylarylsilyl, arylheteroarylsilyl, and heteroarylsilyl. The arylsilyl refers to a silyl group obtained by substituting one, two or three of the hydrogen atoms in —$SiH_3$ with aryl groups. The alkylsilyl refers to a silyl group obtained by substituting one, two or three of the hydrogen atoms in —$SiH_3$ with alkyl groups. The alkylarylsilyl refers to a silyl group obtained by substituting one of the hydrogen atoms in —$SiH_3$ with an alkyl group and the other two hydrogen atoms with aryl groups or substituting two of the hydrogen atoms in —$SiH_3$ with alkyl groups and the remaining hydrogen atom with an aryl group. The arylheteroarylsilyl refers to a silyl group obtained by substituting one of the hydrogen atoms in —$SiH_3$ with an aryl group and the other two hydrogen atoms with heteroaryl groups or substituting two of the hydrogen atoms in —$SiH_3$ with aryl groups and the remaining hydrogen atom with a heteroaryl group. The heteroarylsilyl refers to a silyl group obtained by substituting one, two or three of the hydrogen atoms in —$SiH_3$ with heteroaryl groups. The arylsilyl group may be, for example, substituted or unsubstituted monoarylsilyl, substituted or unsubstituted diarylsilyl, or substituted or unsubstituted triarylsilyl. The same applies to the alkylsilyl and heteroarylsilyl groups.

Each of the aryl groups in the arylsilyl, heteroarylsilyl, and arylheteroarylsilyl groups may be a monocyclic or polycyclic one. Each of the heteroaryl groups in the arylsilyl, heteroarylsilyl, and arylheteroarylsilyl groups may be a monocyclic or polycyclic one.

Specific examples of the silyl groups include trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more of the hydrogen atoms in each of the silyl groups may be substituted with the substituents mentioned in the aryl groups.

The amine group is intended to include —$NH_2$, alkylamine, arylamine, arylheteroarylamine, and heteroarylamine. The arylamine refers to an amine group obtained by substituting one or two of the hydrogen atoms in —$NH_2$ with aryl groups. The alkylamine refers to an amine group obtained by substituting one or two of the hydrogen atoms in —$NH_2$ with alkyl groups. The alkylarylamine refers to an amine group obtained by substituting one of the hydrogen atoms in —$NH_2$ with an alkyl group and the other hydrogen atom with an aryl group. The arylheteroarylamine refers to an amine group obtained by substituting one of the hydrogen atoms in —$NH_2$ with an aryl group and the other hydrogen atom with a heteroaryl group. The heteroarylamine refers to an amine group obtained by substituting one or two of the hydrogen atoms in —$NH_2$ with heteroaryl groups. The arylamine may be, for example, substituted or unsubstituted monoarylamine, substituted or unsubstituted diarylamine, or substituted or unsubstituted triarylamine. The same applies to the alkylamine and heteroarylamine groups.

Each of the aryl groups in the arylamine, heteroarylamine, and arylheteroarylamine groups may be a monocyclic or polycyclic one. Each of the heteroaryl groups in the arylamine, heteroarylamine, and arylheteroarylamine groups may be a monocyclic or polycyclic one.

The germanium group is intended to include —$GeH_3$, alkylgermanium, arylgermanium, heteroarylgermanium, alkylarylgermanium, alkylheteroarylgermanium, and arylheteroarylgermanium. The definitions of the substituents in the germanium groups follow those described for the silyl groups, except that the silicon (Si) atom in each silyl group is changed to a germanium (Ge) atom.

Specific examples of the germanium groups include trimethylgermane, triethylgermane, triphenylgermane, trimethoxygermane, dimethoxyphenylgermane, diphenylmethylgermane, diphenylvinylgermane, methylcyclobutylgermane, and dimethylfurylgermane. One or more of the hydrogen atoms in each of the germanium groups may be substituted with the substituents mentioned in the aryl groups.

The cycloalkyl, aryl, and heteroaryl groups in the cycloalkyloxy, aryloxy, heteroaryloxy, cycloalkylthioxy, arylthioxy, and heteroarylthioxy groups are the same as those exemplified above. Specific examples of the aryloxy groups include, but are not limited to, phenoxy, p-tolyloxy, m-tolyloxy, 3,5-dimethylphenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, and 9-phenanthryloxy groups. Specific examples of the arylthioxy groups include, but are not limited to, phenylthioxy, 2-methylphenylthioxy, and 4-tert-butylphenylthioxy groups.

The halogen group may be, for example, fluorine, chlorine, bromine or iodine.

According to one embodiment of the present invention, the anthracene derivative represented by Formula A may be selected from the following compounds A-1 to A-88:

A-1

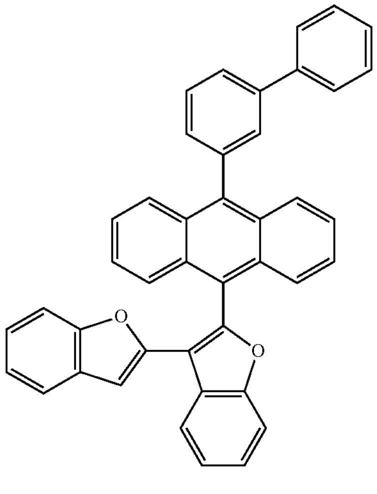

-continued
A-2
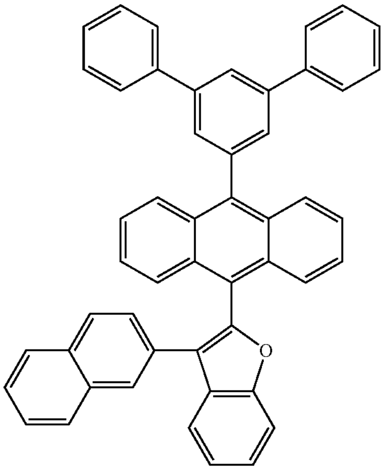
A-3
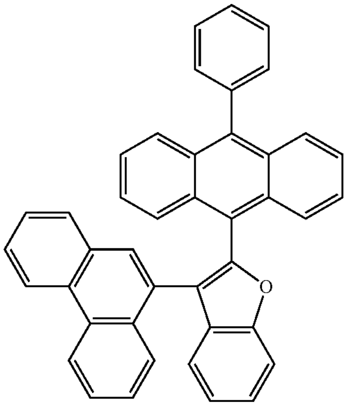
A-4
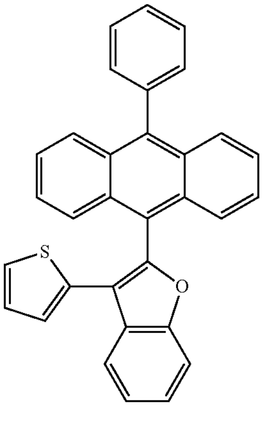
-continued
A-5
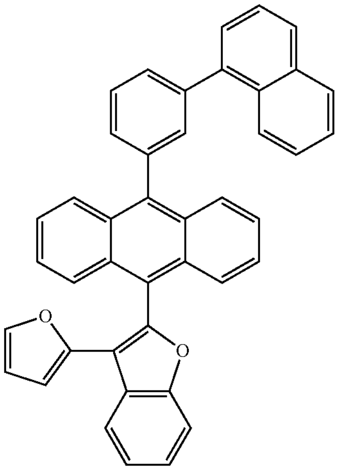
A-6
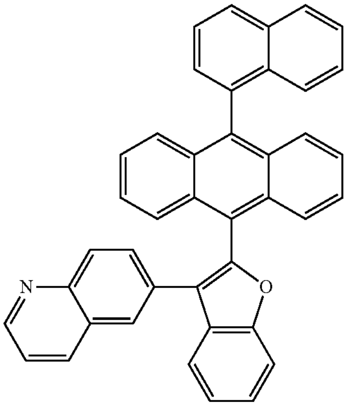
A-7
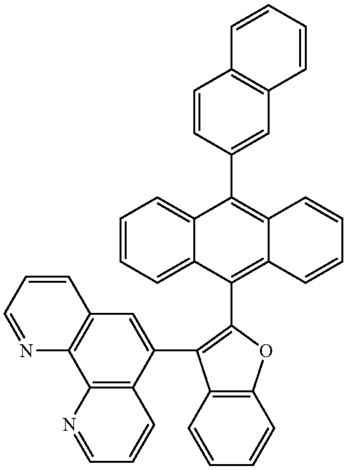

-continued
A-8
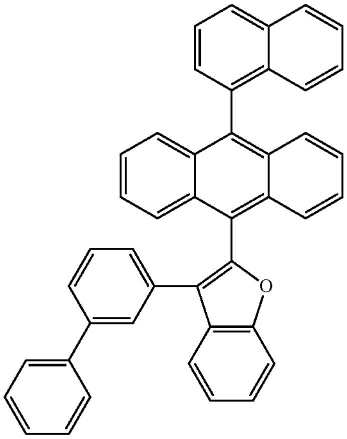
A-9
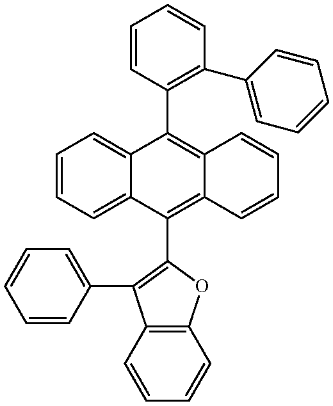
A-10
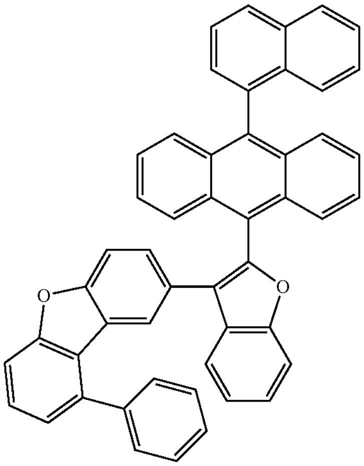
-continued
A-11
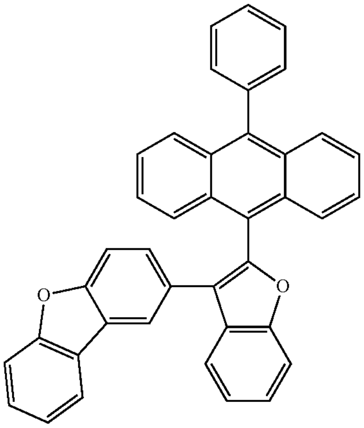
A-12
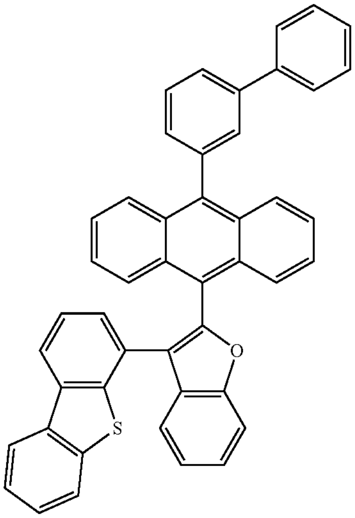
A-13
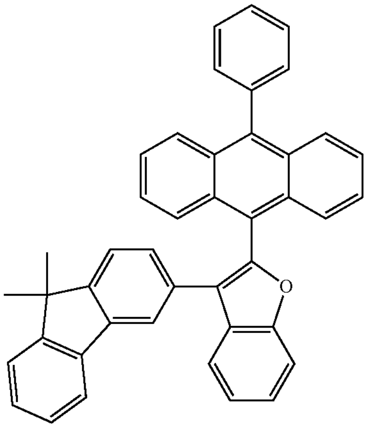

-continued
A-14
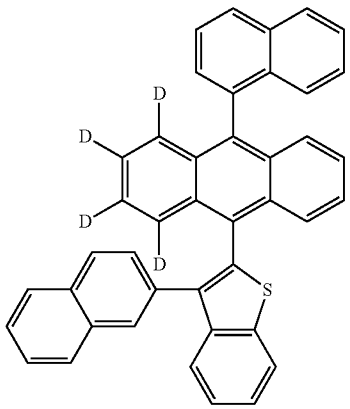
A-15
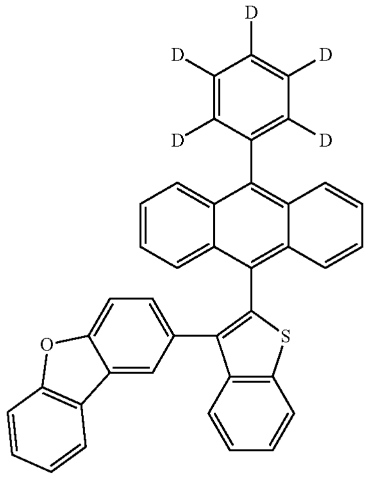
A-16
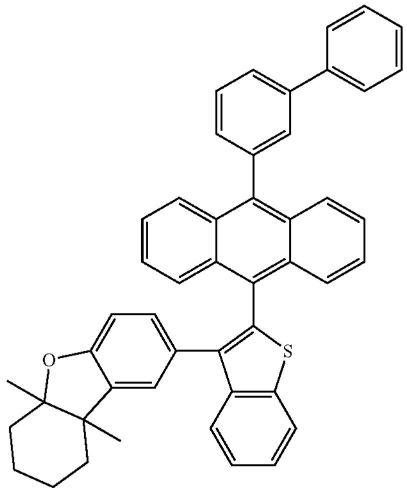
-continued
A-17
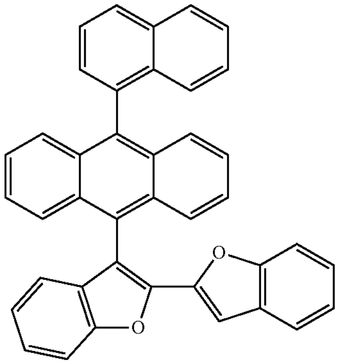
A-18
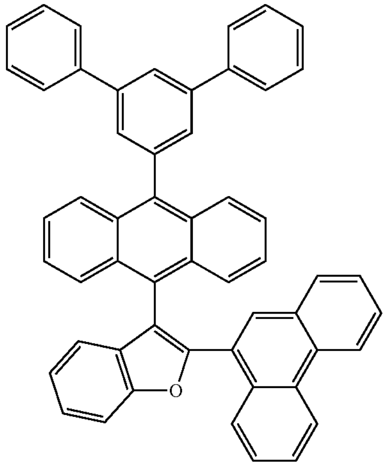
A-19
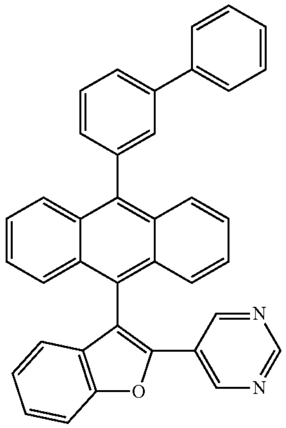
A-20
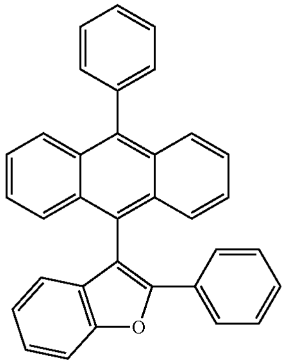

-continued
A-21
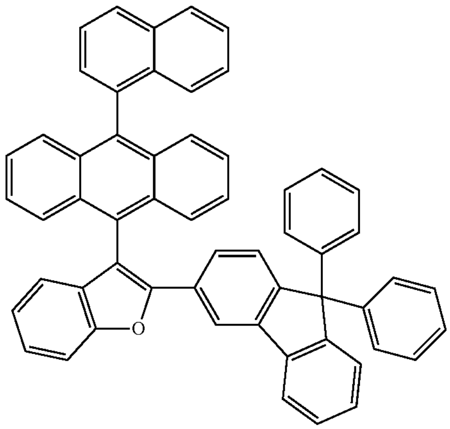
A-22
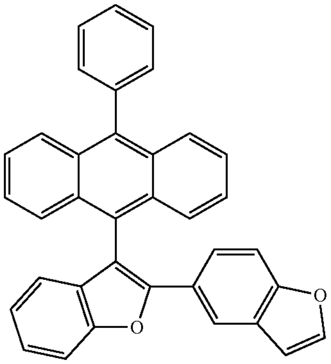
A-23
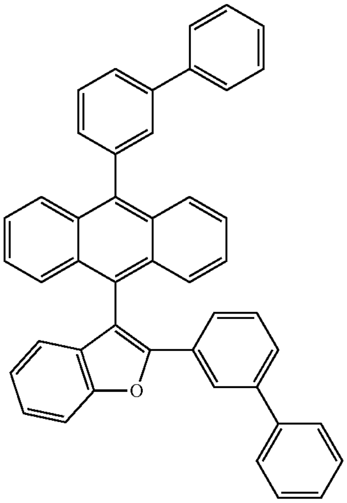
-continued
A-24
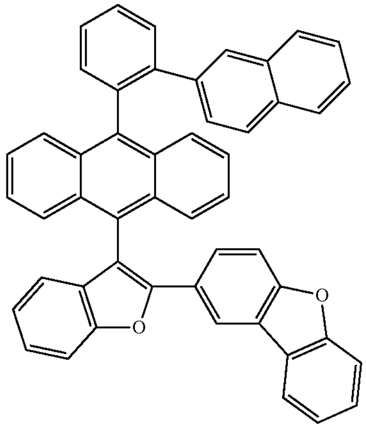
A-25
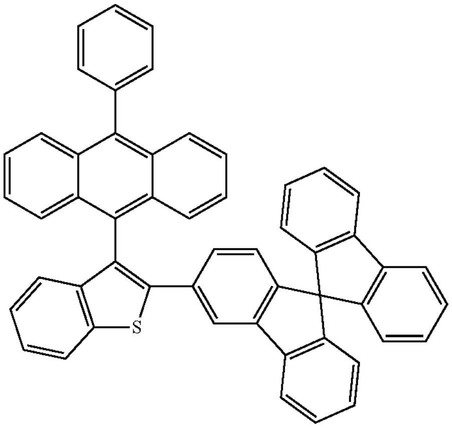
A-26
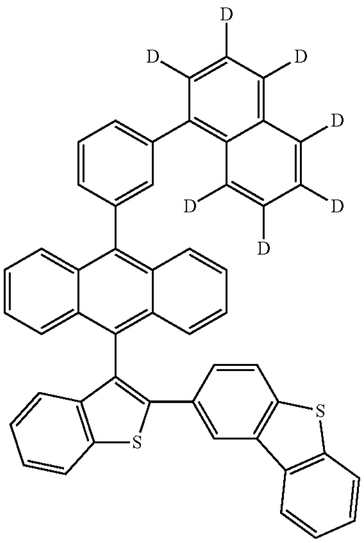

-continued
A-27
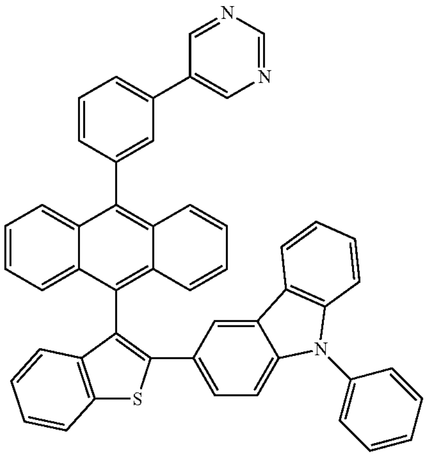
A-28
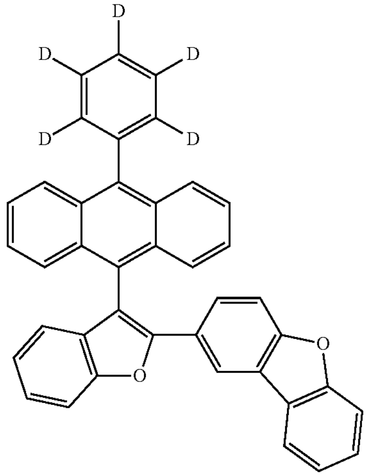
A-29
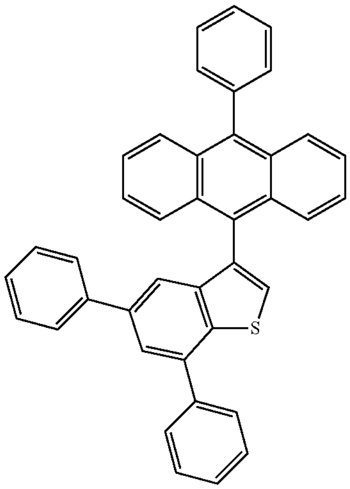
-continued
A-30
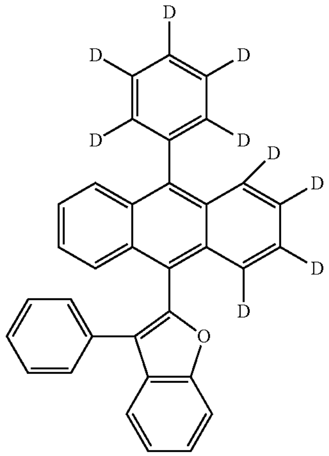
A-31
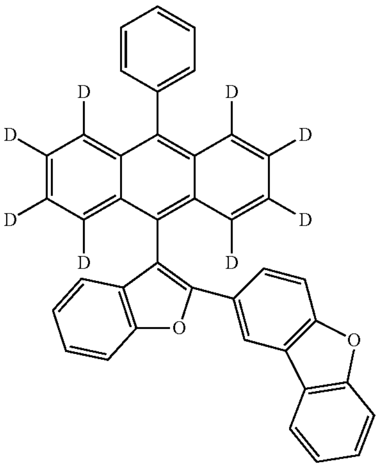
A-32
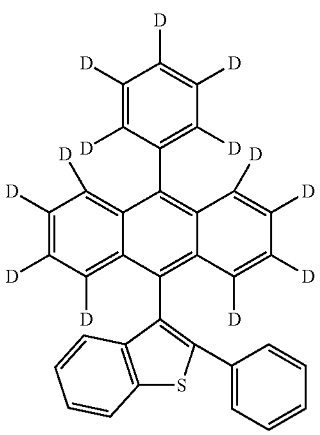

-continued
A-33
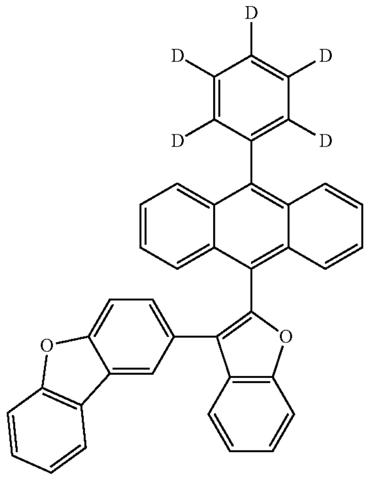
A-34
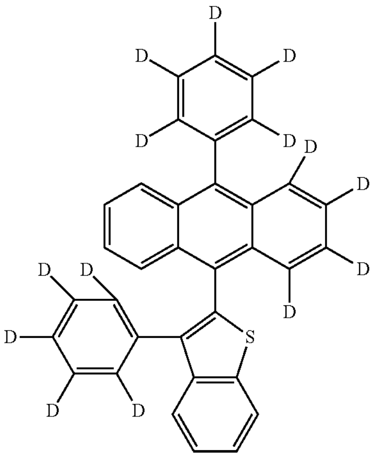
A-35
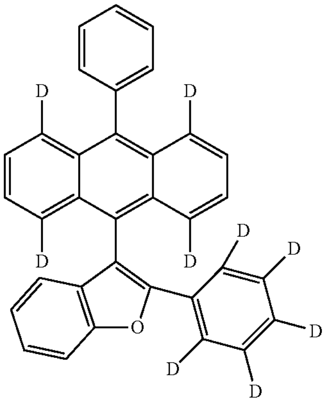
-continued
A-36
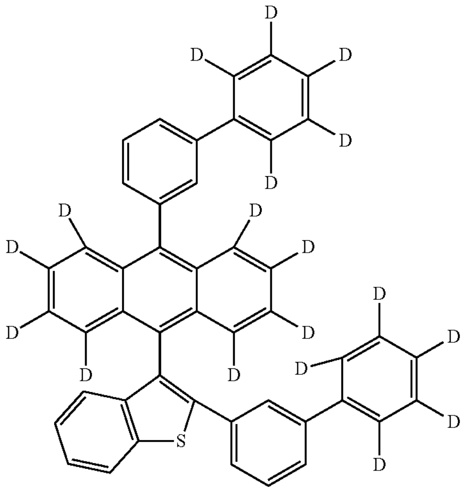
A-37
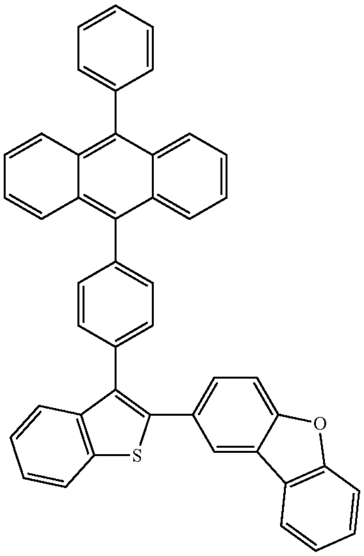
A-38
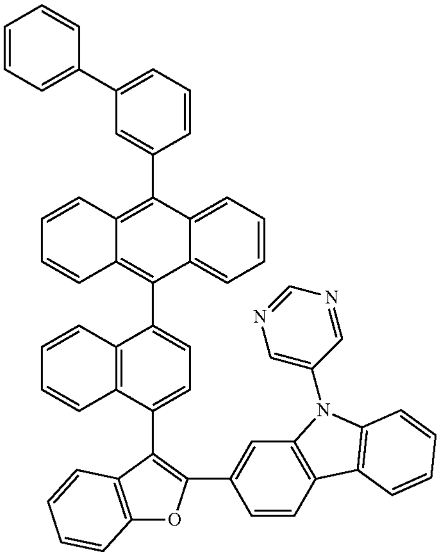

-continued
A-39
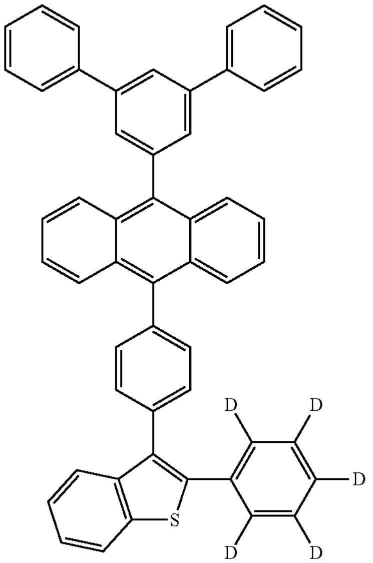
A-40
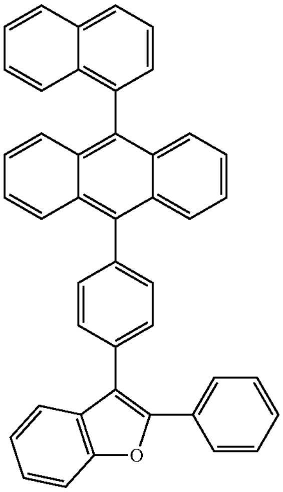
A-41
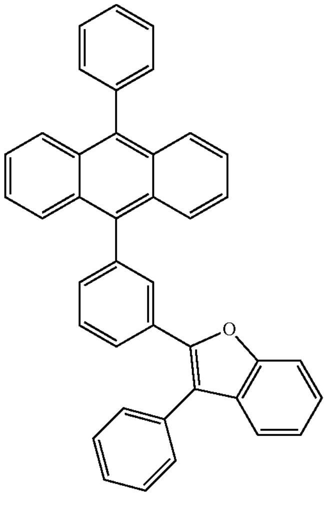
-continued
A-42
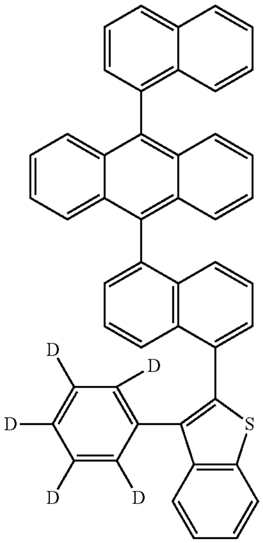
A-43
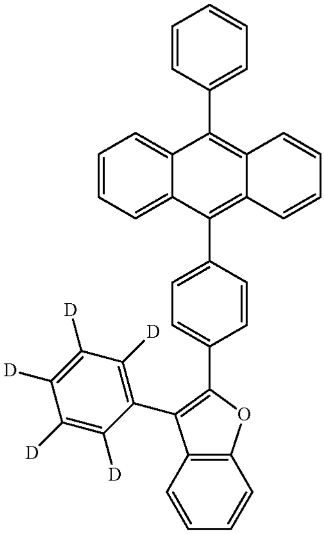

-continued
A-44
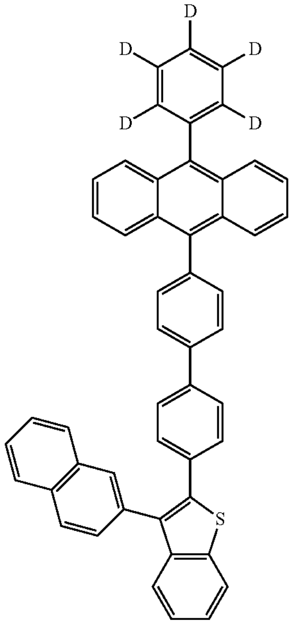
A-45
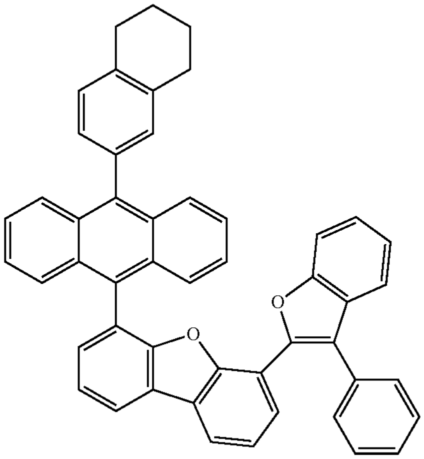
A-46
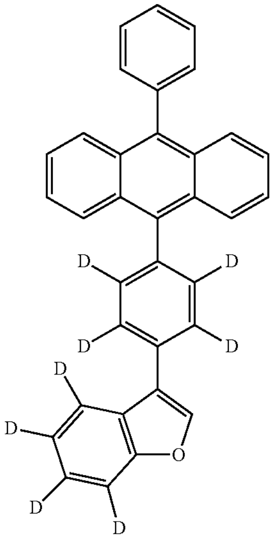
-continued
A-47
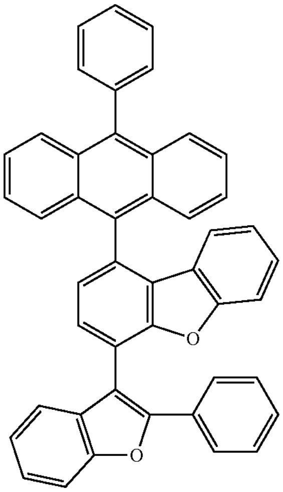
A-48
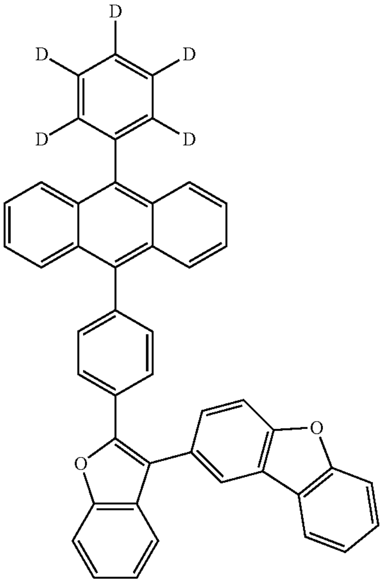
A-49
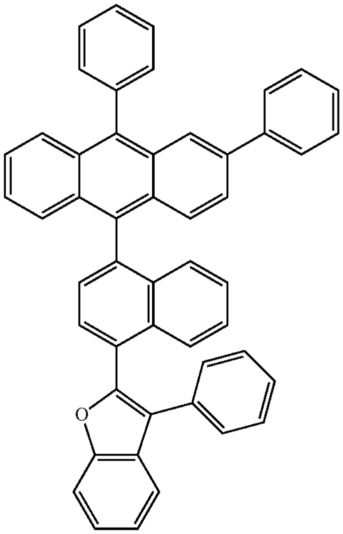

-continued
A-50
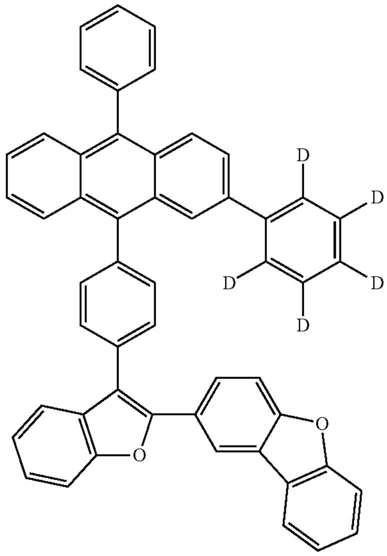
A-51
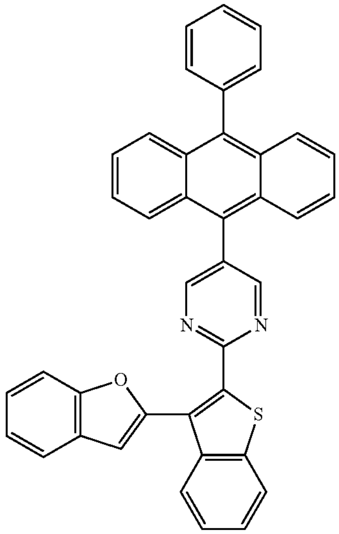
-continued
A-52
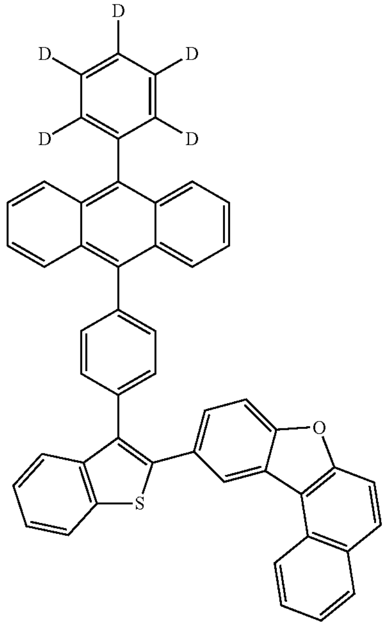
A-53
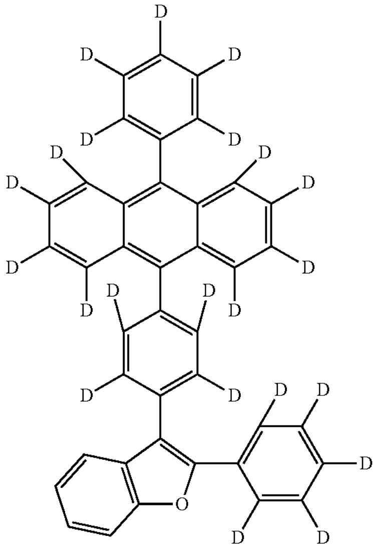
A-54
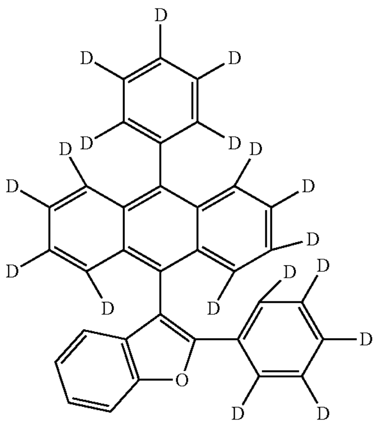

-continued
A-55
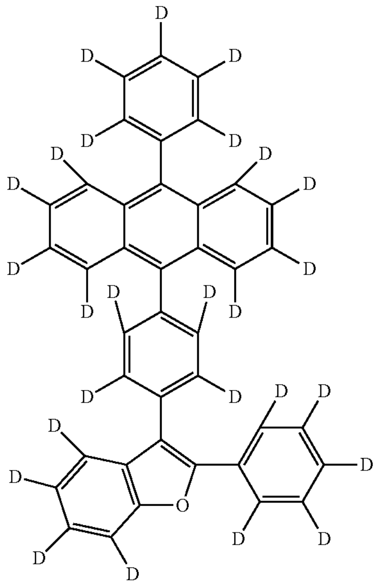
A-56
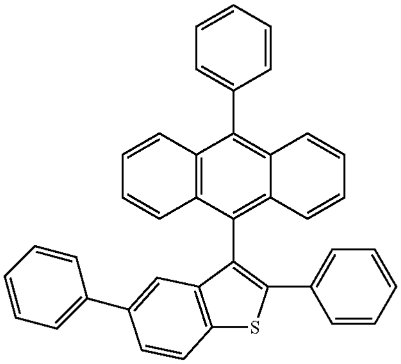
A-57
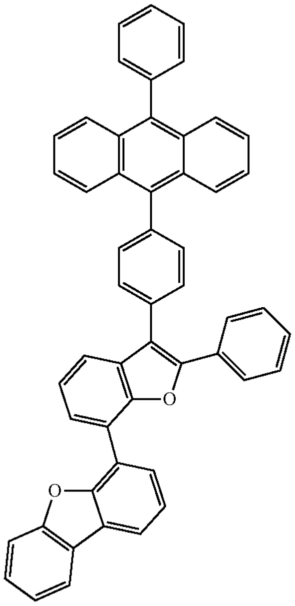
-continued
A-58
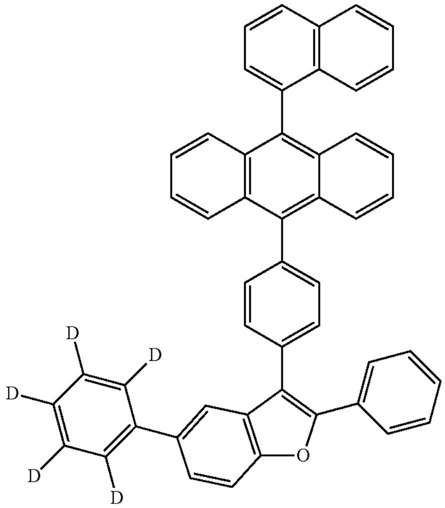
A-59
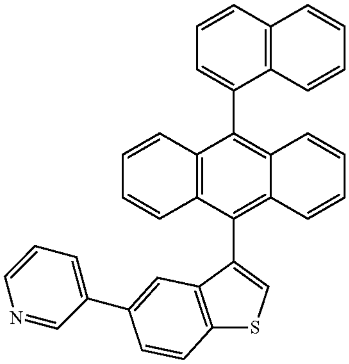
A-60
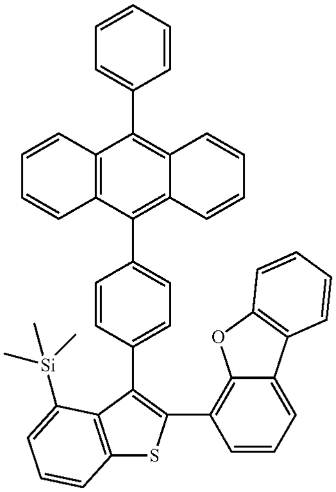

A-61
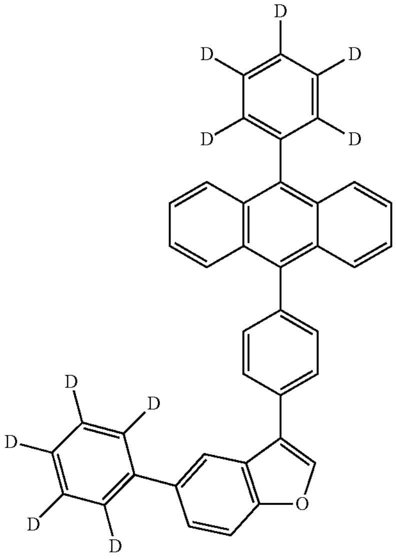
A-62
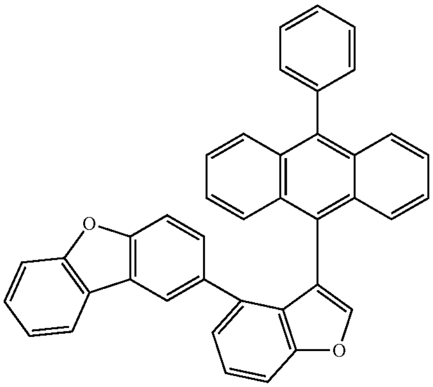
A-63
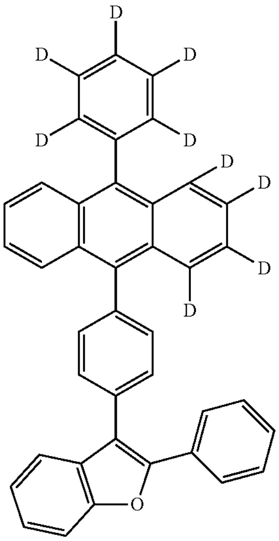
-continued
A-64
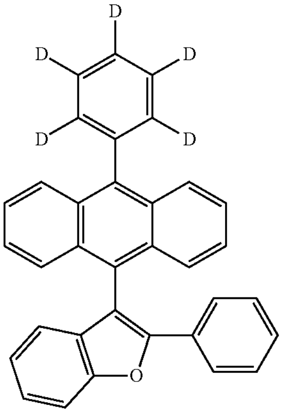
A-65
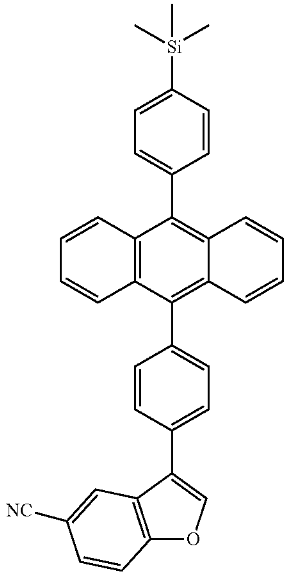
A-66
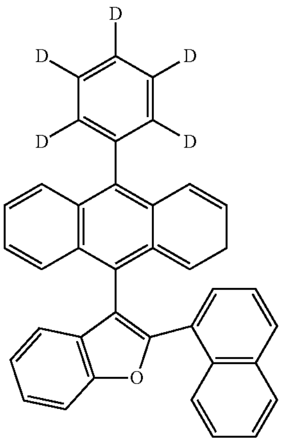

-continued
A-67
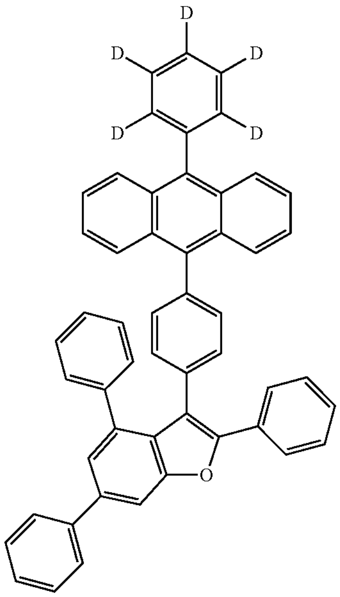
A-68
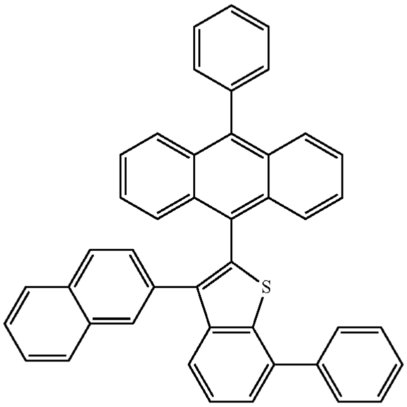
A-69
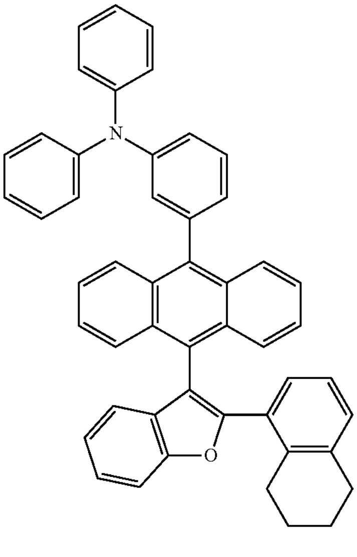
-continued
A-70
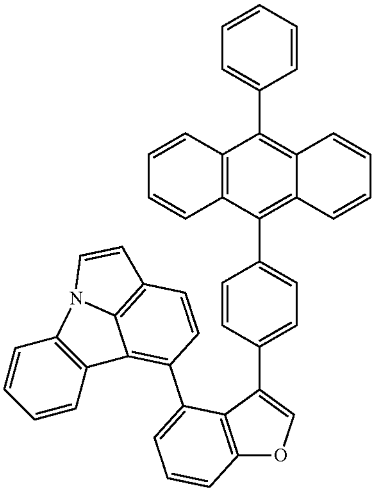
A-71
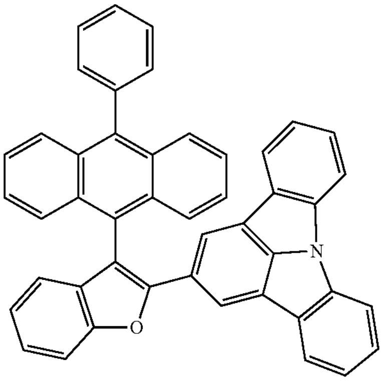
A-72
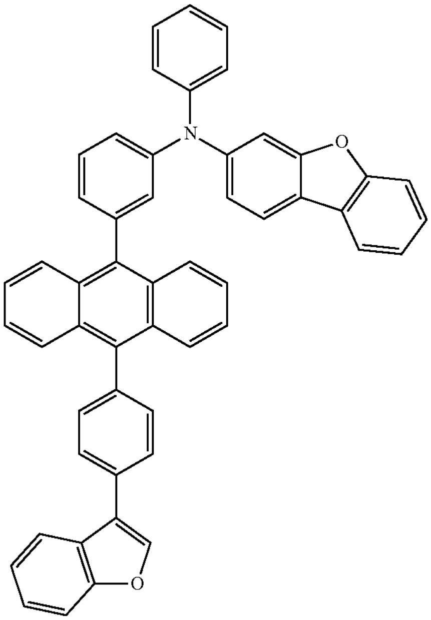

-continued
A-73
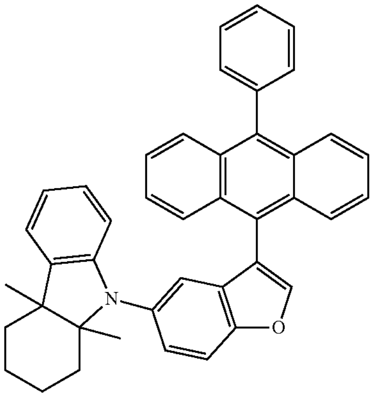
A-74
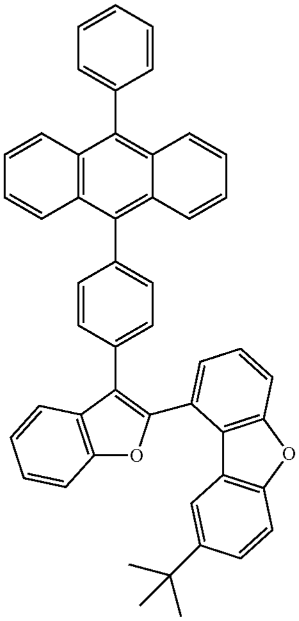
A-75
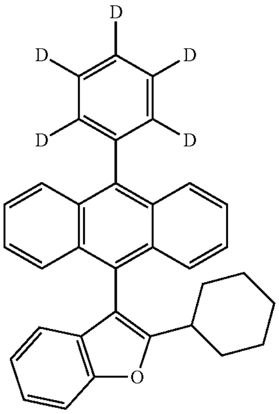
-continued
A-76
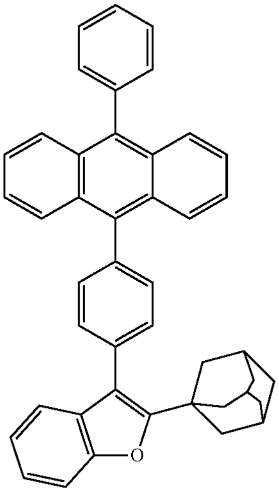
A-77
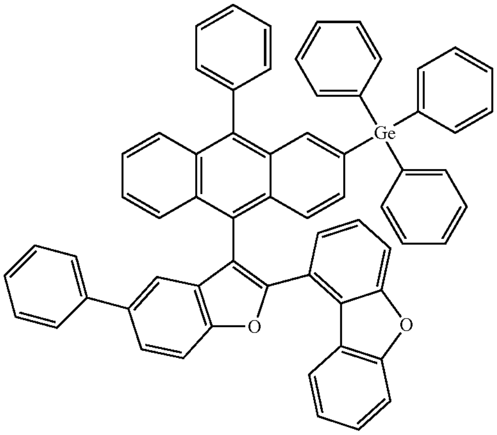
A-78
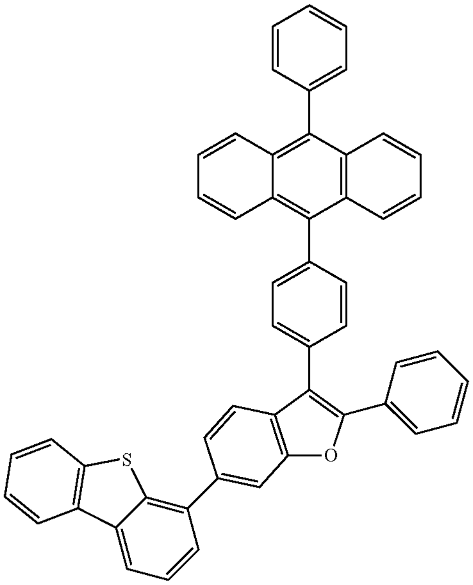

-continued
A-79
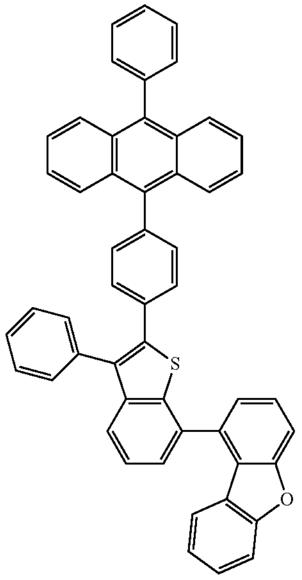
A-80
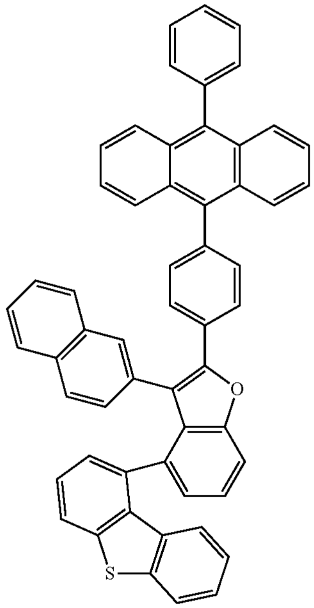
-continued
A-81
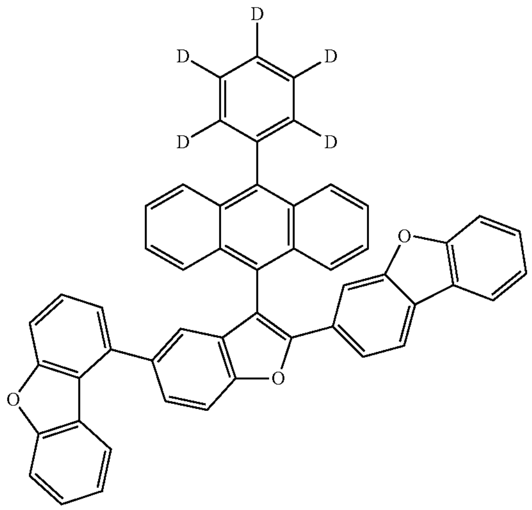
A-82
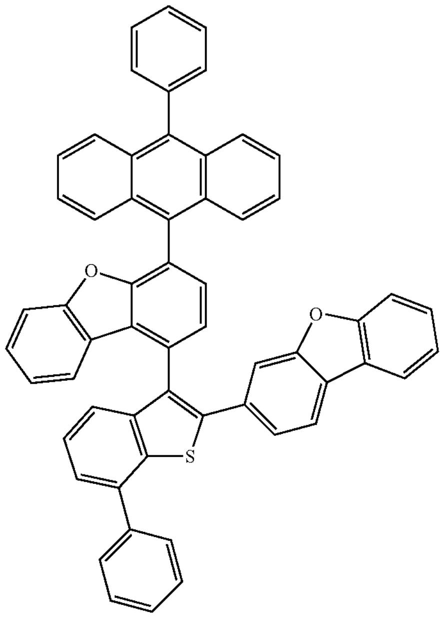
A-83
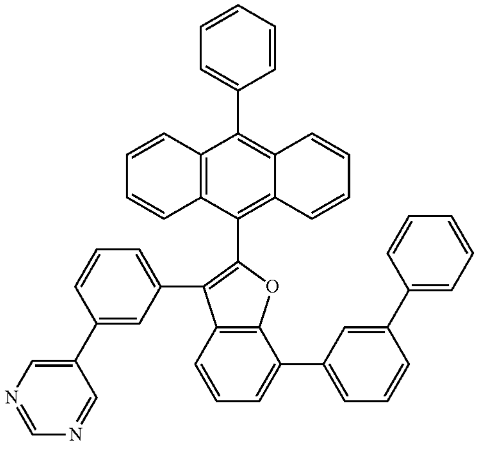

-continued
A-84
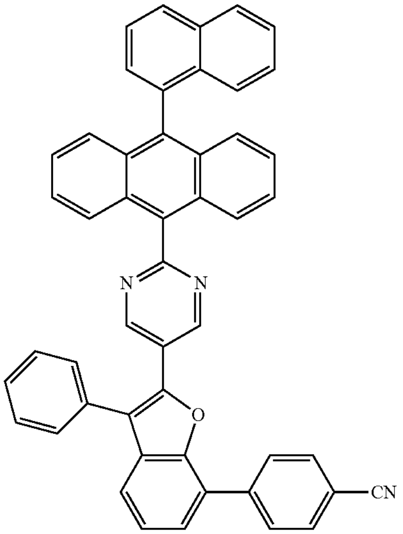
A-85
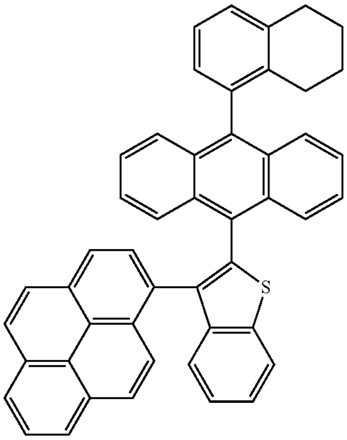
A-86
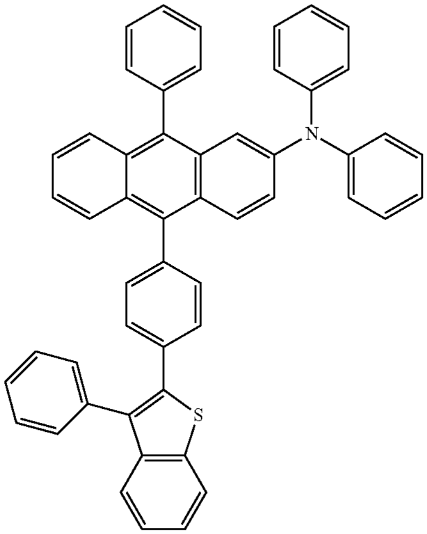
-continued
A-87
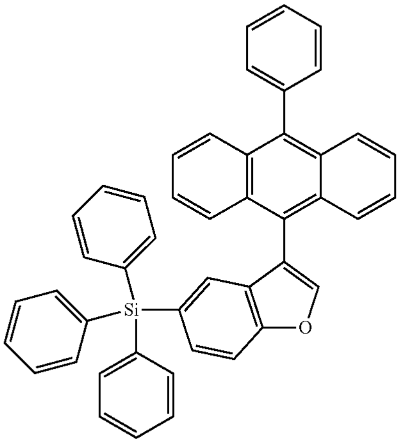
A-88
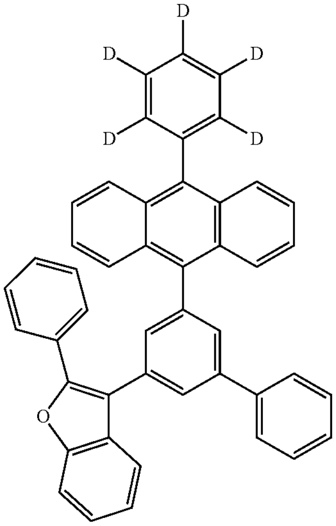
However, these compounds are not intended to limit the scope of Formula A.
According to one embodiment of the present invention, the compound represented by Formula D-1 may be selected from the following compounds D-101 to D-130:
D-101
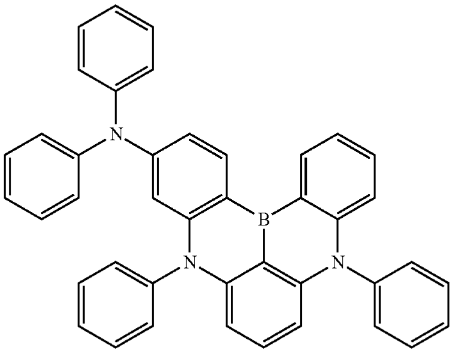

-continued
D-102
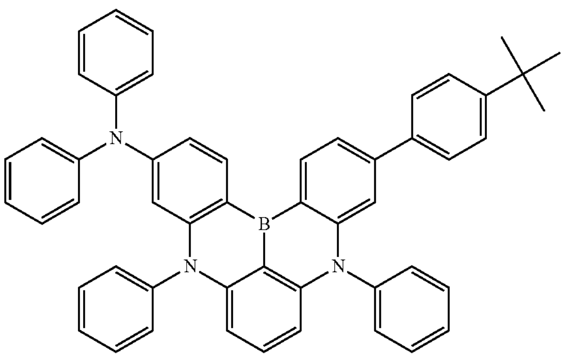
D-103
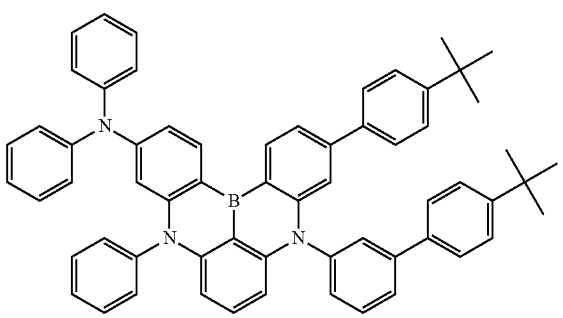
D-104
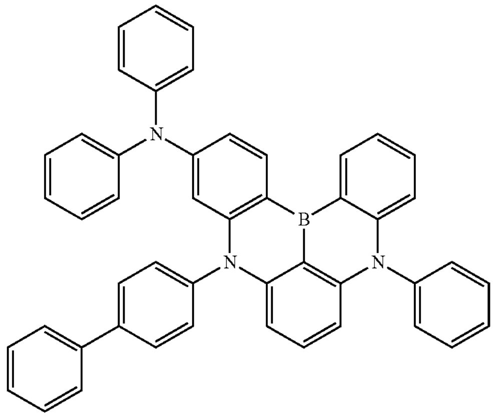
D-105
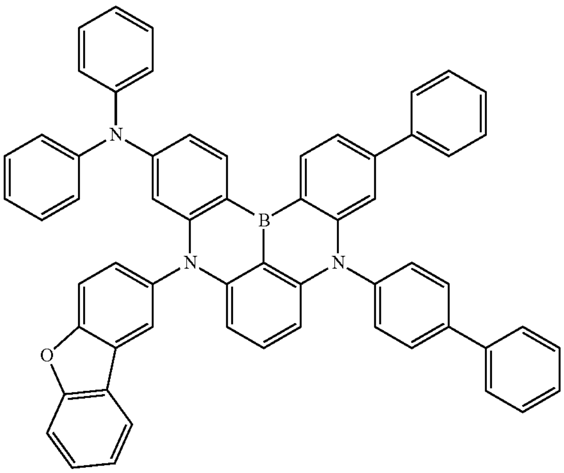
-continued
D-106
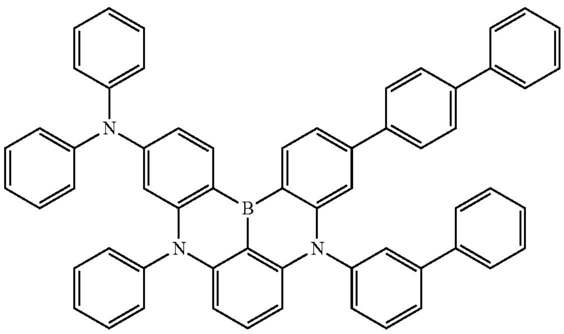
D-107
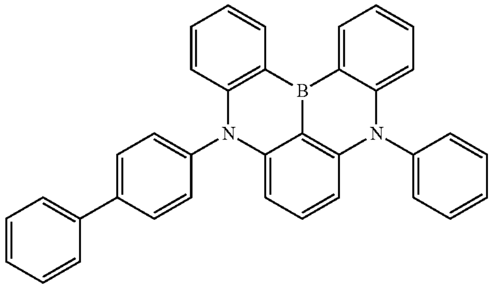
D-108
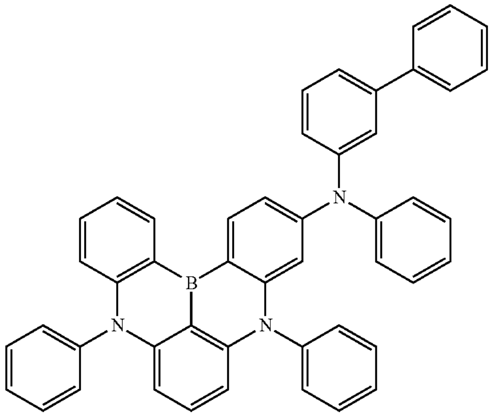
D-109
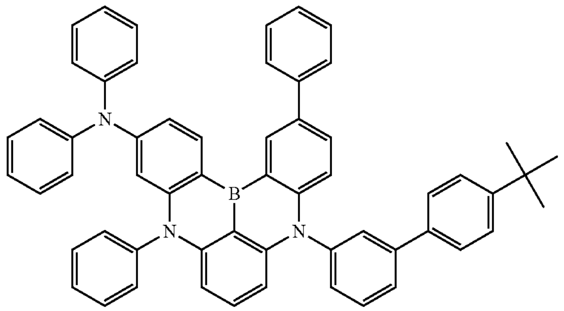
D-110
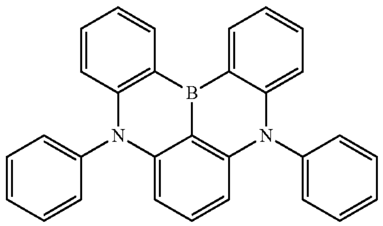

-continued
D-111
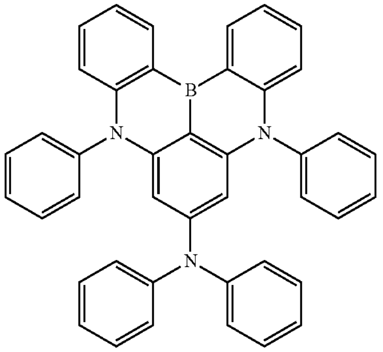
D-112
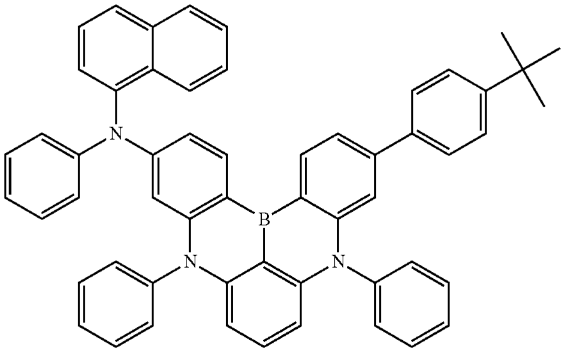
D-113
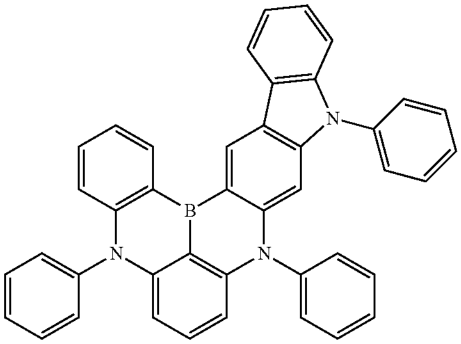
D-114
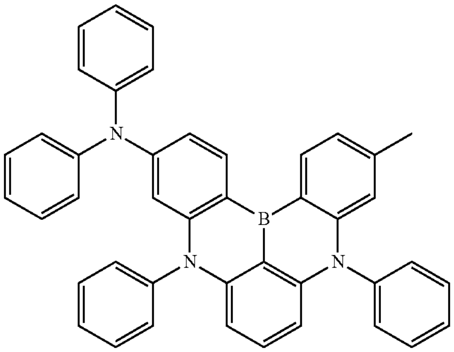
-continued
D-115
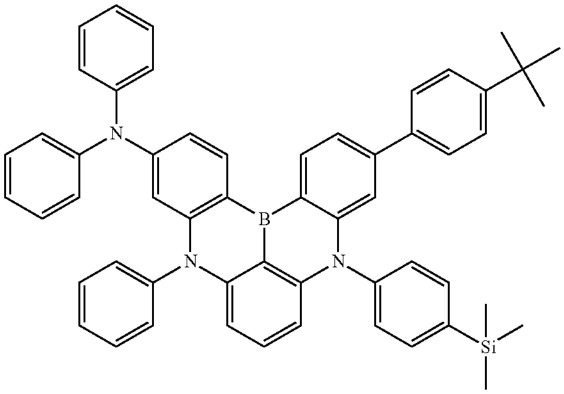
D-116
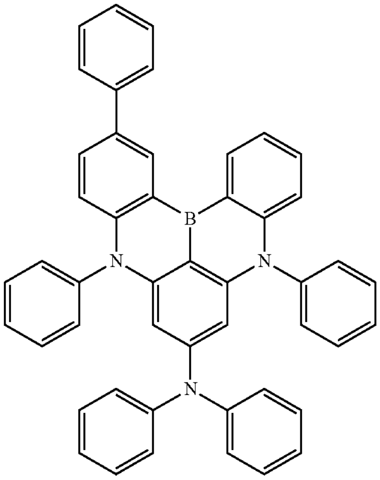
D-117
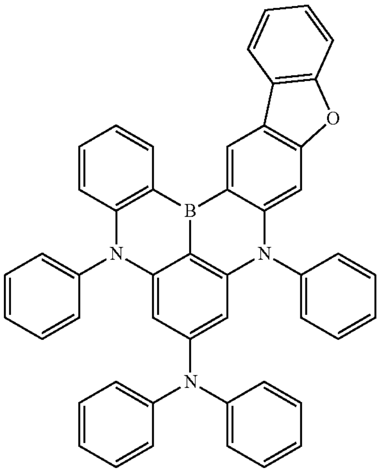

-continued
D-118
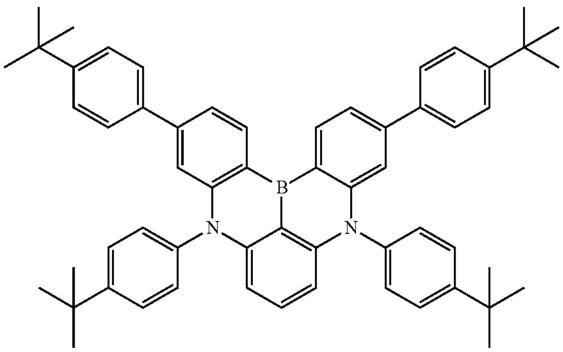
D-119
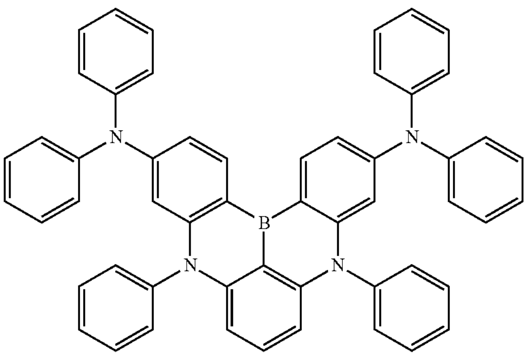
D-120
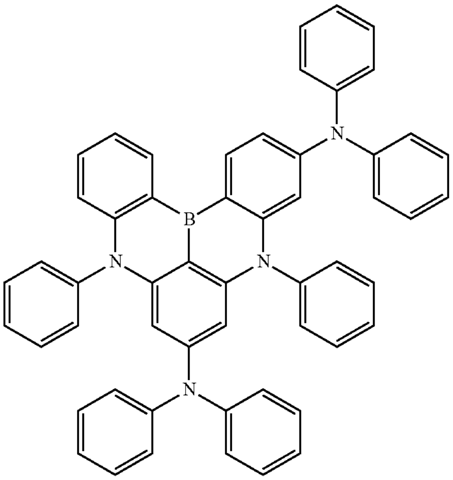
-continued
D-121
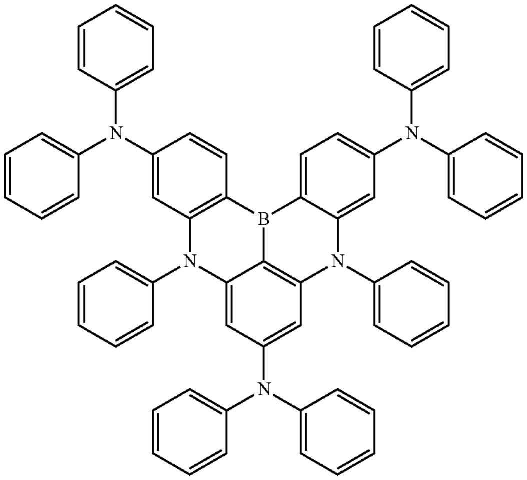
D-122
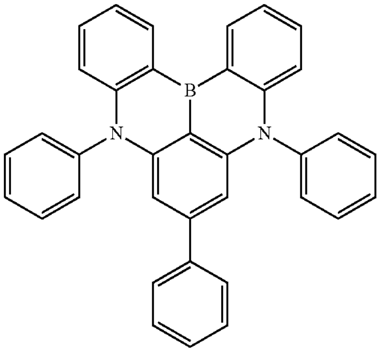
D-123
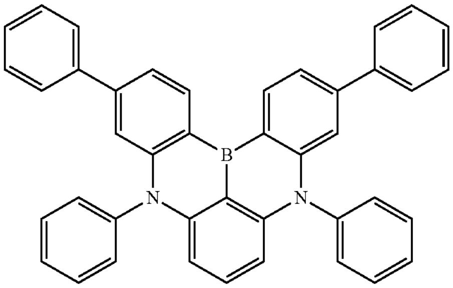
D-124
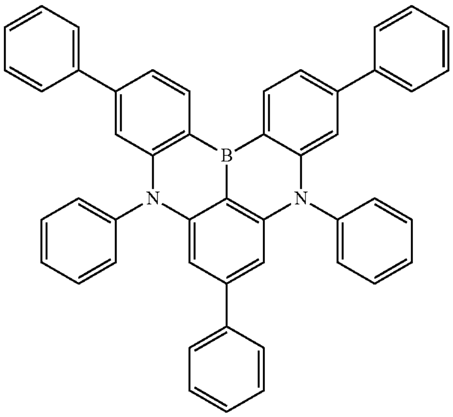

-continued
D-125
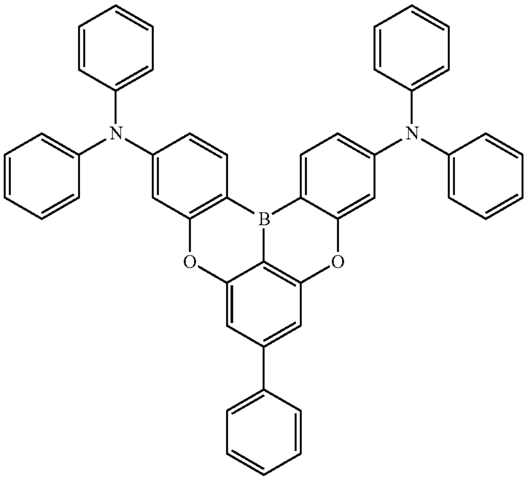
D-126
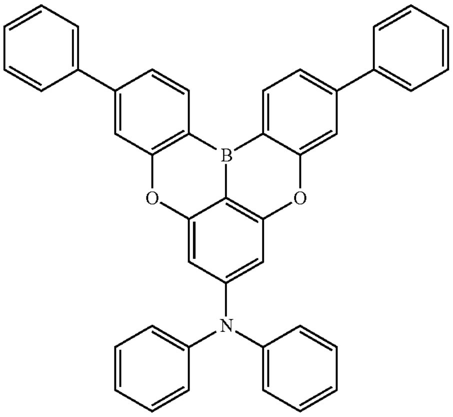
D-127
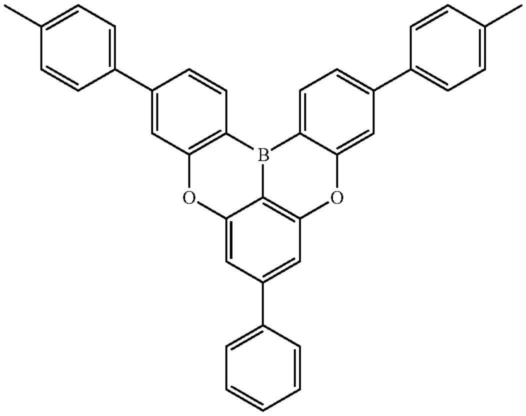
-continued
D-128
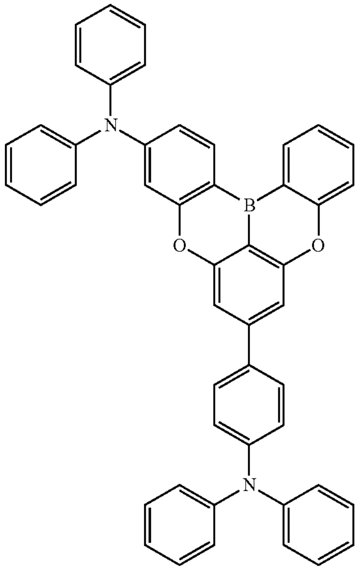
D-129
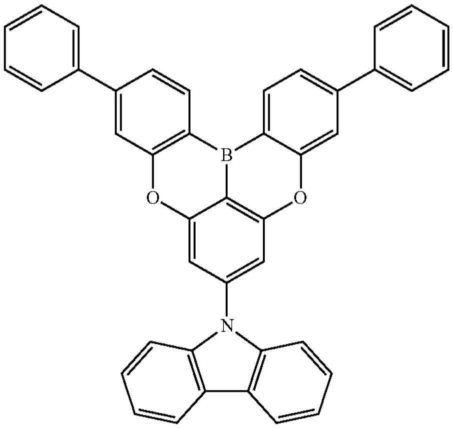
D-130
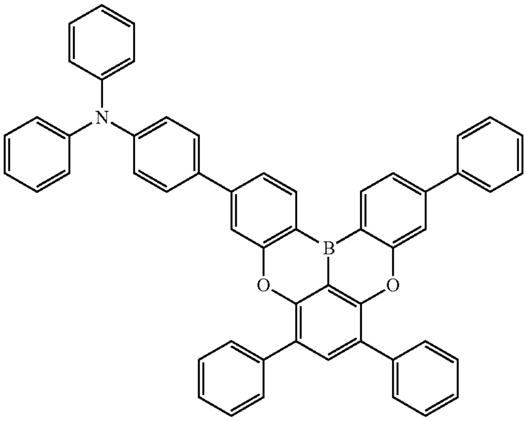
However, these compounds are not intended to limit the scope of Formula D-1.
According to one embodiment of the present invention, the compounds represented by Formulas D-2 and D-3 may be selected from the following compounds D-201 to D-332:

D-201
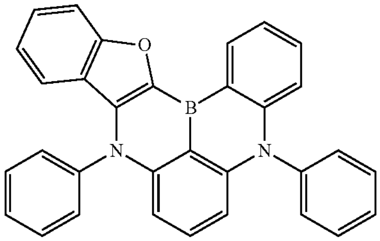
D-202
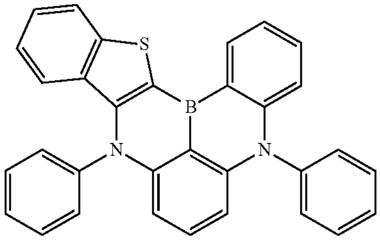
D-203
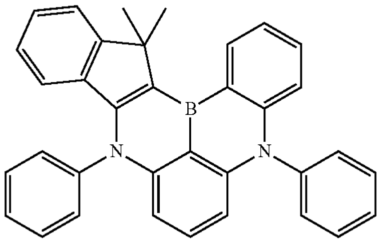
D-204
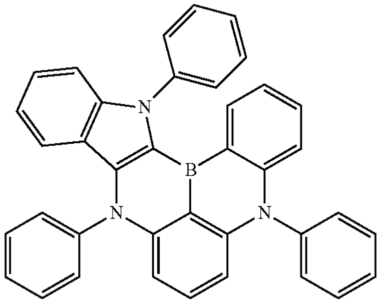
D-205
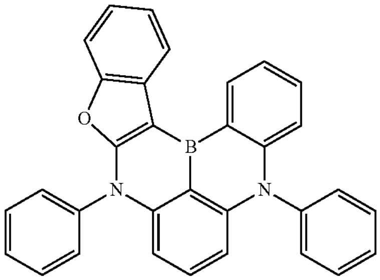
D-206
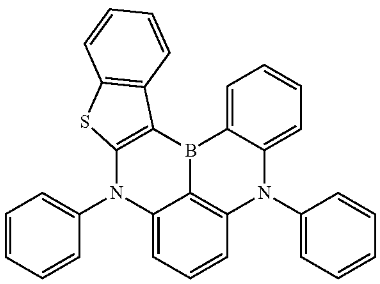
-continued
D-207
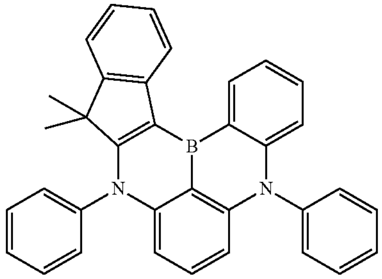
D-208
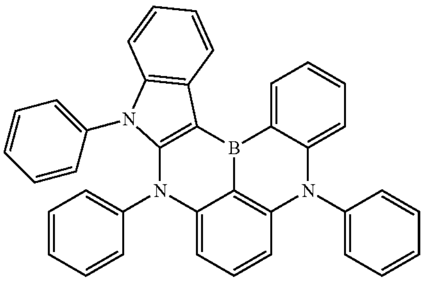
D-209
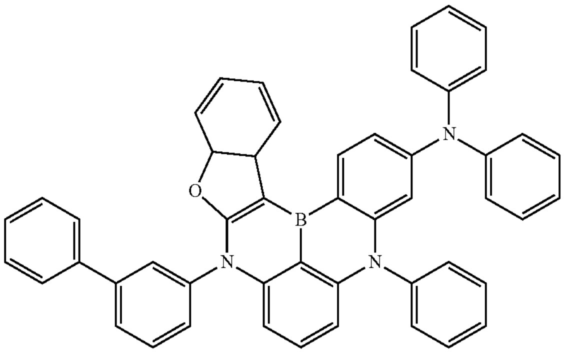
D-210
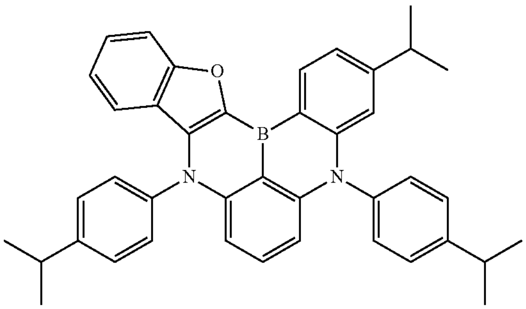
D-211
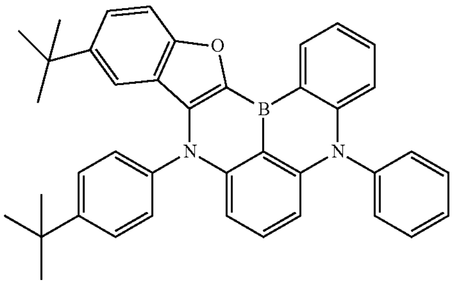

-continued
D-212
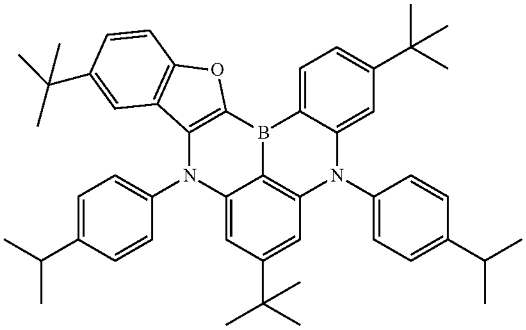
D-213
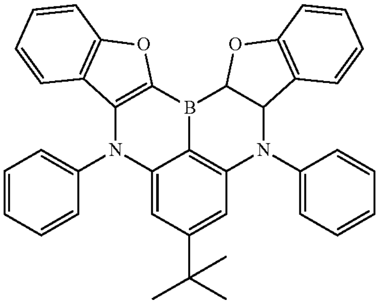
D-214
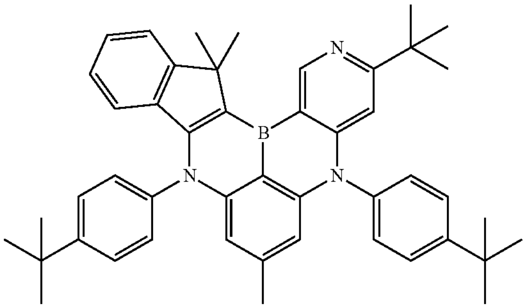
D-215
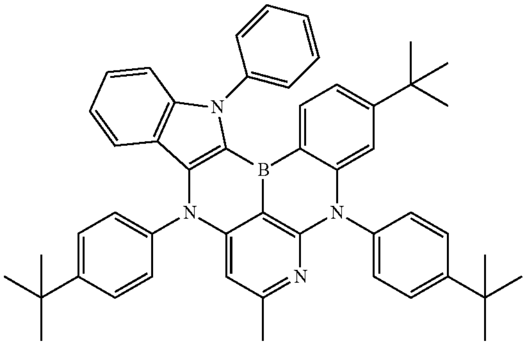
-continued
D-216
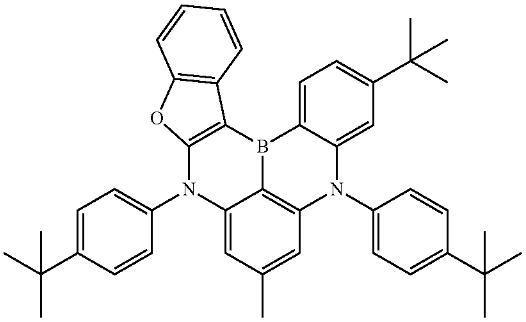
D-217
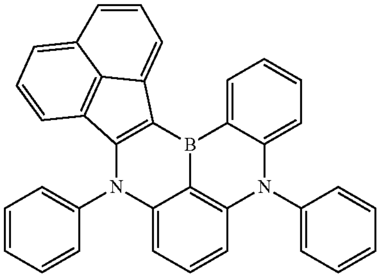
D-218
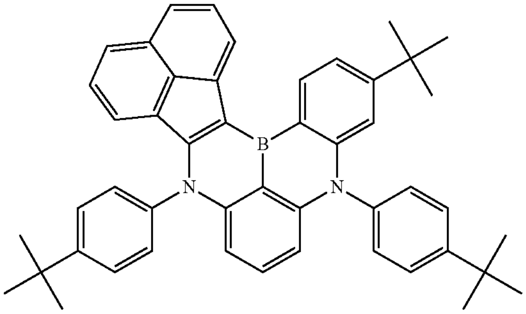
D-219
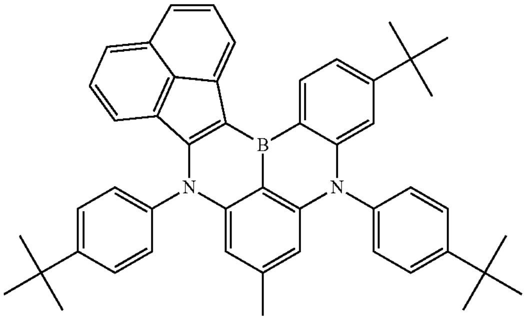

-continued
D-220
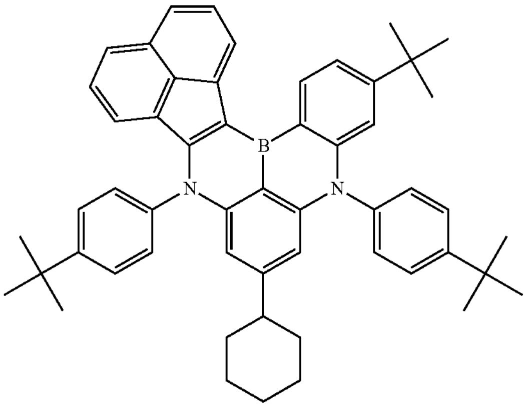
D-221
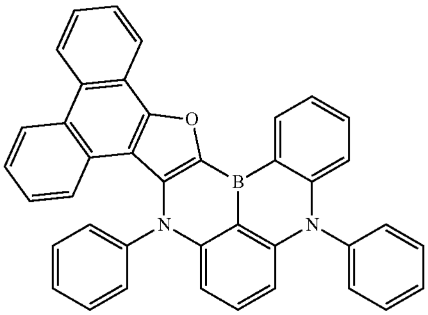
D-222
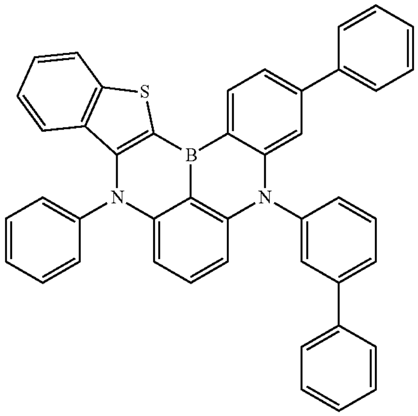
D-223
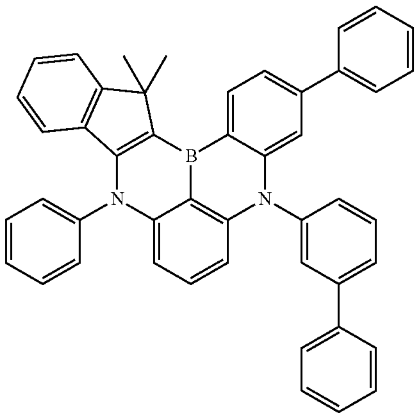
-continued
D-224
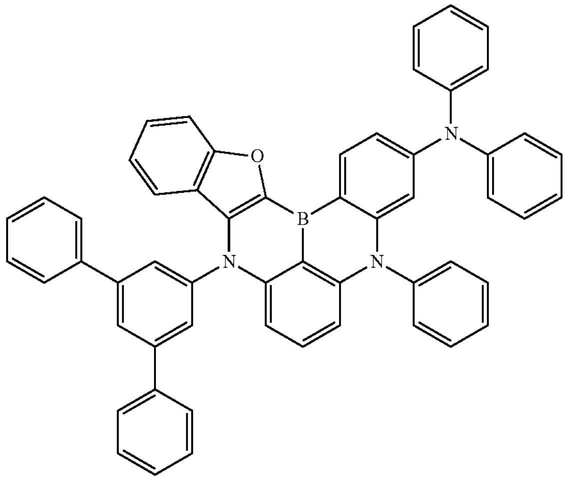
D-225
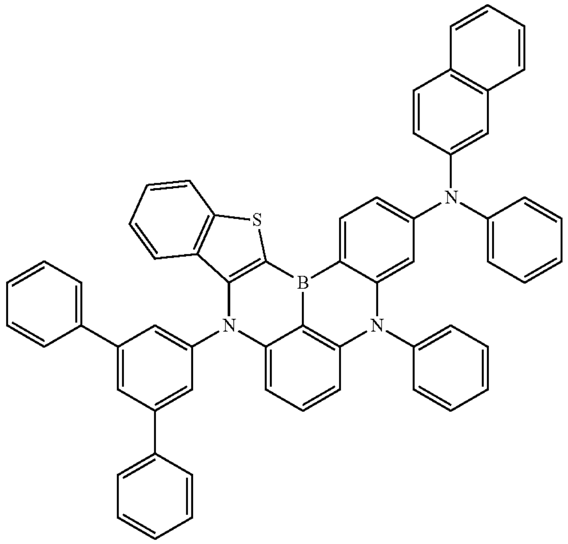
D-226
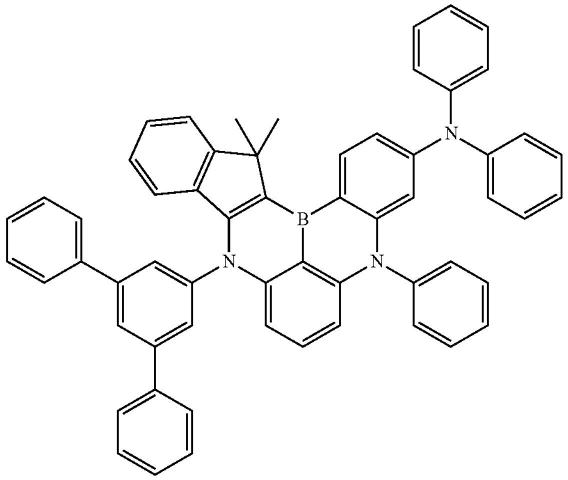

-continued
D-227
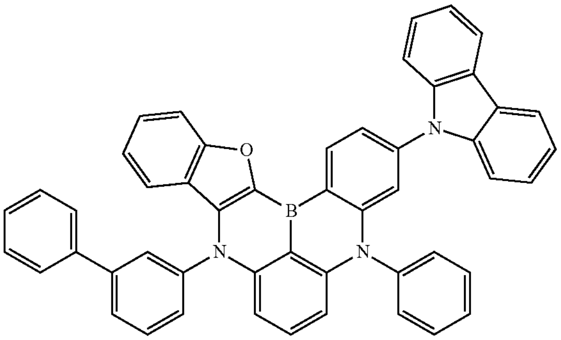
D-228
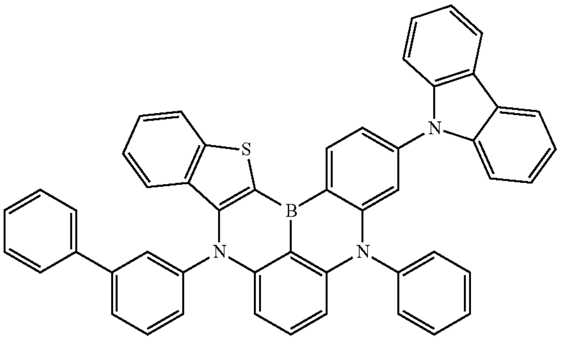
D-229
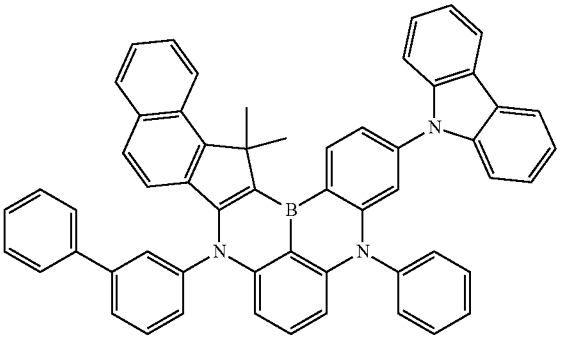
D-230
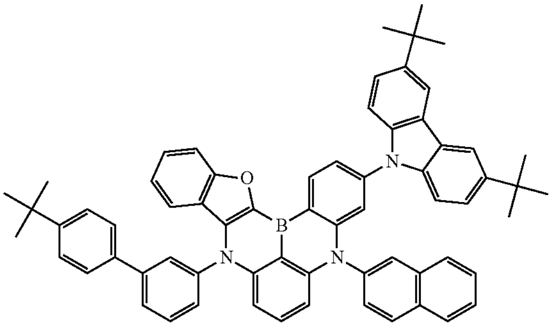
-continued
D-231
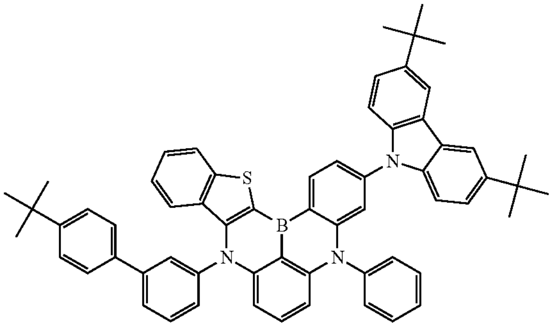
D-232
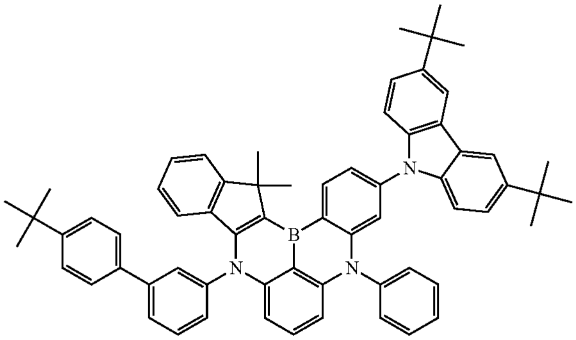
D-233
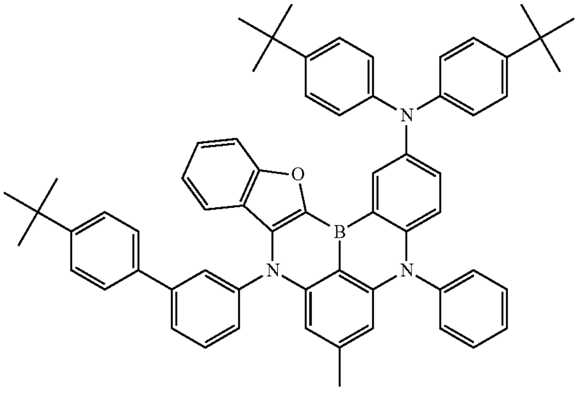
D-234
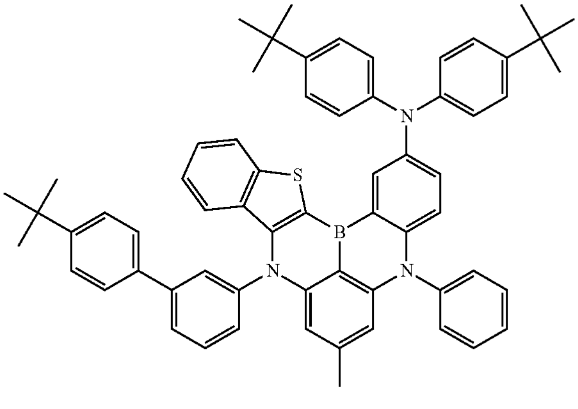

-continued
D-235
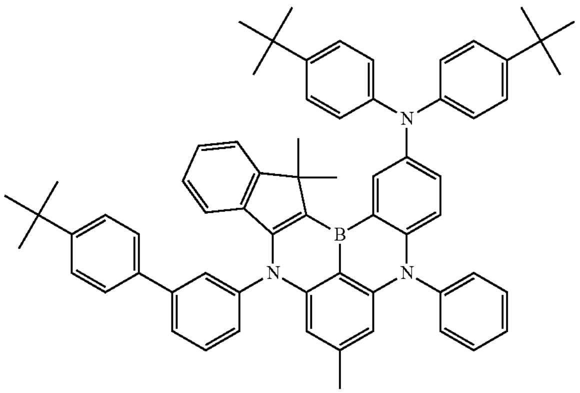
D-236
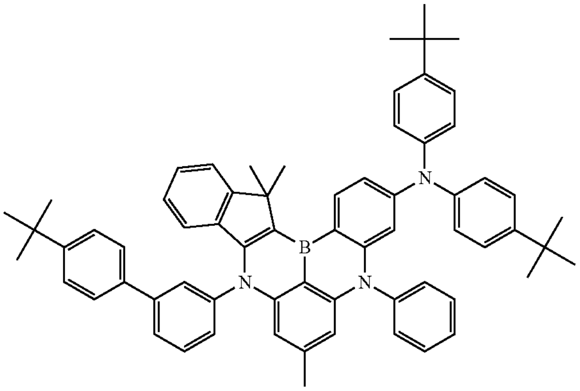
D-237
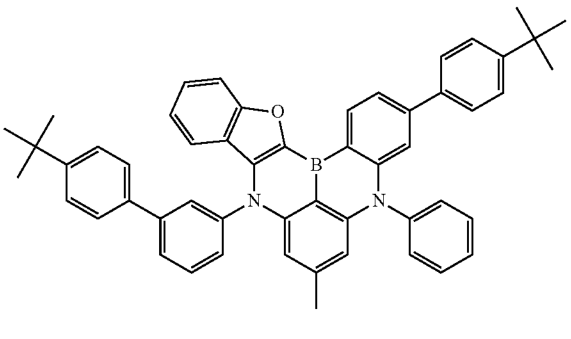
D-238
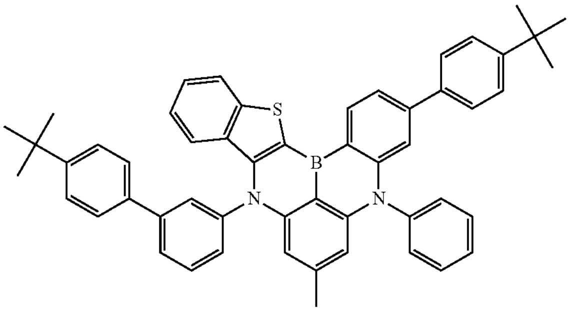
-continued
D-239
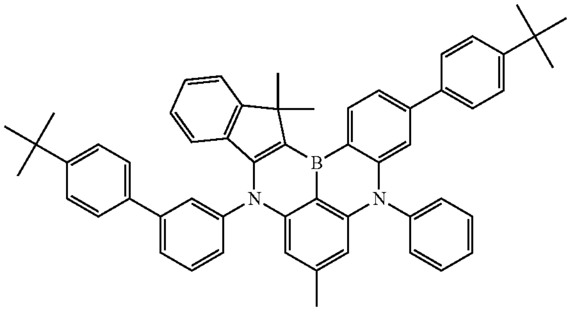
D-240
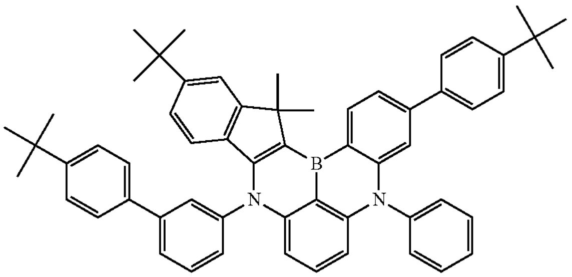
D-241
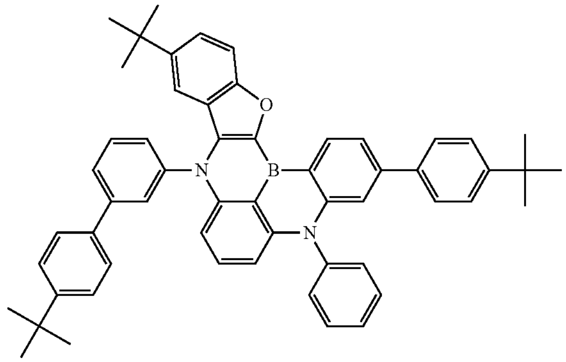
D-242
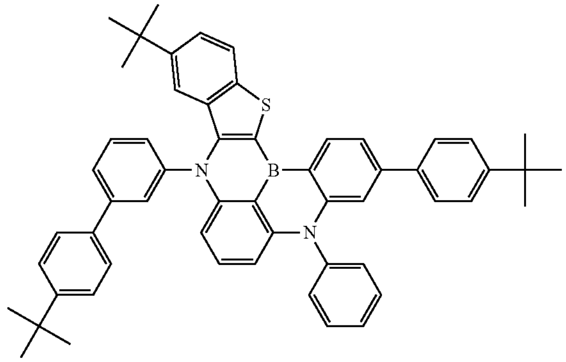

-continued
D-243
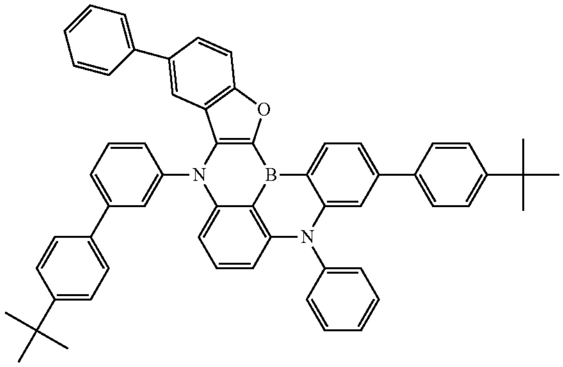
D-244
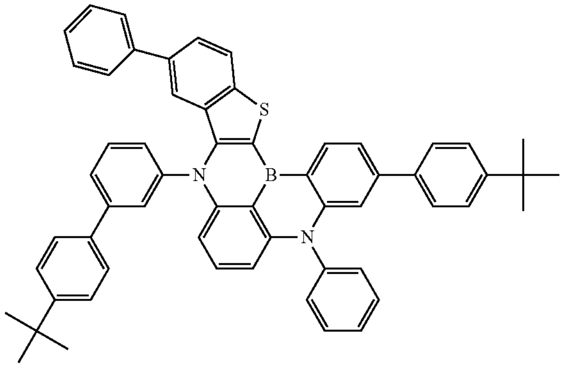
D-245
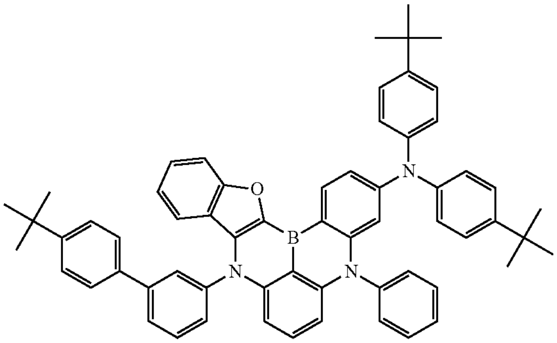
D-246
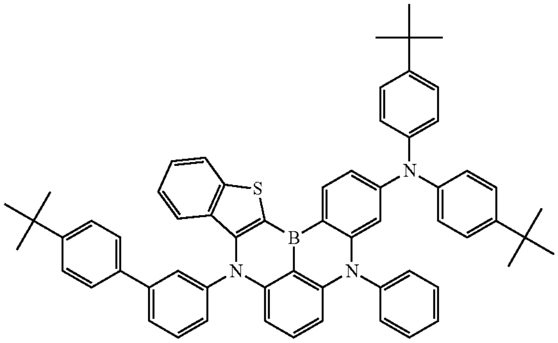
-continued
D-247
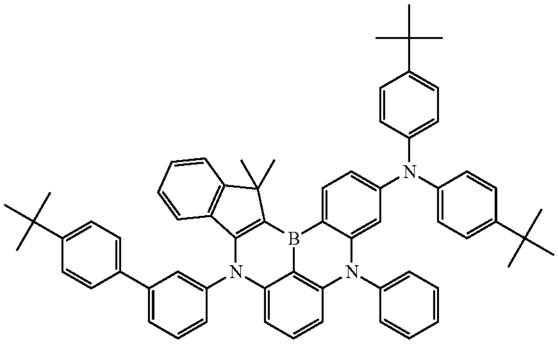
D-248
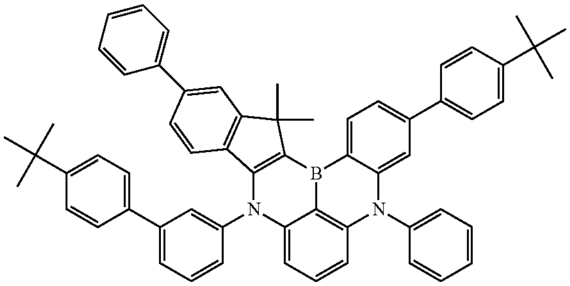
D-249
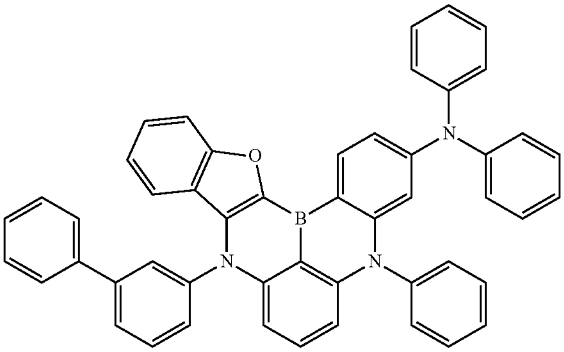
D-250
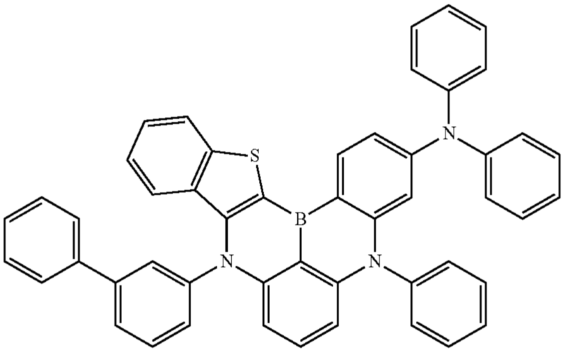

-continued
D-251
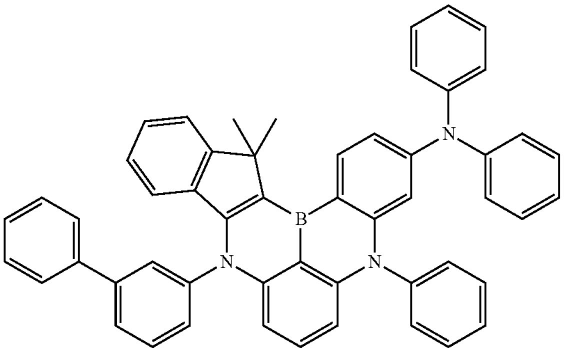
D-252
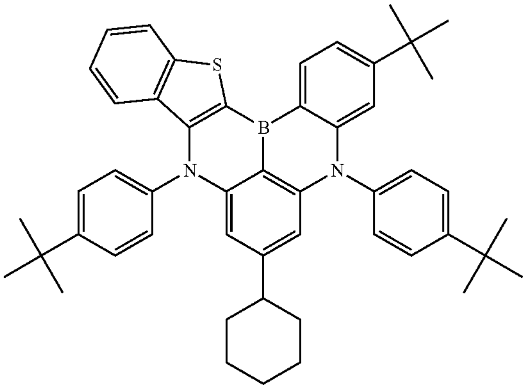
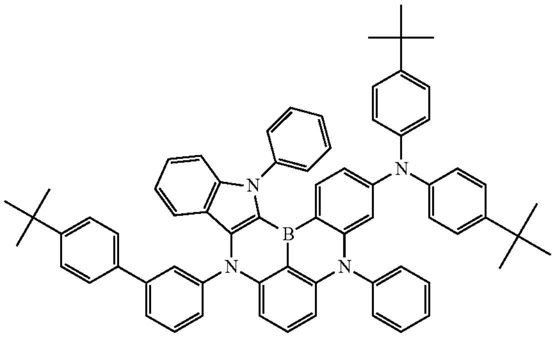
D-254
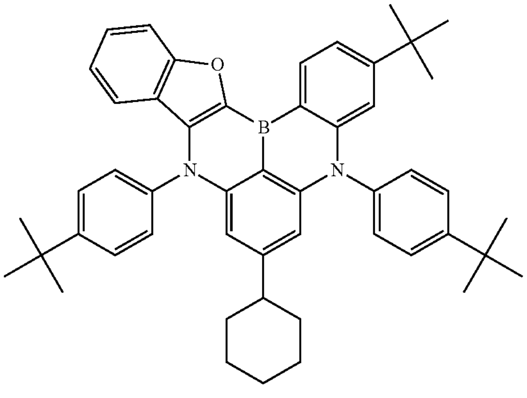
-continued
D-255
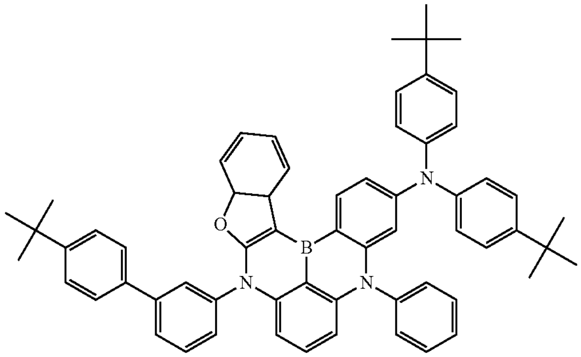
D-256
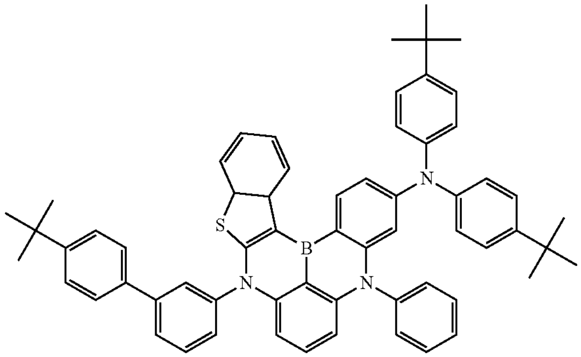
D-257
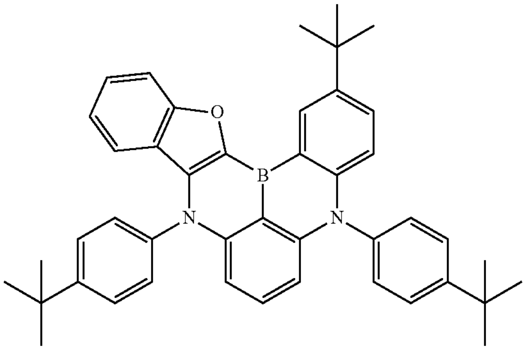
D-258
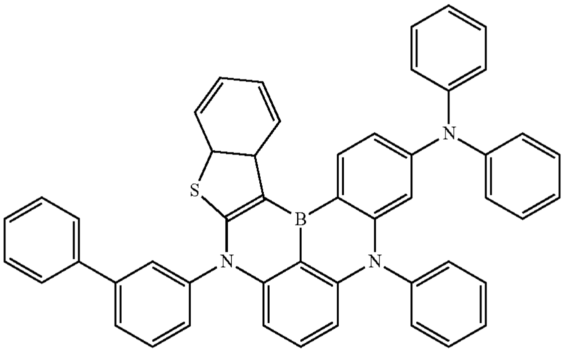

-continued
D-259
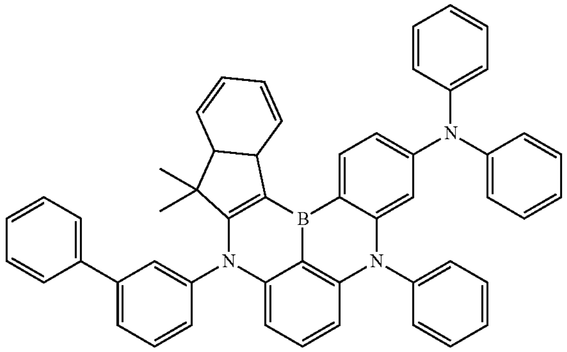
D-260
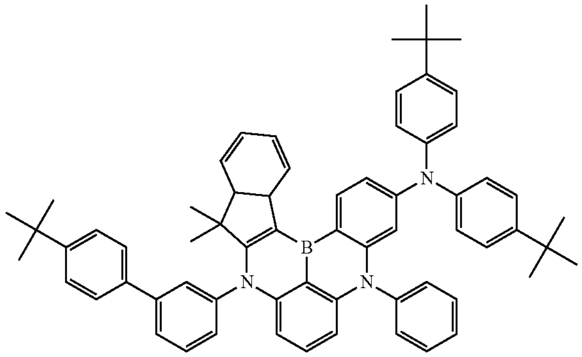
D-261
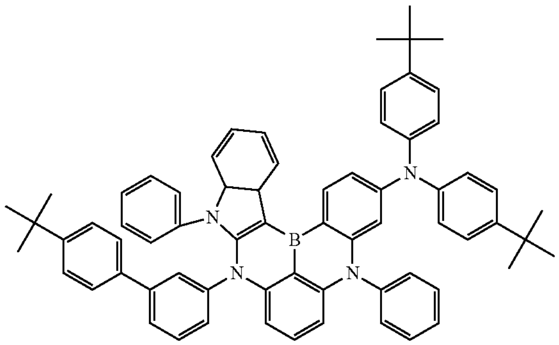
D-262
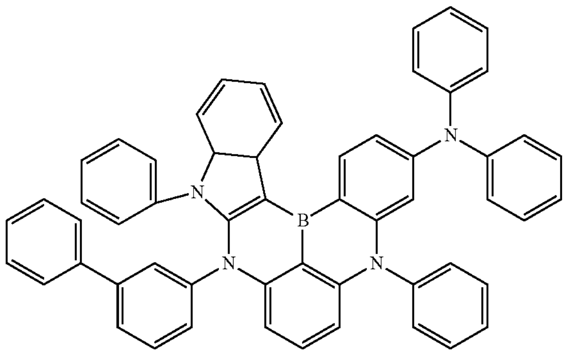
-continued
D-263
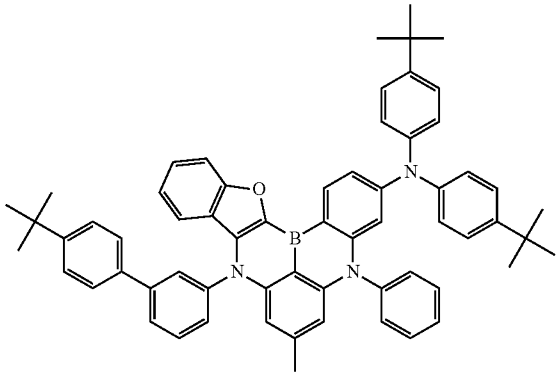
D-264
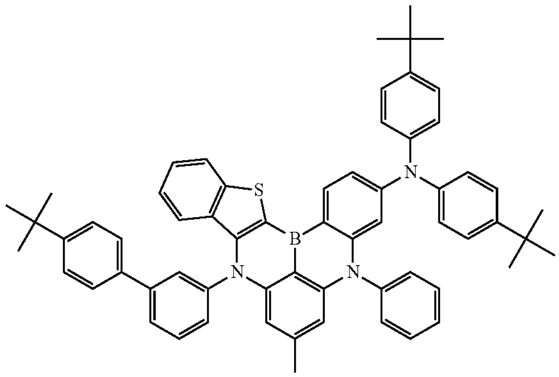
D-265
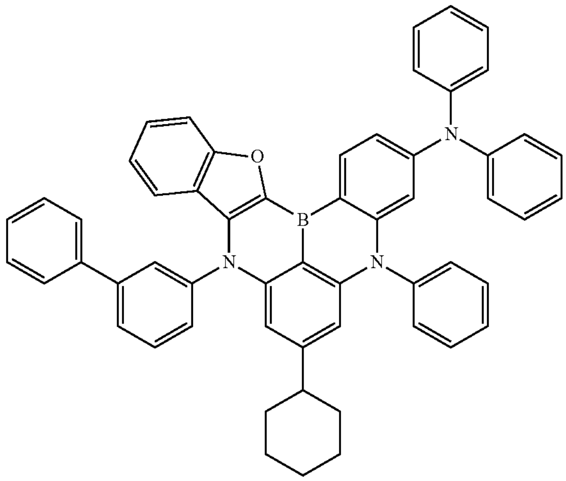

-continued
D-266
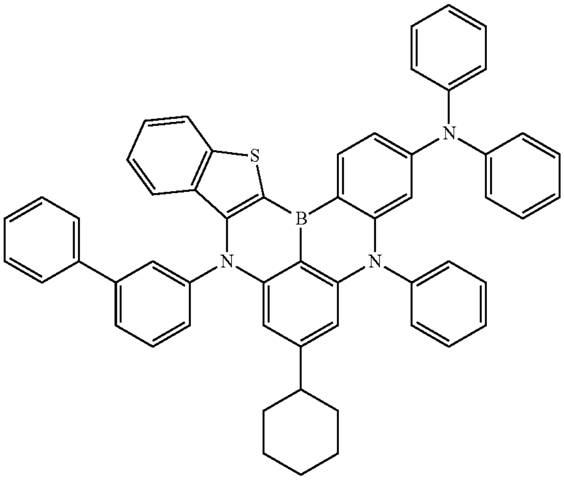
D-267
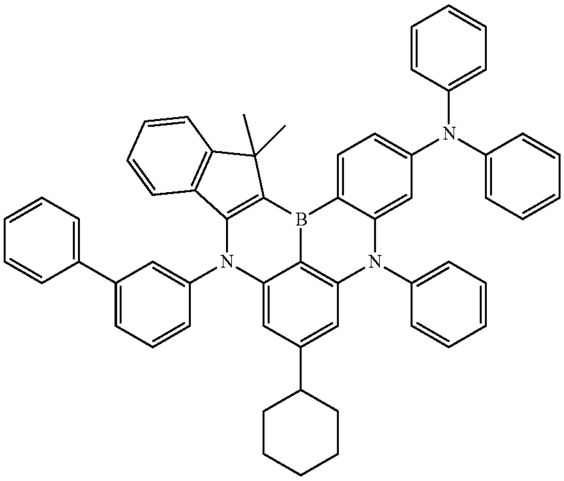
D-268
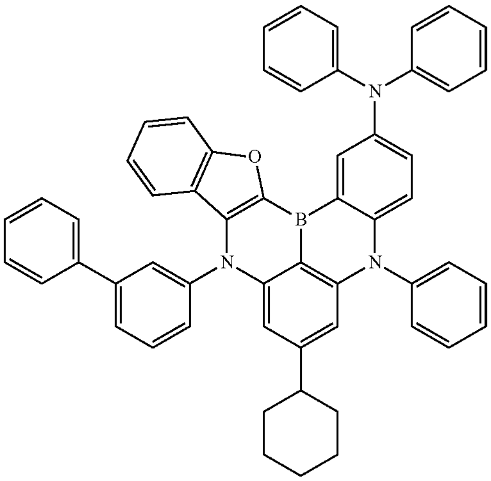
-continued
D-269
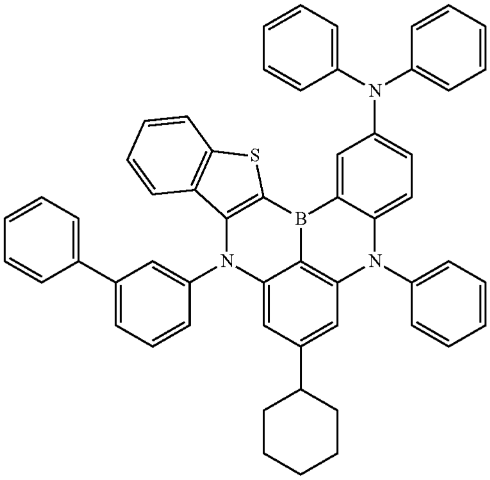
D-270
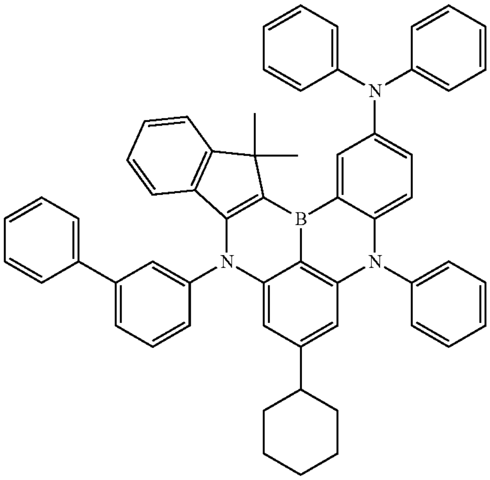
D-271
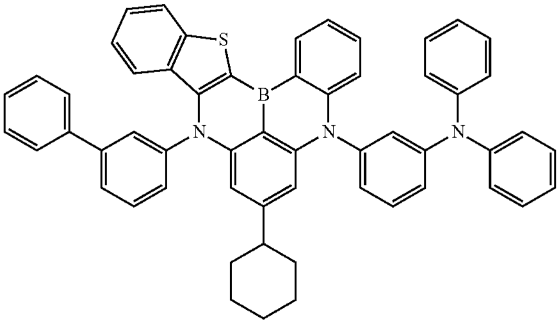

-continued
D-272
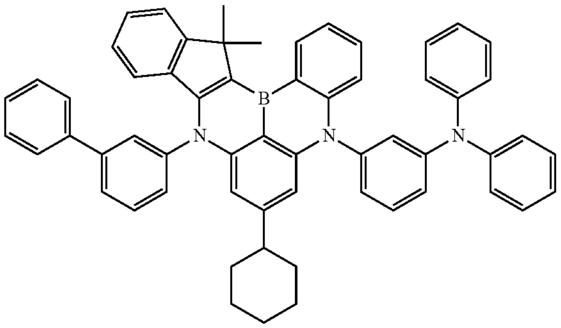
D-273
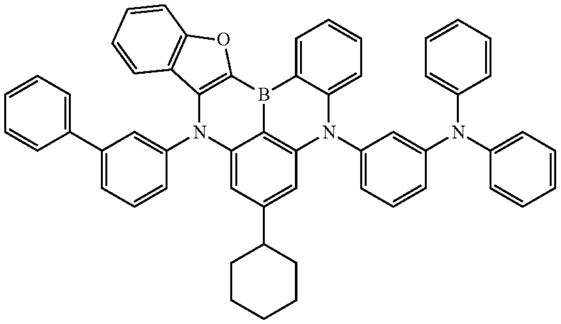
D-274
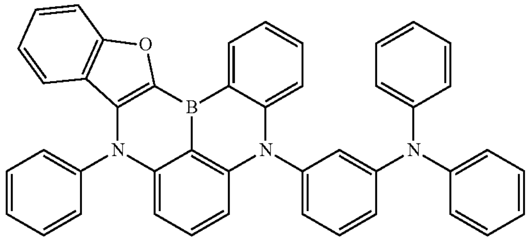
D-275
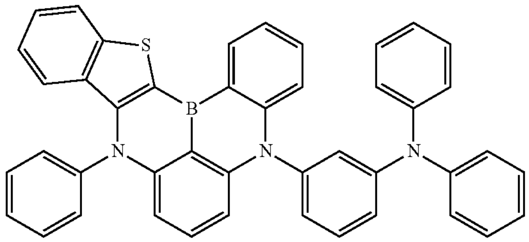
-continued
D-276
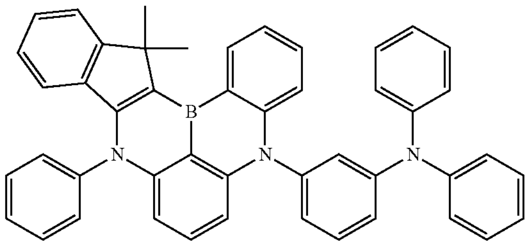
D-277
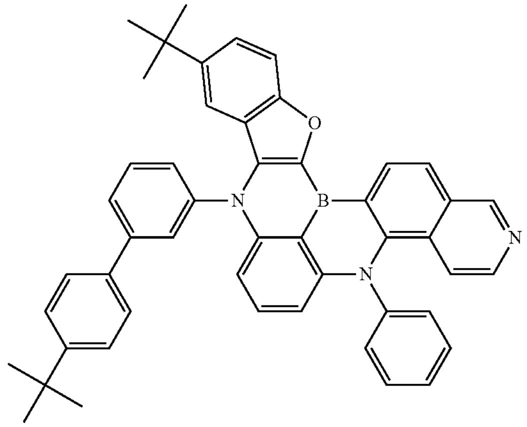
D-278
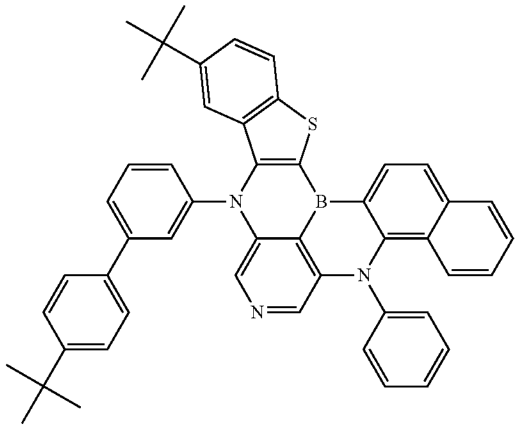
D-279
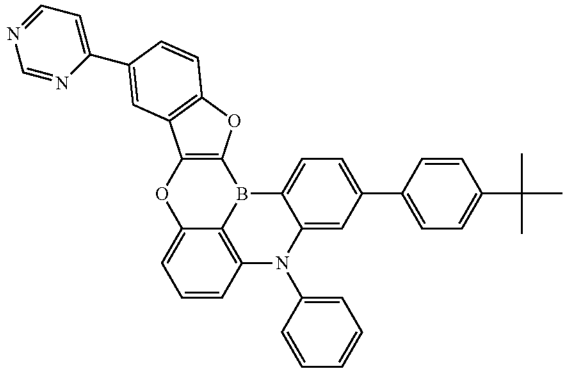

-continued
D-280
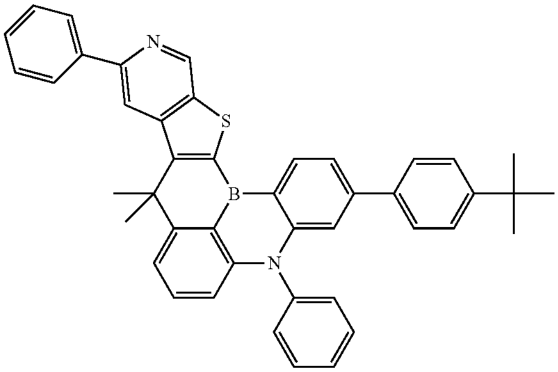
D-281
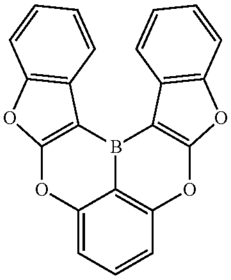
D-282
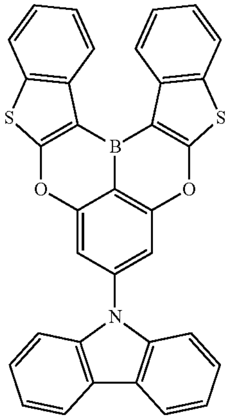
D-283
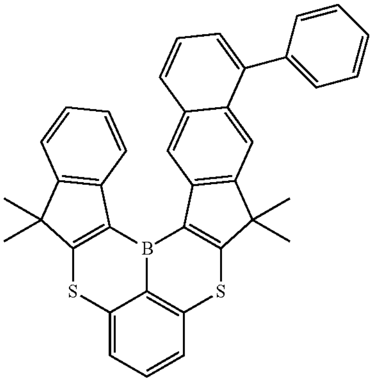
-continued
D-284
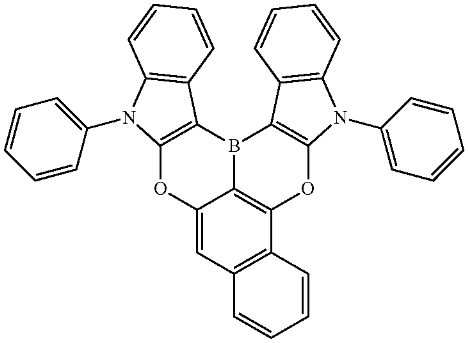
D-285
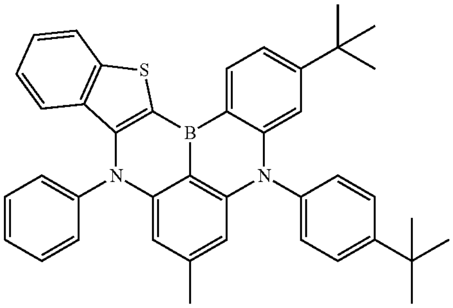
D-286
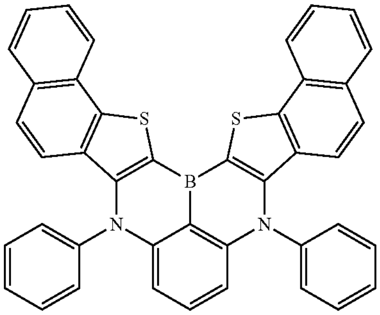
D-287
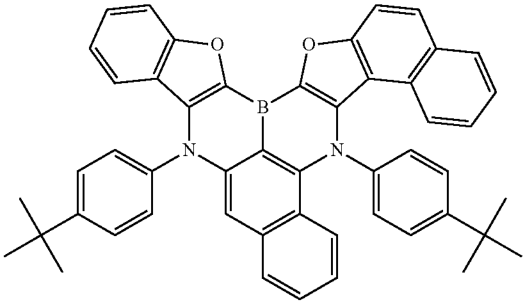
D-288
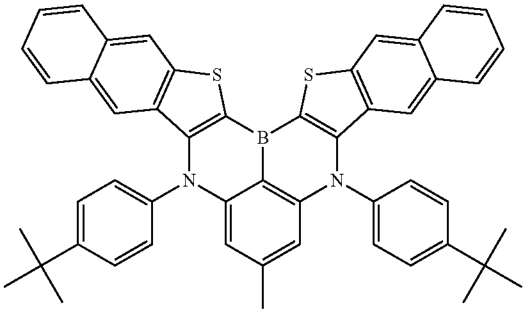

-continued
D-289
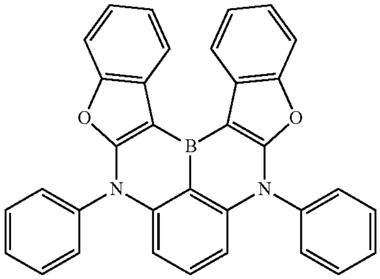
D-290
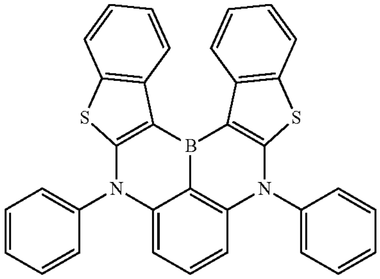
D-291
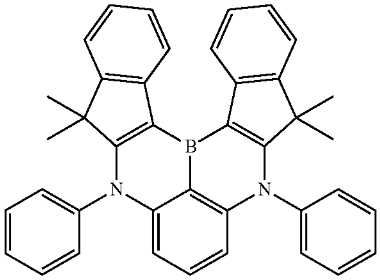
D-292
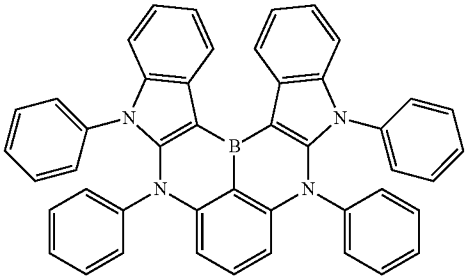
D-293
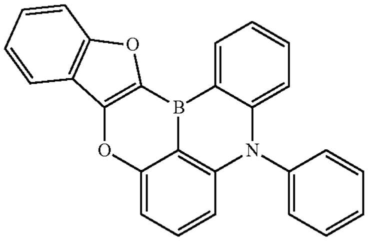
D-294
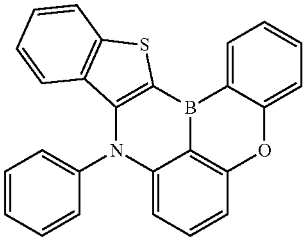
-continued
D-295
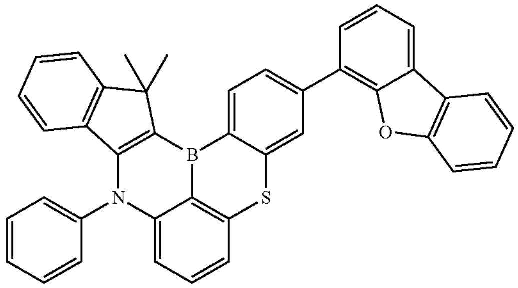
D-296
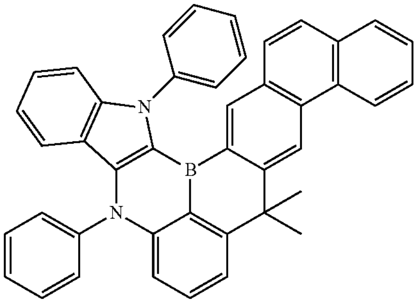
D-297
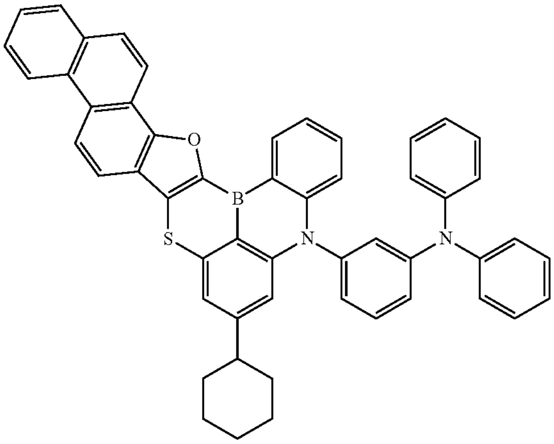
D-298
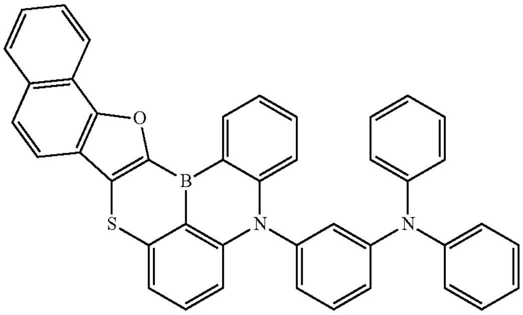

-continued
D-299
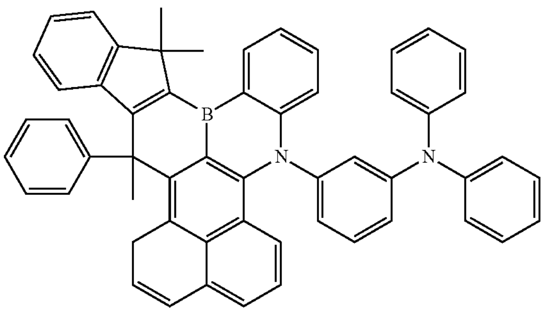
D-300
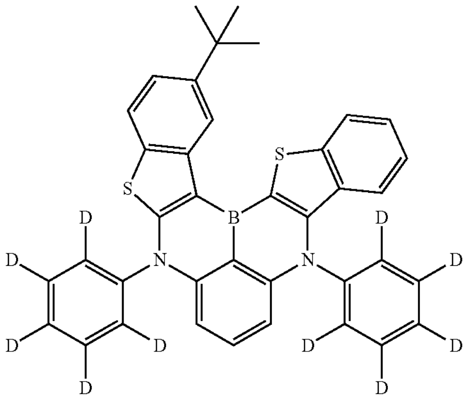
D-301
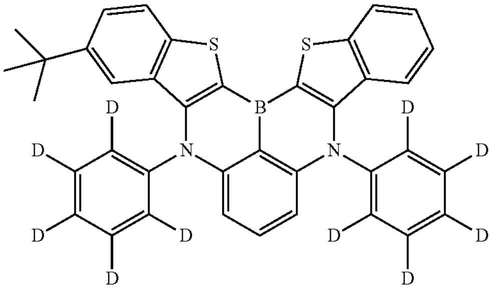
D-302
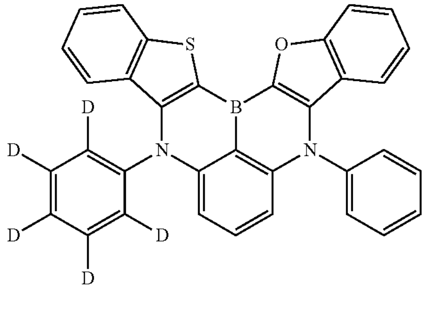
-continued
D-303
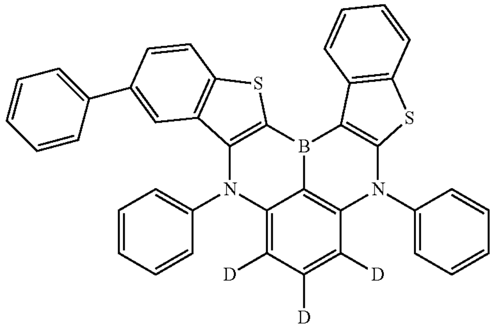
D-304
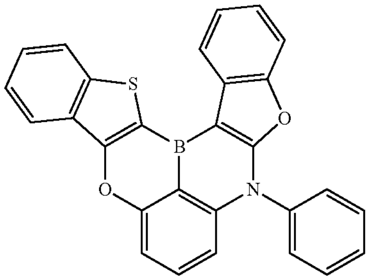
D-305
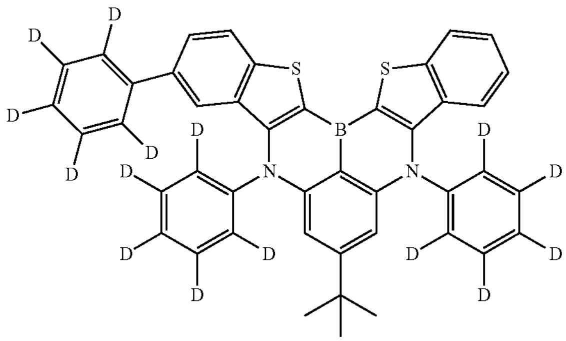
D-306
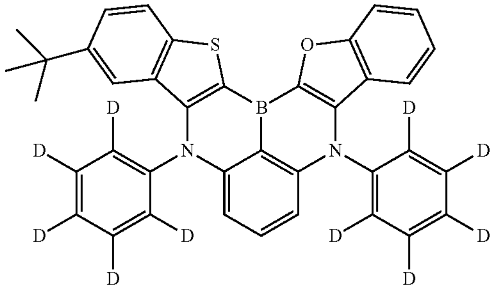
D-307
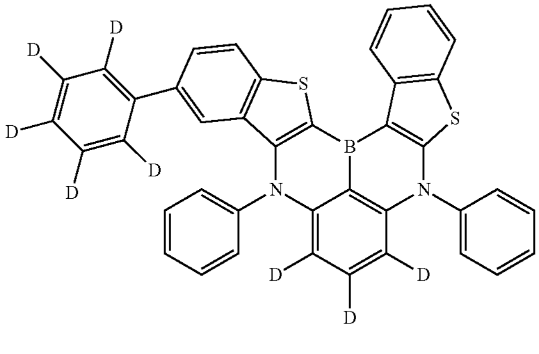

-continued
D-308
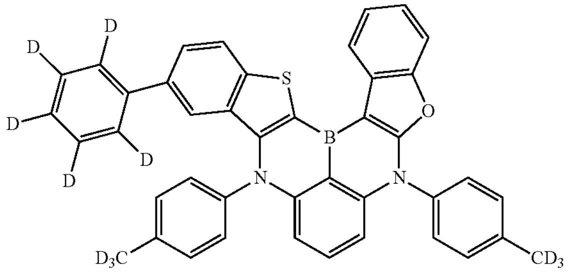
D-309
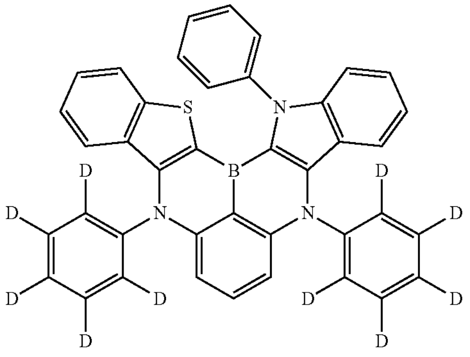
D-310
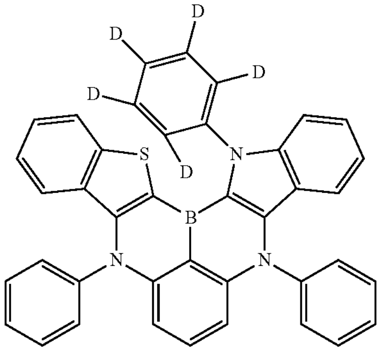
D-311
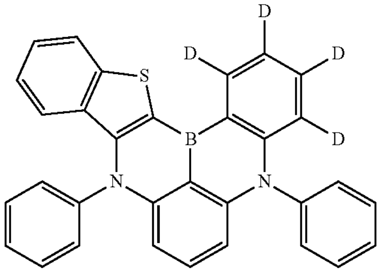
D-312
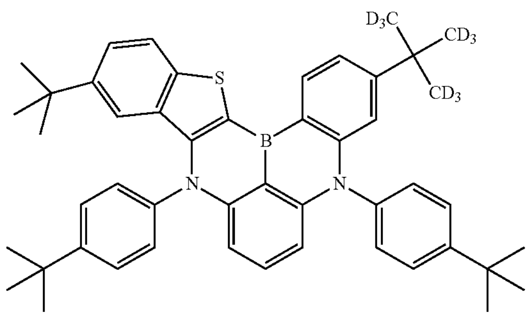
-continued
D-313
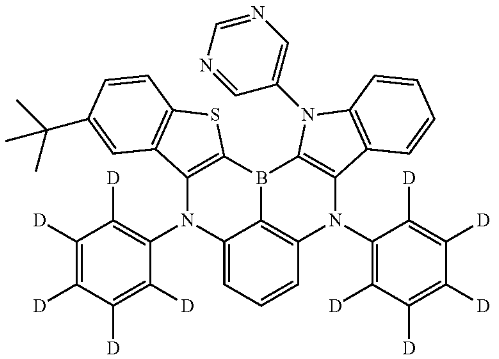
D-314
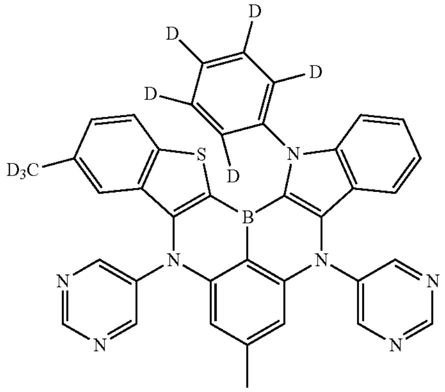
D-315
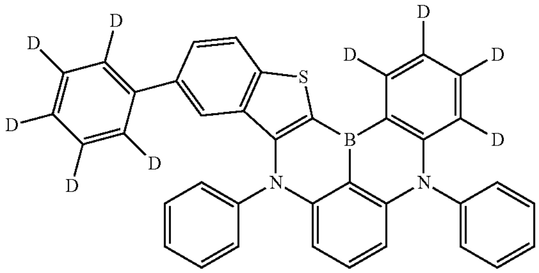
D-316
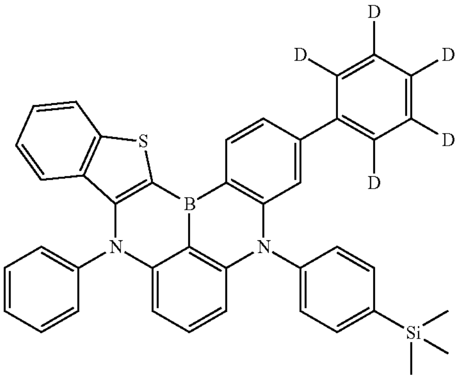

-continued
D-317
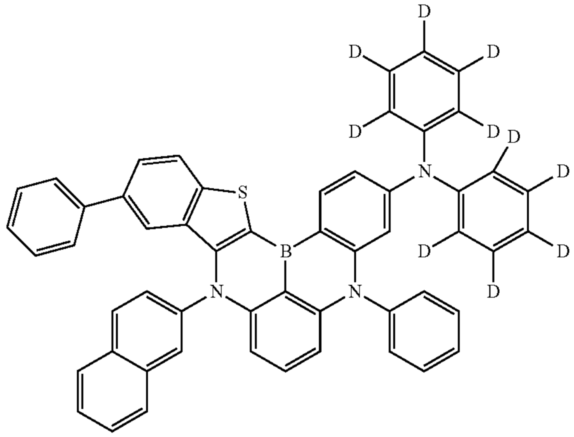
D-318
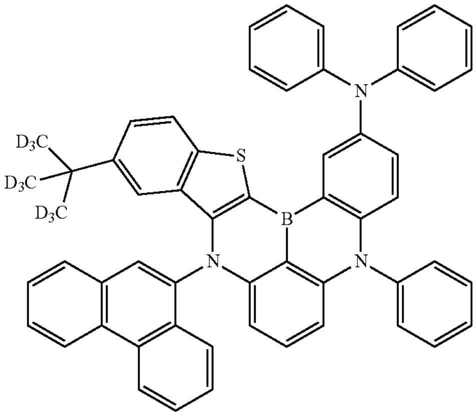
D-319
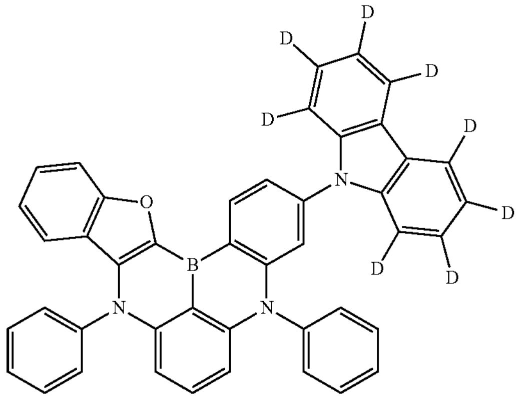
D-320
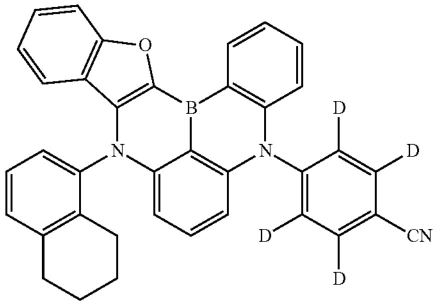
-continued
D-321
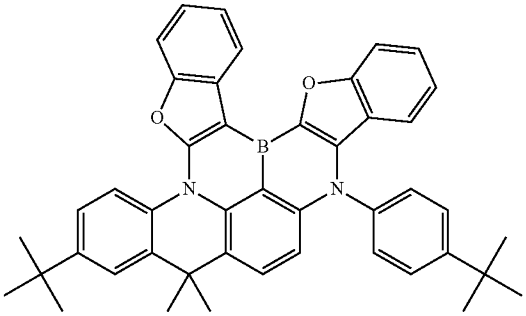
D-322
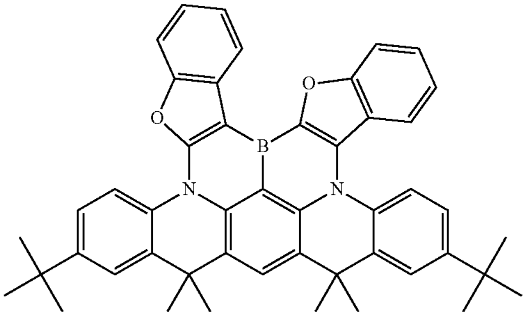
D-323
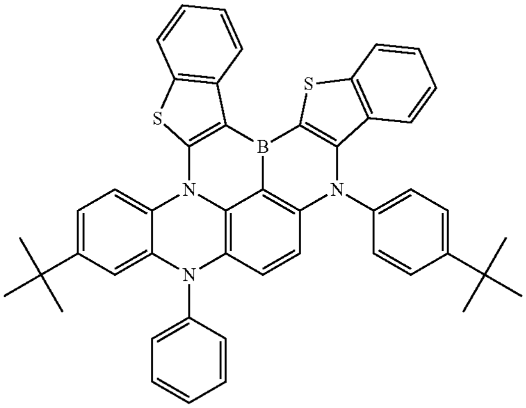
D-324
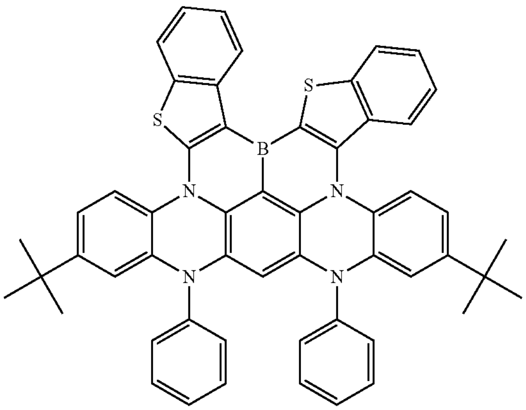

-continued
D-325
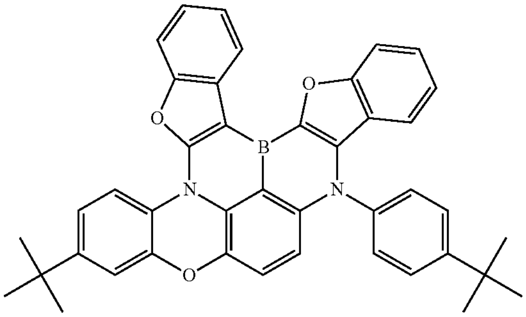
D-326
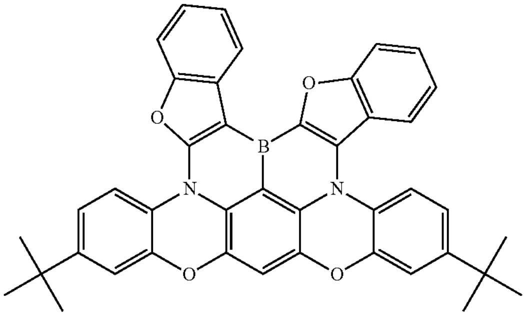
D-327
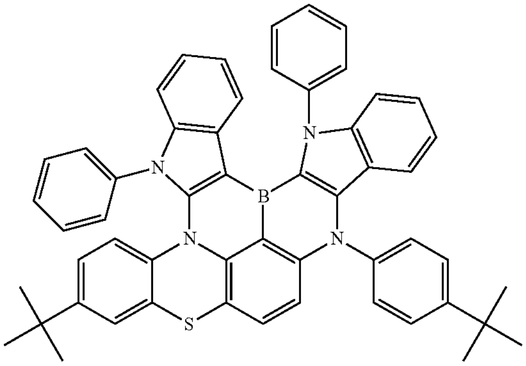
D-328
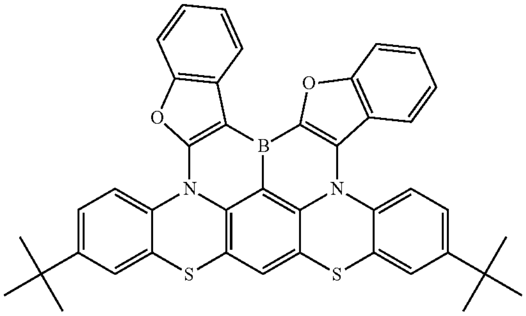
-continued
D-329
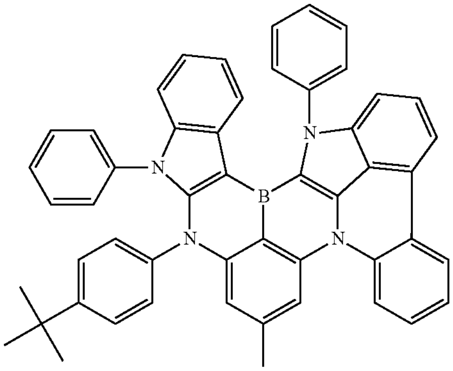
D-330
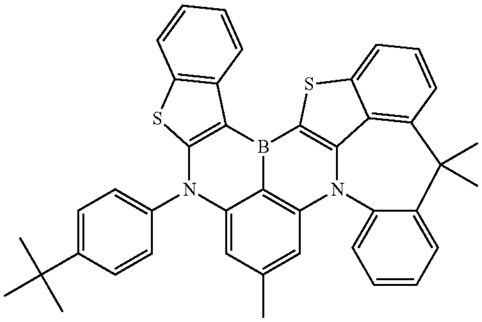
D-331
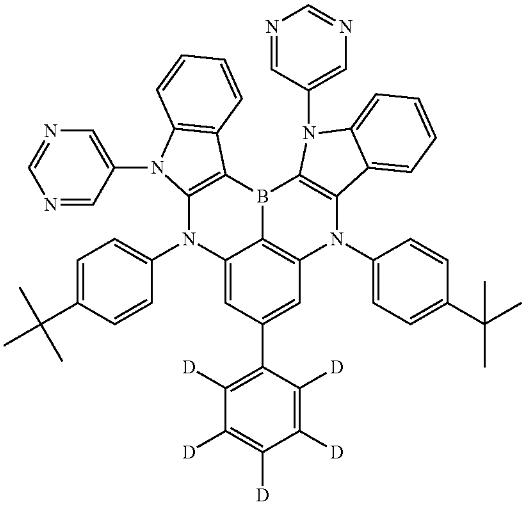
D-332
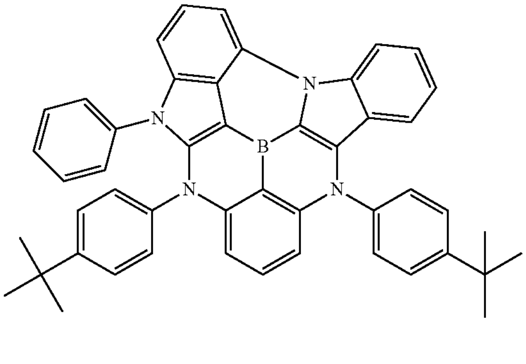

However, these compounds are not intended to limit the scope of Formulas D-2 and D-3.
According to one embodiment of the present invention, the compounds represented by Formulas D-4 to D-6 may be selected from the following compounds D-401 to D-536:
D-401
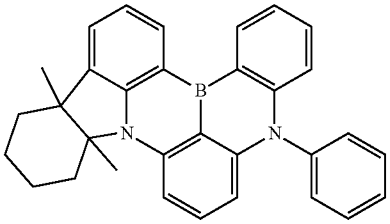
D-402
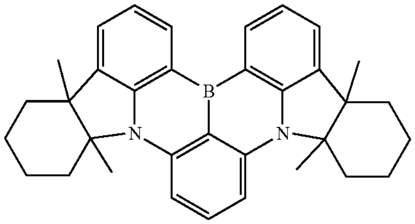
D-403
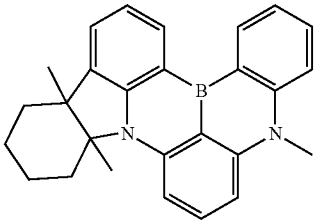
D-404
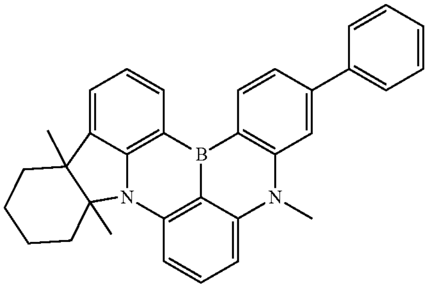
D-405
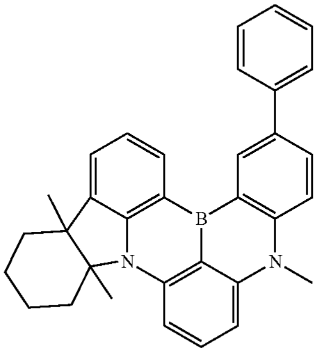
-continued
D-406
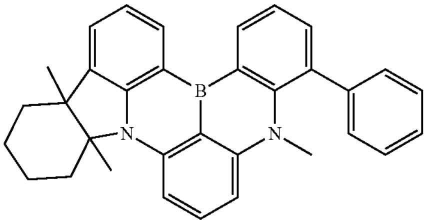
D-407
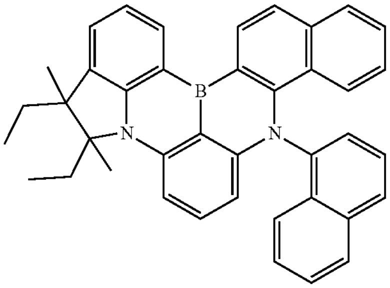
D-408
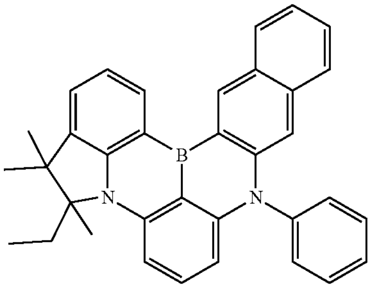
D-409
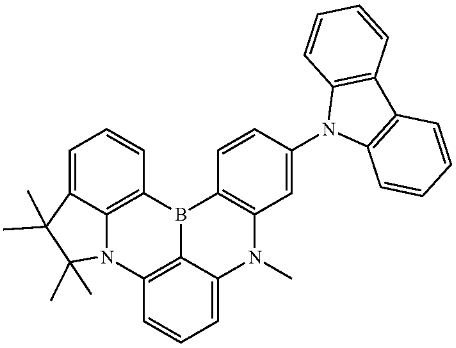
D-410
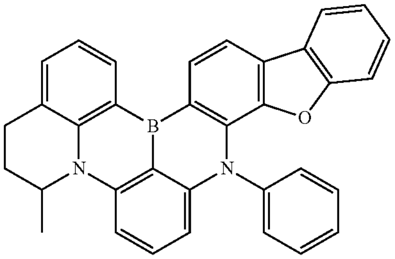

-continued
D-411
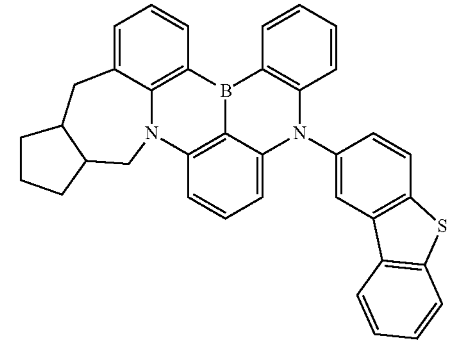
D-412
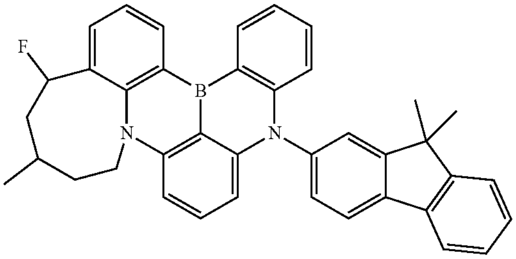
D-413
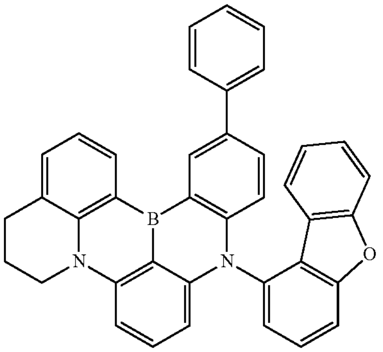
D-414
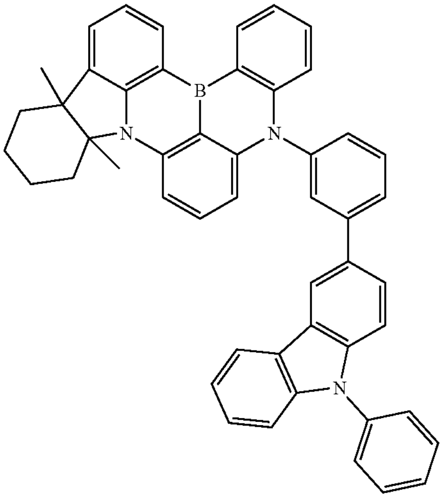
-continued
D-415
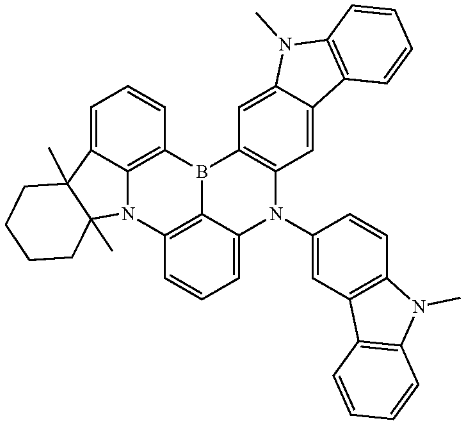
D-416
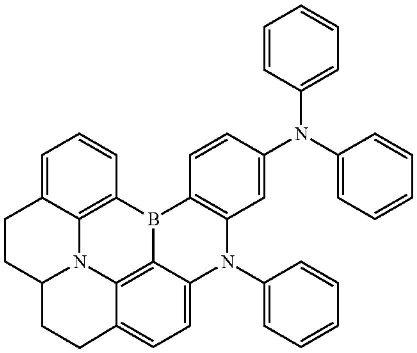
D-417
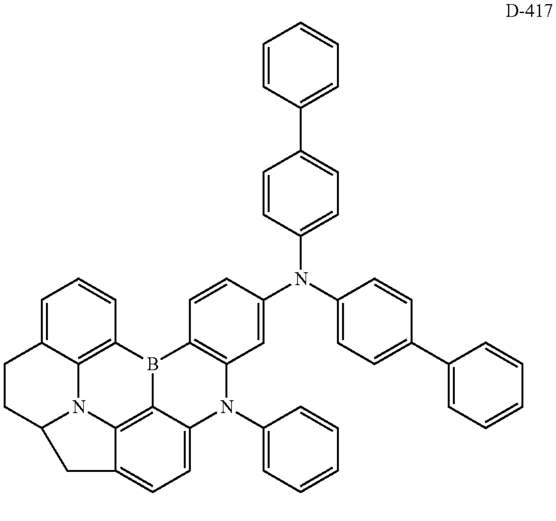

-continued
D-418
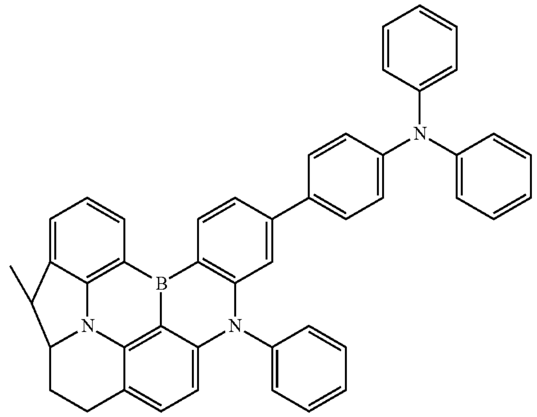
D-419
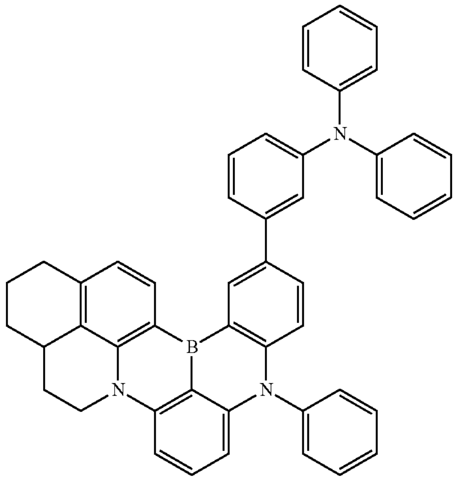
D-420
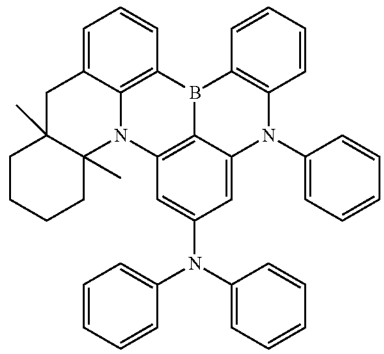
-continued
D-421
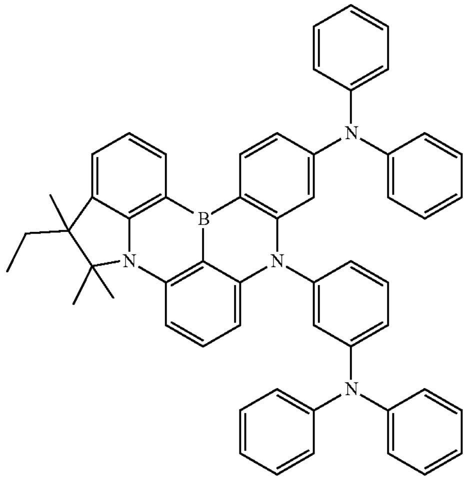
D-422
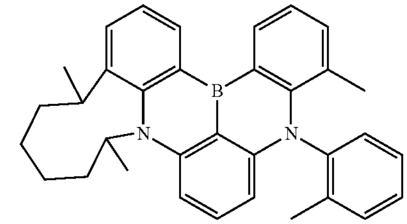
D-423
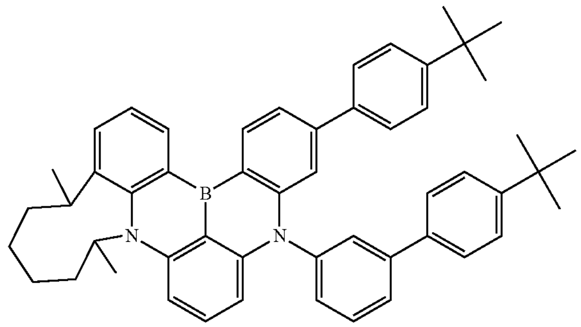
D-424
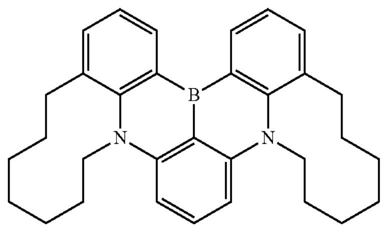
D-425
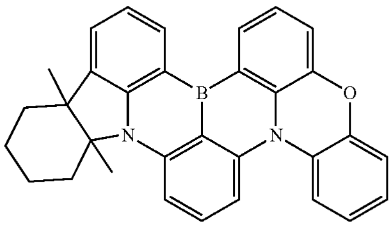

-continued
D-426
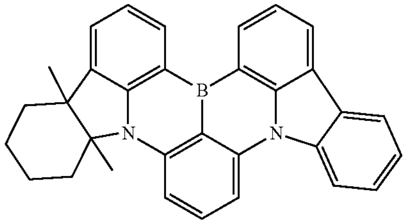
D-427
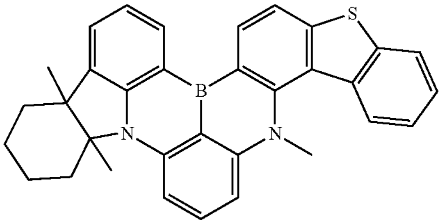
D-428
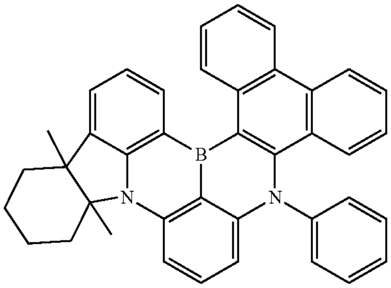
D-429
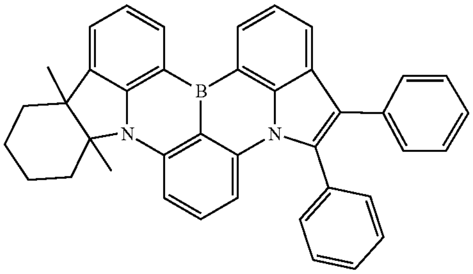
D-430
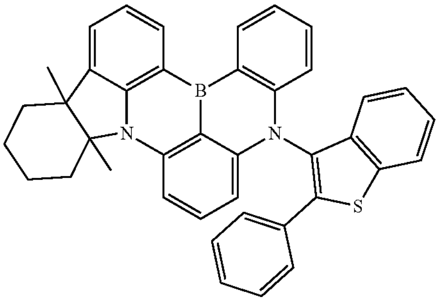
-continued
D-431
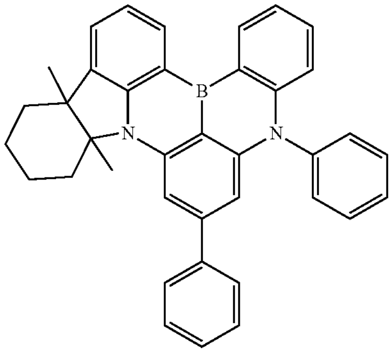
D-432
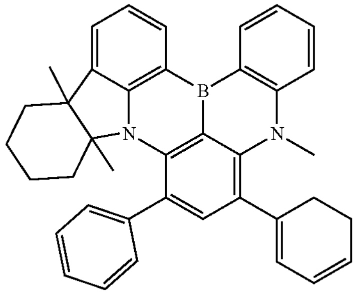
D-433
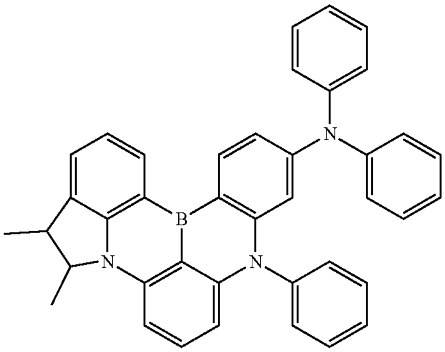
D-434
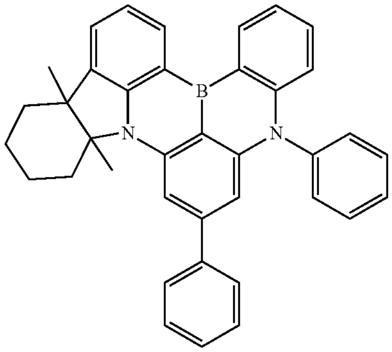

-continued
D-435
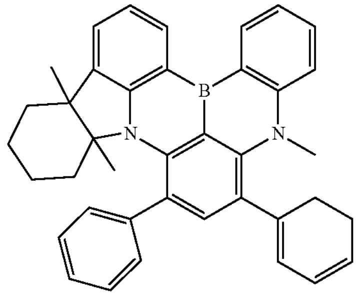
D-436
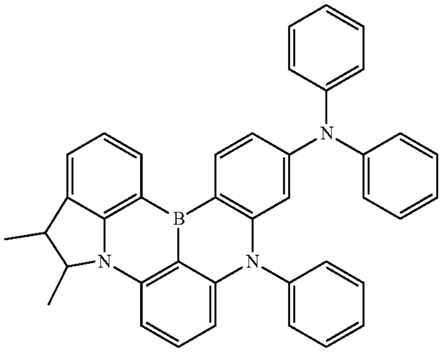
D-437
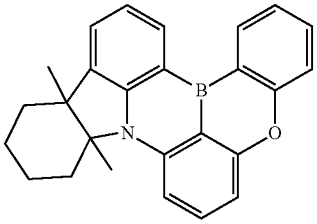
D-438
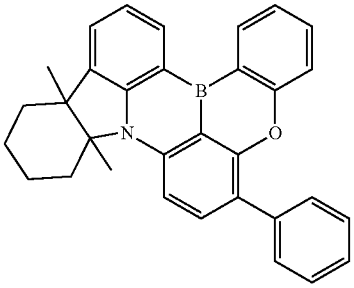
D-439
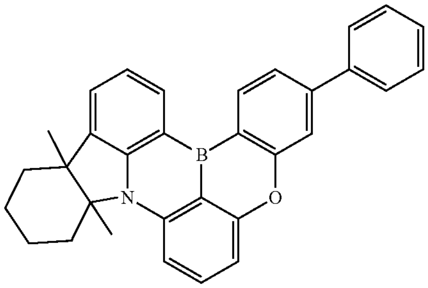
-continued
D-440
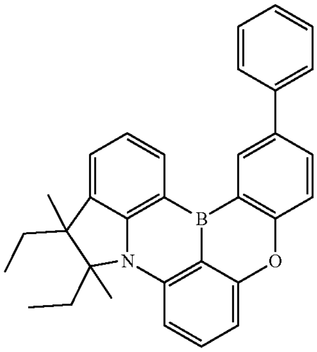
D-441
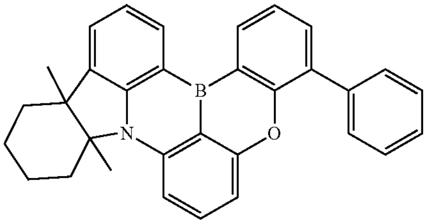
D-442
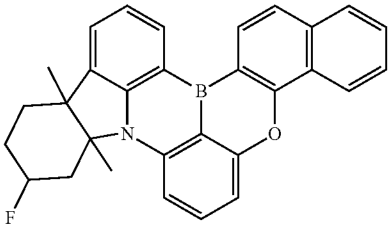
D-443
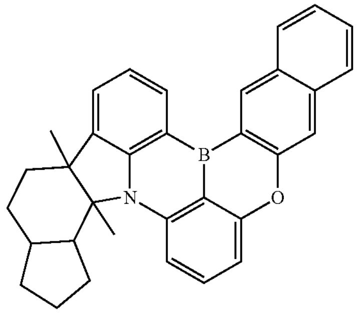
D-444
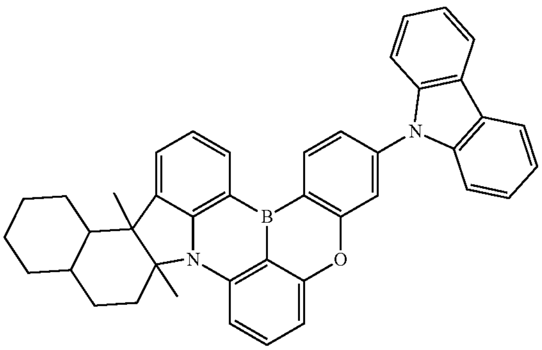

-continued
D-445
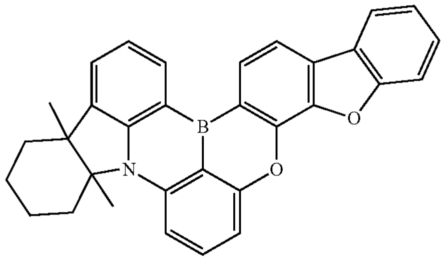
D-446
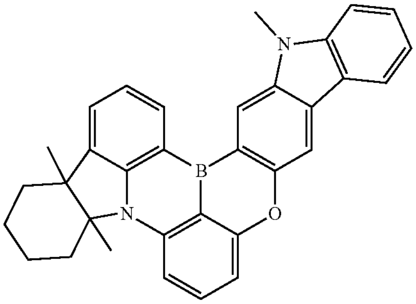
D-447
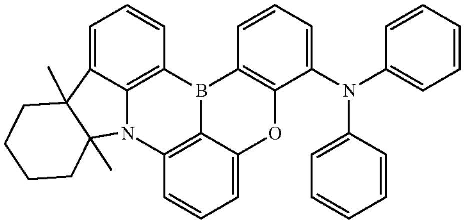
D-448
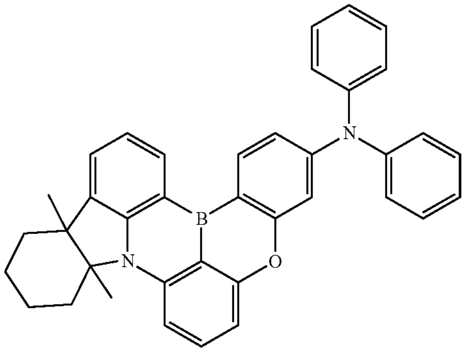
D-449
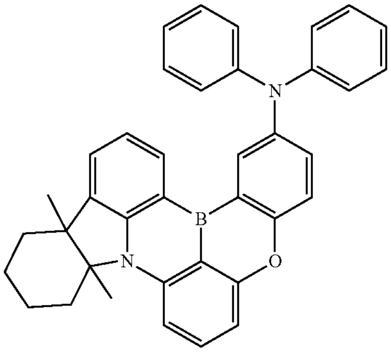
-continued
D-450
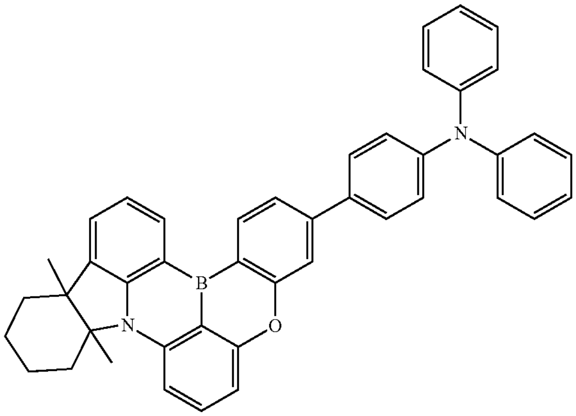
D-451
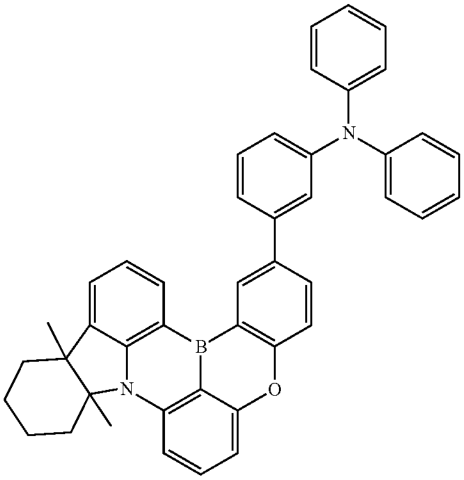
D-452
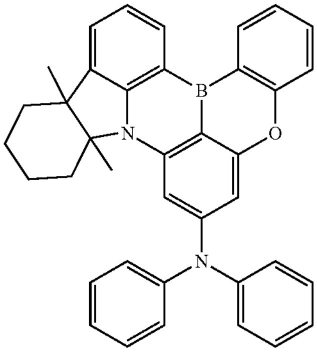
D-453
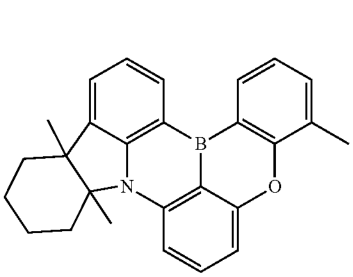

-continued
D-454
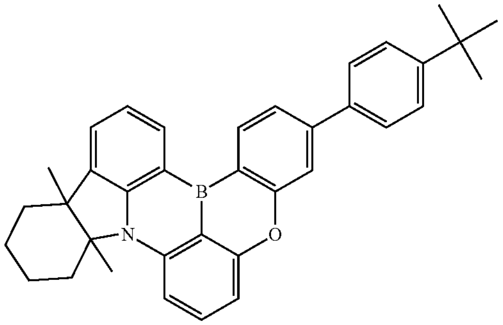
D-455
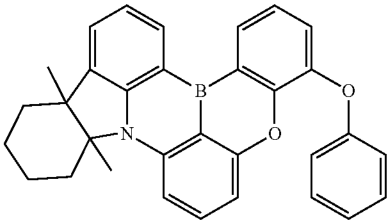
D-456
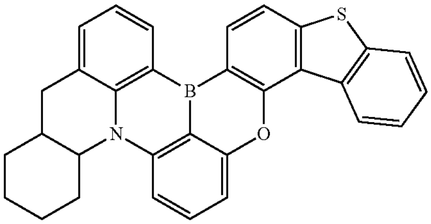
D-457
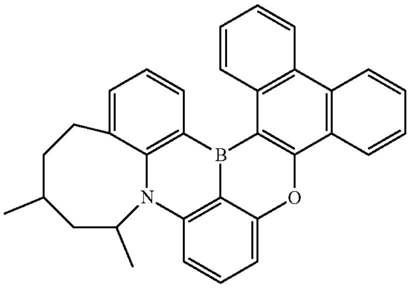
D-458
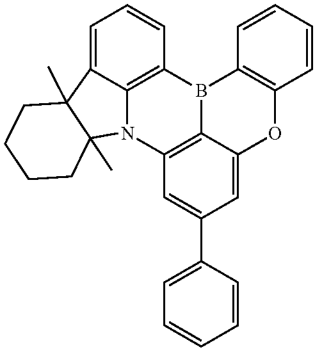
-continued
D-459
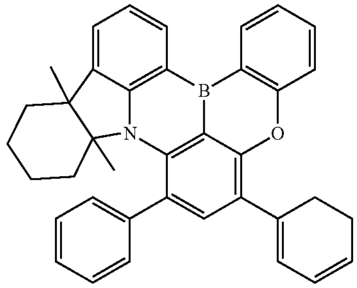
D-460
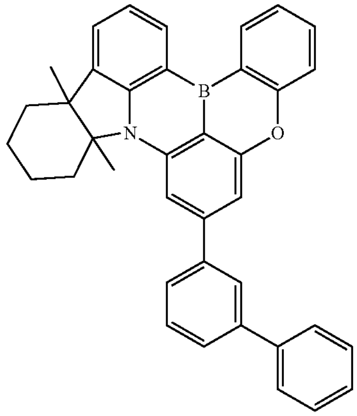
D-461
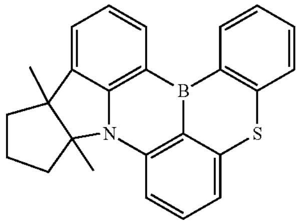
D-462
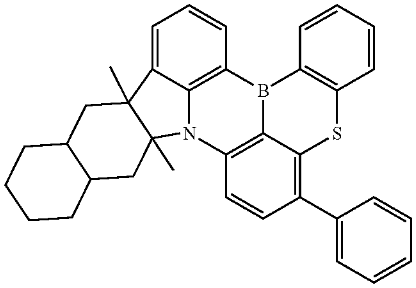
D-463
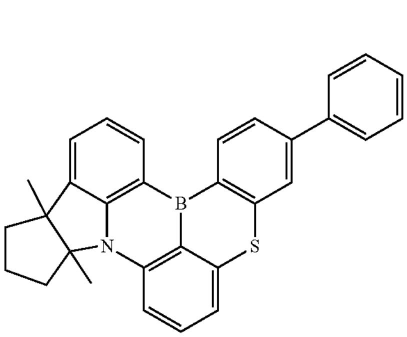

-continued
D-464
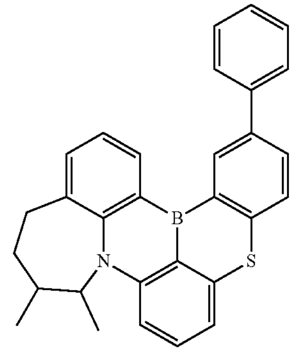
D-465
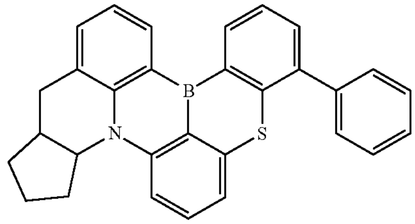
D-466
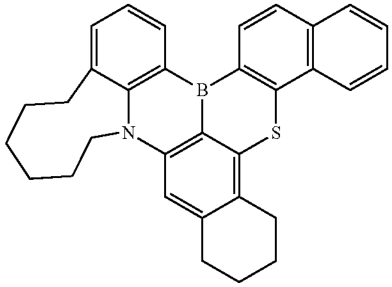
D-467
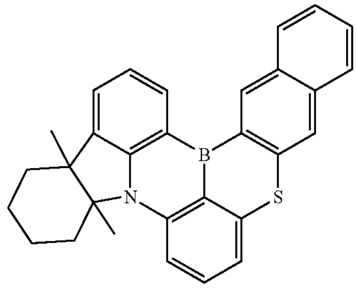
D-468
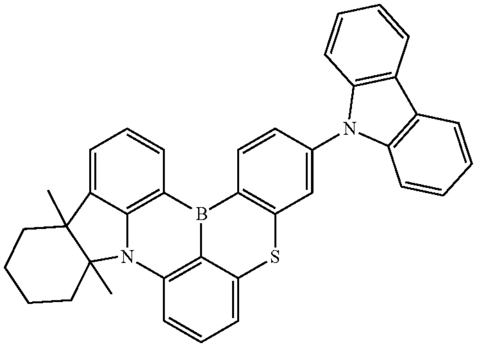
-continued
D-469
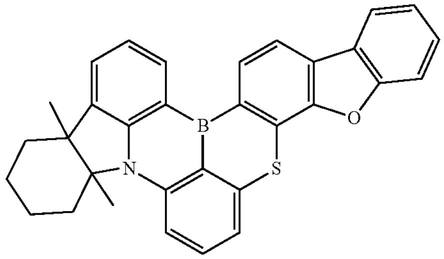
D-470
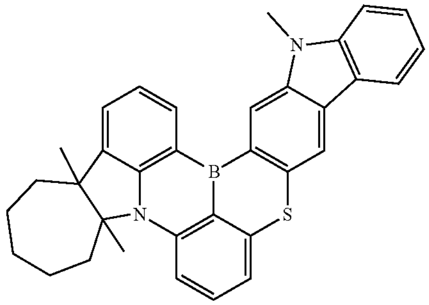
D-471
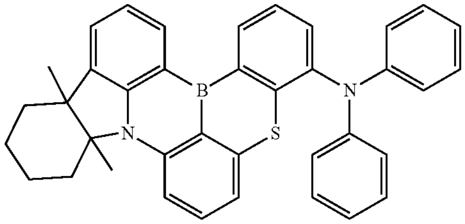
D-472
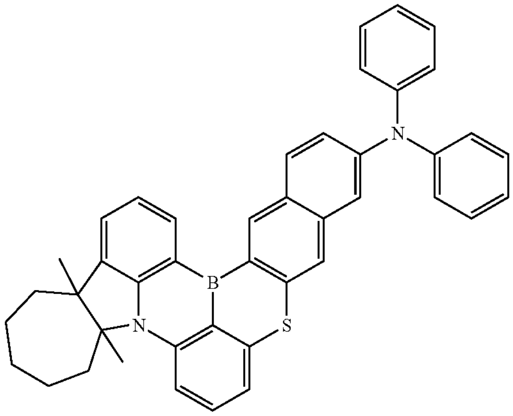
D-473
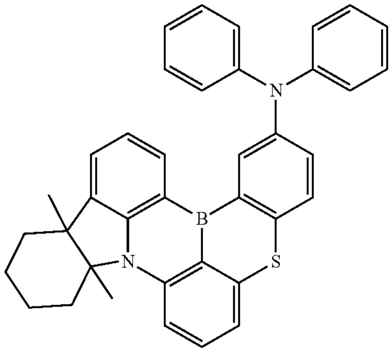

-continued
D-474
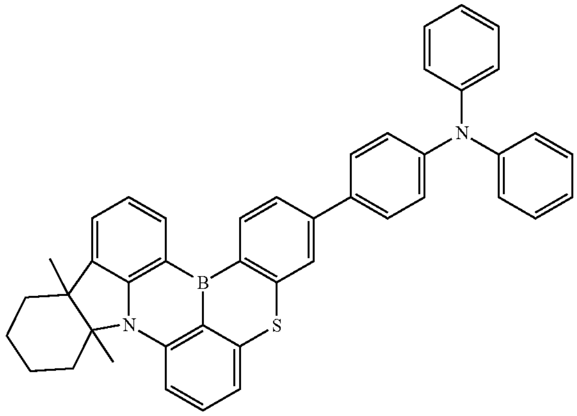
D-475
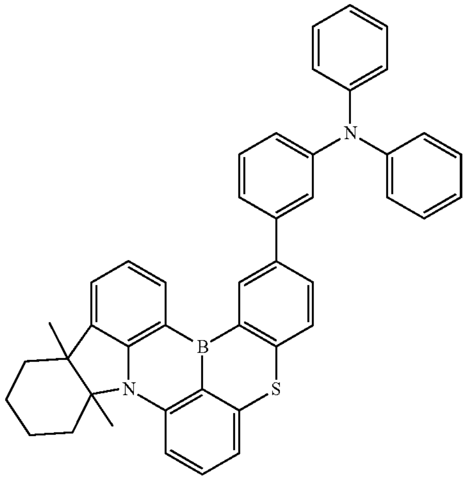
D-476
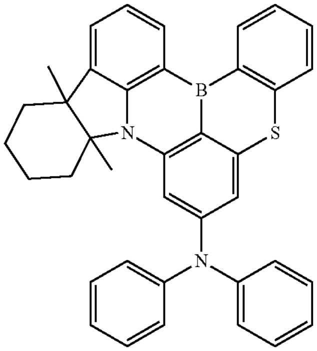
D-477
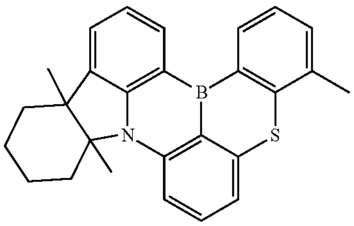
-continued
D-478
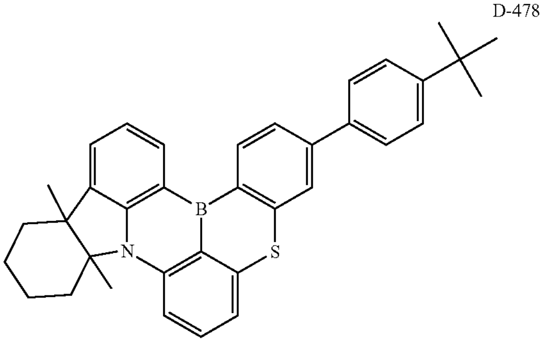
D-479
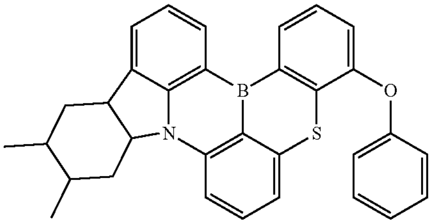
D-480
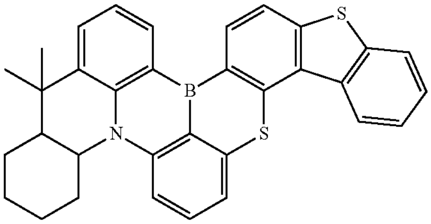
D-481
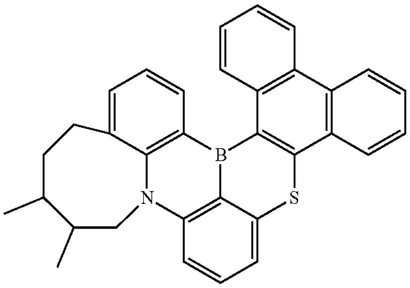
D-482
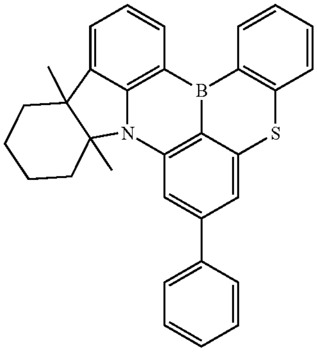

-continued
D-483
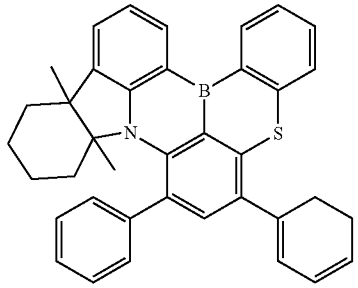
D-484
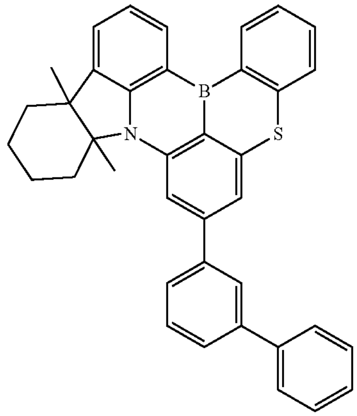
D-485
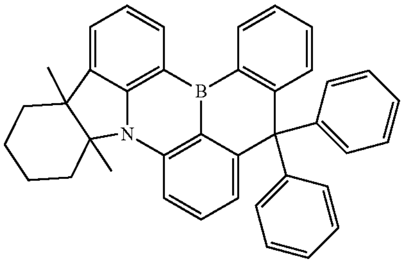
D-486
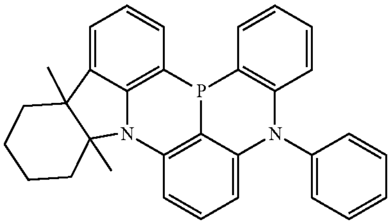
D-487
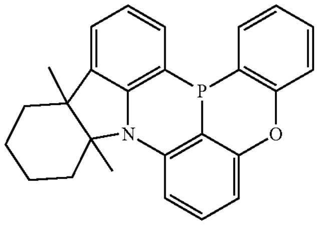
-continued
D-488
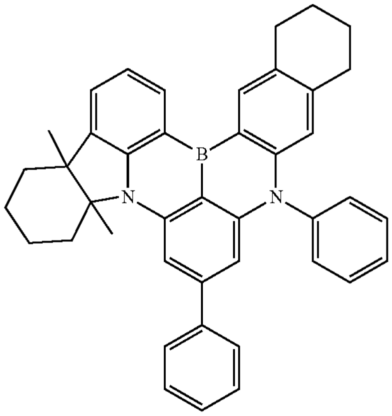
D-489
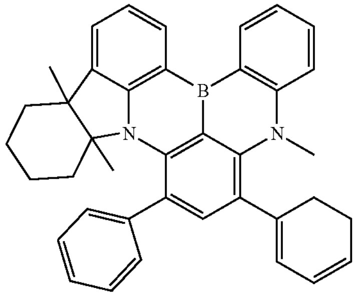
D-490
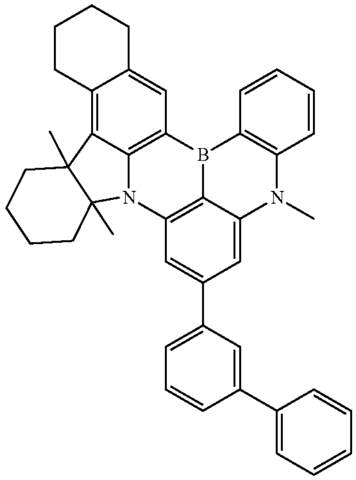
D-491
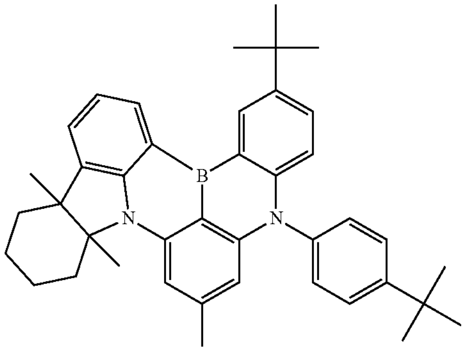

-continued
D-492
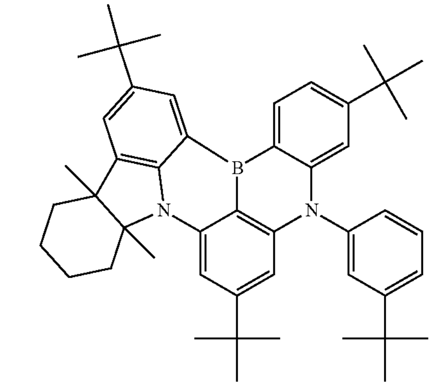
D-493
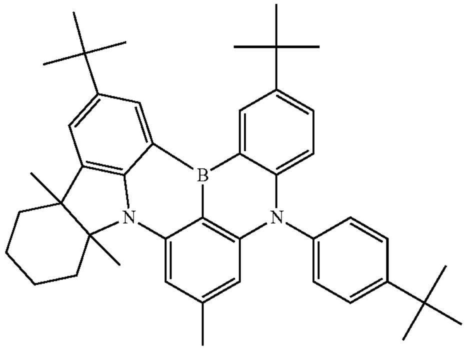
D-494
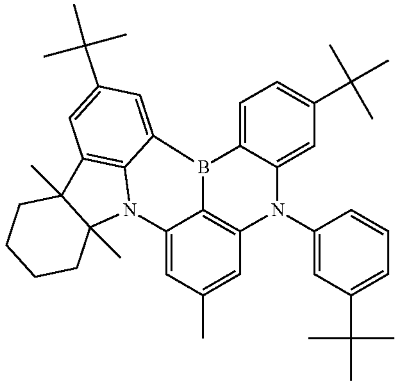
D-495
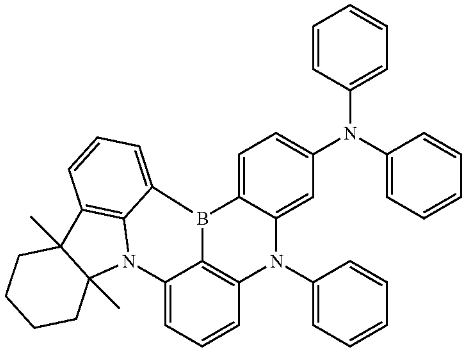
-continued
D-496
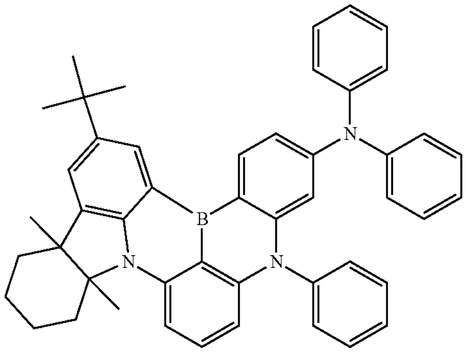
D-497
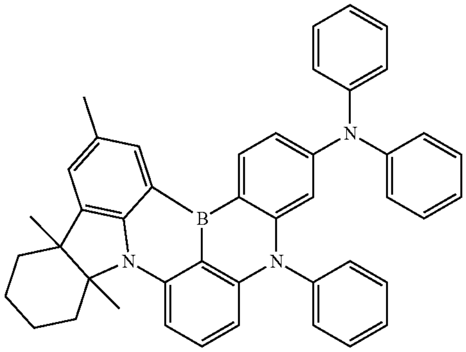
D-498
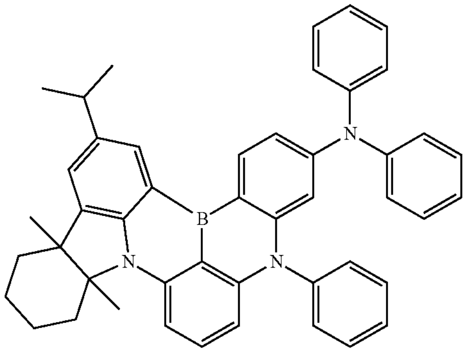
D-499
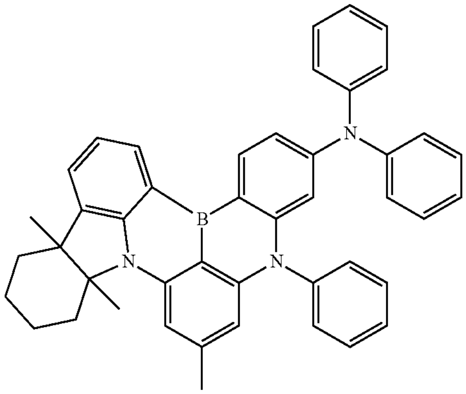

-continued
D-500
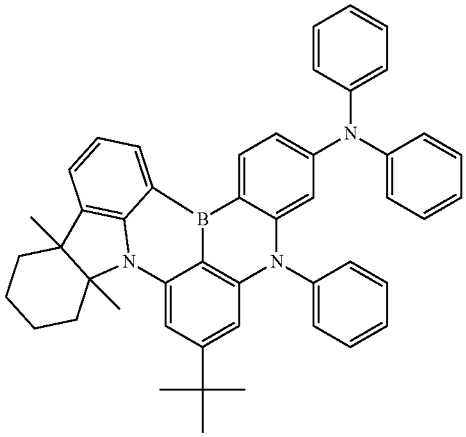
D-501
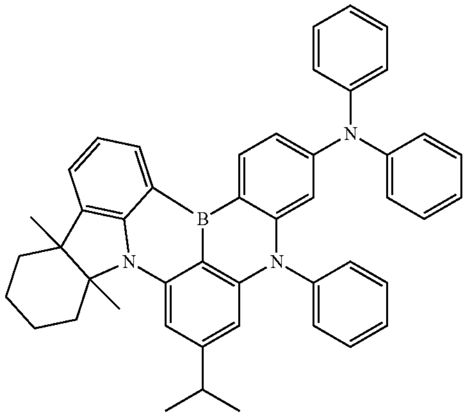
D-502
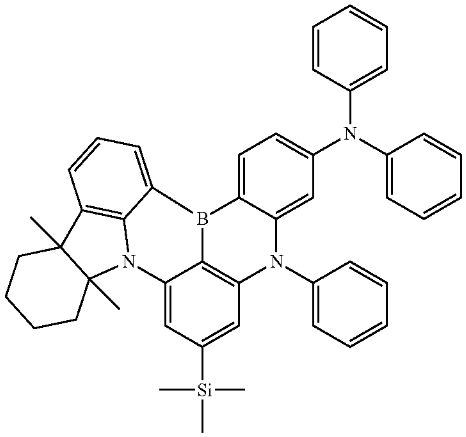
-continued
D-503
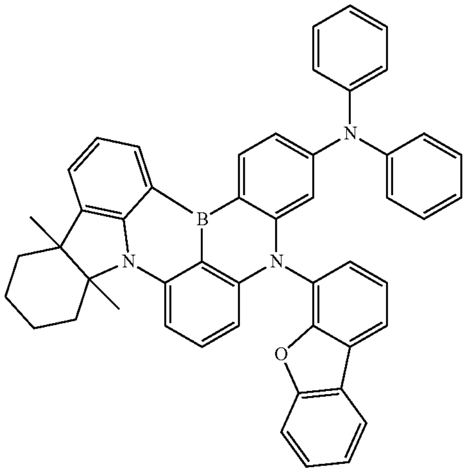
D-504
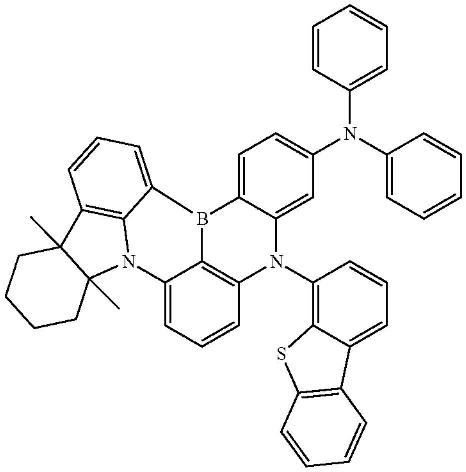
D-505
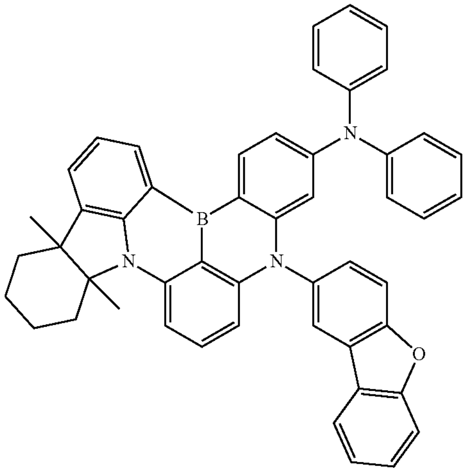

-continued
D-506
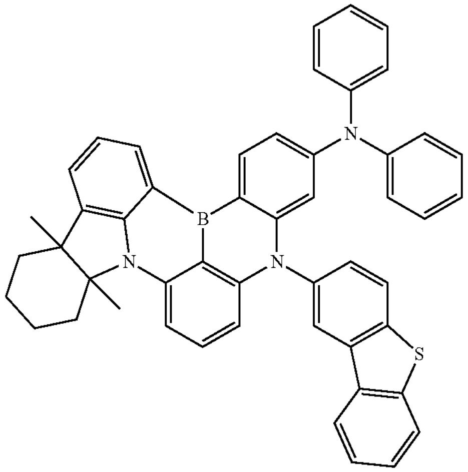
D-507
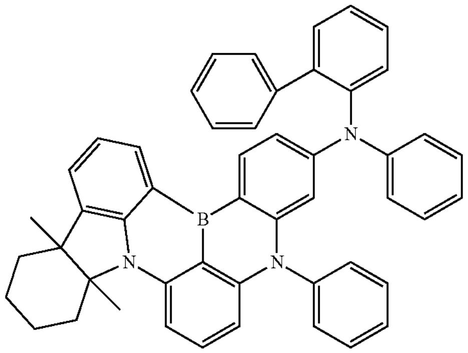
D-508
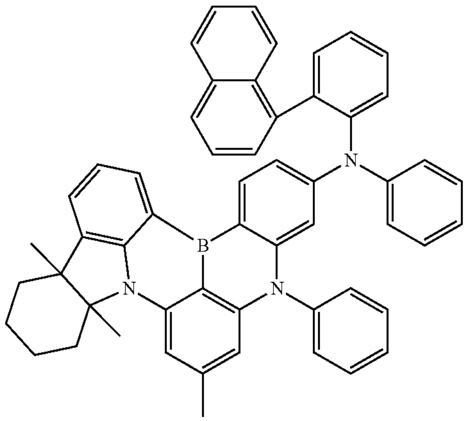
-continued
D-509
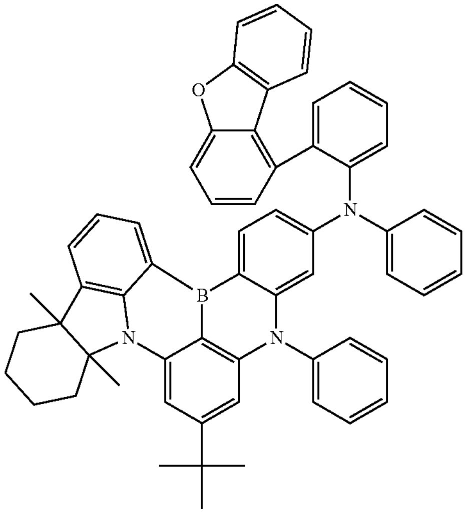
D-510
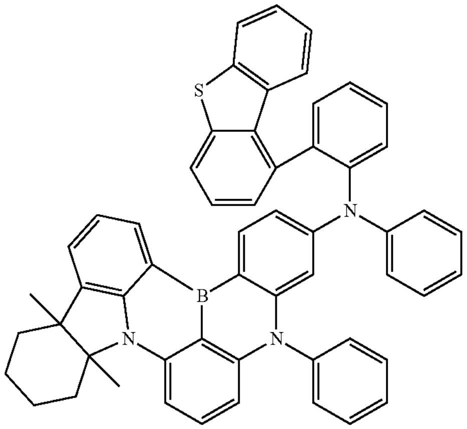
D-511
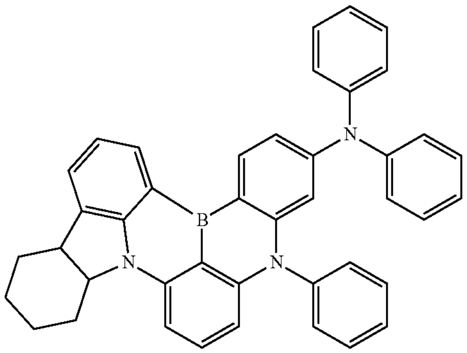

-continued
D-512
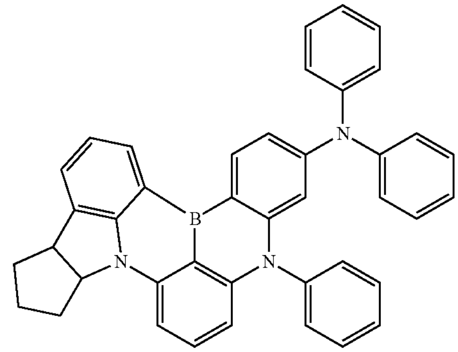
D-513
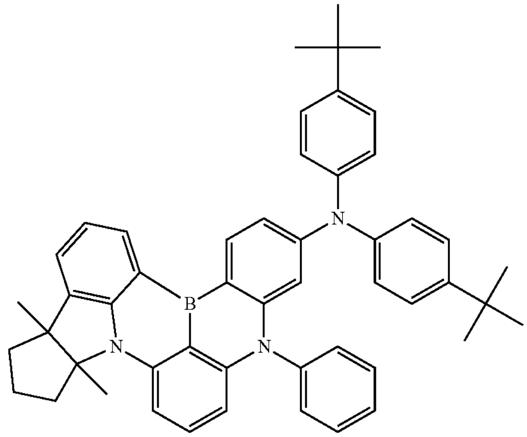
D-514
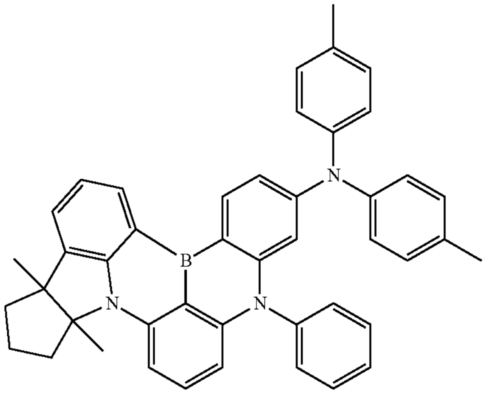
-continued
D-515
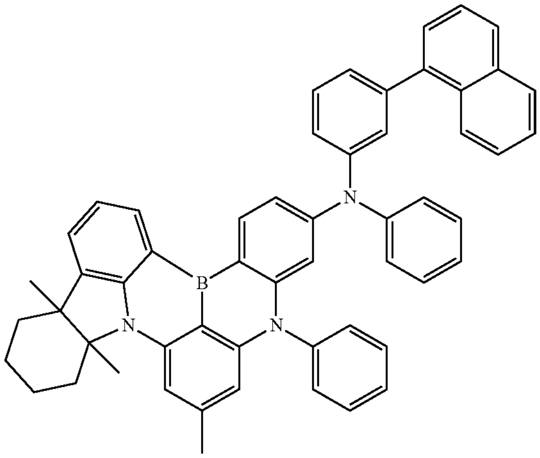
D-516
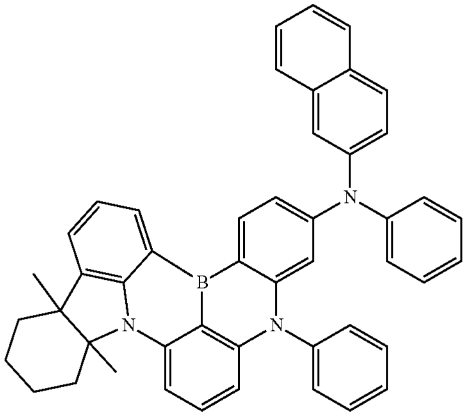
D-517
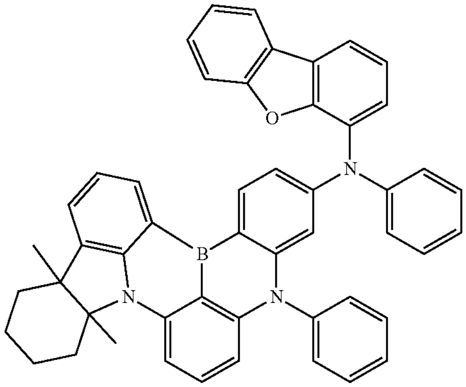
D-518
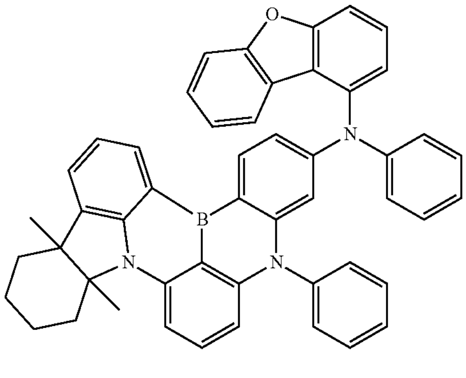

-continued
D-519
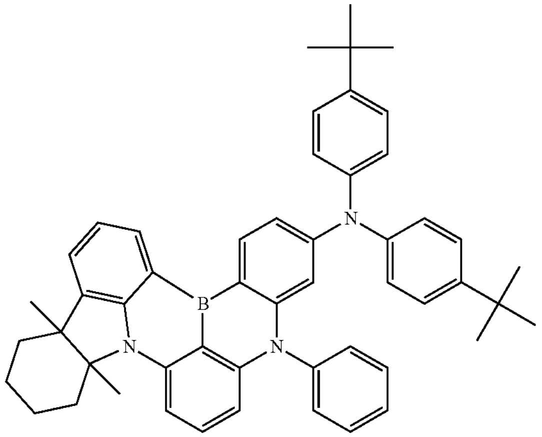
D-520
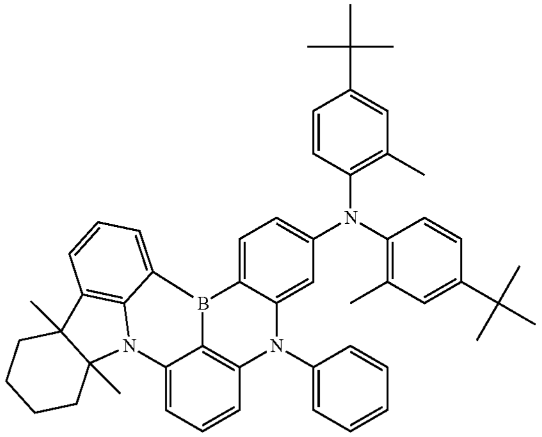
D-521
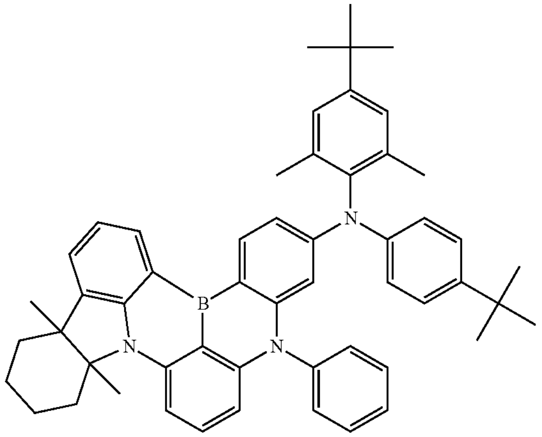
-continued
D-522
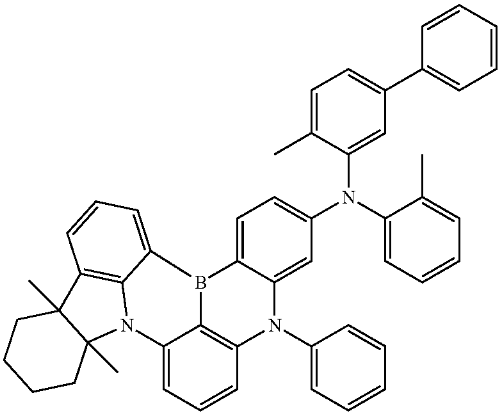
D-523
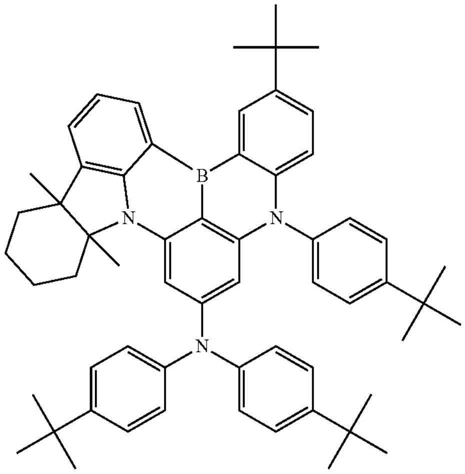
D-524
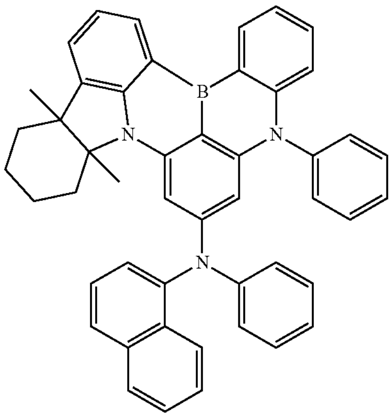

-continued
D-525
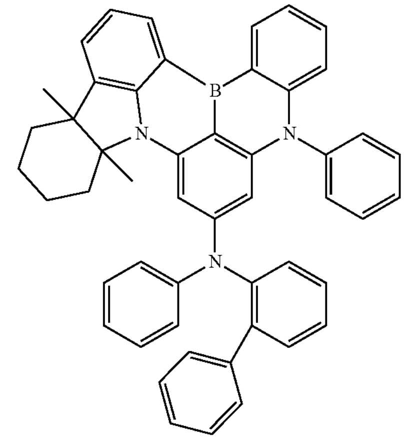
D-526
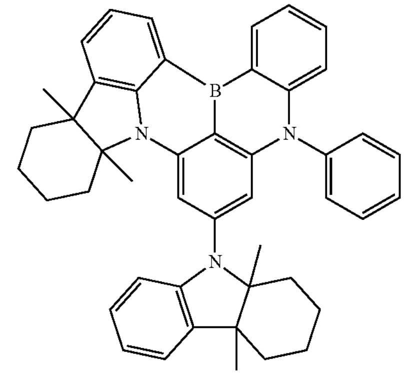
D-527
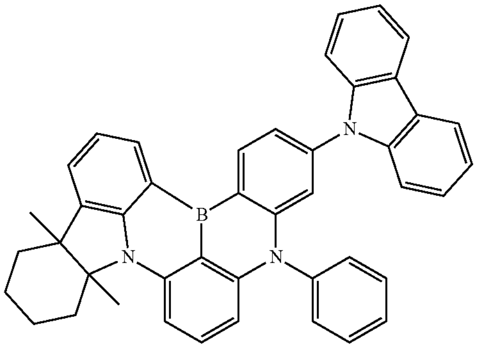
D-528
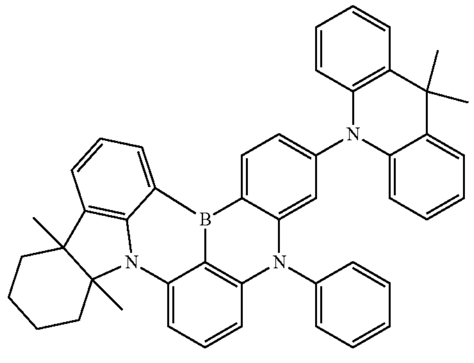
-continued
D-529
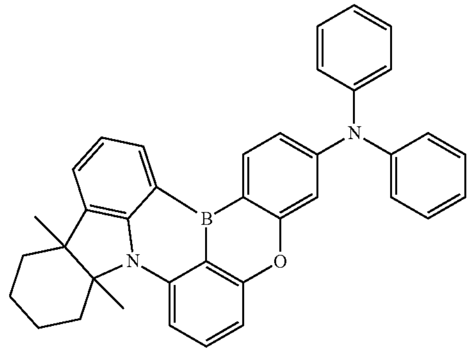
D-530
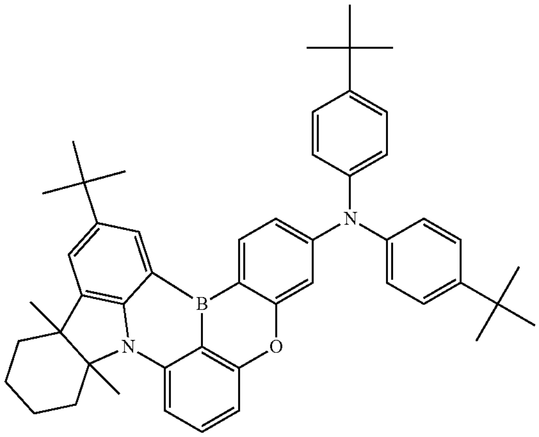
D-531
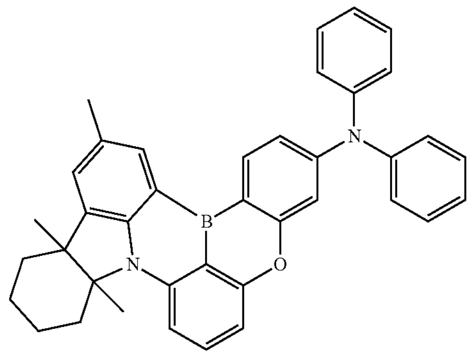
D-532
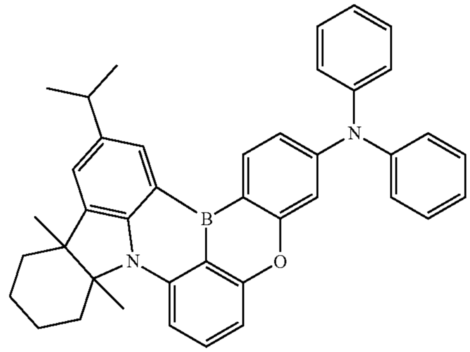

-continued
D-533
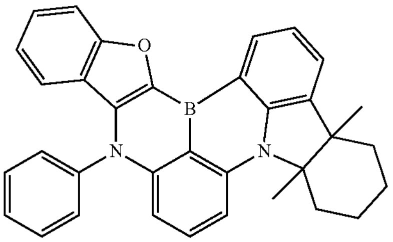
D-534
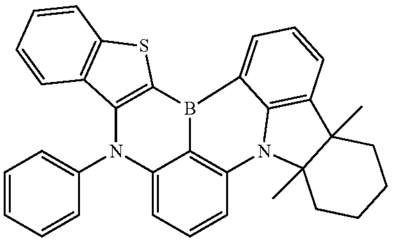
D-535
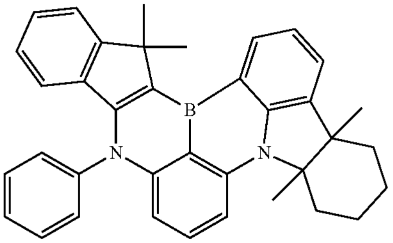
D-536
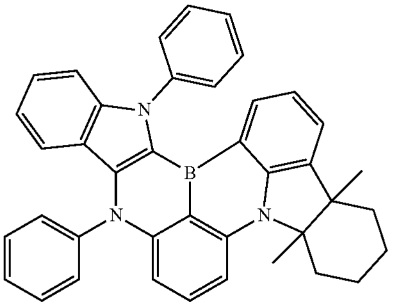
However, these compounds are not intended to limit the scope of Formulas D-4 to D-6.
According to one embodiment of the present invention, the compounds represented by Formulas D-7 and D-8 may be selected from the following compounds D-601 to D-727:
D-601
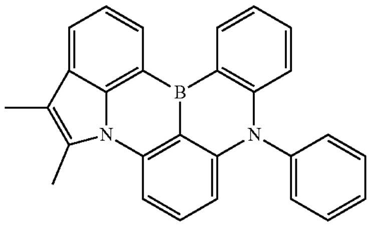
-continued
D-602
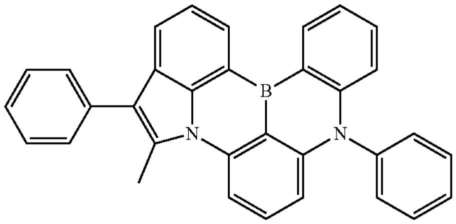
D-603
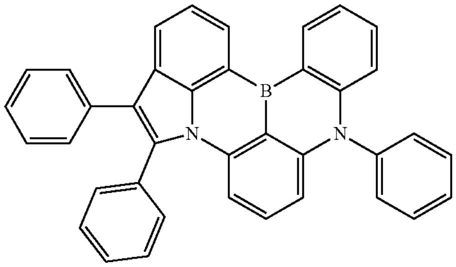
D-604
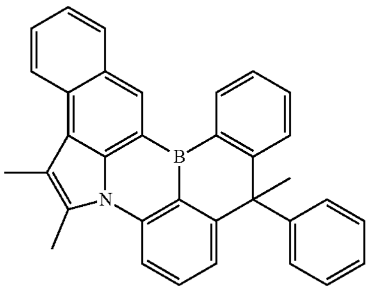
D-605
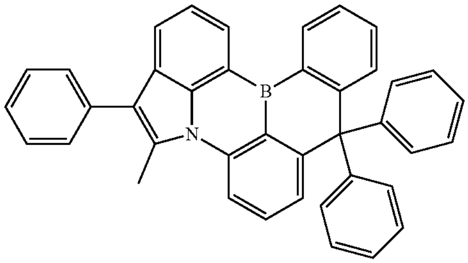
D-606
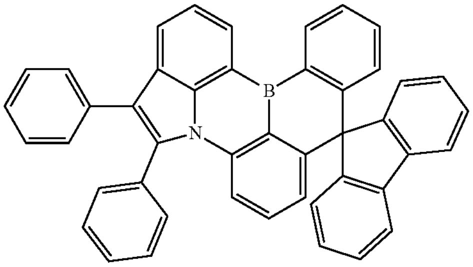
D-607
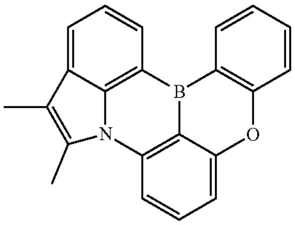

-continued
D-608
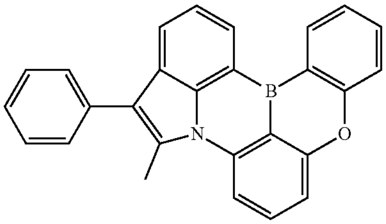
D-609
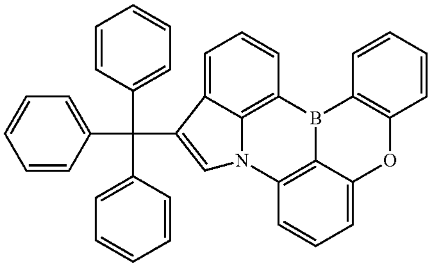
D-610
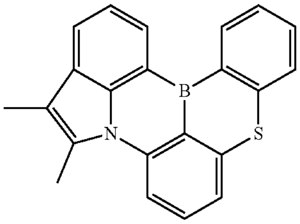
D-611
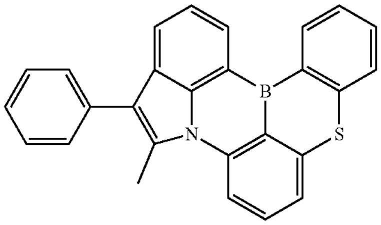
D-612
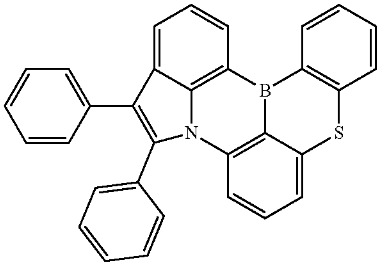
D-613
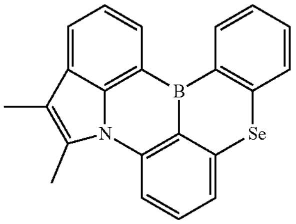
-continued
D-614
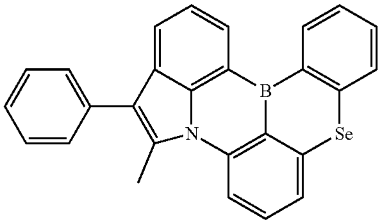
D-615
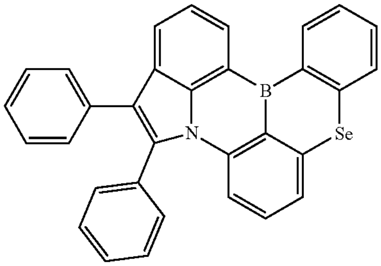
D-616
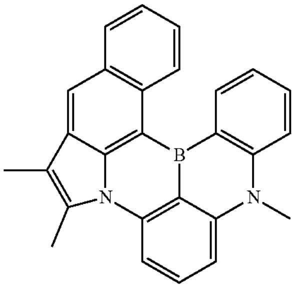
D-617
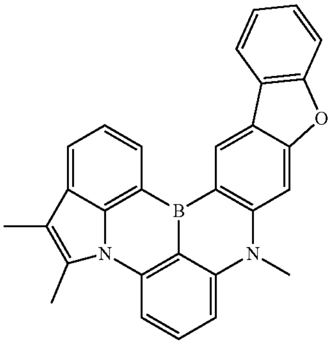
D-618
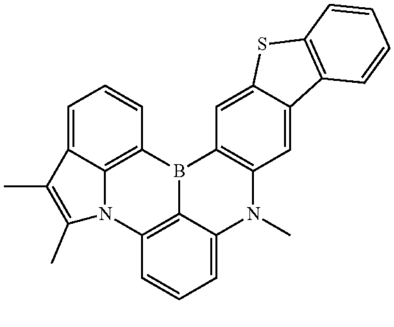

-continued
D-619
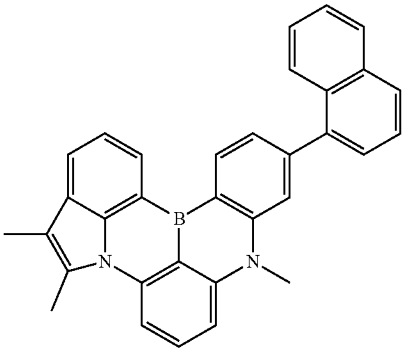
D-620
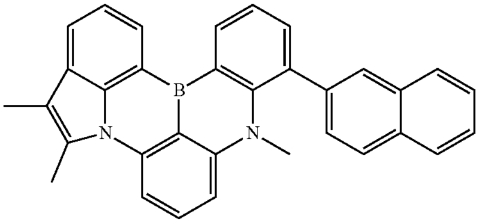
D-621
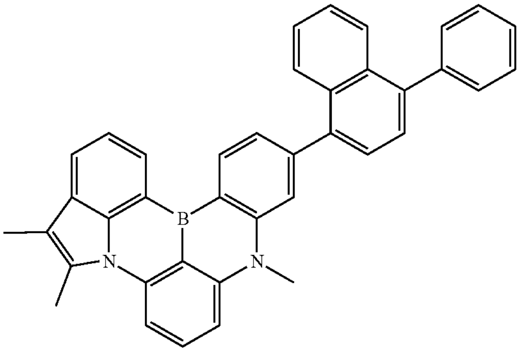
D-622
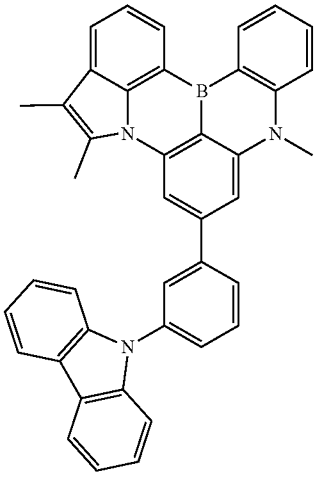
-continued
D-623
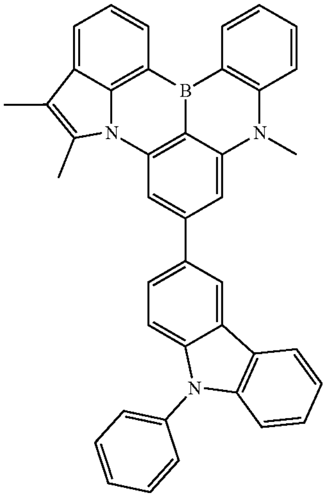
D-624
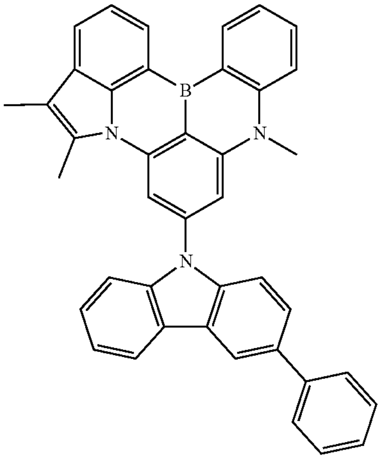
D-625
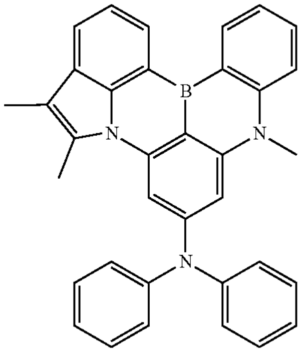

-continued
D-626
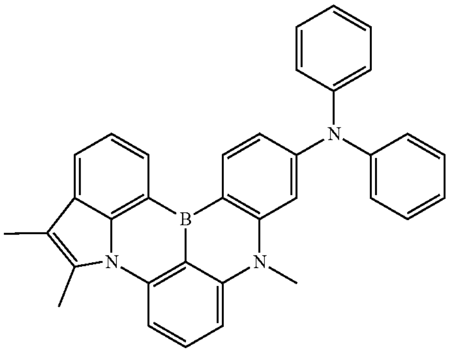
D-627
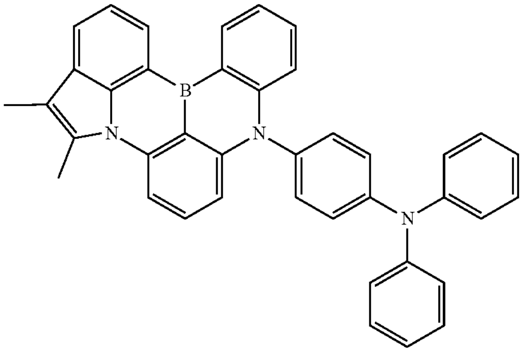
D-628
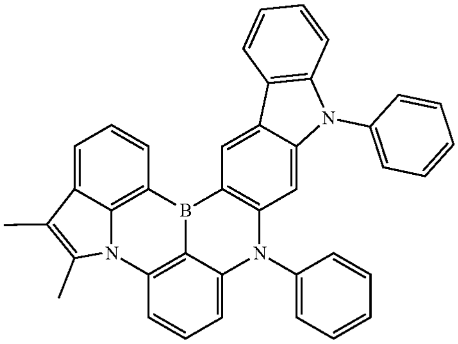
D-629
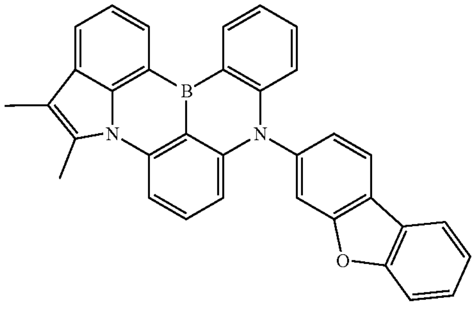
-continued
D-630
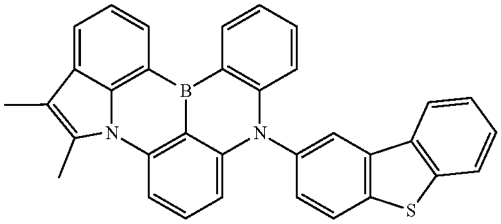
D-631
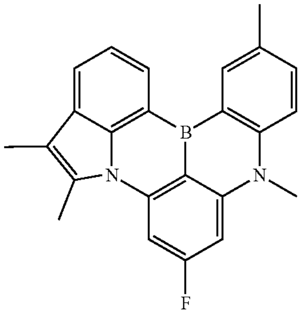
D-632
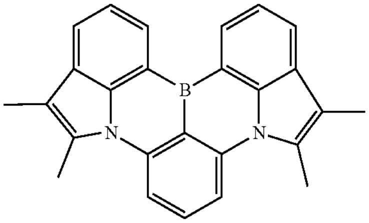
D-633
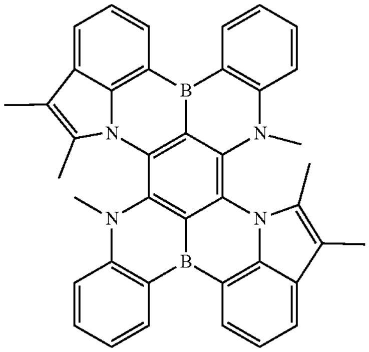
D-634
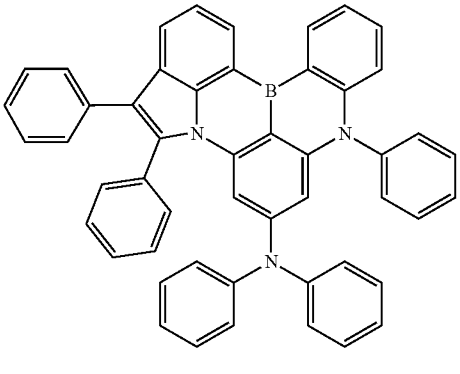

-continued
D-635
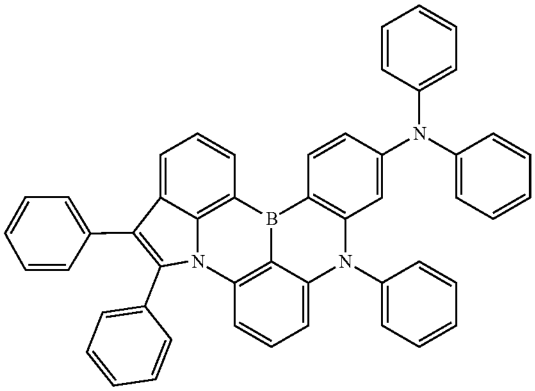
D-636
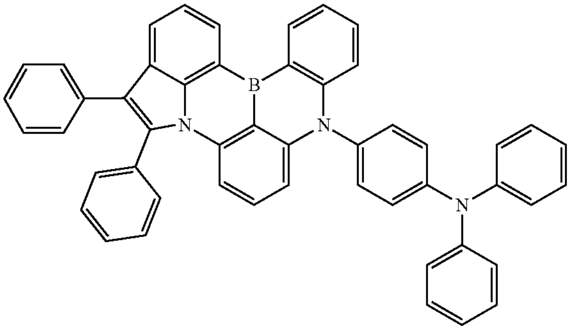
D-637
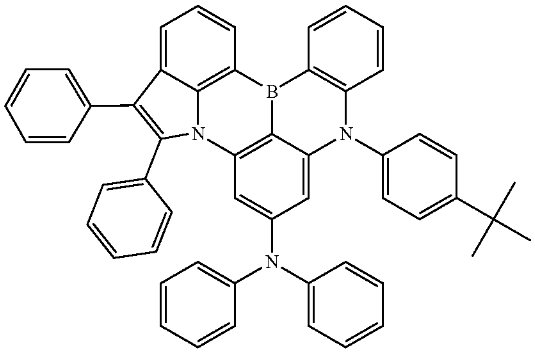
-continued
D-638
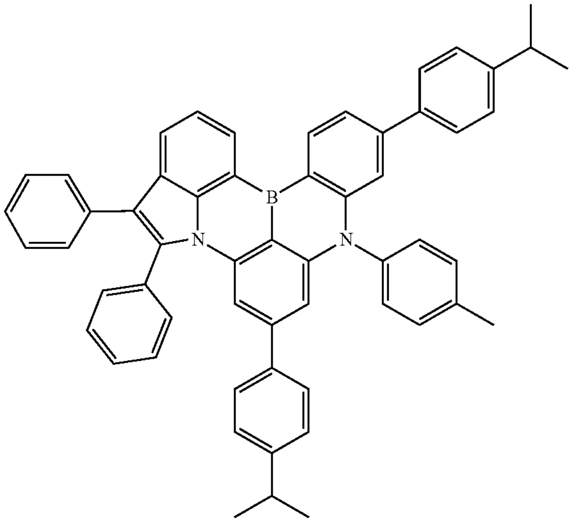
D-639
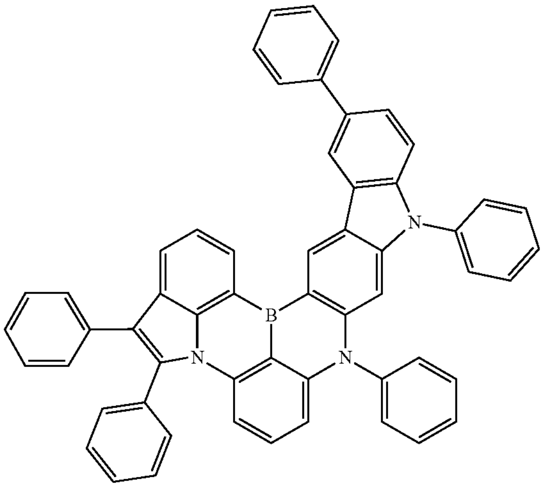
D-640
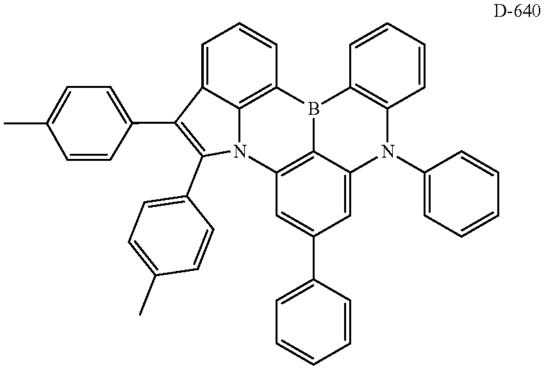

-continued
D-641
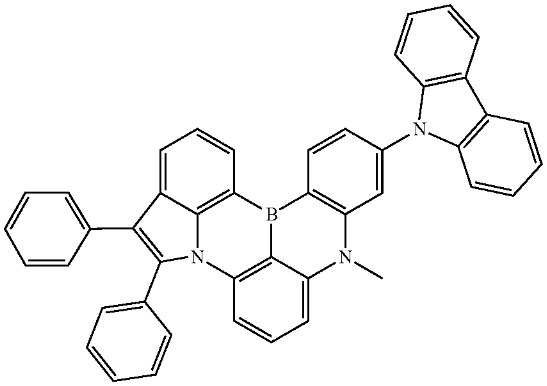
D-642
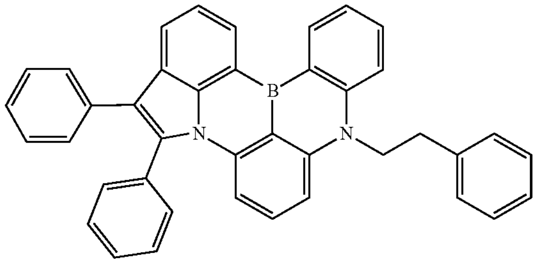
D-643
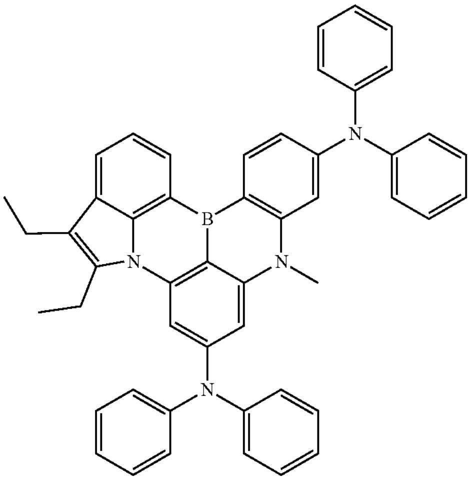
D-644
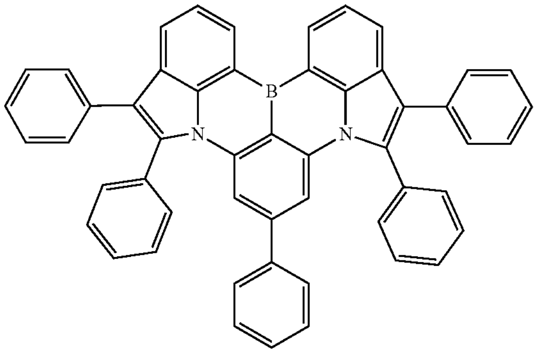
-continued
D-645
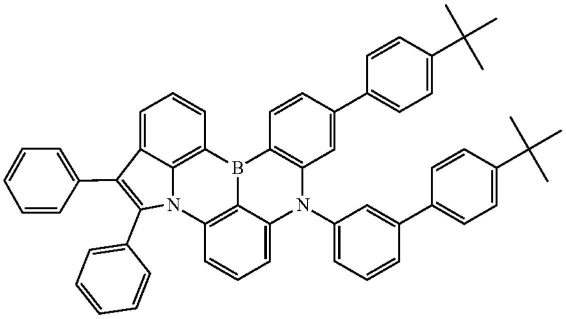
D-646
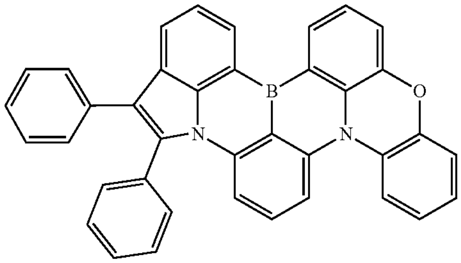
D-647
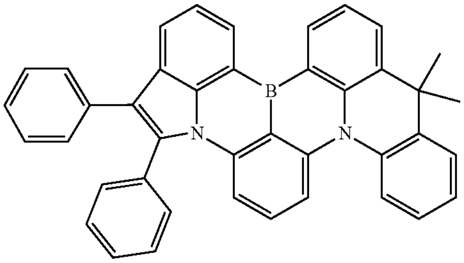
D-648
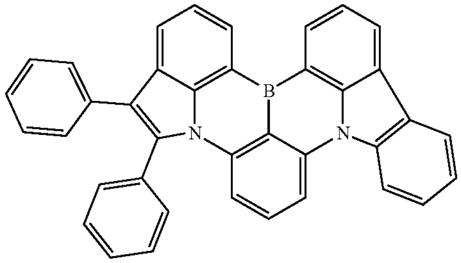
D-649
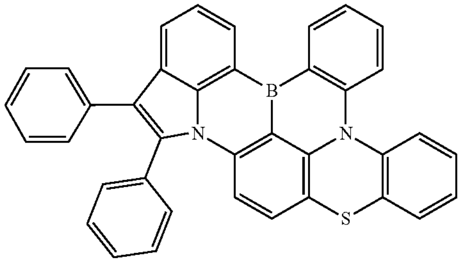

-continued
D-650
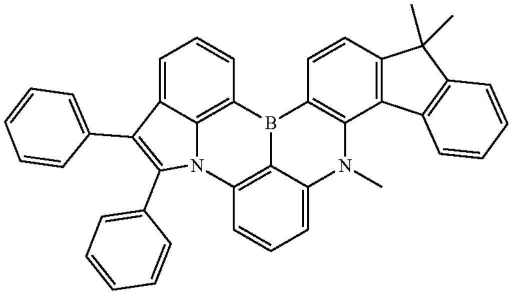
D-651
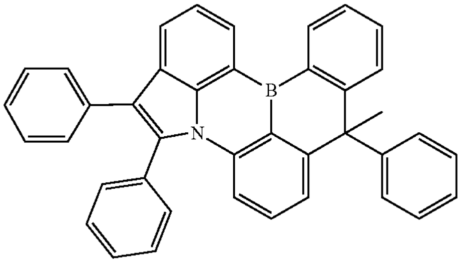
D-652
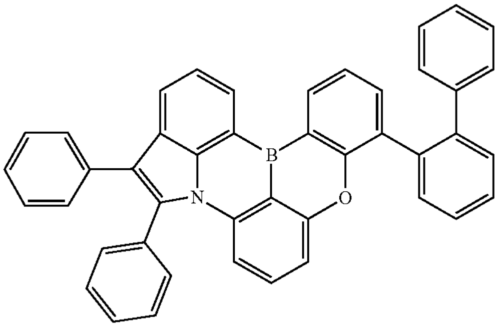
D-653
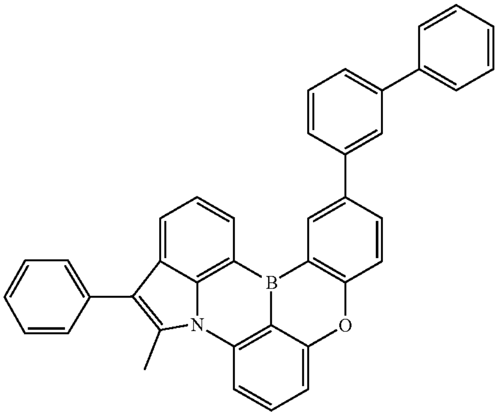
-continued
D-654
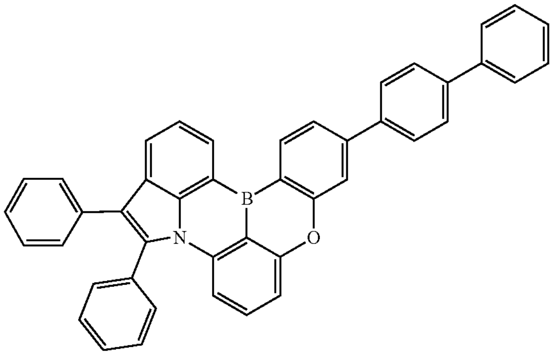
D-655
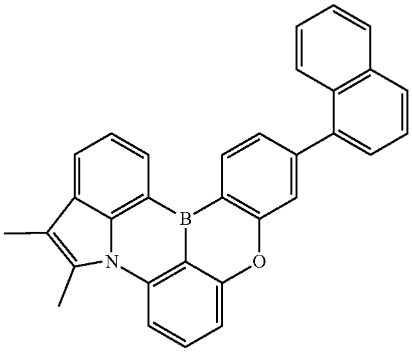
D-656
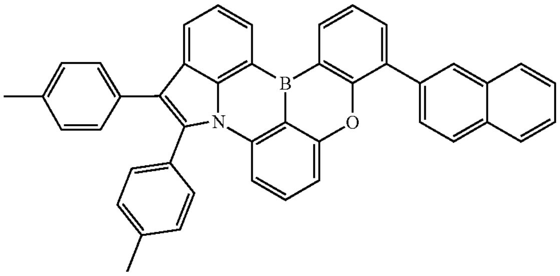
D-657
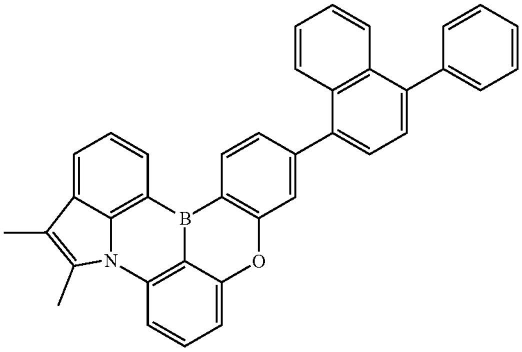

-continued
D-658
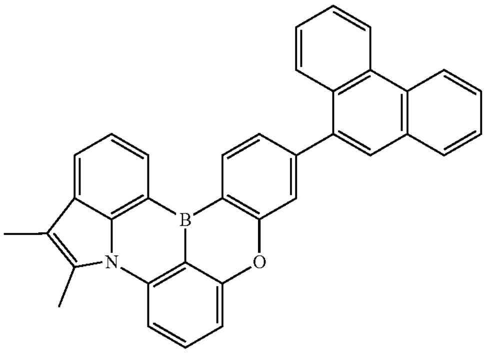
D-659
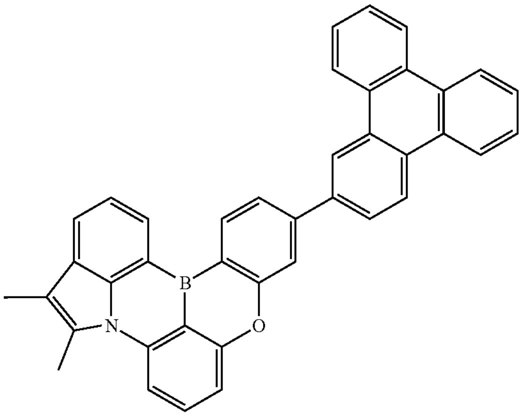
D-660
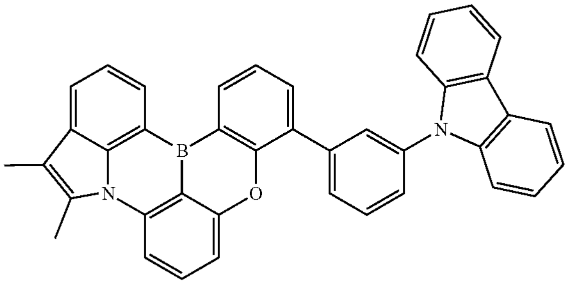
D-661
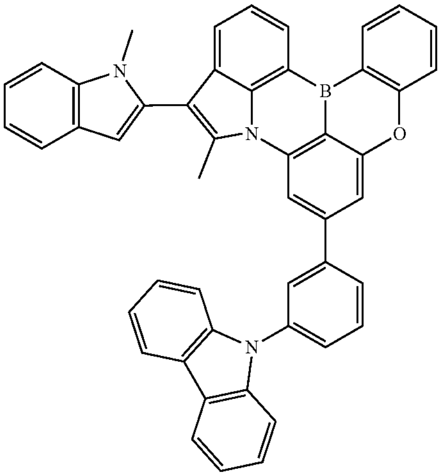
-continued
D-662
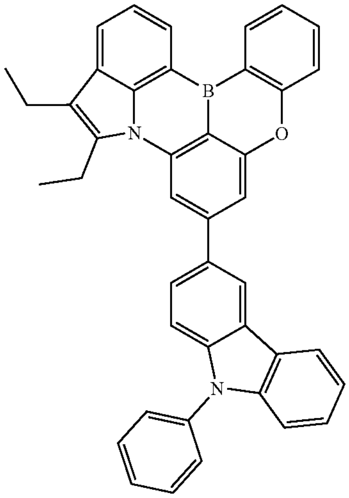
D-663
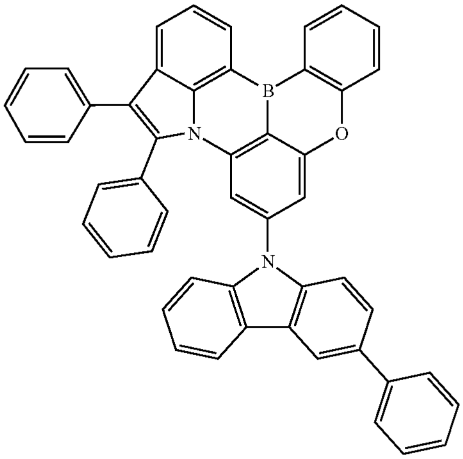
D-664
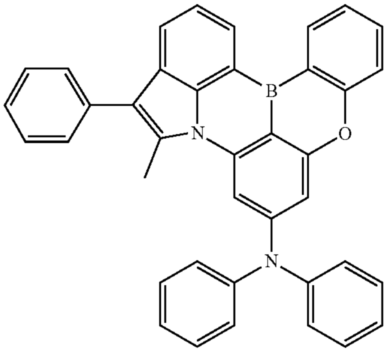

-continued
D-665
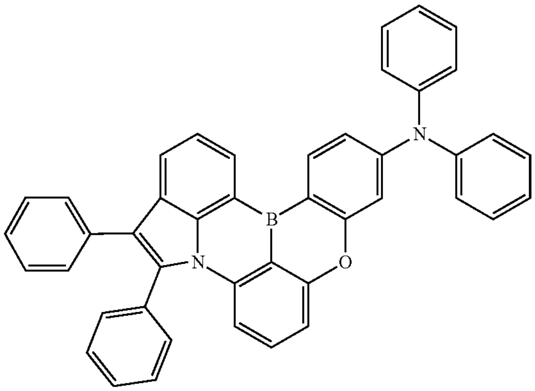
D-666
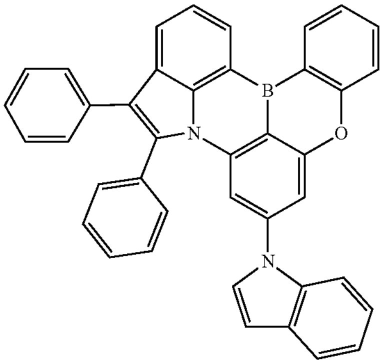
D-667
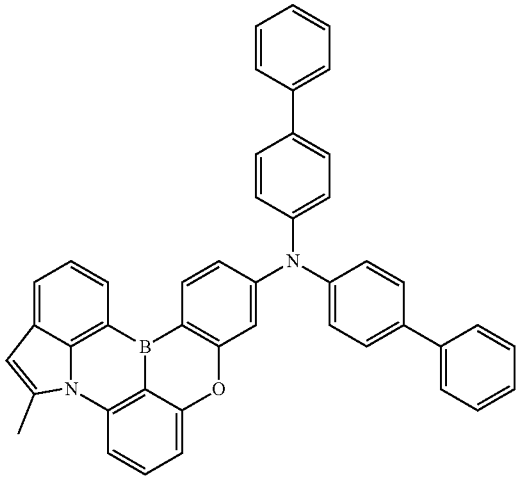
D-668
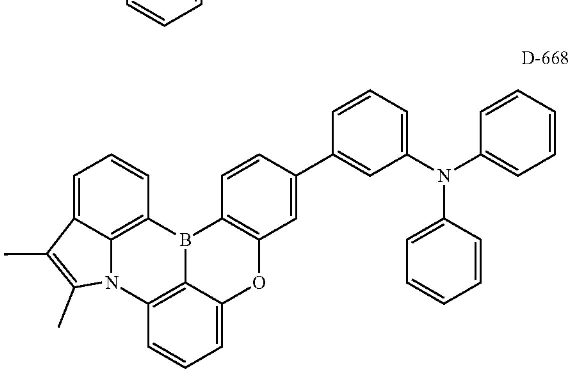
-continued
D-669
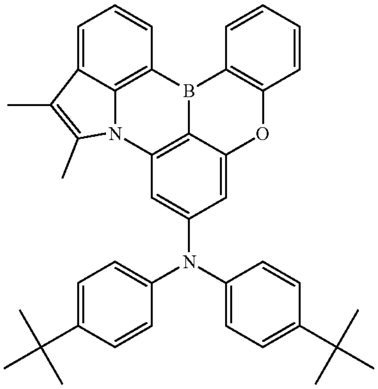
D-670
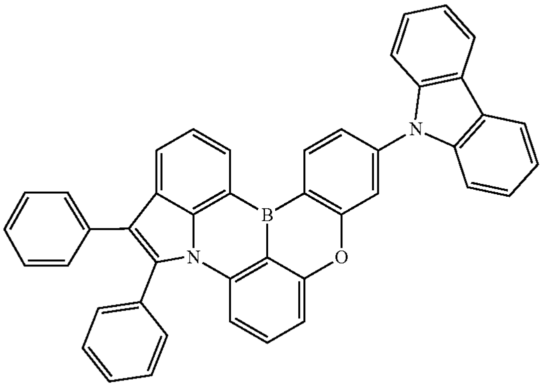
D-671
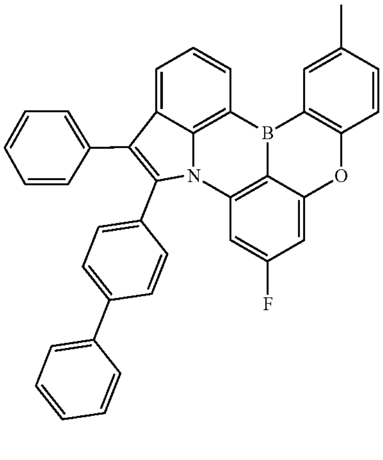

-continued
D-672
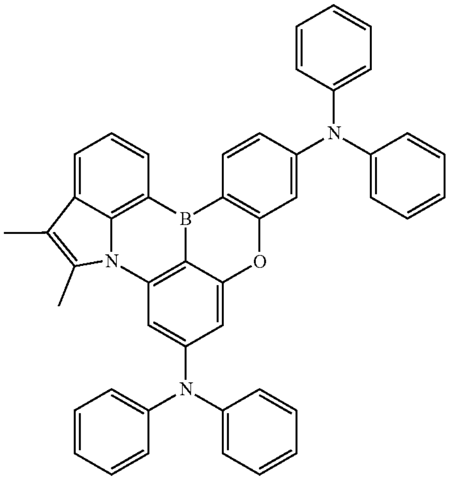
D-673
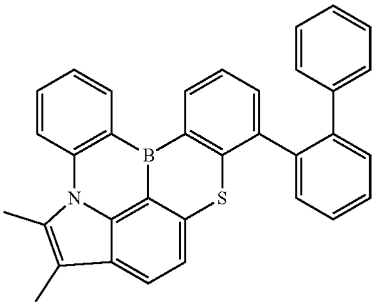
D-674
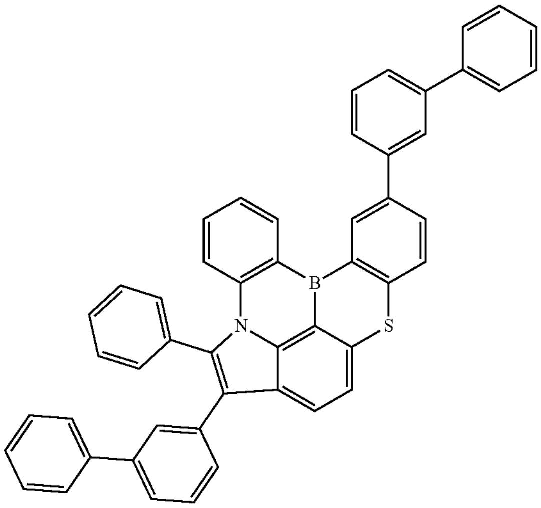
-continued
D-675
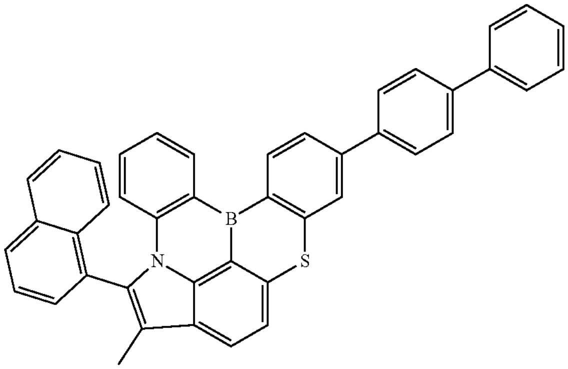
D-676
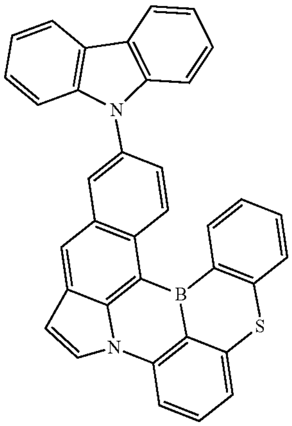
D-677
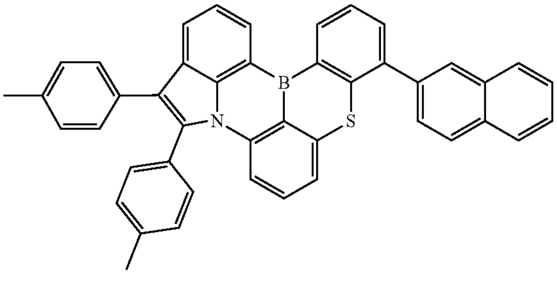
D-678
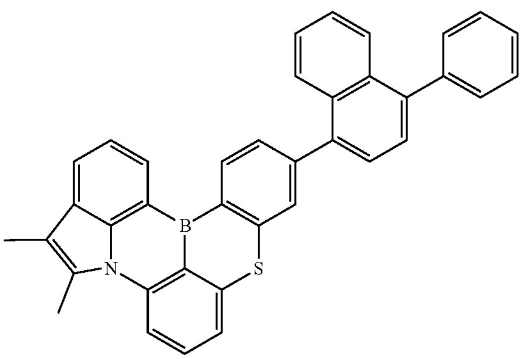

-continued
D-679
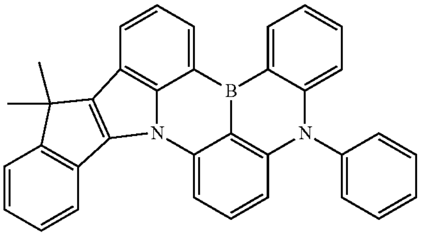
D-680
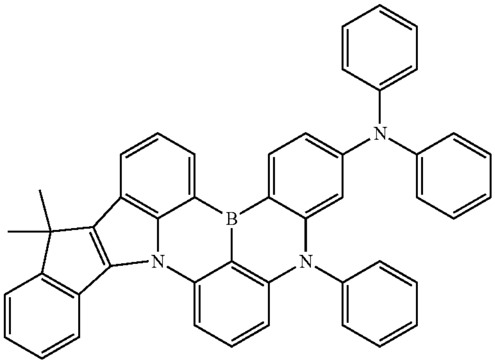
D-681
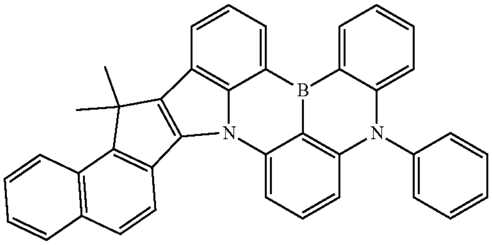
D-682
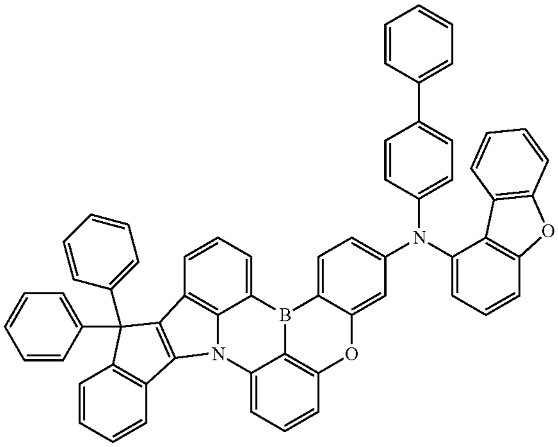
-continued
D-683
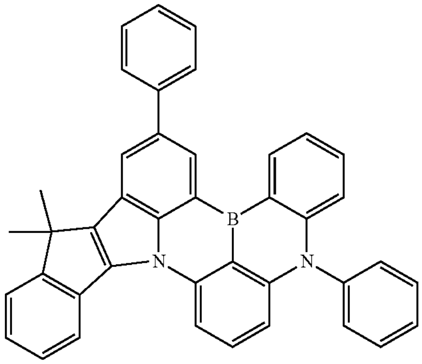
D-684
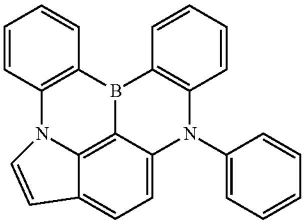
D-685
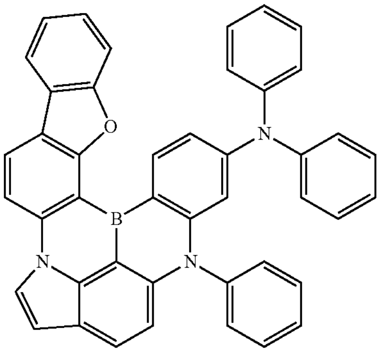
D-686
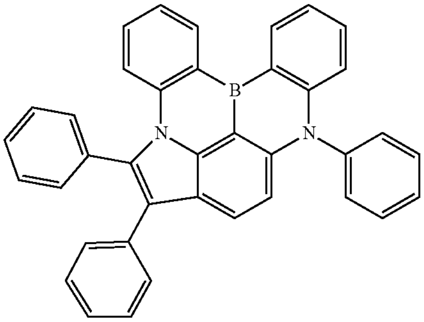
D-687
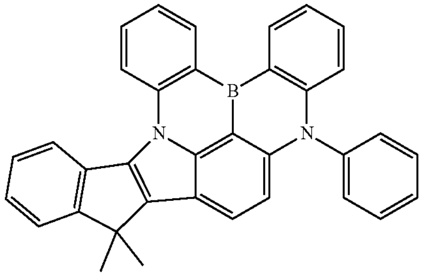

-continued
D-688
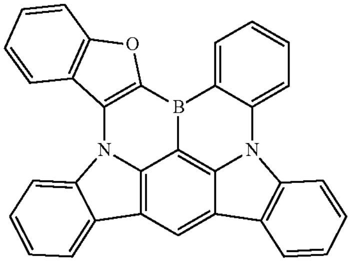
D-689
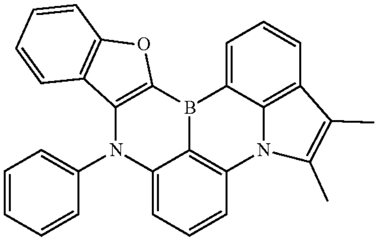
D-690
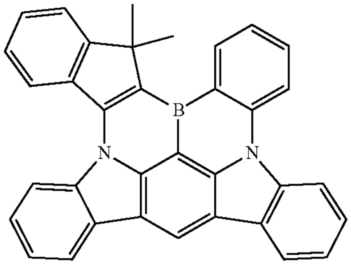
D-691
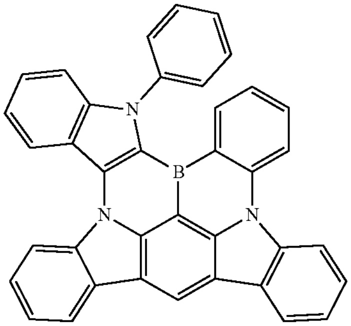
D-692
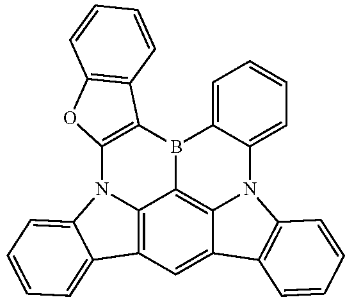
-continued
D-693
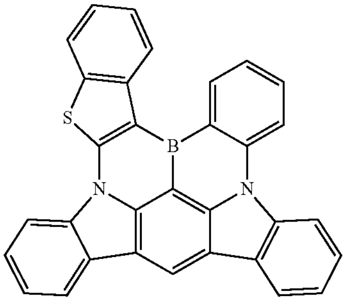
D-694
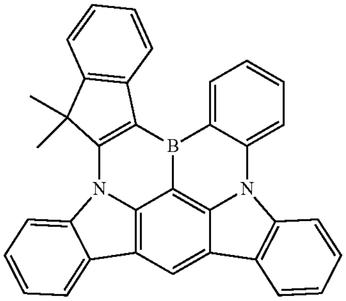
D-695
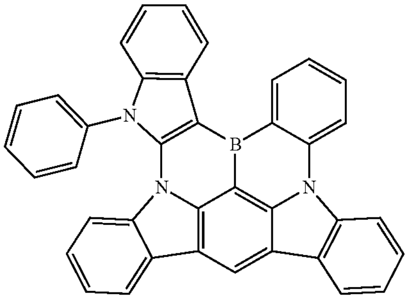
D-696
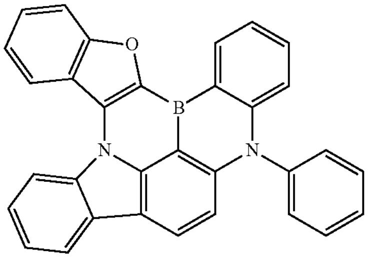
D-697
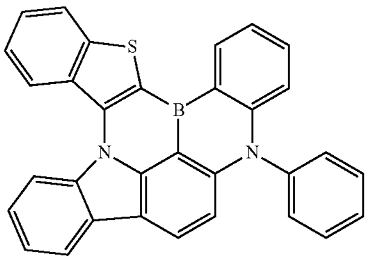

-continued
D-698
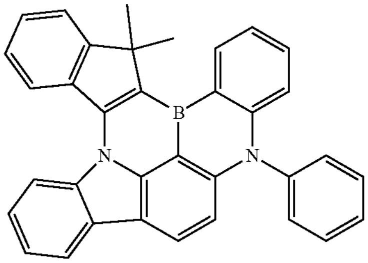
D-699
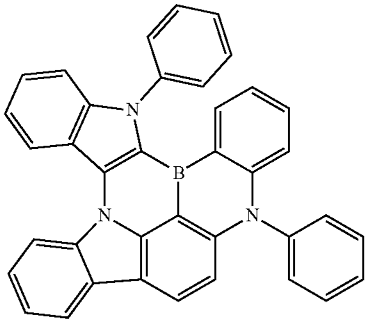
D-700
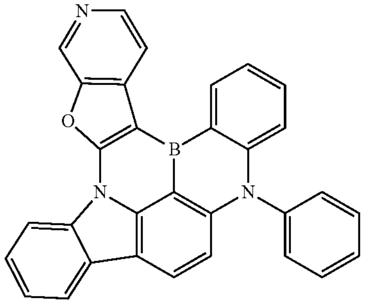
D-701
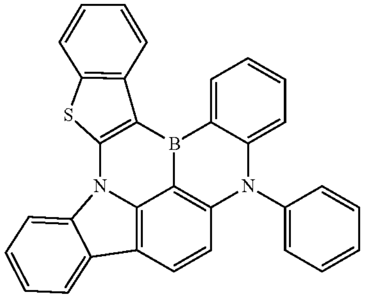
D-702
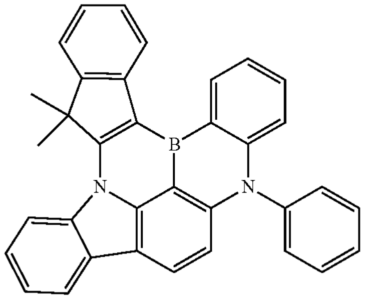
-continued
D-703
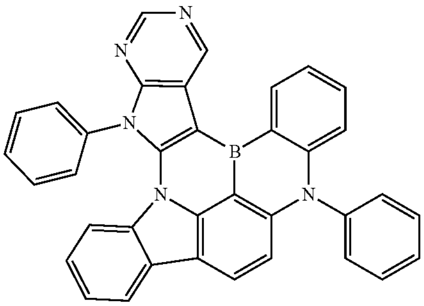
D-704
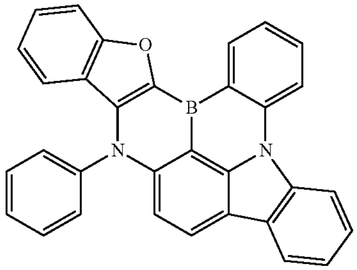
D-705
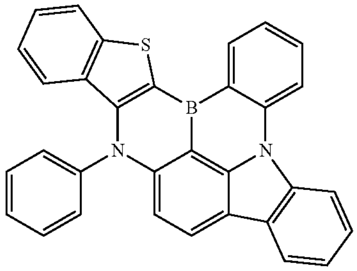
D-706
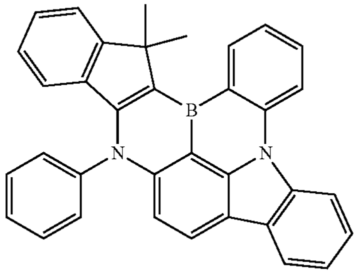
D-707
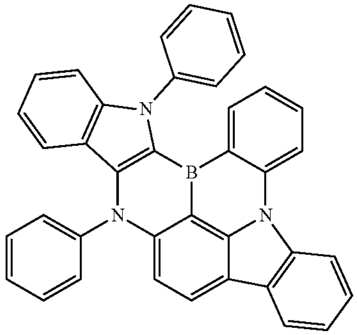

-continued
D-708
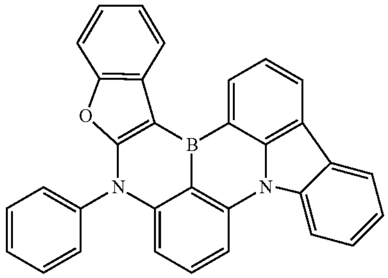
D-709
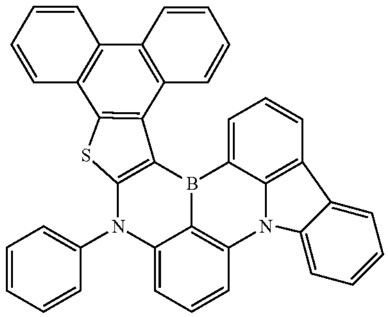
D-710
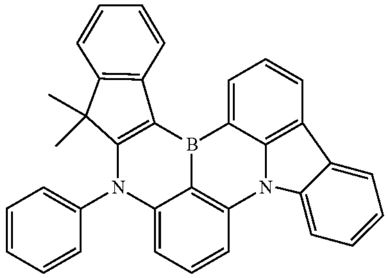
D-711
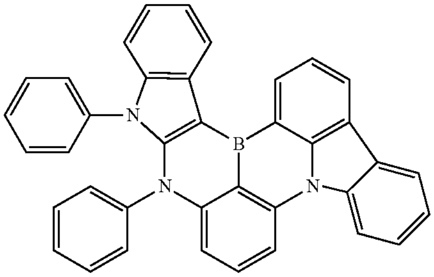
D-712
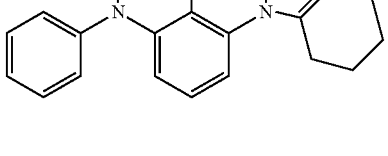
-continued
D-713
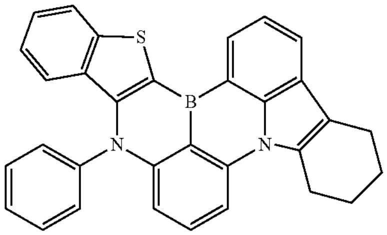
D-714
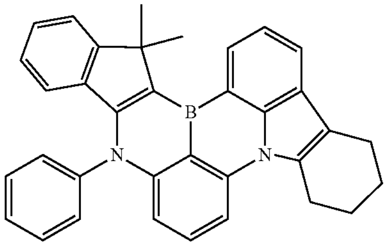
D-715
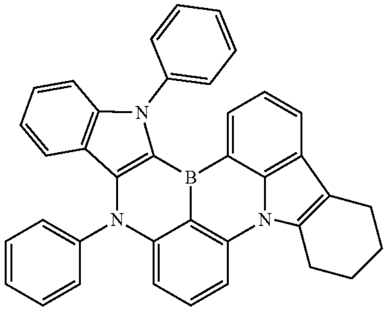
D-716
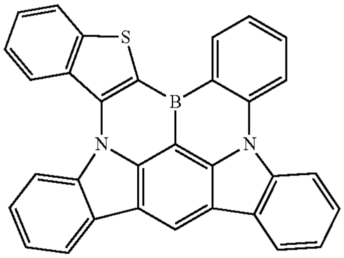
D-717
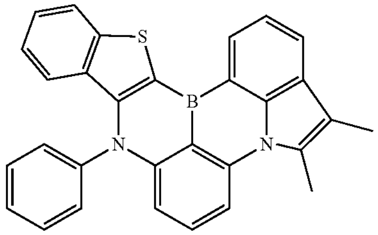
D-718
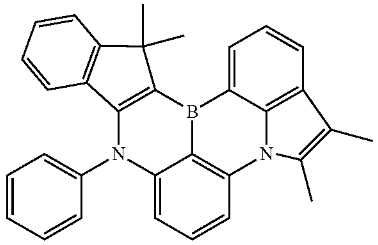

-continued

D-719

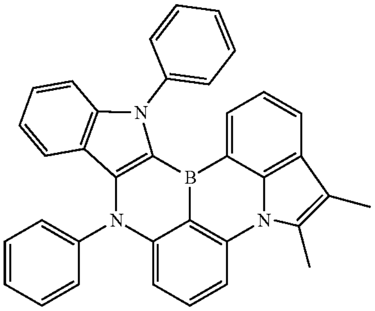

D-720

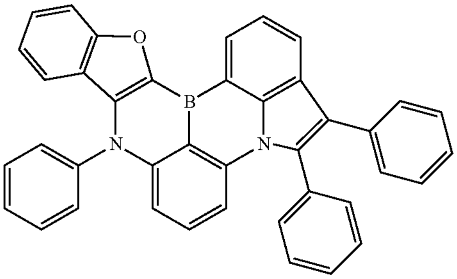

D-721

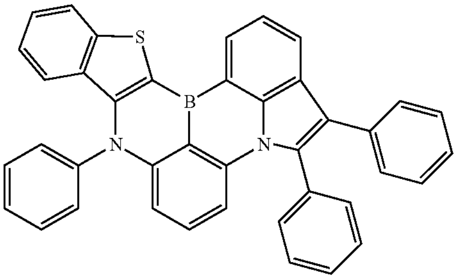

D-722

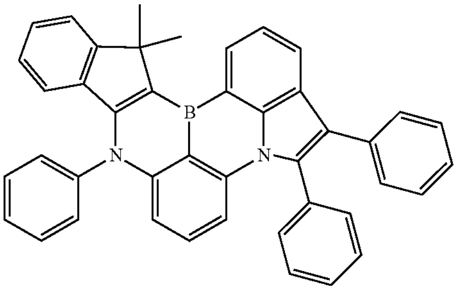

D-723

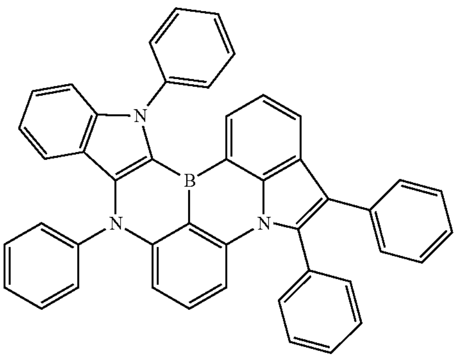

-continued

D-724

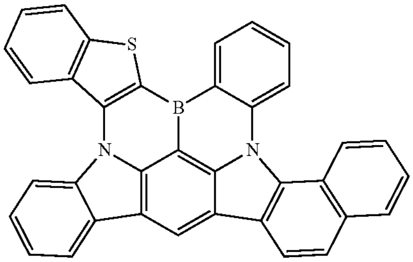

D-725

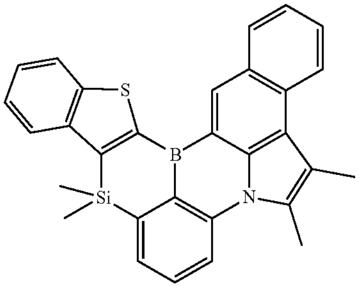

D-726

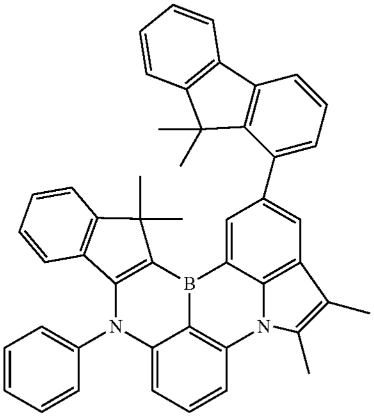

D-727

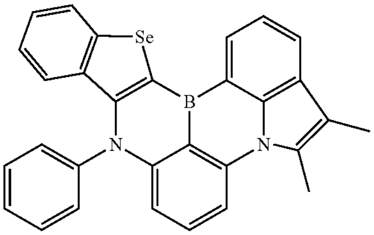

However, these compounds are not intended to limit the scope of Formulas D-7 and D-8.

The content of the dopant in the light emitting layer is typically in the range of about 0.01 to about 20 parts by weight, based on about 100 parts by weight of the host but is not limited to this range.

The light emitting layer may further include one or more hosts other than the host compound represented by Formula A and one or more dopants other than the dopant compound represented by one of Formulas D-1 to D-8.

The organic layers of the organic light emitting device according to the present invention may form a monolayer structure. Alternatively, the organic layers may be stacked together to form a multilayer structure. For example, the organic layers may have a structure including a hole injecting layer, a hole transport layer, a hole blocking layer, a light emitting layer, an electron blocking layer, an electron transport layer, and an electron injecting layer but are not limited to this structure. The number of the organic layers is not limited and may be increased or decreased. Preferred structures of the organic layers of the organic light emitting device according to the present invention will be explained in more detail in the Examples section that follows.

A more detailed description will be given concerning exemplary embodiments of the organic light emitting device according to the present invention.

The organic light emitting device of the present invention includes an anode, a hole transport layer, a light emitting layer, an electron transport layer, and a cathode. The organic light emitting device of the present invention may optionally further include a hole injecting layer between the anode and the hole transport layer and an electron injecting layer between the electron transport layer and the cathode. If necessary, the organic light emitting device of the present invention may further include one or two intermediate layers such as a hole blocking layer or an electron blocking layer. The organic light emitting device of the present invention may further include one or more organic layers such as a capping layer that have various functions depending on the desired characteristics of the device.

A specific structure of the organic light emitting device according to one embodiment of the present invention, a method for fabricating the device, and materials for the organic layers are as follows.

First, an anode material is coated on a substrate to form an anode. The substrate may be any of those used in general organic light emitting devices. The substrate is preferably an organic substrate or a transparent plastic substrate that is excellent in transparency, surface smoothness, ease of handling, and waterproofness. A highly transparent and conductive metal oxide such as indium tin oxide (ITO), indium zinc oxide (IZO), tin oxide ($SnO_2$) or zinc oxide (ZnO) is used as the anode material.

A hole injecting material is coated on the anode by vacuum thermal evaporation or spin coating to form a hole injecting layer. Then, a hole transport material is coated on the hole injecting layer by vacuum thermal evaporation or spin coating to form a hole transport layer.

The hole injecting material is not specially limited so long as it is usually used in the art. Specific examples of such materials include 4,4',4"-tris(2-naphthylphenyl-phenylamino)triphenylamine (2-TNATA), N,N'-di(1-naphthyl)-N,N'-diphenylbenzidine (NPD), N,N'-diphenyl-N,N'-bis(3-methylphenyl)-1,1'-biphenyl-4,4'-diamine (TPD), and N,N'-diphenyl-N,N'-bis(4-(phenyl-m-tolylamino)phenyl) biphenyl-4,4'-diamine (DNTPD).

The hole transport material is not specially limited so long as it is commonly used in the art. Examples of such materials include N,N'-bis(3-methylphenyl)-N,N'-diphenyl-(1,1-biphenyl)-4,4'-diamine (TPD) and N,N'-di(naphthalen-1-yl)-N,N'-diphenylbenzidine (α-NPD).

Subsequently, a hole auxiliary layer and a light emitting layer are sequentially laminated on the hole transport layer. A hole blocking layer may be optionally formed on the light emitting layer by vacuum thermal evaporation or spin coating. The hole blocking layer is formed as a thin film and blocks holes from entering a cathode through the organic light emitting layer. This role of the hole blocking layer prevents the lifetime and efficiency of the device from deteriorating. A material having a very low highest occupied molecular orbital (HOMO) energy level is used for the hole blocking layer. The hole blocking material is not particularly limited so long as it can transport electrons and has a higher ionization potential than the light emitting compound. Representative examples of suitable hole blocking materials include BAlq, BCP, and TPBI.

Examples of materials for the hole blocking layer include, but are not limited to, BAlq, BCP, Bphen, TPBI, TAZ, $BeBq_2$, OXD-7, and Liq.

An electron transport layer is deposited on the hole blocking layer by vacuum thermal evaporation or spin coating, and an electron injecting layer is formed thereon. A cathode metal is deposited on the electron injecting layer by vacuum thermal evaporation to form a cathode, completing the fabrication of the organic light emitting device.

For example, lithium (Li), magnesium (Mg), aluminum (Al), aluminum-lithium (Al—Li), calcium (Ca), magnesium-indium (Mg—In) or magnesium-silver (Mg—Ag) may be used as the metal for the formation of the cathode. The organic light emitting device may be of top emission type. In this case, a transmissive material such as ITO or IZO may be used to form the cathode.

A material for the electron transport layer functions to stably transport electrons injected from the cathode. The electron transport material may be any of those known in the art and examples thereof include, but are not limited to, quinoline derivatives, particularly tris(8-quinolinolate)aluminum (Alq3), TAZ, Balq, beryllium bis(benzoquinolin-10-olate) (Bebq2), ADN, and oxadiazole derivatives such as PBD, BMD, and BND.

Each of the organic layers can be formed by a monomolecular deposition or solution process. According to the monomolecular deposition process, the material for each layer is evaporated into a thin film under heat and vacuum or reduced pressure. According to the solution process, the material for each layer is mixed with a suitable solvent and the mixture is then formed into a thin film by a suitable method such as ink-jet printing, roll-to-roll coating, screen printing, spray coating, dip coating or spin coating.

The organic light emitting device of the present invention can be used in a display or lighting system selected from flat panel displays, flexible displays, monochromatic flat panel lighting systems, white flat panel lighting systems, flexible monochromatic lighting systems, flexible white lighting systems, displays for automotive applications, displays for virtual reality, and displays for augmented reality.

MODE FOR CARRYING OUT THE INVENTION

The present invention will be more specifically explained with reference to the following examples. However, it will be obvious to those skilled in the art that these examples are in no way intended to limit the scope of the invention.

<Formula A>

Synthesis Example 1. Synthesis of A-20

Synthesis Example 1-1: Synthesis of 1-a

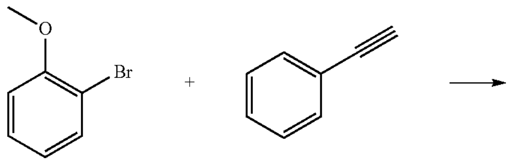

-continued

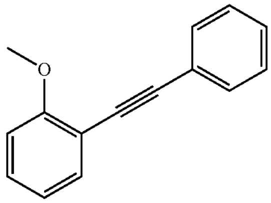

1-a

2-Bromoanisole (30 g, 0.171 mol), phenylacetylene (38.5 g, 0.377 mol), bis(triphenylphosphine)palladium(II) dichloride (2.41 g, 0.003 mol), copper(I) iodide (1.63 g, 0.009 mol), and triphenylphosphine (0.45 g, 0.002 mol) were added to 300 mL of triethylamine in a 1 L reactor. The mixture was stirred under reflux overnight. After completion of the reaction, the reaction mixture was allowed to cool to room temperature and filtered with hexane. The filtrate was concentrated and purified by column chromatography to afford 1-a (25 g, 74%).

Synthesis Example 1-2: Synthesis of 1-b

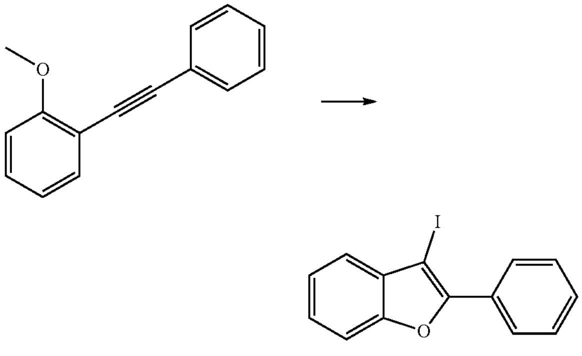

1-b 1-a (25 g, 0.12 mol) was dissolved in dichloromethane in a 1 L reactor and purged with nitrogen. To the resulting solution was added iodine (45.7 g, 0.18 mol). The mixture was stirred at room temperature for 12 h. After completion of the reaction, the reaction mixture was added with an aqueous sodium thiosulfate solution to remove residual iodine, extracted with dichloromethane, and purified by column chromatography to afford 1-b (31 g, 81%).

Synthesis Example 1-3: Synthesis of A-20

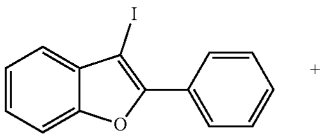

-continued

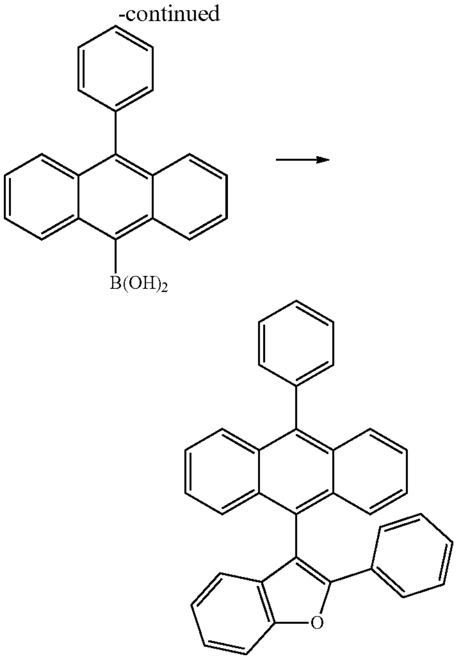

A-20

1-b (31 g, 0.097 mol), 10-phenylanthracene-9-boronic acid (31.7 g, 0.107 mol), potassium carbonate (26.8 g, 0.194 mol), tetrakis(triphenylphosphine)palladium(0) (2.24 g, 0.002 mol), 210 mL of toluene, and 90 mL of ethanol were placed in a 1 L reactor. The mixture was stirred under reflux at 110° C. overnight. The reaction mixture was allowed to cool to room temperature and extracted with ethyl acetate/distilled water. The organic layer was concentrated and purified by column chromatography to afford A-20 (19 g, 44%).

MS (MALDI-TOF): m/z 446.17 [$M^+$]

Synthesis Example 2. Synthesis of A-30

Synthesis Example 2-1: Synthesis of 2-a

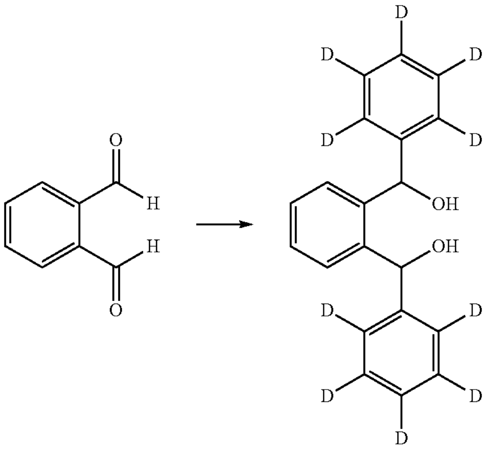

2-a

Bromobenzene(d5) (60.4 g, 0.373 mol) and 480 mL of tetrahydrofuran were placed in a 2 L reactor. The mixture was cooled to −78° C., followed by stirring. To the cooled reaction mixture was added dropwise n-butyllithium (223.6 mL, 0.357 mol). The resulting mixture was stirred at the same temperature for 1 h. To the reaction solution was added dropwise to a solution of o-phthalaldehyde (20 g, 0.149 mol) in 100 mL of tetrahydrofuran, followed by stirring at room temperature. 200 mL of an aqueous ammonium chloride solution was added to quench the reaction. The reaction solution was extracted with ethyl acetate, concentrated under reduced pressure, and purified by column chromatography to afford 2-a (40 g, 89%).

Synthesis Example 2-2: Synthesis of 2-b

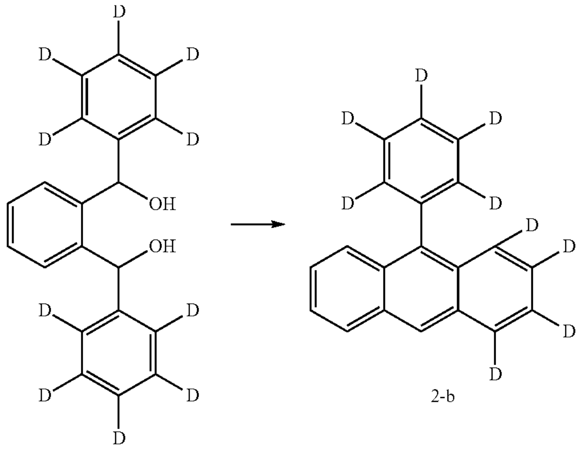 [SMILES: [2H]c1c([2H])c([2H])c(C(O)c2ccccc2C(O)c2c([2H])c([2H])c([2H])c([2H])c2[2H])c([2H])c1[2H] ; [2H]c1c([2H])c([2H])c(-c2c3ccccc3cc3c([2H])c([2H])c([2H])c([2H])c23)c([2H])c1[2H]]

2-b 2-a (40 g, 0.133 mol) was dissolved in 200 mL of acetic acid in a 500 mL reactor, followed by stirring. To the reaction solution was added 2 mL of hydrogen bromide. The mixture was stirred at 80° C. for 2 h. After completion of the reaction, the reaction mixture was allowed to cool to room temperature, slowly poured into 500 mL of distilled water in a beaker, followed by stirring. The resulting solid was collected by filtration, washed with distilled water, and purified by column chromatography to afford 2-b (13 g, 37%).

Synthesis Example 2-3: Synthesis of 2-c

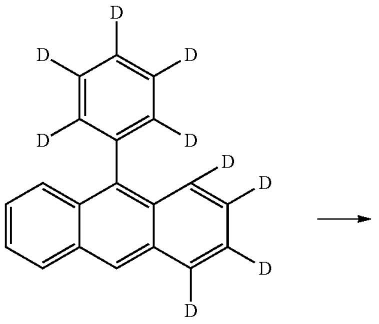

-continued

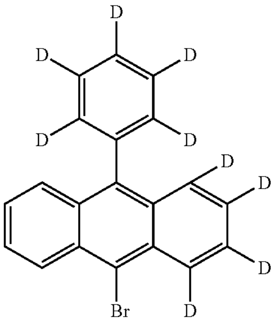

2-c 2-b (13 g, 0.049 mol) was dissolved in 130 mL of N,N-dimethylamide in a 500 mL reactor. The solution was stirred at room temperature. To the reaction solution was added dropwise a solution of N-bromosuccinimide (10.5 g, 0.059 mol) in 40 mL of N,N-dimethylamide. The completion of the reaction was confirmed by thin layer chromatography. The reaction mixture was poured into 500 mL of distilled water in a beaker, followed by stirring. The resulting solid was collected by filtration, washed with distilled water, and purified by column chromatography to afford 2-c (14 g, 83%).

Synthesis Example 2-4: Synthesis of 2-d

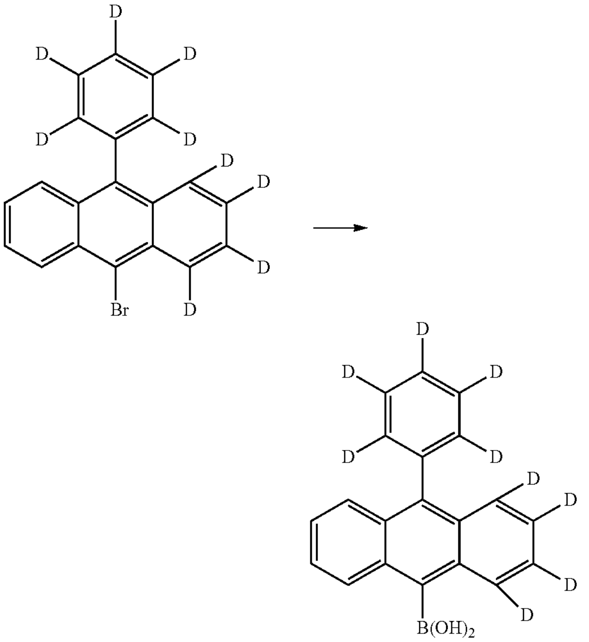

2-d 2-c (50 g, 0.146 mol) was dissolved in 500 mL of tetrahydrofuran in a 500 mL reactor. The temperature of the solution was lowered to −78° C. To the solution was added dropwise n-butyllithium (100 mL, 0.161 mol). After stirring for 5 h, the reaction mixture was added with trimethyl borate (18 mL, 0.161 mol). The resulting mixture was stirred at room temperature overnight. After completion of the reaction, the reaction mixture was acidified with 2 N hydrochloric acid and recrystallized to afford 2-d (25 g, 56%).

Synthesis Example 2-5: Synthesis of A-30

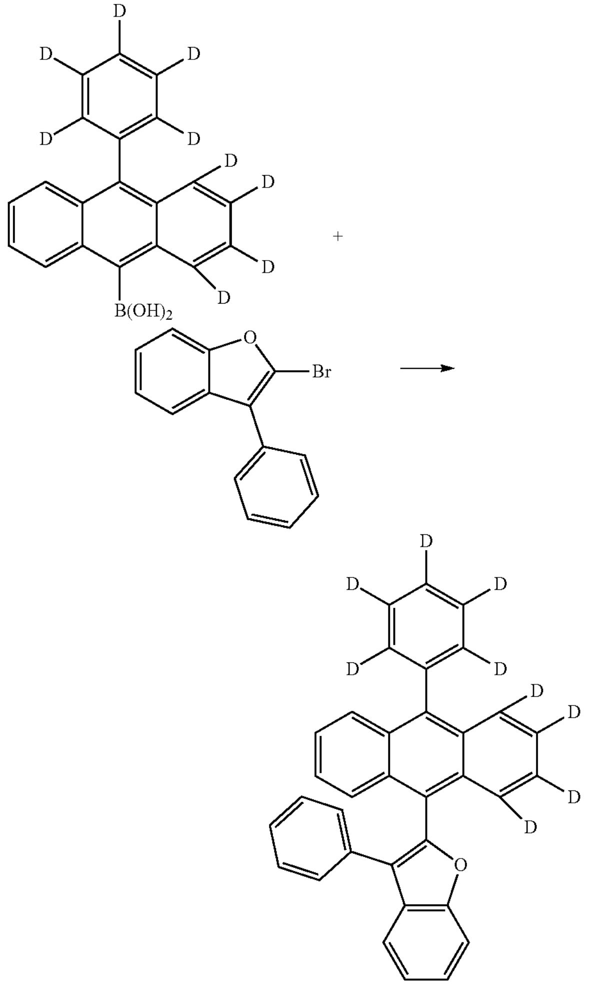

A-30

A-30 (yield 30%) was synthesized in the same manner as in Synthesis Example 1-3, except that 2-bromo-3-phenyl-benzofuran and 2-d were used instead of 1-b and 10-phenylanthracene-9-boronic acid, respectively.

MS (MALDI-TOF): m/z 455.22 [$M^+$]

Synthesis Example 3. Synthesis of A-57

Synthesis Example 3-1: Synthesis of 3-a

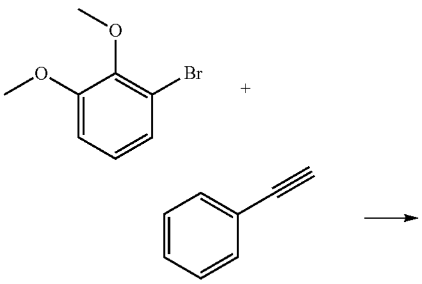

-continued

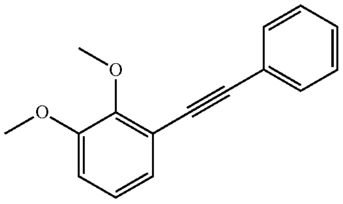

3-a 3-a (yield 79%) was synthesized in the same manner as in Synthesis Example 1-1, except that 3-bromoveratrol was used instead of 2-bromoanisole.

Synthesis Example 3-2: Synthesis of 3-b

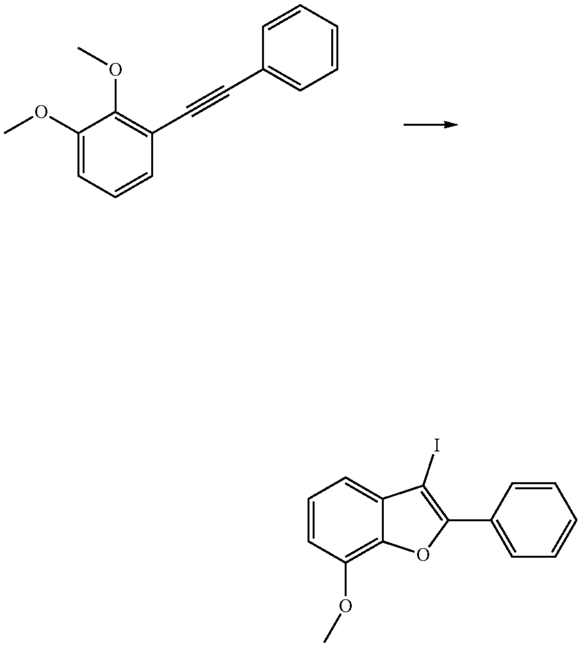

3-b 3-b (yield 63%) was synthesized in the same manner as in Synthesis Example 1-2, except that 3-a was used instead of 1-a.

Synthesis Example 3-3: Synthesis of 3-c

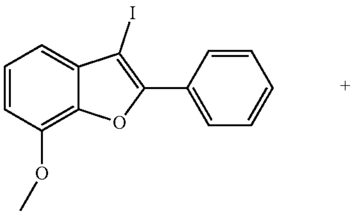

-continued

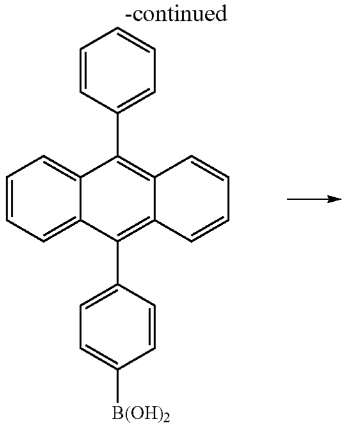

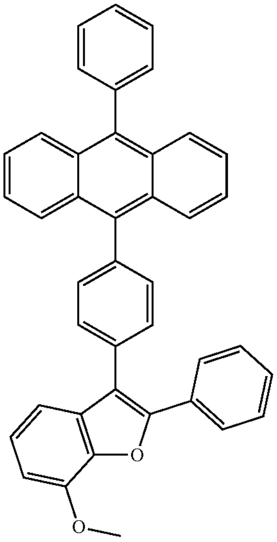

3-c 3-c (yield 61%) was synthesized in the same manner as in Synthesis Example 1-3, except that 3-b and (4-(10-phenylanthracen-9-yl)phenyl)boronic acid were used instead of 1-b and 10-phenylanthracene-9-boronic acid, respectively.

Synthesis Example 3-4: Synthesis of 3-d

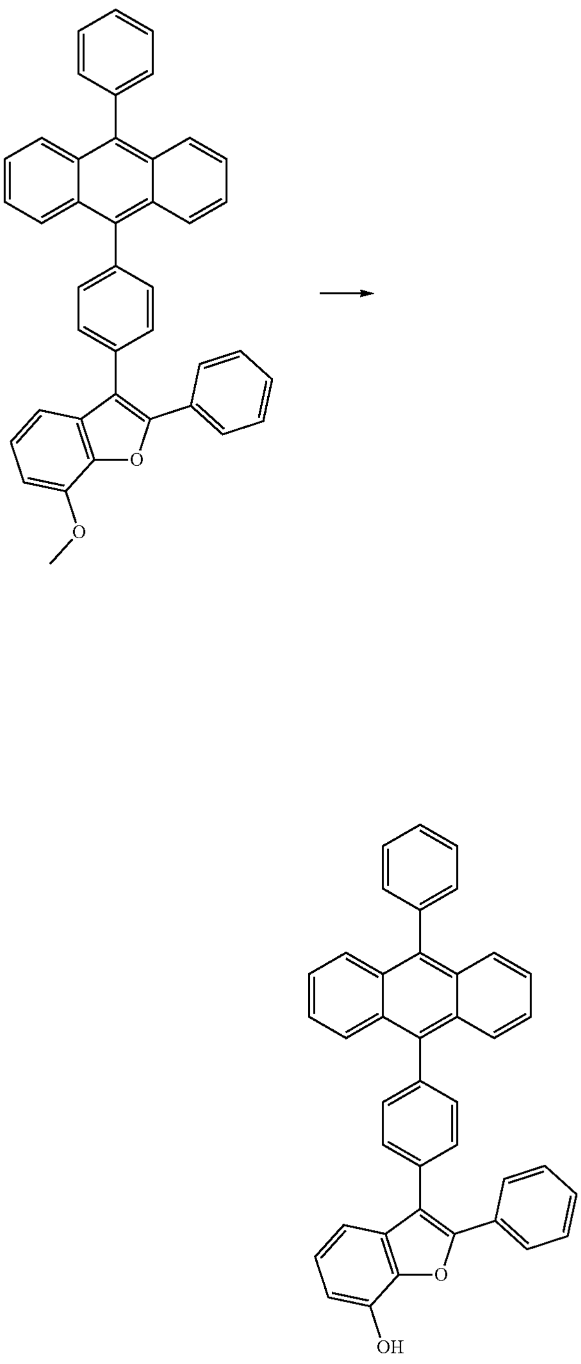

3-d 3-c (20 g, 0.036 mol) was dissolved in dichloromethane in a 500 mL reactor. After the temperature of the reactor was lowered to 0° C., $BBr_3$ (13.6 g, 0.054 mol) was slowly added to the solution. Thereafter, the temperature was raised to room temperature. The mixture was stirred for 2 h. Cold distilled water was slowly added to quench the reaction. The reaction mixture was extracted with dichloromethane and distilled water. The organic layer was concentrated and purified by column chromatography to afford 3-d (17 g, 87%).

Synthesis Example 3-5: Synthesis of 3-e

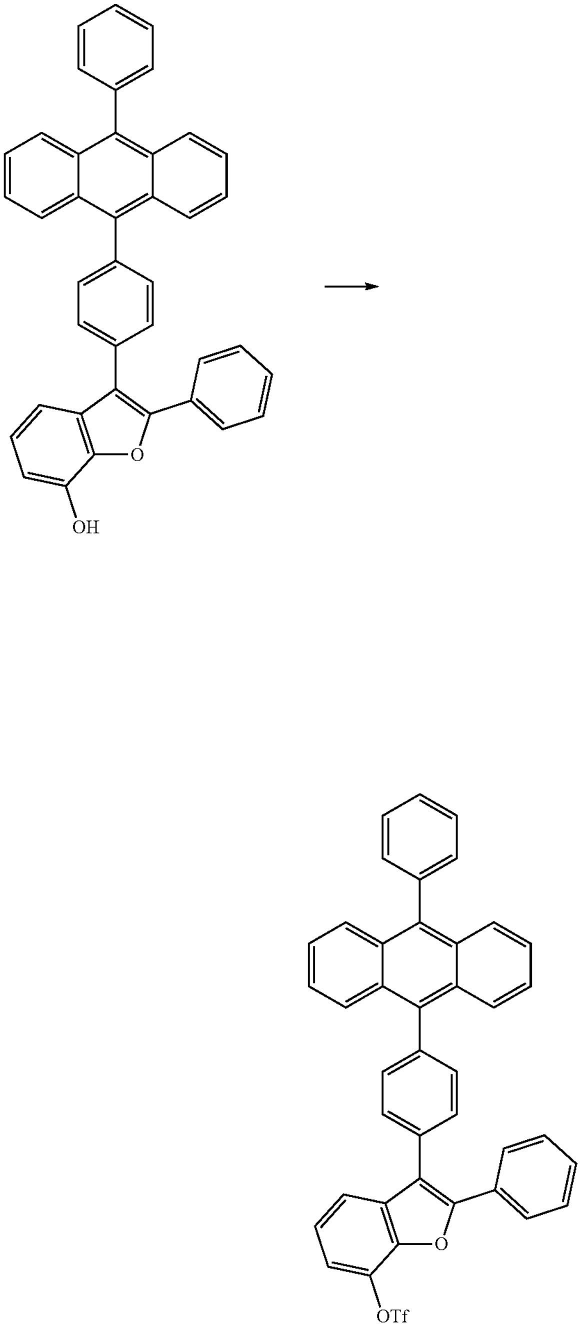

3-e 3-d (17 g, 0.032 mol) was dissolved in 170 mL of dichloromethane in a 500 mL reactor. After the temperature of the reactor was lowered to 0° C., trifluoromethanesulfonic anhydride (10.7 g, 0.048 mol) was slowly added to the solution. Thereafter, the temperature was raised to room temperature. The mixture was stirred for 3 h. Cold distilled water was slowly added to quench the reaction. The reaction mixture was extracted with dichloromethane and distilled water. The organic layer was concentrated and purified by column chromatography to afford 3-e (17 g, 80%).

Synthesis Example 3-6: Synthesis of A-57

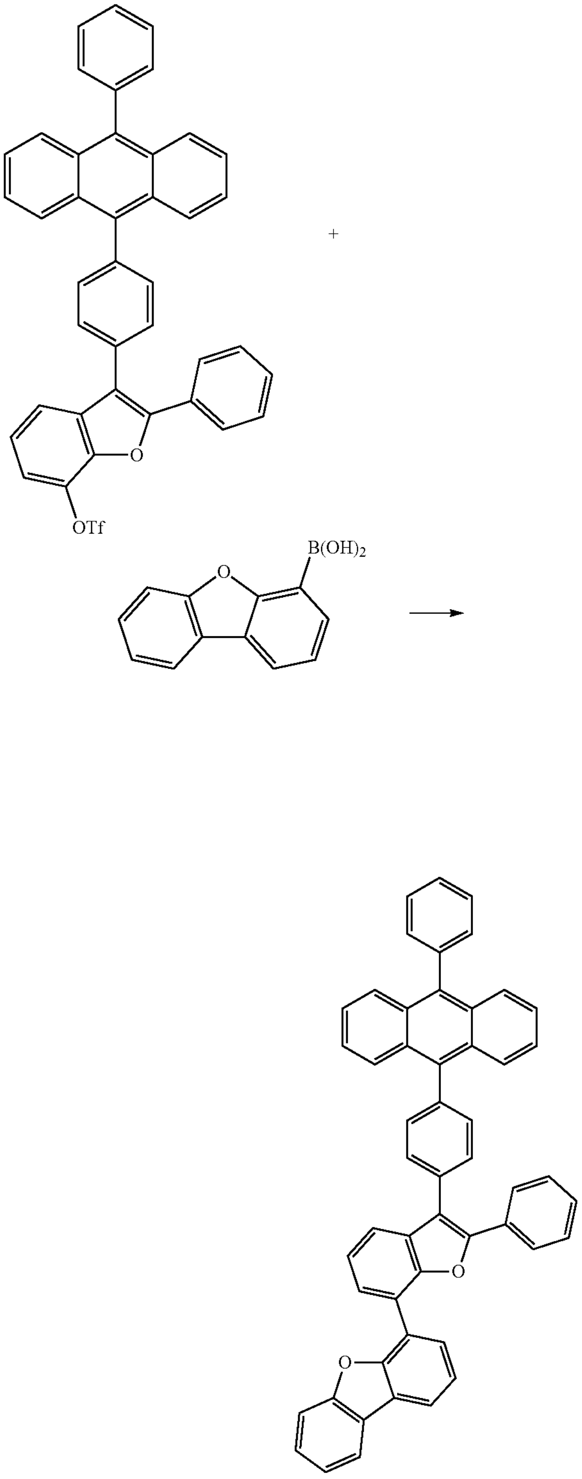

A-57

A-57 (yield 45%) was synthesized in the same manner as in Synthesis Example 1-3, except that 3-e and dibenzo[b,d]furan-4-ylboronic acid were used instead of 1-b and 10-phenylanthracene-9-boronic acid, respectively.

MS (MALDI-TOF): m/z 688.24 [$M^+$]

Synthesis Example 4. Synthesis of A-58

Synthesis Example 4-1: Synthesis of 4-a

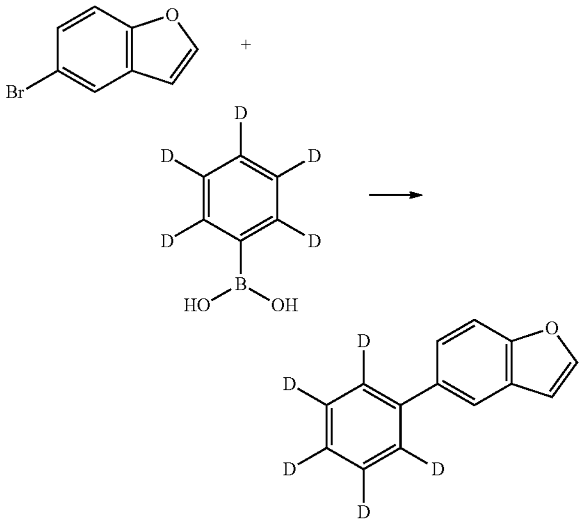

4-a 4-a (yield 70%) was synthesized in the same manner as in Synthesis Example 1-3, except that 5-bromobenzofuran and (phenyl-d5)boronic acid were used instead of 1-b and 10-phenylanthracene-9-boronic acid, respectively.

Synthesis Example 4-2: Synthesis of 4-b

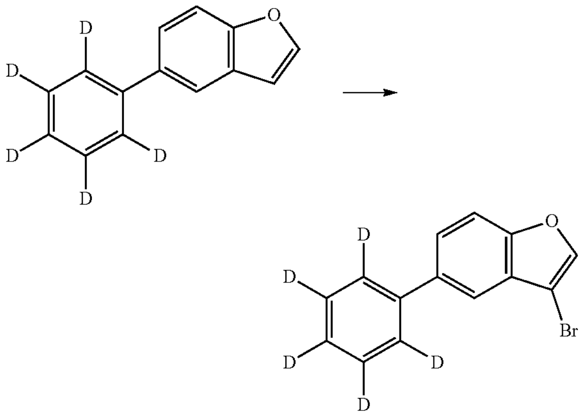

4-b 4-a (21.2 g, 0.106 mol) and dichloromethane were placed in a 500 mL reactor. The mixture was cooled to −10° C. and bromine was added thereto. The resulting mixture was stirred for 1 h. To the reaction mixture was added an aqueous sodium thiosulfate solution, followed by stirring. Thereafter, the mixture was allowed to stand for layer separation. The organic layer was concentrated under reduced pressure. The concentrate was added with ethanol, cooled to −10° C., and added with a solution of potassium hydroxide in ethanol. The mixture was heated to reflux for 4 h. After completion of the reaction, the reaction mixture was allowed to stand for layer separation. The organic layer was concentrated under reduced pressure and purified by column chromatography to afford 4-b (20 g, 70%).

Synthesis Example 4-3: Synthesis of 4-c

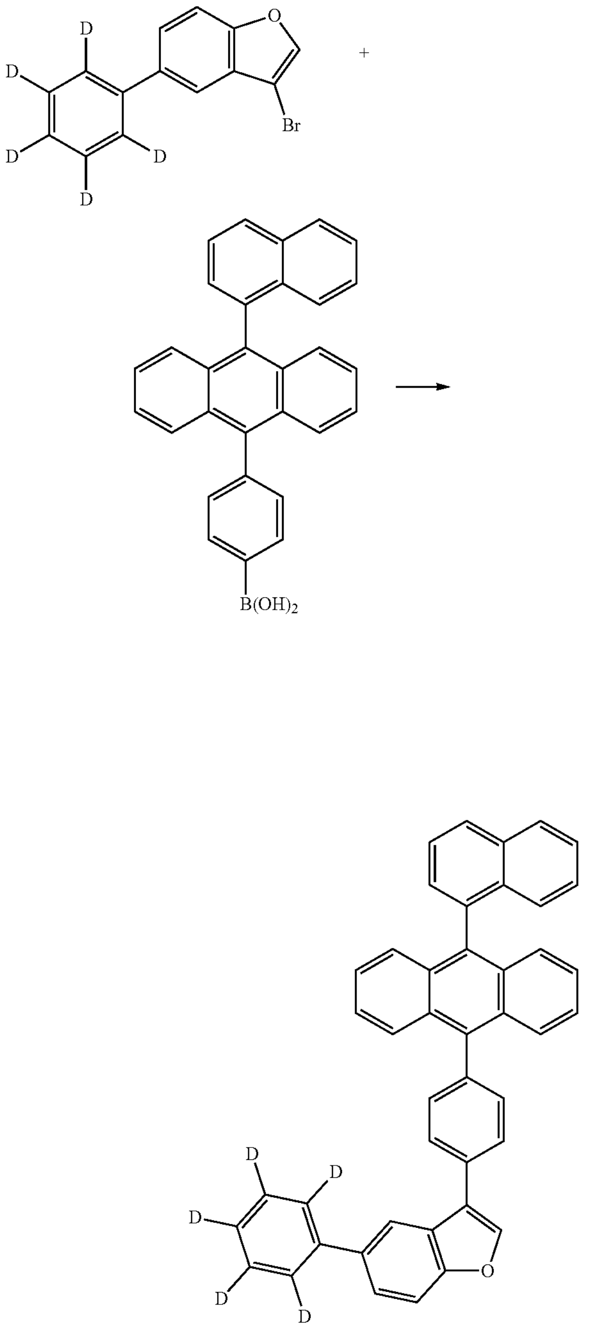

4-c 4-c (yield 72%) was synthesized in the same manner as in Synthesis Example 1-3, except that 4-b and (4-(10-naphthalen-1-yl)anthracen-9-yl)benzeneboronic acid were used instead of 1-b and 10-phenylanthracene-9-boronic acid, respectively.

Synthesis Example 4-4: Synthesis of 4-d

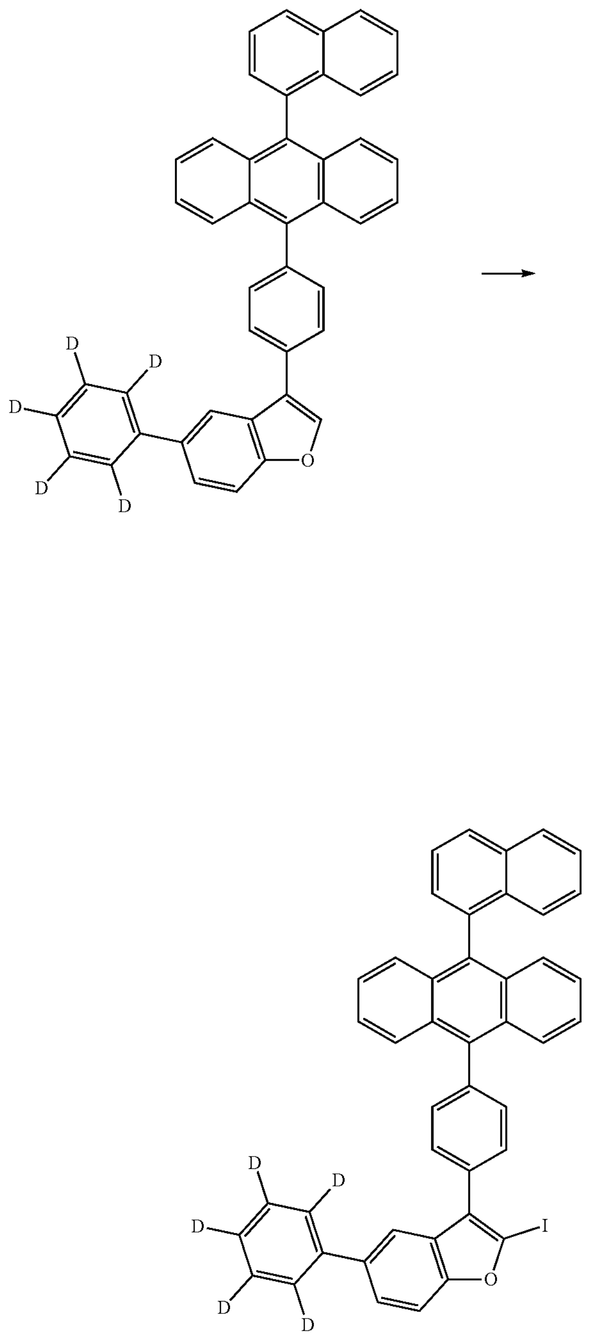

4-d 4-c (20 g, 0.035 mol) and 250 mL of THF were placed in a 500 mL reactor. The mixture was cooled to −50° C. and n-butyllithium (1.6 M) was added thereto. 1 h later, to the resulting mixture was slowly added iodine. The temperature was slowly allowed to rise to room temperature. An aqueous sodium thiosulfate solution was added at room temperature for layer separation. The organic layer was concentrated under reduced pressure and purified by column chromatography to afford 4-d (17 g, 70%).

Synthesis Example 4-5: Synthesis of A-58

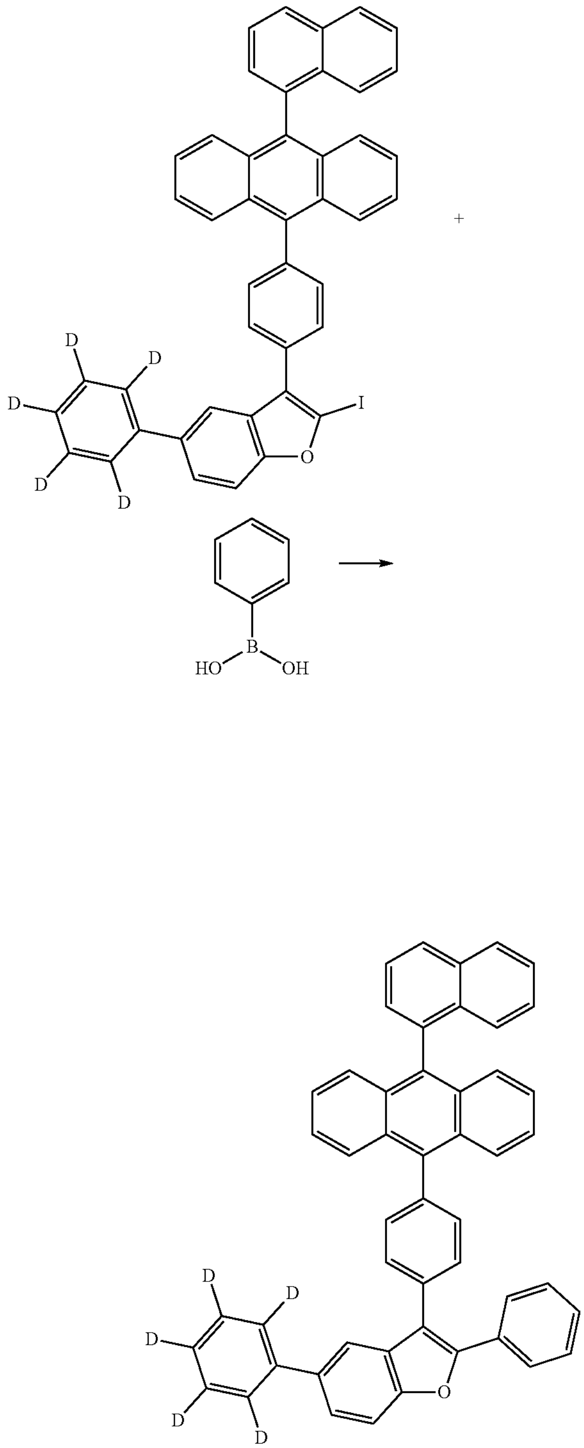

A-58

A-58 (yield 47%) was synthesized in the same manner as in Synthesis Example 1-3, except that 4-d and phenylboronic acid were used instead of 1-b and 10-phenylanthracene-9-boronic acid, respectively.

MS (MALDI-TOF): m/z 653.28 [$M^+$]

Synthesis Example 5. Synthesis of A-68

Synthesis Example 5-1: Synthesis of 5-a

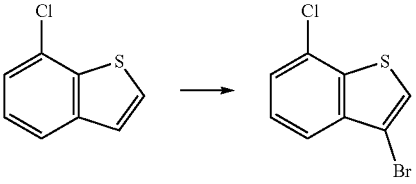

5-a

7-Chlorobenzo[b]thiophene (30 g, 0.178 mol) and DMF were placed in a 500 mL reactor. The mixture was stirred and NBS was added thereto. Thereafter, the resulting mixture was stirred under reflux for 6 h. Distilled water was added for layer separation. The organic layer was concentrated under reduced pressure and purified by column chromatography to afford 5-a (27 g, 62%).

Synthesis Example 5-2: Synthesis of 5-b

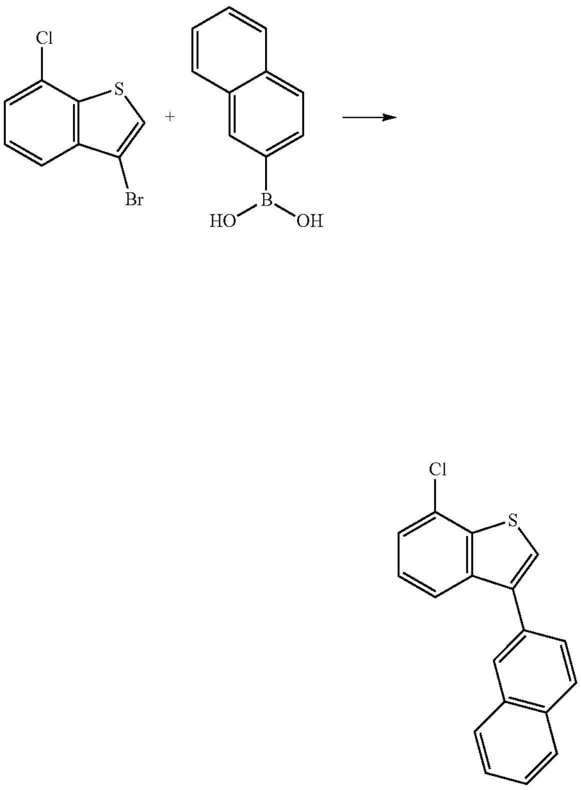

5-b 5-b (yield 68%) was synthesized in the same manner as in Synthesis Example 1-3, except that 5-a and 2-naphthylboronic acid were used instead of 1-b and 10-phenylanthracene-9-boronic acid, respectively.

Synthesis Example 5-3: Synthesis of 5-c

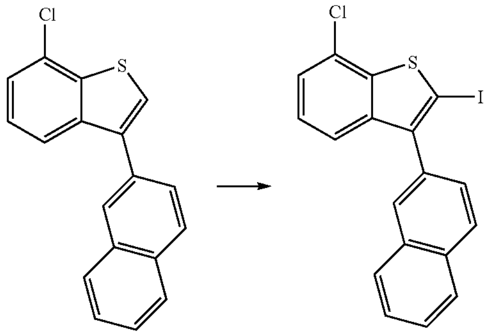

5-c 5-c (yield 70%) was synthesized in the same manner as in Synthesis Example 4-4, except that 5-b was used instead of 4-c.

Synthesis Example 5-4: Synthesis of 5-d

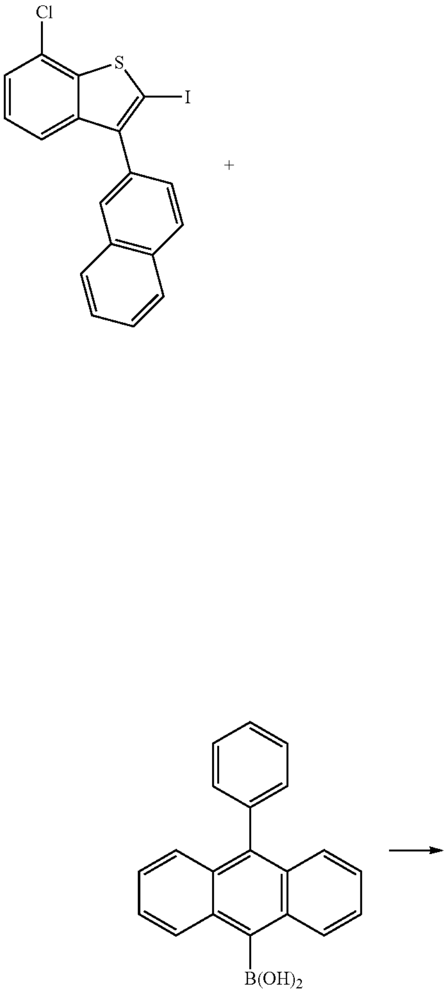

-continued

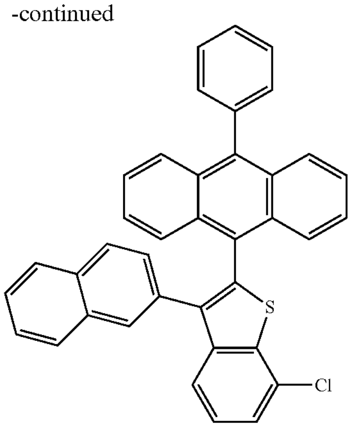

5-d 5-d (yield 63%) was synthesized in the same manner as in Synthesis Example 1-3, except that 5-c was used instead of 1-b.

Synthesis Example 5-5: Synthesis of A-68

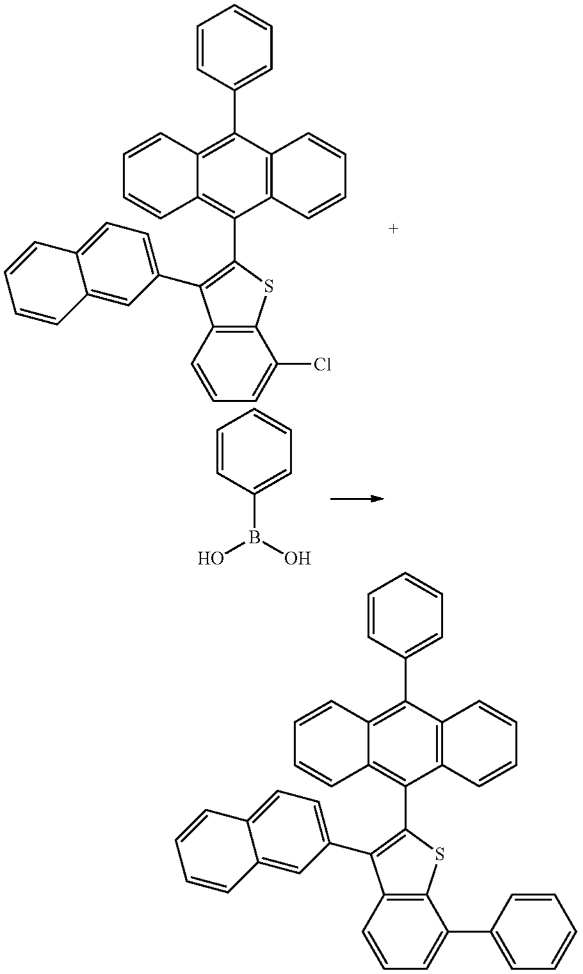

A-68

A-68 (yield 11%) was synthesized in the same manner as in Synthesis Example 1-3, except that 5-d and phenylboronic acid were used instead of 1-b and 10-phenylanthracene-9-boronic acid, respectively.

MS (MALDI-TOF): m/z 588.19 [M$^+$]

Synthesis Example 6. Synthesis of A-79

Synthesis Example 6-1: Synthesis of 6-a

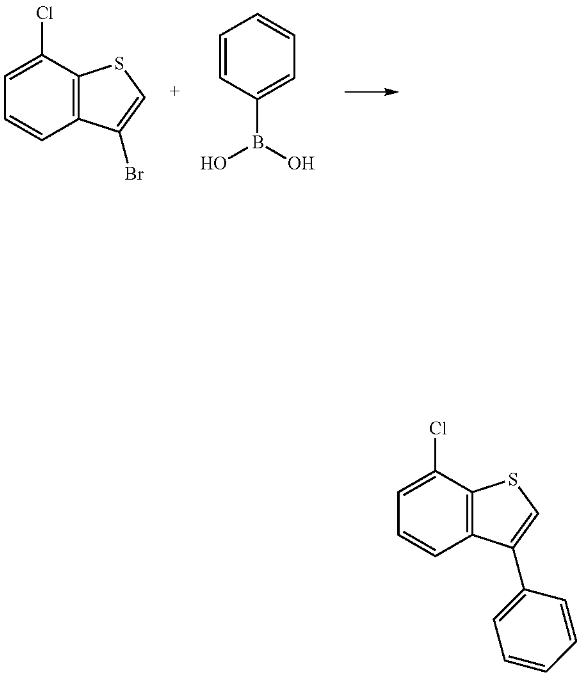

6-a 6-a (yield 70%) was synthesized in the same manner as in Synthesis Example 5-2, except that phenylboronic acid was used instead of 2-naphthylboronic acid.

Synthesis Example 6-2: Synthesis of 6-b

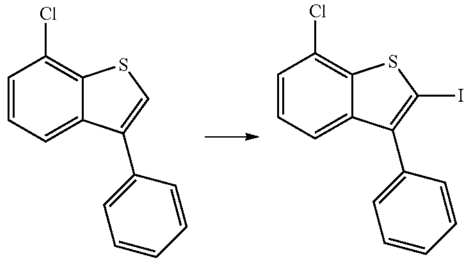

6-b 6-b (yield 70%) was synthesized in the same manner as in Synthesis Example 4-4, except that 6-a was used instead of 4-c.

Synthesis Example 6-3: Synthesis of 6-c

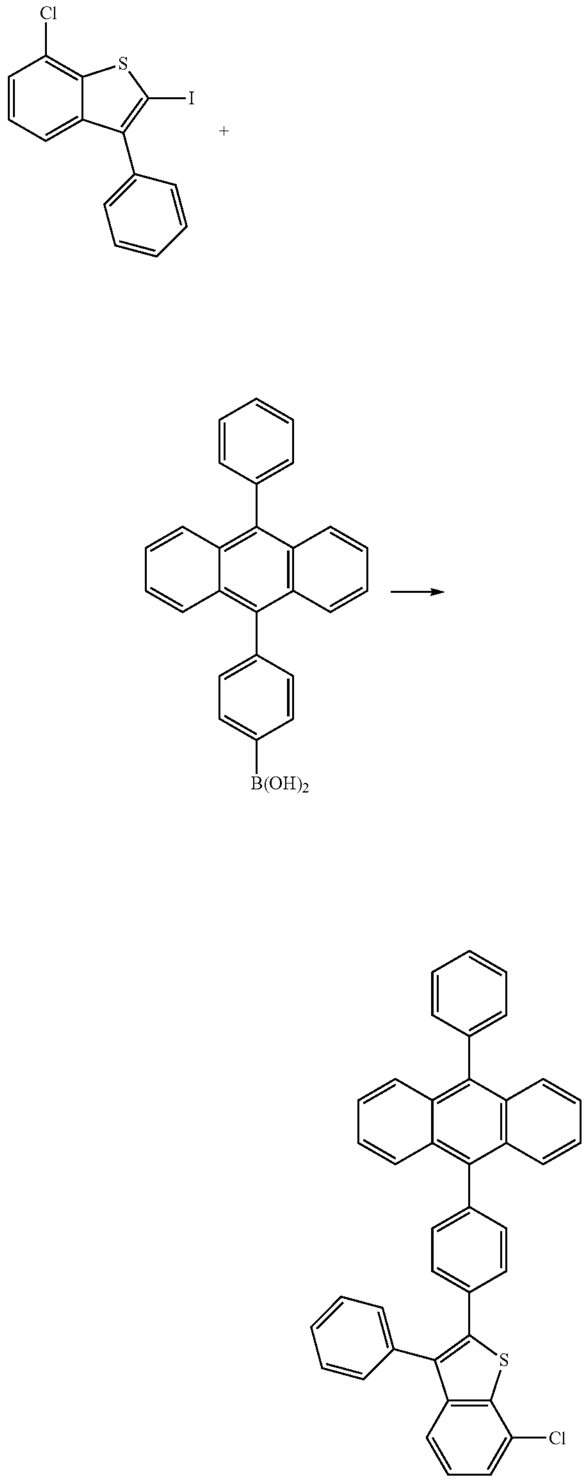

6-c 6-c (yield 65%) was synthesized in the same manner as in Synthesis Example 1-3, except that 6-b and 4-(10-phenylanthracen-9-yl)benzeneboronic acid were used instead of 1-b and 10-phenylanthracene-9-boronic acid, respectively.

Synthesis Example 6-4: Synthesis of A-79

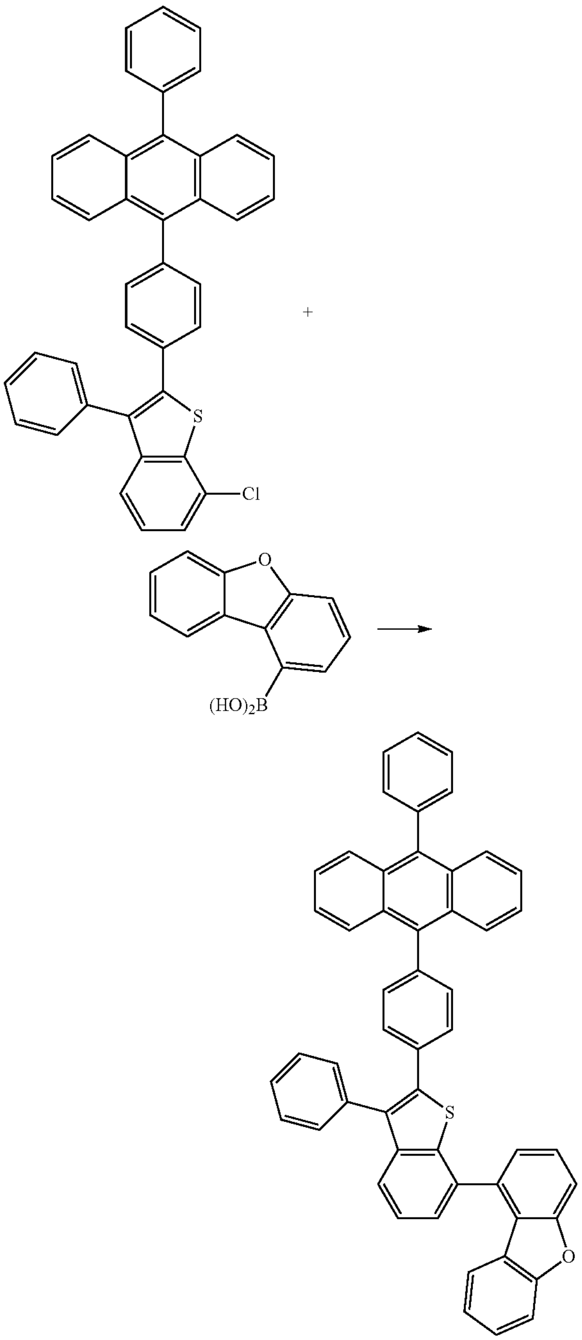

A-79

A-79 (yield 10%) was synthesized in the same manner as in Synthesis Example 1-3, except that 6-c and dibenzo[b,d]furan-1-ylboronic acid were used instead of 1-b and 10-phenylanthracene-9-boronic acid, respectively.

MS (MALDI-TOF): m/z 704.22 [$M^+$]

<Formulas D-1 to D-8>

Synthesis Example 7. Synthesis of D-202

Synthesis Example 7-1: Synthesis of 7-a

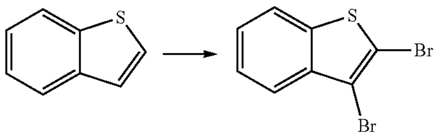

7-a

Benzothiophene (50 g, 0.373 mol) and 500 mL of dichloromethane were stirred in a 1 L reactor. The reaction mixture was cooled to −10° C. and a dilute solution of bromine (59.5 g, 0.745 mol) in 100 mL of dichloromethane was added dropwise thereto. The mixture was stirred at 0° C. for 2 h. After completion of the reaction, the reaction mixture was added with an aqueous sodium thiosulfate solution, followed by stirring. The resulting mixture was extracted with ethyl acetate and distilled water and recrystallized from ethanol to afford 7-a (100 g, 91%).

Synthesis Example 7-2: Synthesis of 7-b

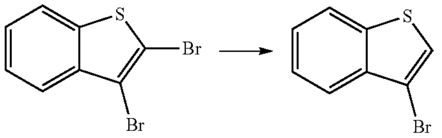

7-b

Potassium hydroxide (38.2 g, 0.68 mol) was dissolved in 500 mL of ethanol in a 1 L reactor. 7-a (100 g, 0.34 mol) was dissolved in ethanol at 0° C. and added dropwise to the reactor. The mixture was stirred for 2 h. After completion of the reaction, the reaction mixture was concentrated under reduced pressure and extracted with ethyl acetate and distilled water. The organic layer was concentrated and purified by column chromatography to afford 7-b (40 g, 55%).

Synthesis Example 7-3: Synthesis of 7-c

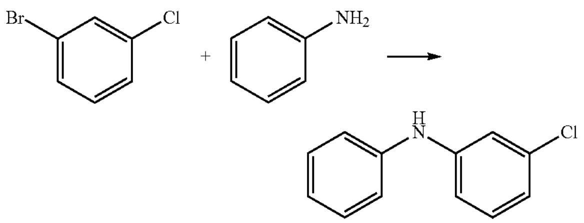

7-c

1-Bromo-3-chlorobenzene (4.5 g, 0.023 mol), aniline (2.2 g, 0.023 mol), palladium acetate (0.1 g, 0.003 mol), sodium tert-butoxide (3.4 g, 0.035 mol), bis(diphenylphosphino)-1,1'-binaphthyl (0.2 g, 0.003 mol), and 50 mL of toluene were placed in a 100 mL reactor. The mixture was stirred under reflux for 24 h. After completion of the reaction, the reaction mixture was filtered, concentrated, and purified by column chromatography to afford 7-c (3.9 g, 82%).

Synthesis Example 7-4: Synthesis of 7-d

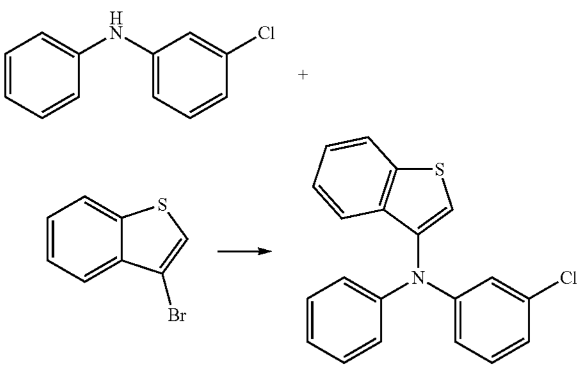

7-d 7-b (209 g, 0.094 mol), 7-c (19.29 g, 0.094 mol), palladium acetate (0.49 g, 0.002 mol), sodium tert-butoxide (18 g, 0.188 mol), tri-tert-butylphosphine (0.8 g, 0.004 mol), and 200 mL of toluene were placed in a 250 mL reactor. The mixture was stirred under reflux. After completion of the reaction, the reaction mixture was filtered, concentrated, and purified by column chromatography to afford 7-d (23 g, 73%).

Synthesis Example 7-5: Synthesis of 7-e

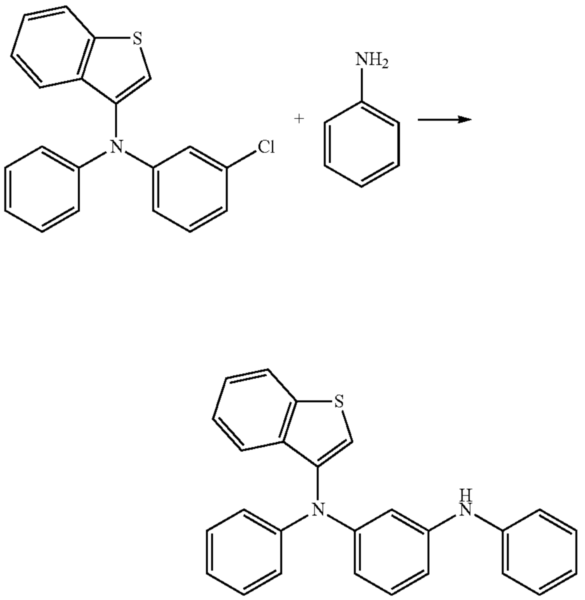

7-e 7-e (yield 74%) was synthesized in the same manner as in Synthesis Example 7-3, except that 7-d was used instead of 1-bromo-3-chlorobenzene.

Synthesis Example 7-6: Synthesis of 7-f

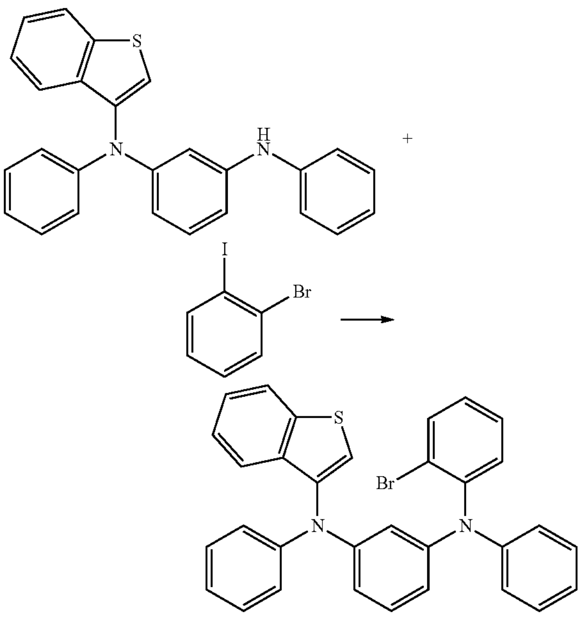

7-f 7-f (yield 82%) was synthesized in the same manner as in Synthesis Example 7-4, except that 1-bromo-2-iodobenzene and 7-e were used instead of 7-b and 7-c, respectively.

Synthesis Example 7-7: Synthesis of D-202

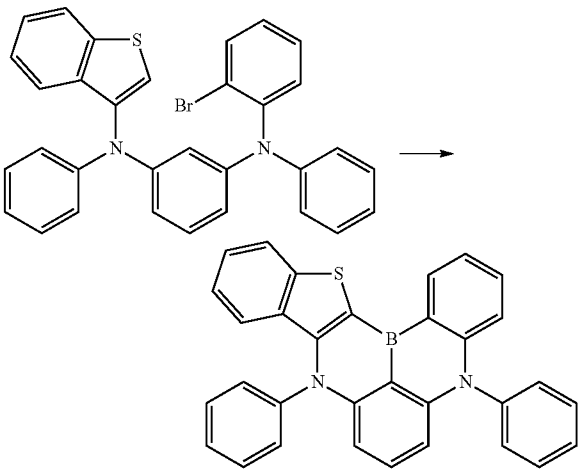

D-202

7-f (12 g, 0.022 mol) and 120 mL of tert-butylbenzene were placed in a 300 mL reactor and n-butyllithium (42 mL, 0.068 mol) was added dropwise thereto at −78° C. The mixture was stirred at 60° C. for 3 h. Nitrogen was blown into the mixture to remove heptane. After cooling to −78° C., boron tribromide (11.3 g, 0.045 mol) was added dropwise. The resulting mixture was stirred at room temperature for 1 h. After dropwise addition of N,N-diisopropylethylamine (5.8 g, 0.045 mol) at 0° C., stirring was continued at 120° C. for 2 h. After completion of the reaction, an aqueous sodium acetate solution was added at room temperature, followed by stirring. The reaction mixture was extracted with ethyl acetate. The organic layer was concentrated and purified by column chromatography to afford D-202 (1.2 g, 11%).

MS (MALDI-TOF): m/z 476.15 [$M^+$]

Synthesis Example 8. Synthesis of D-304

Synthesis Example 8-1: Synthesis of 8-a

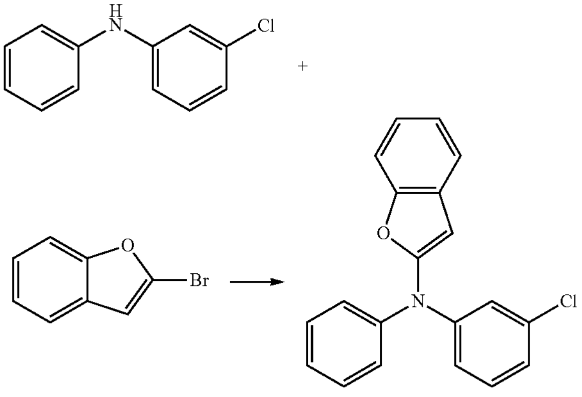

8-a 8-a (yield 73%) was synthesized in the same manner as in Synthesis Example 7-4, except that 2-bromobenzofuran was used instead of 7-b.

Synthesis Example 8-2: Synthesis of 8-b

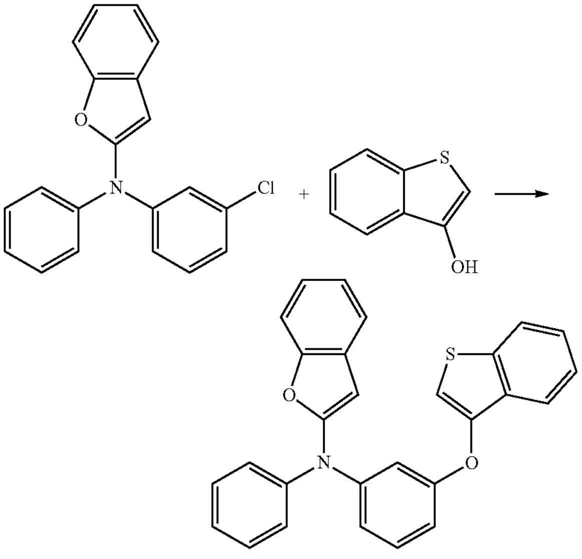

8-b 8-a (30 g, 0.094 mol), benzothiophen-3-ol (15.5 g, 0.103 mol), potassium carbonate (25.9 g, 0.188 mol), and 200 mL of NMP were placed in a 500 mL reactor. The mixture was stirred under reflux for 12 h. After completion of the reaction, the reaction mixture was allowed to cool to room temperature and NMP was distilled off under reduced pressure. The residue was extracted with distilled water and ethyl acetate, concentrated under reduced pressure to remove the solvent, and purified by column chromatography to afford 8-b (26 g, 64%).

Synthesis Example 8-3: Synthesis of D-304

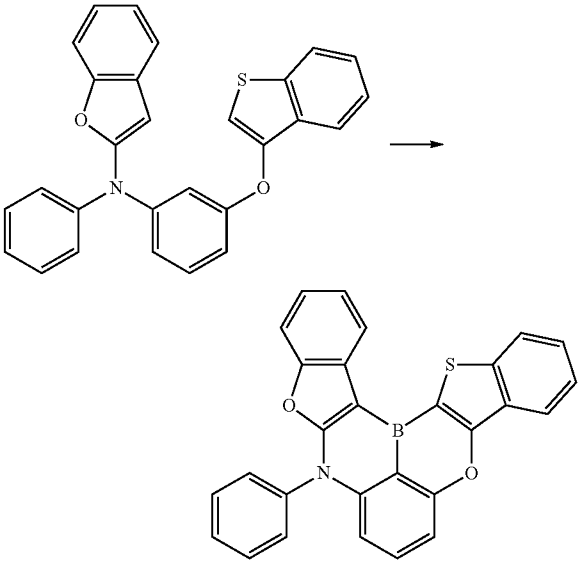

D-304

D-304 (yield 10%) was synthesized in the same manner as in Synthesis Example 7-7, except that 8-b was used instead of 7-f.

MS (MALDI-TOF): m/z 441.10 [$M^+$]

Synthesis Example 9. Synthesis of D-401

Synthesis Example 9-1: Synthesis of 9-a

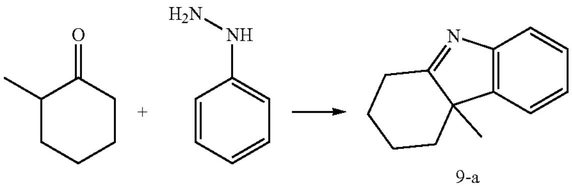

9-a

Phenylhydrazine (100 g, 0.924 mol) and 500 mL of acetic acid were stirred in a round-bottom flask. The mixture was heated to 60° C. and 2-methylcyclohexanone (103.6 g, 0.924 mol) was slowly added dropwise thereto. The resulting mixture was refluxed for 8 h. After completion of the reaction, the reaction mixture was extracted with ethyl acetate/distilled water, concentrated under reduced pressure, and purified by column chromatography to afford 9-a (130 g, 76%).

Synthesis Example 9-2: Synthesis of 9-b

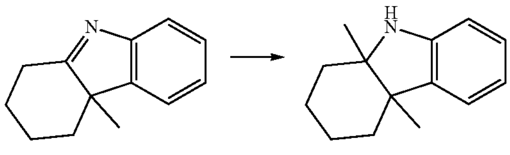

9-b 9-a (75 g, 0.405 mol) was added to 750 mL of toluene in a round-bottom flask under a nitrogen atmosphere. The mixture was cooled to −10° C. and 1.6 M methyl lithium (380 mL, 0.608 mol) was slowly added dropwise thereto. The resulting mixture was stirred for ~3 h. After completion of the reaction, the reaction mixture was extracted with ethyl acetate/distilled water, concentrated under reduced pressure, and purified by column chromatography to afford 9-b (50.5 g, 62%).

Synthesis Example 9-3: Synthesis of 9-c

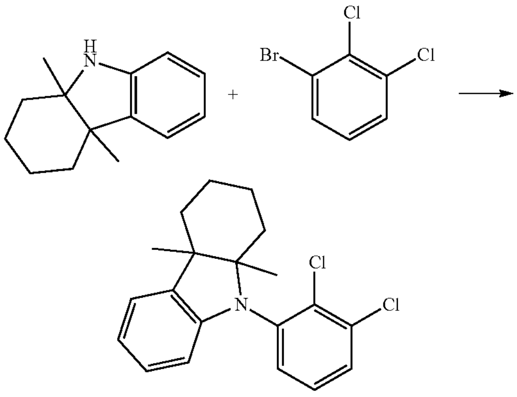

9-c 9-b (50 g, 0.251 mol), 1-bromo-2,3-dichlorobenzene (56.7 g, 0.251 mol), tris(dibenzylideneacetone)dipalladium (4.5 g, 0.005 mol), tri-tert-butylphosphine (2 g, 0.01 mol), sodium tert-butoxide (35.8 g, 0.373 mol), and 500 mL of toluene were placed in a round-bottom flask under a nitrogen atmosphere. The mixture was refluxed for 24 h. After completion of the reaction, the organic layer was concentrated under reduced pressure and purified by column chromatography to afford 9-c (35.6 g, 41%).

Synthesis Example 9-4: Synthesis of 9-d

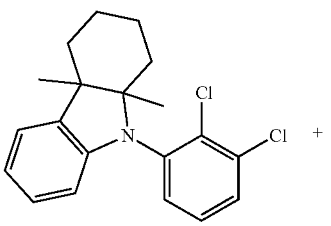

-continued

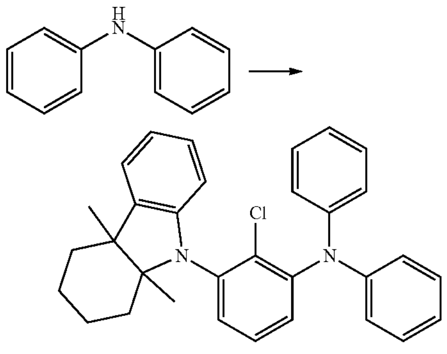

9-d 9-d (yield 73%) was synthesized in the same manner as in Synthesis Example 9-3, except that diphenylamine and 9-c were used instead of 9-b and 1-bromo-2,3-dichlorobenzene, respectively.

Synthesis Example 9-5: Synthesis of D-401

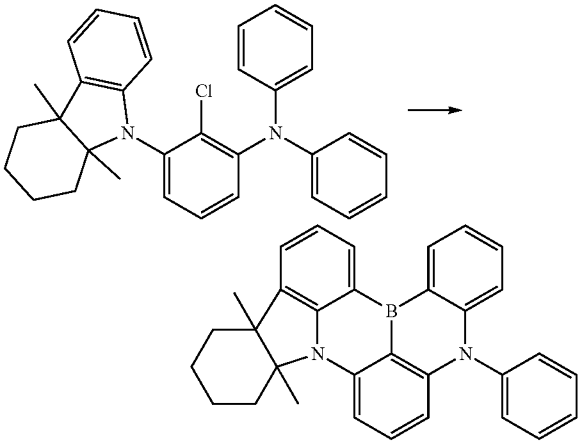

D-401

9-d (20 g, 0.042 mol) was added to 200 mL of tert-butylbenzene in a round-bottom flask under a nitrogen atmosphere. The mixture was cooled to −30° C. and a 1.7 M tert-butyllithium pentane solution (49.1 mL, 0.084 mol) was slowly added dropwise thereto. After completion of the dropwise addition, the resulting mixture was heated to 60° C. After stirring for 3 h, pentane was distilled off. The residue was cooled to −50° C. and boron tribromide (20.8 g, 0.084 mol) was added dropwise thereto. The mixture was allowed to warm to room temperature, followed by stirring for 1 h. The mixture was again cooled to 0° C., N,N-diisopropylethylamine (10.7 g, 0.084 mol) was added dropwise thereto, followed by stirring at 120° C. for 3 h. After completion of the reaction, the reaction mixture was distilled under reduced pressure to remove tert-butylbenzene, extracted with ethyl acetate/distilled water, concentrated under reduced pressure, and purified by column chromatography to afford D-401 (5.3 g, 28%).

MS (MALDI-TOF): m/z 452.24 [$M^+$]

Synthesis Example 10. Synthesis of D-413

Synthesis Example 10-1: Synthesis of 10-a

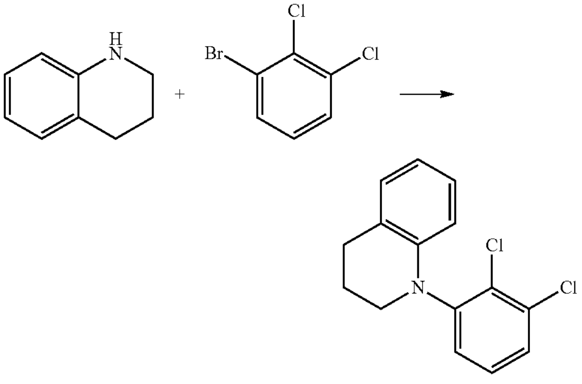

10-a 10-a (yield 63%) was synthesized in the same manner as in Synthesis Example 9-3, except that 1,2,3,4-tetrahydroisoquinoline was used instead of 9-b.

Synthesis Example 10-2: Synthesis of 10-b

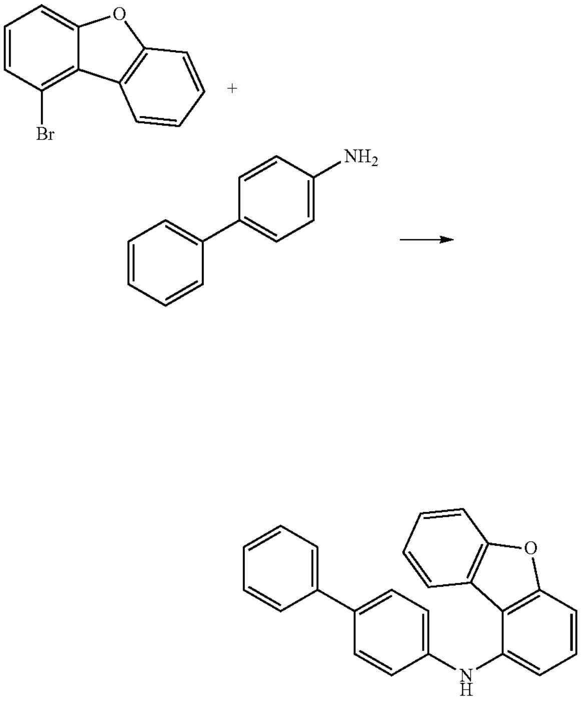

10-b 10-b (yield 61%) was synthesized in the same manner as in Synthesis Example 9-3, except that 4-aminobiphenyl and 1-bromodibenzofuran were used instead of 9-b and 1-bromo-2,3-dichlorobenzene, respectively.

Synthesis Example 10-3: Synthesis of 10-c

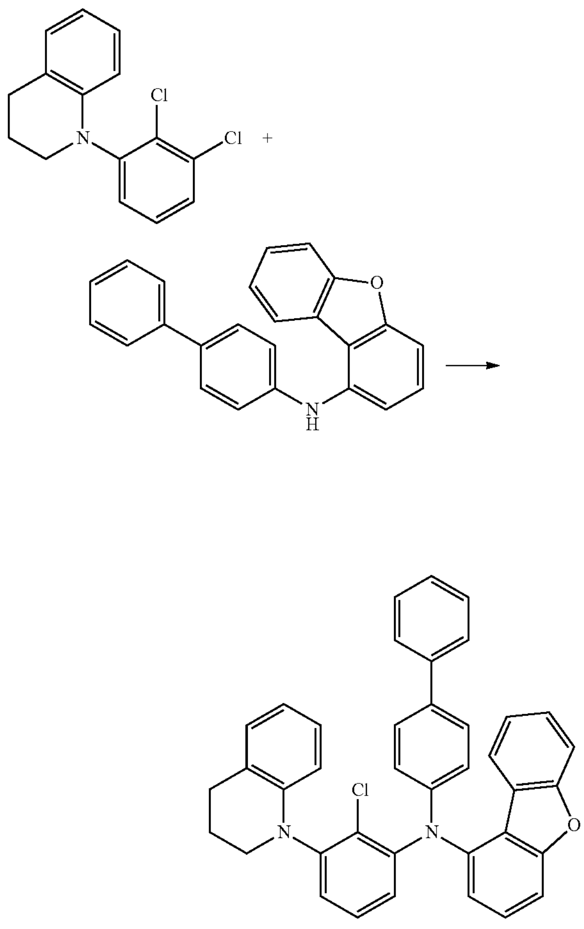

10-c 10-c (yield 67%) was synthesized in the same manner as in Synthesis Example 9-3, except that 10-b and 10-a were used instead of 9-b and 1-bromo-2,3-dichlorobenzene, respectively.

Synthesis Example 10-4: Synthesis of D-413

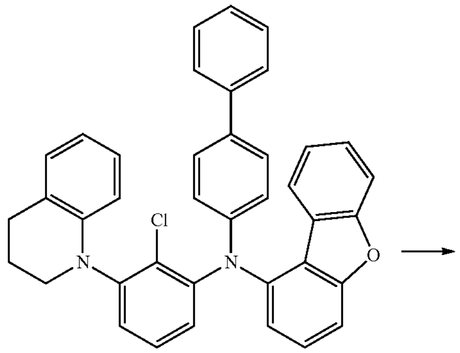

-continued

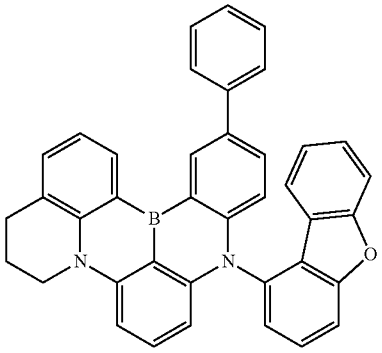

D-413

D-413 (yield 66%) was synthesized in the same manner as in Synthesis Example 9-5, except that 10-c was used instead of 9-d.

MS (MALDI-TOF): m/z 550.22 [$M^+$]

Synthesis Example 11. Synthesis of D-433

Synthesis Example 11-1: Synthesis of 11-a

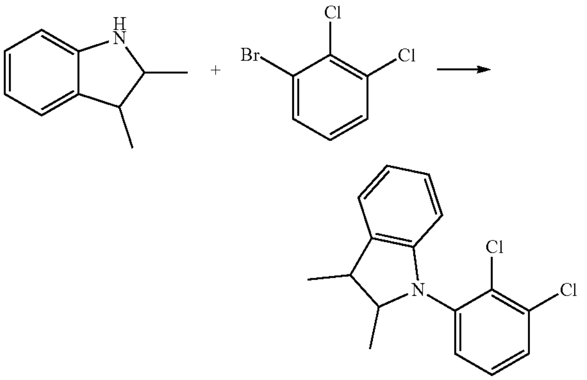

11-a 11-a (yield 52%) was synthesized in the same manner as in Synthesis Example 9-3, except that 2,3-dimethyl-2,3-dihydro-1H-indole was used instead of 9-b.

Synthesis Example 11-2: Synthesis of 11-b

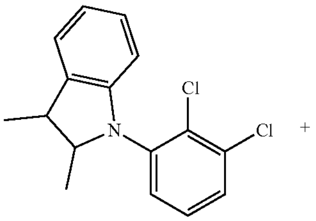

-continued

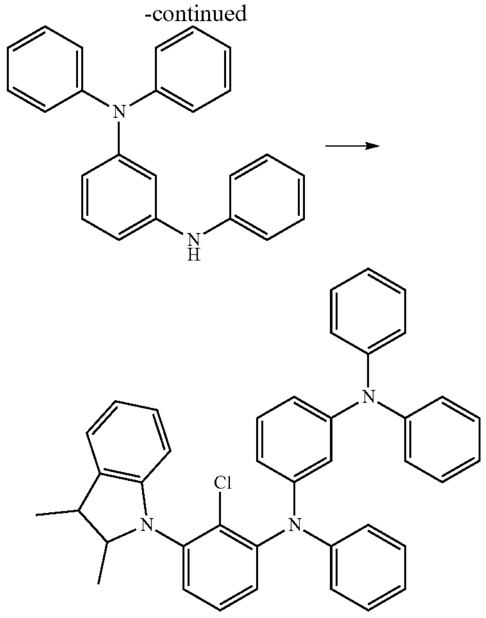

11-b 11-b (yield 55%) was synthesized in the same manner as in Synthesis Example 9-3, except that N,N,N-triphenylbenzene-1,3-diamine and 11-a were used instead of 9-b and 1-bromo-2,3-dichlorobenzene, respectively.

Synthesis Example 11-3: Synthesis of D-433

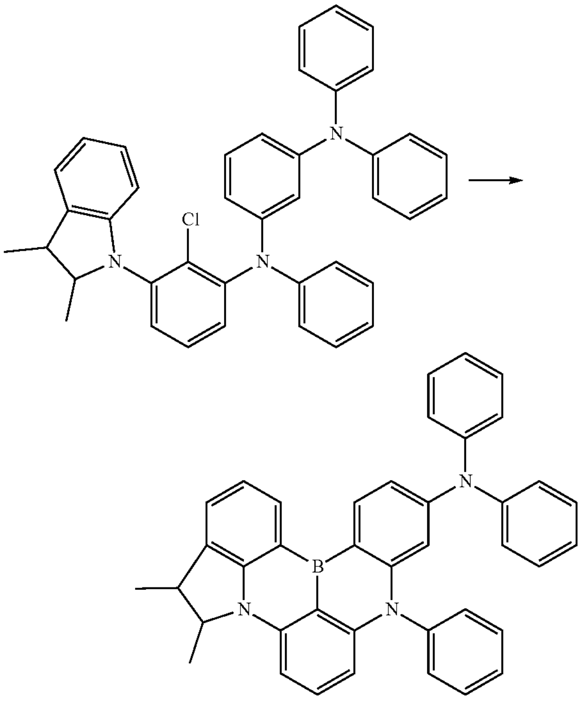

D-433

D-433 (yield 68%) was synthesized in the same manner as in Synthesis Example 9-5, except that 11-b was used instead of 9-d.

MS (MALDI-TOF): m/z 565.27 [$M^+$]

Synthesis Example 12. Synthesis of D-515

Synthesis Example 12-1: Synthesis of 12-a

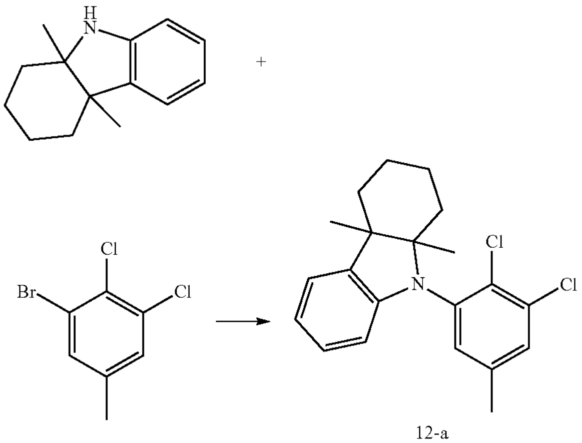

12-a 12-a (yield 62%) was synthesized in the same manner as in Synthesis Example 9-3, except that 1-bromo-2,3-dichloro-5-methylbenzene was used instead of 1-bromo-2,3-dichlorobenzene.

Synthesis Example 12-2: Synthesis of 12-b

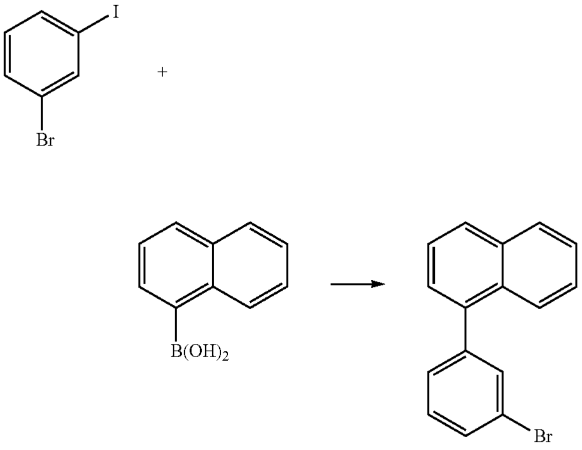

12-b

1-Bromo-3-iodobenzene (30 g, 0.106 mol), 1-naphthaleneboronic acid (16.4 g, 0.095 mol), tetrakis(triphenylphosphine)palladium (1.8 g, 0.002 mol), potassium carbonate (17.6 g, 0.127 mol), 300 mL of tetrahydrofuran, 300 mL of toluene, and 120 mL of distilled water were placed in a round-bottom flask under a nitrogen atmosphere. The mixture was refluxed for 24 h. After completion of the reaction, the reaction mixture was allowed to cool to room temperature, followed by extraction. The organic layer was concentrated under reduced pressure and purified by column chromatography to afford 12-b (19 g, 70%).

Synthesis Example 12-3: Synthesis of 12-c

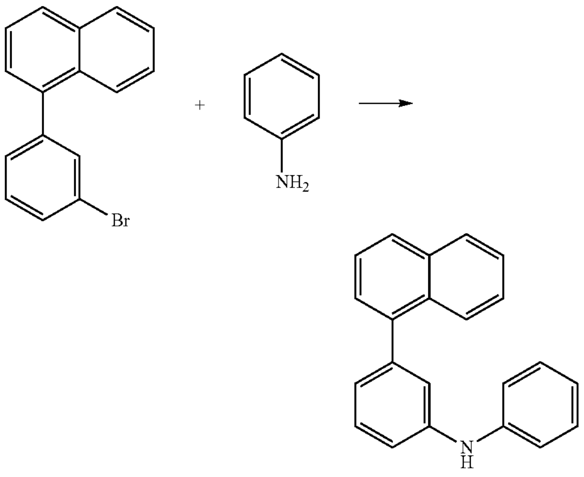

12-c 12-b (19 g, 0.067 mol), aniline (6.2 g, 0.067 mol), tris(dibenzylideneacetone)dipalladium(0) (1.2 g, 0.001 mol), sodium tert-butoxide (7.7 g, 0.81 mol), bis(diphenylphosphino)-1,1'-binaphthyl (0.8 g, 0.001 mol), and 200 mL of toluene were placed in a round-bottom flask. The mixture was stirred under reflux for 24 h. After completion of the reaction, the reaction mixture was extracted. The organic layer was concentrated under reduced pressure and purified by column chromatography to afford 12-c (15 g, 77%).

Synthesis Example 12-4: Synthesis of 12-d

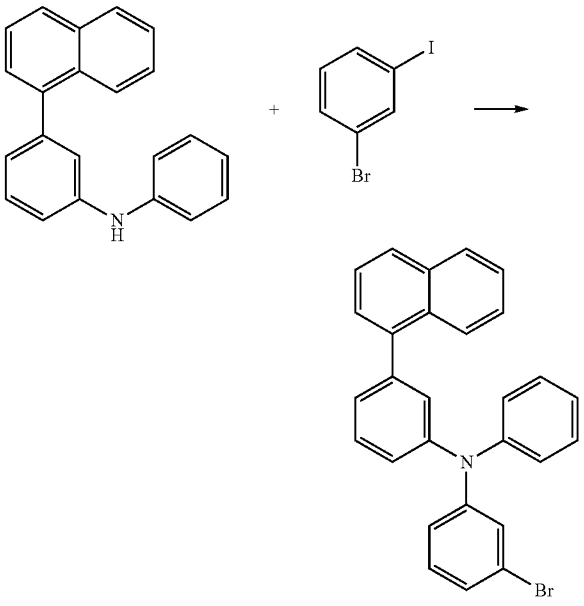

12-d 12-d (yield 64%) was synthesized in the same manner as in Synthesis Example 12-3, except that 1-bromo-3-iodobenzene and 12-c were used instead of 12-b and aniline, respectively.

Synthesis Example 12-5: Synthesis of 12-e

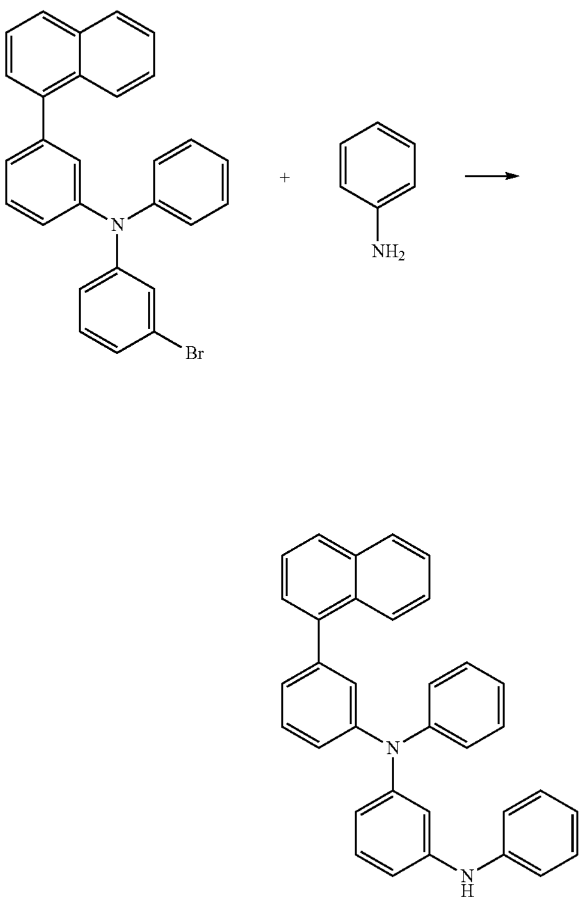

12-e 12-e (yield 75%) was synthesized in the same manner as in Synthesis Example 12-3, except that 12-d was used instead of 12-b.

Synthesis Example 12-6: Synthesis of 12-f

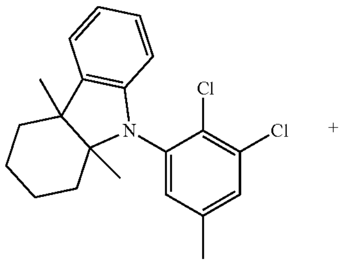

-continued

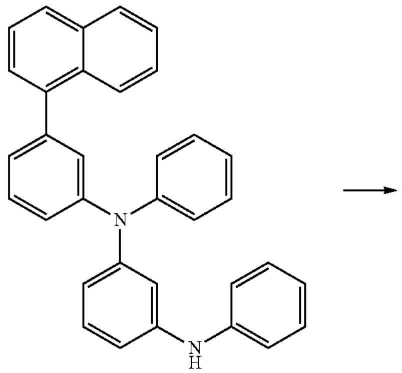

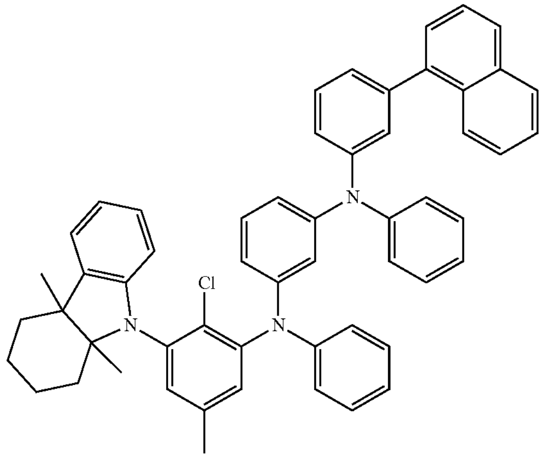

12-f 12-f (yield 65%) was synthesized in the same manner as in Synthesis Example 12-3, except that 12-a and 12-e were used instead of 12-b and aniline, respectively. The product was further purified by recrystallization from dichloromethane and methanol.

Synthesis Example 12-7: Synthesis of D-515

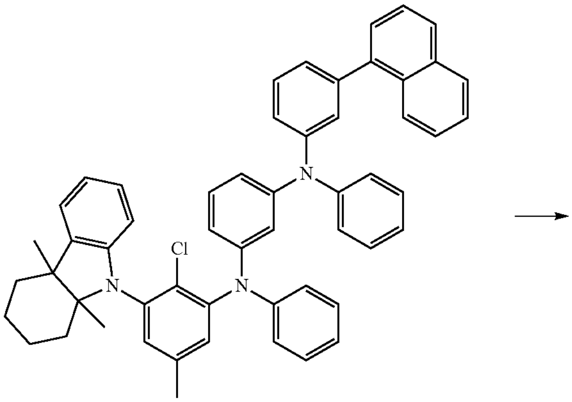

-continued

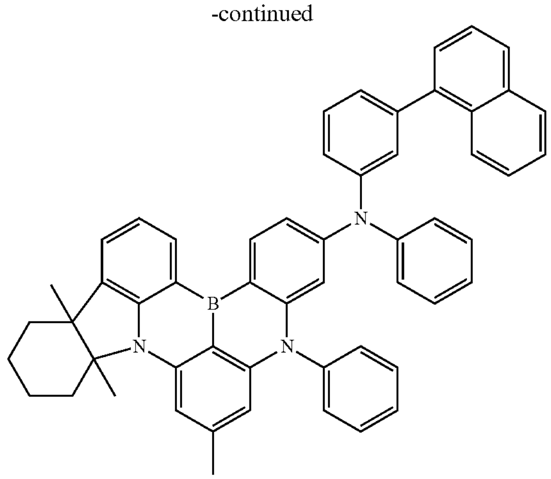

D-515

D-515 (yield 11%) was synthesized in the same manner as in Synthesis Example 9-5, except that 12-f was used instead of 9-d.

MS (MALDI-TOF): m/z 759.38 [$M^+$]

Synthesis Example 13. Synthesis of D-601

Synthesis Example 13-1: Synthesis of 13-a

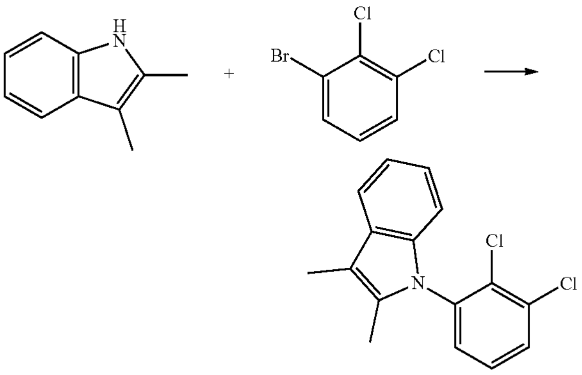

13-a 13-a (yield 47%) was synthesized in the same manner as in Synthesis Example 9-3, except that 2,3-dimethylindole was used instead of 9-b.

Synthesis Example 13-2: Synthesis of 13-b

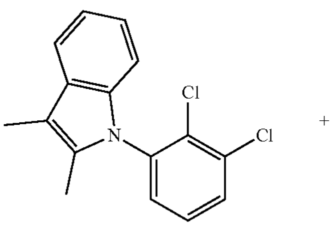

-continued

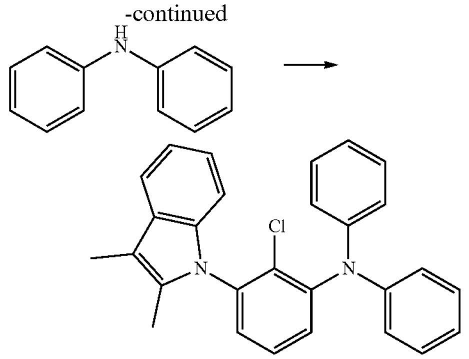

13-b 13-b (yield 72%) was synthesized in the same manner as in Synthesis Example 9-4, except that 13-a was used instead of 9-c.

Synthesis Example 13-3: Synthesis of D-601

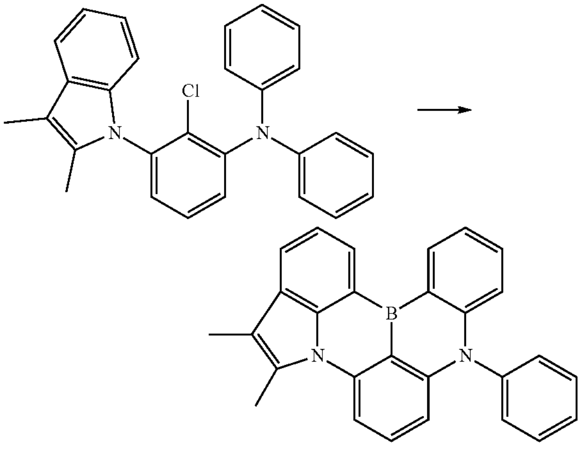

D-601

D-601 (yield 25%) was synthesized in the same manner as in Synthesis Example 9-5, except that 13-b was used instead of 9-d.

MS (MALDI-TOF): m/z 396.18 [$M^+$]

Synthesis Example 14. Synthesis of D-685

Synthesis Example 14-1: Synthesis of 14-a

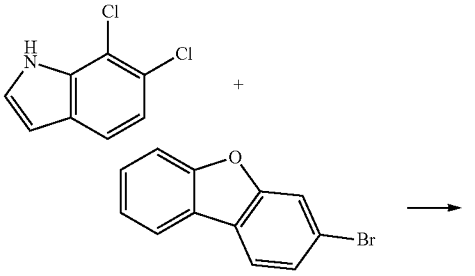

-continued

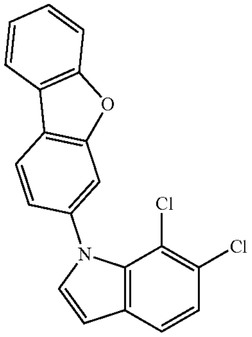

14-a 14-a (yield 52%) was synthesized in the same manner as in Synthesis Example 13-1, except that 6,7-dichloroindole and 3-bromodibenzofuran were used instead of 2,3-dimethylindole and 1-bromo-2,3-dichlorobenzene, respectively.

Synthesis Example 14-2: Synthesis of 14-b

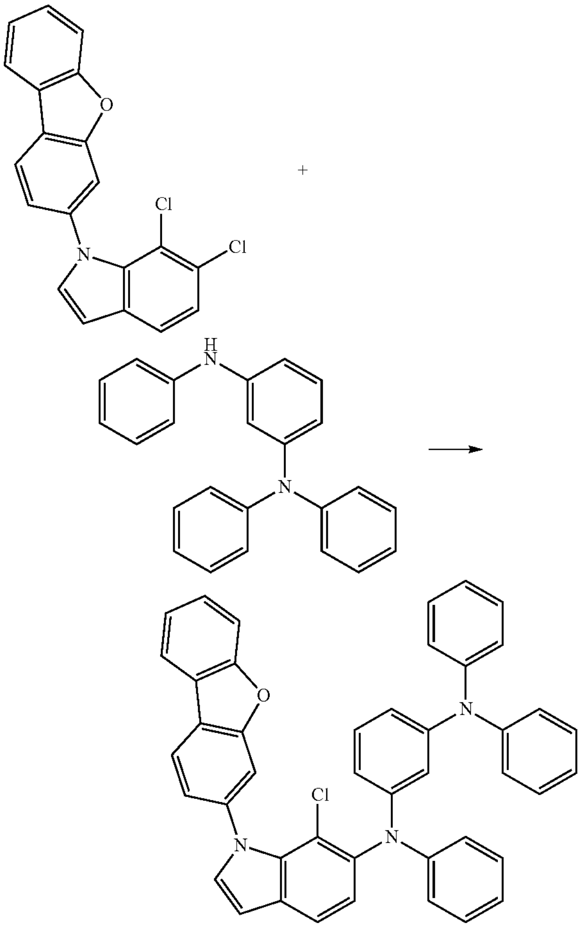

14-b 14-b (yield 59%) was synthesized in the same manner as in Synthesis Example 13-2, except that 14-a and N,N,N-triphenylbenzene-1,3-diamine were used instead of 13-a and diphenylamine, respectively.

Synthesis Example 14-3: Synthesis of D-685

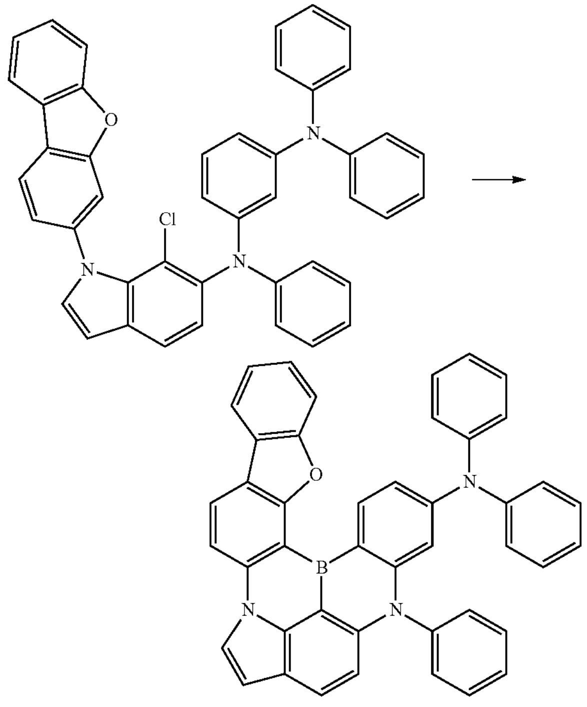

D-685

D-685 (yield 52%) was synthesized in the same manner as in Synthesis Example 13-3, except that 14-b was used instead of 13-b.

MS (MALDI-TOF): m/z 625.23 [$M^+$]

Synthesis Example 15. Synthesis of D-110

Synthesis Example 15-1: Synthesis of 15-a

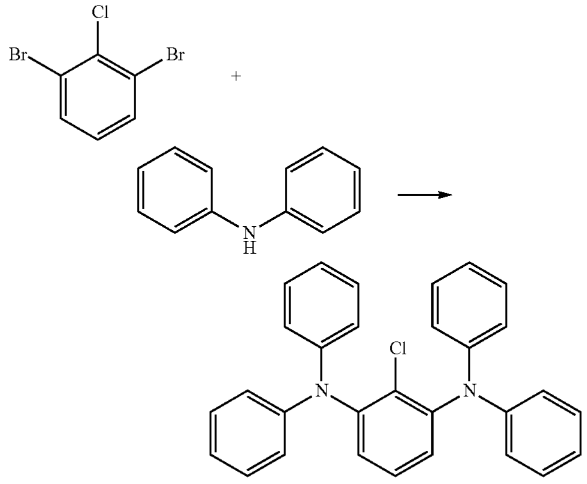

15-a 15-a (yield 50%) was synthesized in the same manner as in Synthesis Example 13-1, except that diphenylamine and 1,3-dibromo-2-chlorobenzene were used instead of 2,3-dimethylindole and 1-bromo-2,3-dichlorobenzene, respectively.

Synthesis Example 15-2: Synthesis of D-110

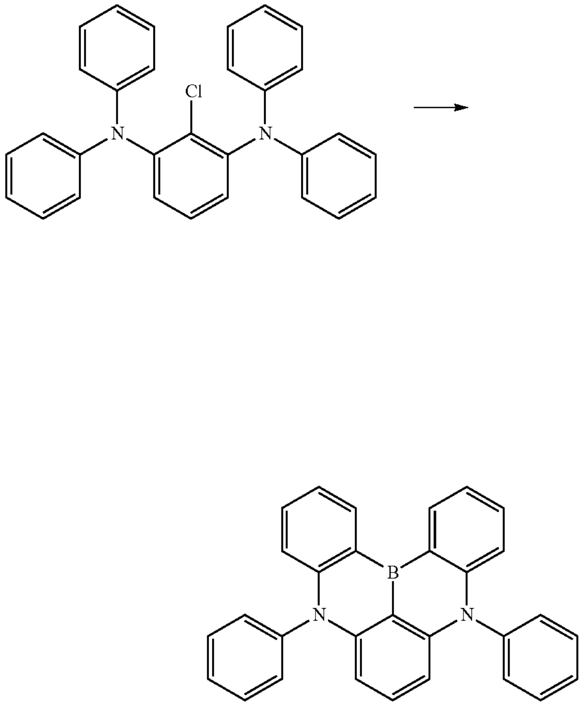

D-110

D-110 (yield 23%) was synthesized in the same manner as in Synthesis Example 13-3, except that 15-a was used instead of 13-b.

MS (MALDI-TOF): m/z 420.18 [$M^+$]

Examples 1 to 36: Fabrication of Organic Light Emitting Devices

ITO glass was patterned to have a light emitting area of 2 mm×2 mm, followed by cleaning. After the cleaned ITO glass was mounted in a vacuum chamber, the base pressure was adjusted to $1\times10^{-7}$ torr. DNTPD (700 Å) and α-NPD (300 Å) were sequentially formed into layers on the ITO. A mixture of the host compound shown in Table 1 and the dopant compound (3 wt %) shown in Table 1 was formed into a 300 Å thick light emitting layer. Thereafter, a mixture of the compound represented by Formula E-1 and the compound represented by Formula E-2 in a ratio of 1:1 was formed into a 300 Å thick electron transport layer on the light emitting layer. The compound represented by Formula E-2 was formed into a 10 Å thick electron injecting layer on the electron transport layer. Al was formed into a 1000 Å thick electrode on the electron injecting layer, completing the fabrication of an organic light emitting device. The luminescent properties of the organic light emitting device were measured at 10 mA/$cm^2$.

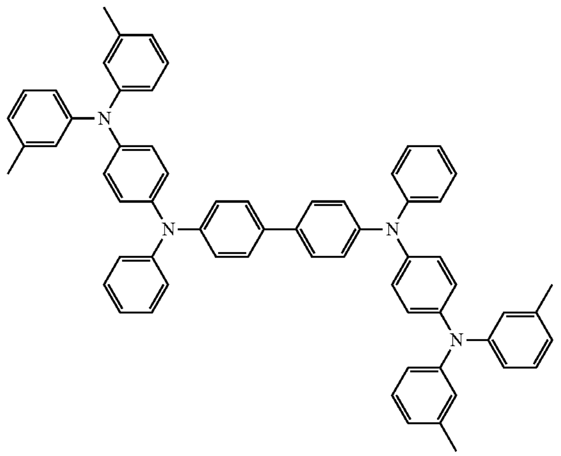

[DNTPD]

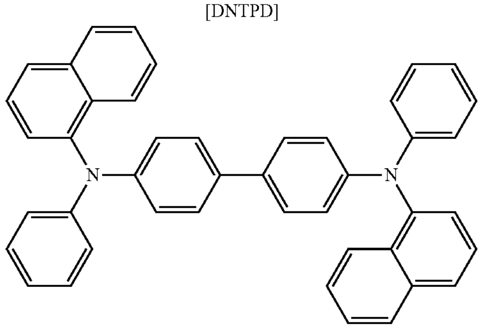

[α-NPD]

[E-1]

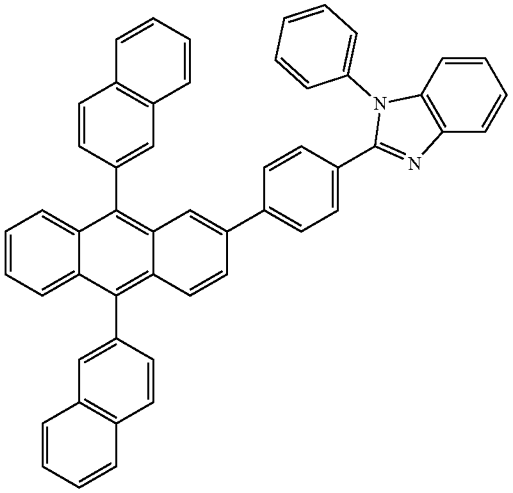

[E-2]

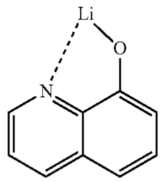

Comparative Examples 1 to 30

Organic light emitting devices were fabricated in the same manner as in Examples 1-36, except that the host and dopant compounds shown in Table 1 were used to form a light emitting layer instead of the inventive compounds. The luminescent properties of the organic light emitting devices were measured at 10 mA/$cm^2$. The structures of BH1 to BH3 and BD-1 are as follow:

[BH-1]

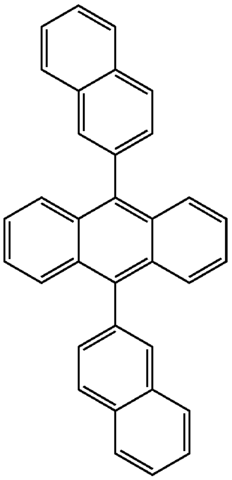

[BH-2]

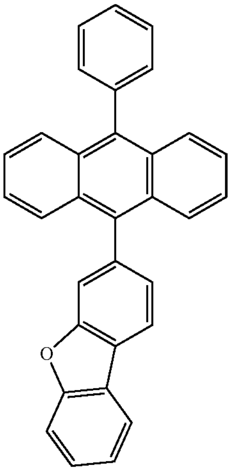

[BH-3]

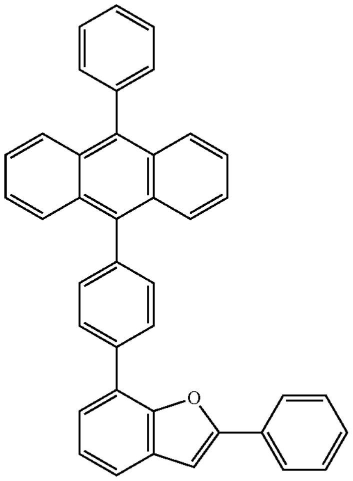

-continued

[BD-1]

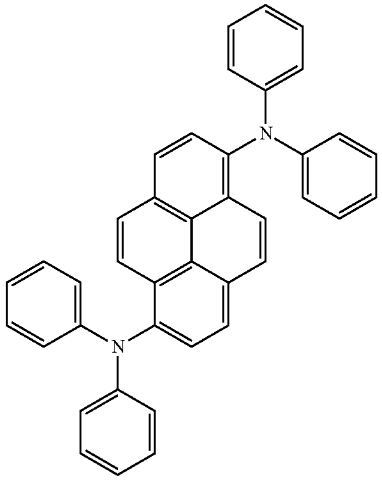

TABLE 1

| Example No. | Host | Dopant | Current density (mA/cm$^2$) | External quantum efficiency (EQE, %) |
|---|---|---|---|---|
| Example 1 | A-20 | D-110 | 10 | 11.1 |
| Example 2 | A-20 | D-401 | 10 | 11.0 |
| Example 3 | A-20 | D-515 | 10 | 11.3 |
| Example 4 | A-20 | D-601 | 10 | 10.8 |
| Example 5 | A-20 | D-685 | 10 | 11.0 |
| Example 6 | A-30 | D-110 | 10 | 10.2 |
| Example 7 | A-30 | D-401 | 10 | 10.2 |
| Example 8 | A-30 | D-515 | 10 | 10.4 |
| Example 9 | A-30 | D-601 | 10 | 10.0 |
| Example 10 | A-30 | D-685 | 10 | 10.2 |
| Example 11 | A-57 | D-110 | 10 | 11.0 |
| Example 12 | A-57 | D-202 | 10 | 11.4 |
| Example 13 | A-57 | D-304 | 10 | 11.3 |
| Example 14 | A-57 | D-401 | 10 | 11.0 |
| Example 15 | A-57 | D-515 | 10 | 11.3 |
| Example 16 | A-57 | D-601 | 10 | 10.8 |
| Example 17 | A-57 | D-685 | 10 | 11.0 |
| Example 18 | A-58 | D-110 | 10 | 11.2 |
| Example 19 | A-58 | D-401 | 10 | 11.1 |
| Example 20 | A-58 | D-515 | 10 | 11.3 |
| Example 21 | A-58 | D-601 | 10 | 10.9 |
| Example 22 | A-58 | D-685 | 10 | 11.0 |
| Example 23 | A-68 | D-110 | 10 | 10.0 |
| Example 24 | A-68 | D-202 | 10 | 10.4 |
| Example 25 | A-68 | D-304 | 10 | 10.2 |
| Example 26 | A-68 | D-401 | 10 | 10.0 |
| Example 27 | A-68 | D-515 | 10 | 10.3 |
| Example 28 | A-68 | D-601 | 10 | 10.1 |
| Example 29 | A-68 | D-685 | 10 | 10.2 |
| Example 30 | A-79 | D-110 | 10 | 10.8 |
| Example 31 | A-79 | D-202 | 10 | 11.1 |
| Example 32 | A-79 | D-304 | 10 | 11.0 |
| Example 33 | A-79 | D-401 | 10 | 10.7 |
| Example 34 | A-79 | D-515 | 10 | 10.9 |
| Example 35 | A-79 | D-601 | 10 | 10.6 |
| Example 36 | A-79 | D-685 | 10 | 10.7 |
| Comparative Example 1 | BH-1 | D-110 | 10 | 9.6 |
| Comparative Example 2 | BH-1 | D-202 | 10 | 9.8 |
| Comparative Example 3 | BH-1 | D-304 | 10 | 9.9 |
| Comparative Example 4 | BH-1 | D-401 | 10 | 9.5 |
| Comparative Example 5 | BH-1 | D-515 | 10 | 9.7 |
| Comparative Example 6 | BH-1 | D-601 | 10 | 9.4 |
| Comparative Example 7 | BH-1 | D-685 | 10 | 9.6 |
| Comparative Example 8 | BH-2 | D-110 | 10 | 9.8 |
| Comparative Example 9 | BH-2 | D-202 | 10 | 9.9 |
| Comparative Example 10 | BH-2 | D-304 | 10 | 9.9 |
| Comparative Example 11 | BH-2 | D-401 | 10 | 9.7 |
| Comparative Example 12 | BH-2 | D-515 | 10 | 9.8 |
| Comparative Example 13 | BH-2 | D-601 | 10 | 9.6 |
| Comparative Example 14 | BH-2 | D-685 | 10 | 9.8 |
| Comparative Example 15 | BH-3 | D-110 | 10 | 9.7 |
| Comparative Example 16 | BH-3 | D-202 | 10 | 9.9 |
| Comparative Example 17 | BH-3 | D-304 | 10 | 9.6 |
| Comparative Example 18 | BH-3 | D-401 | 10 | 9.5 |
| Comparative Example 19 | BH-3 | D-515 | 10 | 9.7 |
| Comparative Example 20 | BH-3 | D-601 | 10 | 9.8 |
| Comparative Example 21 | BH-3 | D-685 | 10 | 9.7 |
| Comparative Example 22 | A-20 | BD-1 | 10 | 8.4 |
| Comparative Example 23 | A-30 | BD-1 | 10 | 7.8 |
| Comparative Example 24 | A-57 | BD-1 | 10 | 8.4 |
| Comparative Example 25 | A-58 | BD-1 | 10 | 8.6 |
| Comparative Example 26 | A-68 | BD-1 | 10 | 7.7 |
| Comparative Example 27 | A-79 | BD-1 | 10 | 7.9 |
| Comparative Example 28 | BH-1 | BD-1 | 10 | 7.5 |
| Comparative Example 29 | BH-2 | BD-1 | 10 | 7.7 |
| Comparative Example 30 | BH-3 | BD-1 | 10 | 7.7 |

As can be seen from the results in Table 1, the organic light emitting devices of Examples 1-36, each of which employed the inventive host and dopant compounds for the light emitting layer, showed significantly high external quantum efficiencies compared to the organic light emitting devices of Comparative Examples 1-30, each of which employed the host and dopant compounds whose structural features are contrasted with those of the inventive compounds. These results concluded that the use of the inventive compounds makes the organic light emitting devices highly efficient.

INDUSTRIAL APPLICABILITY

The organic light emitting device of the present invention includes a light emitting layer employing, as a host, an anthracene derivative with a specific structure in which a benzofuran structure is introduced to the anthracene skeleton and, as a dopant, a polycyclic compound with a specific structure. The use of the host and dopant ensures significantly improved external quantum efficiency and high efficiency of the device. Due to these advantages, the organic light emitting device of the present invention can find useful industrial applications in not only lighting systems but also a variety of displays, including flat panel displays, flexible displays, and wearable displays.

What is claimed is:

1. An organic light emitting device comprising a first electrode, a second electrode opposite to the first electrode, and a light emitting layer interposed between the first and second electrodes wherein the light emitting layer comprises at least one host and at least one dopant, wherein the host is an anthracene derivative represented by Formula A:

[Formula A]

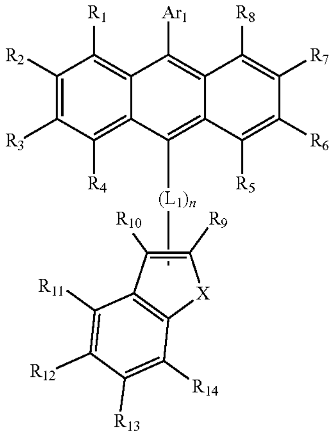

wherein $Ar_1$ is selected from substituted or unsubstituted $C_6$-$C_{50}$ aryl, substituted or unsubstituted $C_2$-$C_{50}$ heteroaryl, and substituted or unsubstituted $C_3$-$C_{50}$ mixed aliphatic-aromatic cyclic groups, $R_1$ to $R_{14}$ are the same as or different from each other and are each independently selected from hydrogen, deuterium, substituted or unsubstituted $C_1$-$C_{30}$ alkyl, substituted or unsubstituted $C_6$-$C_{50}$ aryl, substituted or unsubstituted $C_2$-$C_{30}$ alkenyl, substituted or unsubstituted $C_2$-$C_{30}$ alkynyl, substituted or unsubstituted $C_3$-$C_{30}$ cycloalkyl, substituted or unsubstituted $C_3$-$C_{30}$ cycloalkenyl, substituted or unsubstituted $C_2$-$C_{50}$ heteroaryl, substituted or unsubstituted $C_2$-$C_{30}$ heterocycloalkyl, substituted or unsubstituted $C_1$-$C_{30}$ alkoxy, substituted or unsubstituted $C_6$-$C_{50}$ aryloxy, substituted or unsubstituted $C_1$-$C_{30}$ alkylthioxy, substituted or unsubstituted $C_6$-$C_{50}$ arylthioxy, substituted or unsubstituted amine, substituted or unsubstituted silyl, substituted or unsubstituted germanium, substituted or unsubstituted $C_3$-$C_{50}$ mixed aliphatic-aromatic cyclic groups, cyano, and halogen, with the proviso that either one of $R_9$ and $R_{10}$ is optionally bonded to the linker $L_1$, X is an oxygen (O) or sulfur (S) atom, $L_1$ is a single bond or is selected from substituted or unsubstituted $C_6$-$C_{50}$ arylene and substituted or unsubstituted $C_2$-$C_{50}$ heteroarylene, and n is an integer from 1 to 3, provided that when n is 2 or more, the linkers $L_1$ are the same as or different from each other, and wherein the dopant is a polycyclic compound represented by one of Formulas D-1 to D-8:

[Formula D-1]

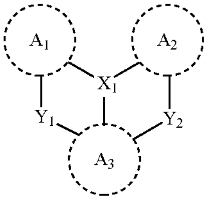

wherein $X_1$ is selected from B, P═O, and P═S, $Y_1$ and $Y_2$ are each independently selected from $NR_{21}$, $CR_{22}R_{23}$, O, S, Se, and $SiR_{24}R_{25}$, $A_1$ to $A_3$ are each independently selected from substituted or unsubstituted $C_6$-$C_{50}$ aromatic hydrocarbon rings, substituted or unsubstituted $C_2$-$C_{50}$ aromatic heterocyclic rings, substituted or unsubstituted $C_3$-$C_{30}$ aliphatic rings, and substituted or unsubstituted $C_3$-$C_{30}$ mixed aliphatic-aromatic rings, and $R_{21}$ to $R_{25}$ are the same as or different from each other and are each independently selected from hydrogen, deuterium, substituted or unsubstituted $C_1$-$C_{30}$ alkyl, substituted or unsubstituted $C_2$-$C_{30}$ alkenyl, substituted or unsubstituted $C_2$-$C_{30}$ alkynyl, substituted or unsubstituted $C_6$-$C_{50}$ aryl, substituted or unsubstituted $C_3$-$C_{30}$ cycloalkyl, substituted or unsubstituted $C_3$-$C_{30}$ heterocycloalkyl, substituted or unsubstituted $C_2$-$C_{50}$ heteroaryl, substituted or unsubstituted $C_1$-$C_{30}$ alkoxy, substituted or unsubstituted $C_6$-$C_{30}$ aryloxy, substituted or unsubstituted $C_1$-$C_{30}$ alkylthioxy, substituted or unsubstituted $C_6$-$C_{30}$ arylthioxy, substituted or unsubstituted amine, substituted or unsubstituted silyl, substituted or unsubstituted $C_3$-$C_{20}$ mixed aliphatic-aromatic cyclic groups, nitro, cyano, and halogen, with the proviso that each of $R_{21}$ to $R_{25}$ is optionally bonded to one or more of the rings $A_1$ to $A_3$ to form an alicyclic or aromatic monocyclic or polycyclic ring or a mixed aliphatic-aromatic ring, the substituents of each of the rings $A_1$ to $A_3$ are optionally linked to each other to form an alicyclic or aromatic monocyclic or polycyclic ring or a mixed aliphatic-aromatic ring, $R_{22}$ and $R_{23}$ are optionally linked to each other to form an alicyclic or aromatic monocyclic or polycyclic ring or a mixed aliphatic-aromatic ring, and $R_{24}$ and $R_{25}$ are optionally linked to each other to form an alicyclic or aromatic monocyclic or polycyclic ring or a mixed aliphatic-aromatic ring,

[Formula D-2]

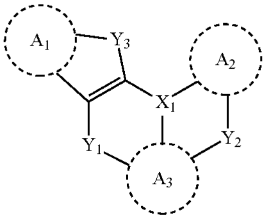

wherein $Y_3$ is selected from $NR_{21}$, $CR_{22}R_{23}$, O, S, Se, and $SiR_{24}R_{25}$ and $X_1$, $Y_1$, $Y_2$, $A_1$ to $A_3$, and $R_{21}$ to $R_{25}$ are as defined in Formula D-1,

[Formula D-3]

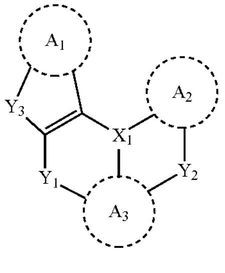

wherein $Y_3$ is as defined in Formula D-2 and $X_1$, $Y_1$, $Y_2$, $A_1$ to $A_3$, and $R_{21}$ to $R_{25}$ are as defined in Formula D-1,

[Formula D-4]

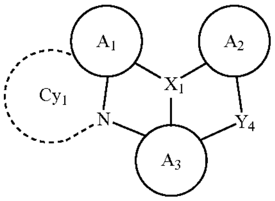

wherein $Y_4$ is selected from $NR_{21}$, $CR_{22}R_{23}$, O, S, Se, and $SiR_{24}R_{25}$, $X_1$, $A_1$ to $A_3$, and $R_{21}$ to $R_{25}$ are as defined in Formula D-1, and $Cy_1$ represents a ring formed by a substituted or unsubstituted $C_2$-$C_5$ alkylene group with the adjacent nitrogen (N) atom, the aromatic carbon atom in the ring $A_1$ to which the nitrogen (N) atom is bonded, and the aromatic carbon atom in the ring $A_1$ to which $Cy_1$ is to be bonded,

[Formula D-5]

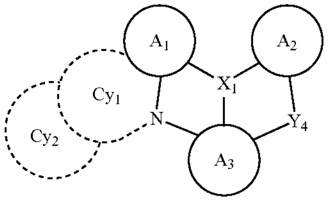

wherein $Y_4$ is selected from $NR_{21}$, $CR_{22}R_{23}$, O, S, Se, and $SiR_{24}R_{25}$, and $X_1$, $A_1$ to $A_3$, and $R_{21}$ to $R_{25}$ are as defined in Formula D-1, $Cy_1$ is as defined in Formula D-4, $Cy_2$ represents a saturated hydrocarbon ring attached to $Cy_1$ and formed by a substituted or unsubstituted $C_2$-$C_5$ alkylene group with carbon atoms in $Cy_1$,

[Formula D-6]

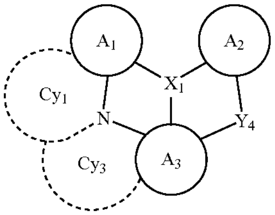

wherein $Y_4$ is selected from $NR_{21}$, $CR_{22}R_{23}$, O, S, Se, and $SiR_{24}R_{25}$, $X_1$, $A_1$ to $A_3$, and $R_{21}$ to $R_{25}$ are as defined in Formula D-1, $Cy_1$ is as defined in Formula D-4, and $Cy_3$ represents a ring formed by a substituted or unsubstituted $C_1$-$C_4$ alkylene group with the aromatic carbon atom in the ring $A_3$ to which $Cy_3$ is to be bonded, the nitrogen (N) atom, the aromatic carbon atom in the ring $A_3$ to which the nitrogen atom is bonded, and the carbon atom in $Cy_1$ to which the nitrogen atom is bonded,

[Formula D-7]

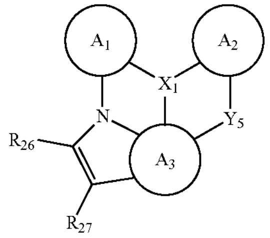

wherein $Y_5$ is selected from $NR_{21}$, $CR_{22}R_{23}$, O, S, Se, and $SiR_{24}R_{25}$ and $X_1$, $A_1$ to $A_3$, and $R_{21}$ to $R_{27}$ are as defined in Formula D-1, and

[Formula D-8]

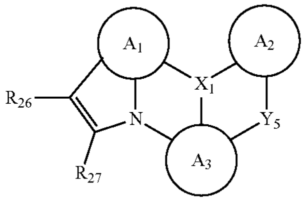

wherein $Y_5$ is as defined in Formula D-7 and $X_1$, $A_1$ to $A_3$, and $R_{21}$ to $R_{27}$ are as defined in Formula D-1, the "substituted" in the definitions of $Ar_1$, $R_1$ to $R_{14}$, and $L_1$ in Formula A and $Y_1$ to $Y_5$, $A_1$ to $A_3$, $Cy_1$ to $Cy_3$, $R_{26}$, and $R_{27}$ in Formulas D-1 to D-8 indicating substitution with one or more substituents selected from deuterium, cyano, halogen, hydroxyl, nitro, $C_1$-$C_{24}$ alkyl, $C_1$-$C_{24}$ haloalkyl, $C_3$-$C_{30}$ cycloalkyl, $C_2$-$C_{24}$ alkenyl, $C_2$-$C_{24}$ alkynyl, $C_1$-$C_{24}$ heteroalkyl, $C_6$-$C_{30}$ aryl, $C_7$-$C_{30}$ arylalkyl, $C_7$-$C_{30}$ alkylaryl, $C_2$-$C_{30}$ heteroaryl, $C_2$-$C_{30}$ heteroarylalkyl, $C_1$-$C_{24}$ alkoxy, $C_6$-$C_{30}$ aryloxy, $C_1$-$C_{24}$ amine, $C_1$-$C_{24}$ silyl, $C_3$-$C_{30}$ mixed aliphatic-aromatic cyclic groups, boron, aluminum, phosphoryl, hydroxyl, selenium, tellurium, nitro, and halogen and one or more hydrogen atoms in each of the substituents being optionally replaced by deuterium atoms.

2. The organic light emitting device according to claim 1, wherein the anthracene derivative of Formula A is represented by Formula A-1 or A-2:

[Formula A-1]

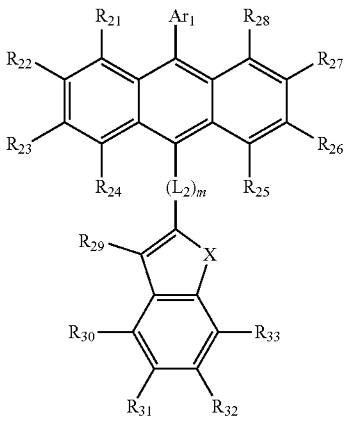

wherein $Ar_{11}$ is selected from substituted or unsubstituted $C_6$-$C_{50}$ aryl, substituted or unsubstituted $C_2$-$C_{50}$ heteroaryl, and substituted or unsubstituted $C_3$-$C_{50}$ mixed aliphatic-aromatic cyclic groups, $R_{21}$ to $R_{33}$ are the same as or different from each other and are each independently selected from hydrogen, deuterium, substituted or unsubstituted $C_1$-$C_{30}$ alkyl, substituted or unsubstituted $C_6$-$C_{50}$ aryl, substituted or unsubstituted $C_2$-$C_{30}$ alkenyl, substituted or unsubstituted $C_2$-$C_{30}$ alkynyl, substituted or unsubstituted $C_3$-$C_{30}$ cycloalkyl, substituted or unsubstituted $C_3$-$C_{30}$ cycloalkenyl, substituted or unsubstituted $C_2$-$C_{50}$ heteroaryl, substituted or unsubstituted $C_2$-$C_{30}$ heterocycloalkyl, substituted or unsubstituted $C_1$-$C_{30}$ alkoxy, substituted or unsubstituted $C_6$-$C_{50}$ aryloxy, substituted or unsubstituted $C_1$-$C_{30}$ alkylthioxy, substituted or unsubstituted $C_6$-$C_{50}$ arylthioxy, substituted or unsubstituted amine, substituted or unsubstituted silyl, substituted or unsubstituted germanium, substituted or unsubstituted $C_3$-$C_{50}$ mixed aliphatic-aromatic cyclic groups, cyano, and halogen, X is an oxygen (O) or sulfur (S) atom, $L_2$ is a single bond or is selected from substituted or unsubstituted $C_6$-$C_{20}$ arylene and substituted or unsubstituted $C_2$-$C_{20}$ heteroarylene, and m is an integer from 1 to 3, provided that when m is 2 or more, the linkers $L_2$ are the same as or different from each other,

[Formula A-2]

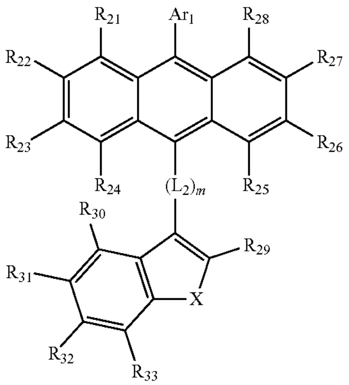

wherein $A_{11}$, $R_{21}$ to $R_{33}$, X, $L_2$, and m are as defined in Formula A-1, the "substituted" in the definitions of $A_{11}$, $R_{21}$ to $R_{33}$, and $L_2$ in Formulas A-1 and A-2 having the same meaning as defined in claim 1.

3. The organic light emitting device according to claim 1, wherein the compound represented by Formula A is selected from the following compounds A-1 to A-88:

A-1

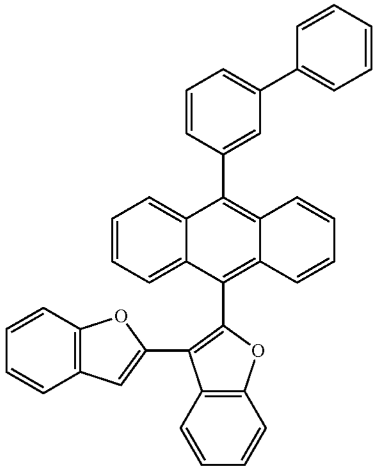

A-2

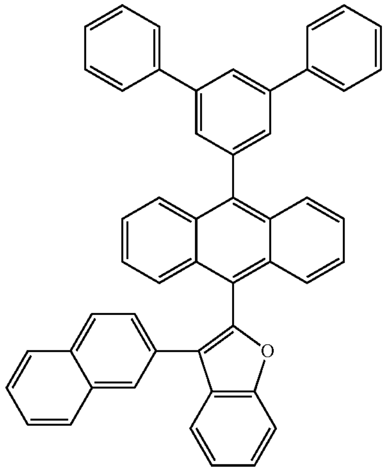

A-3

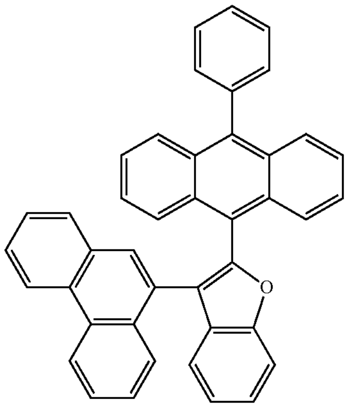

-continued
A-4
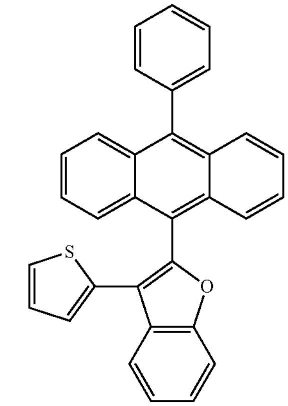
A-5
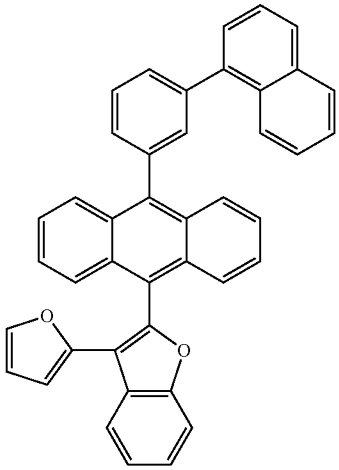
A-6
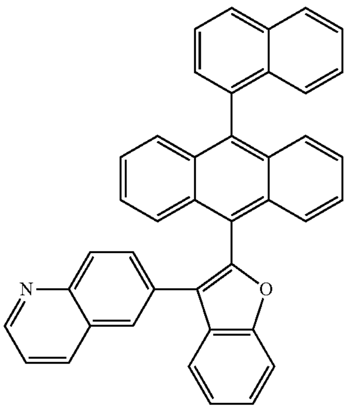
-continued
A-7
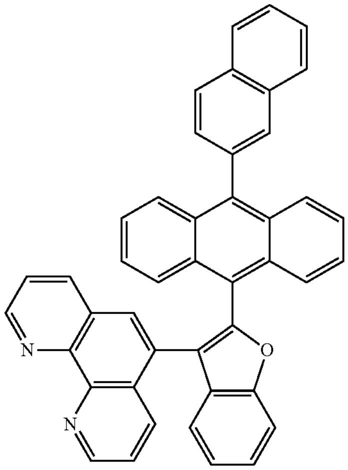
A-8
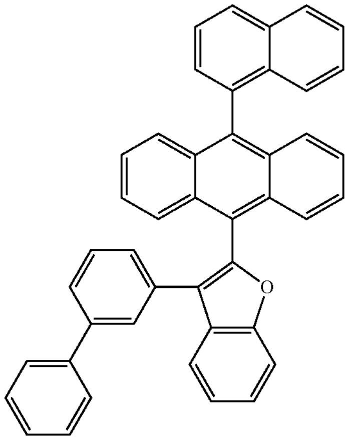
A-9
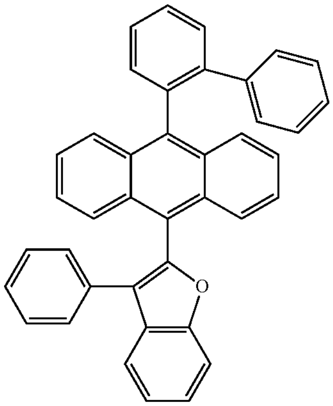

-continued
A-10
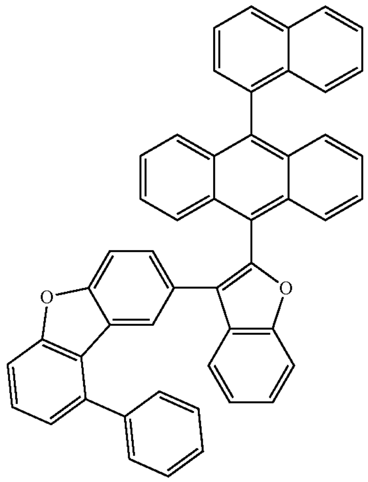
A-11
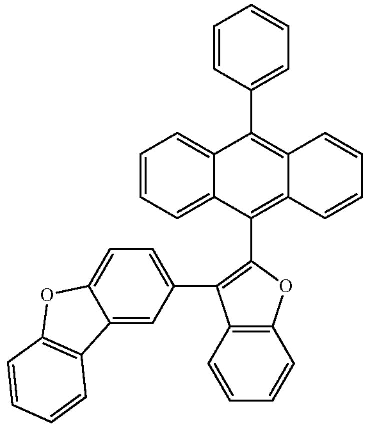
A-12
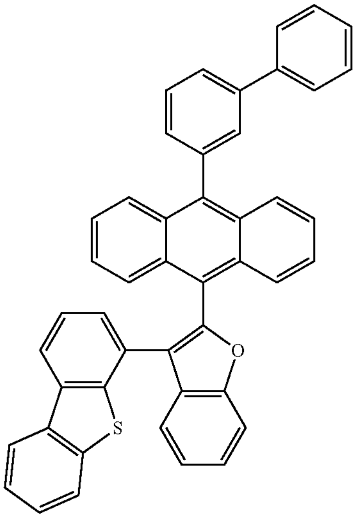
-continued
A-13
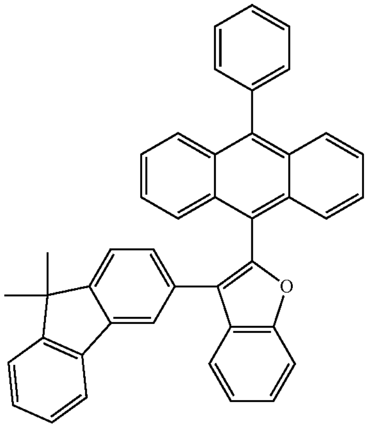
A-14
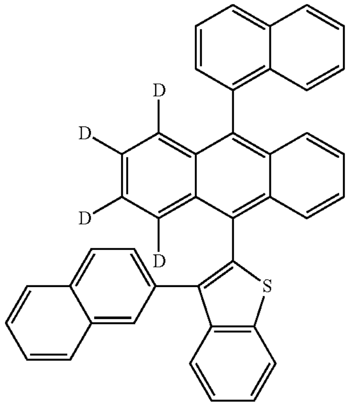
A-15
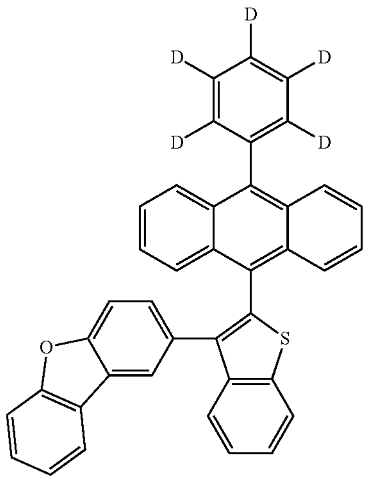

A-16
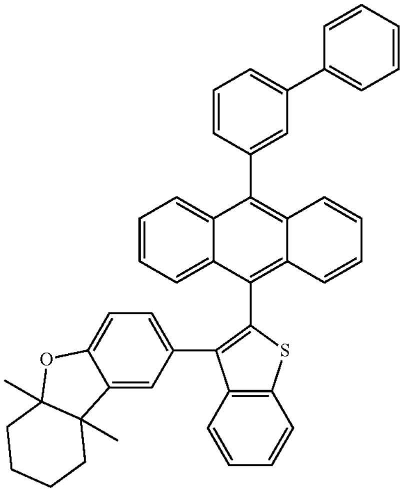
A-17
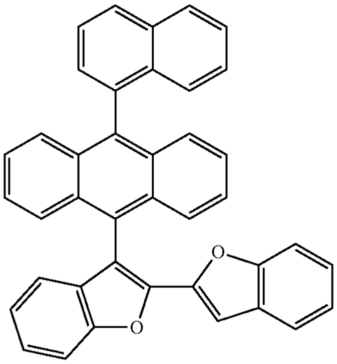
A-18
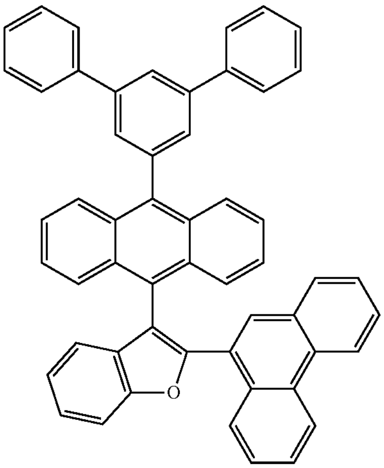
A-19
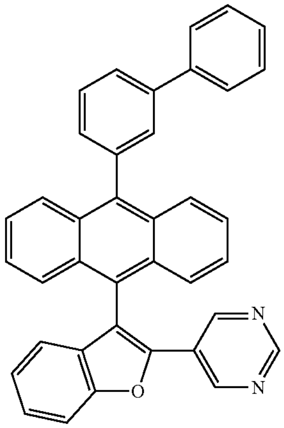
A-20
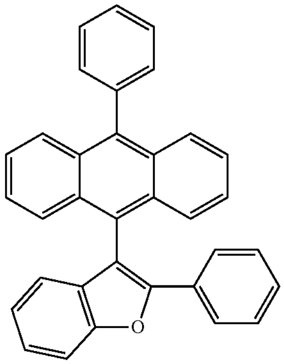
A-21
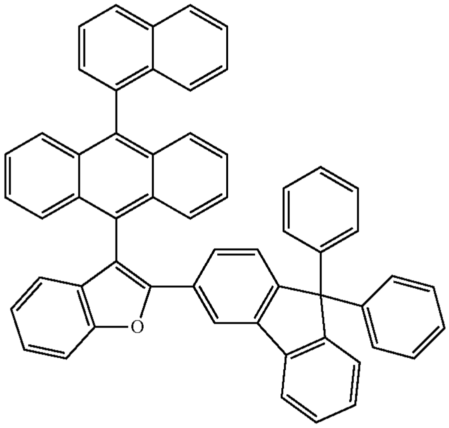
A-22
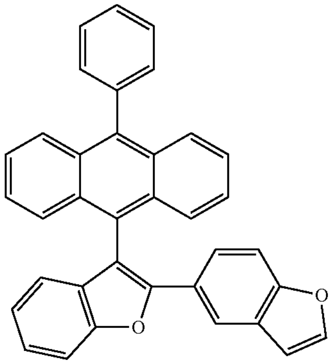

-continued
A-23
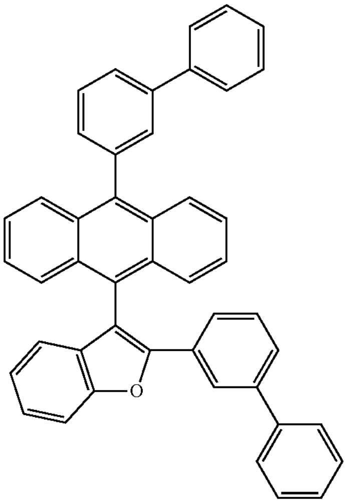
A-24
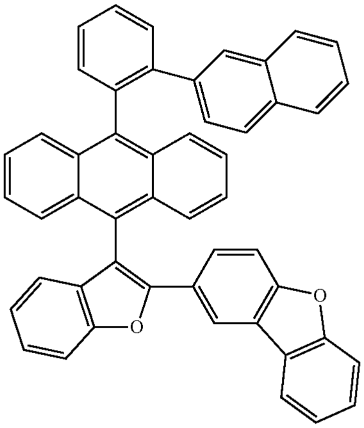
A-25
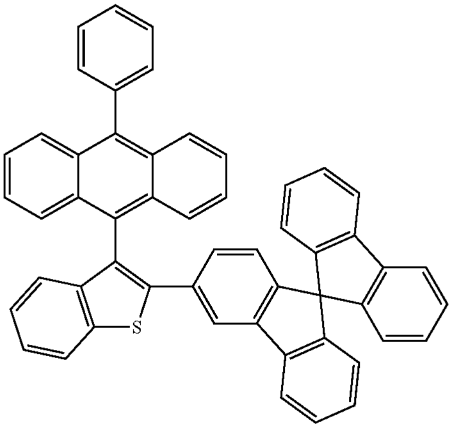
-continued
A-26
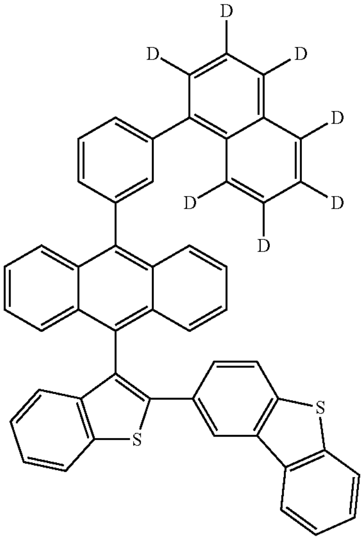
A-27
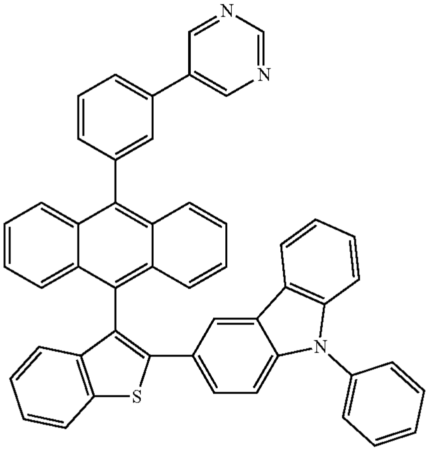
A-28
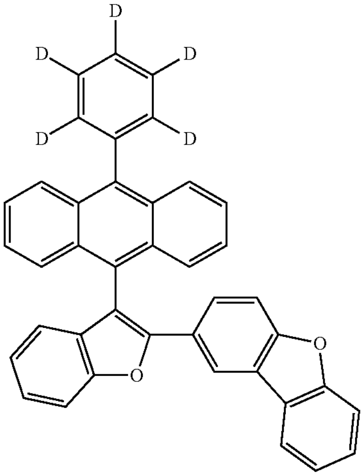

-continued
A-29
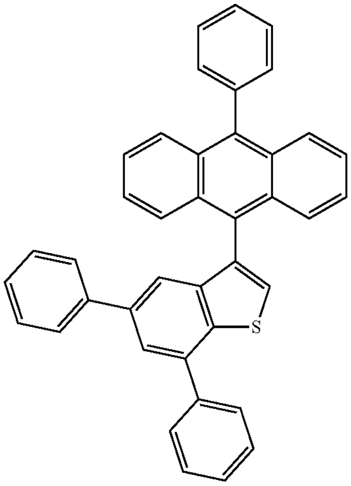
A-30
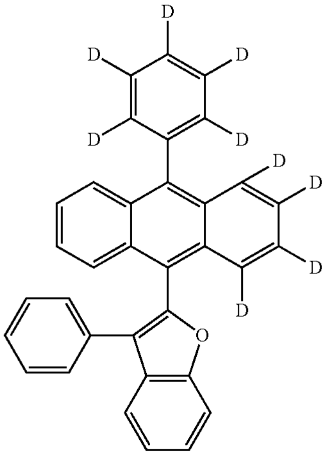
A-31
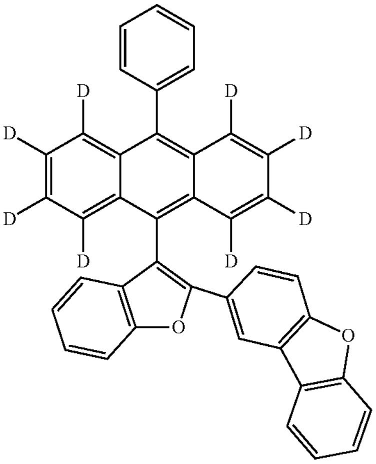
-continued
A-32
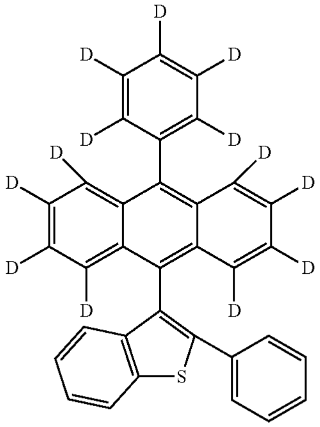
A-33
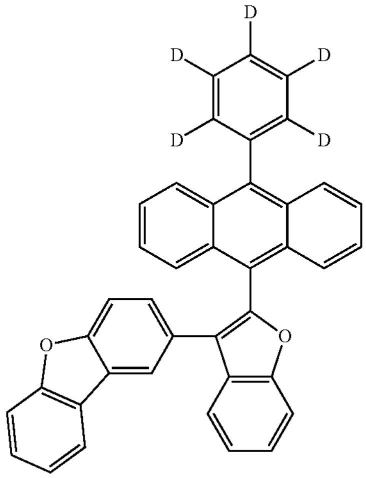
A-34
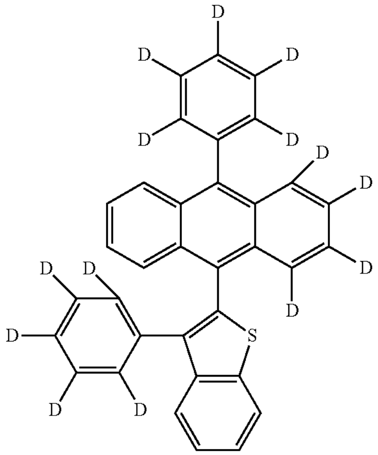

-continued
A-35
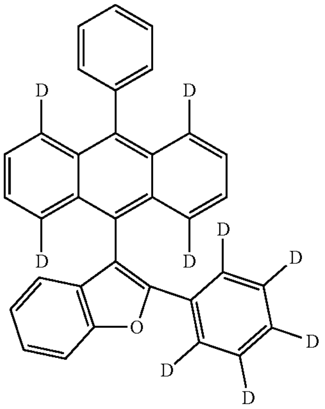
A-36
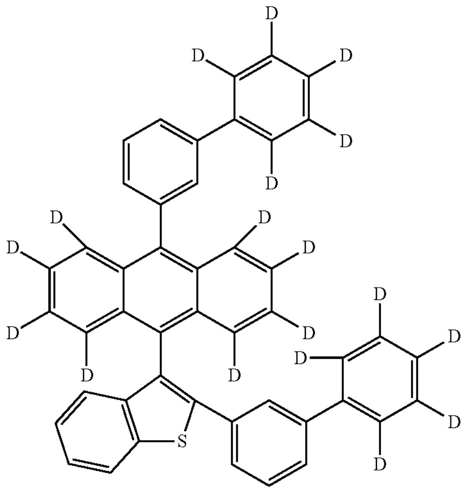
A-37
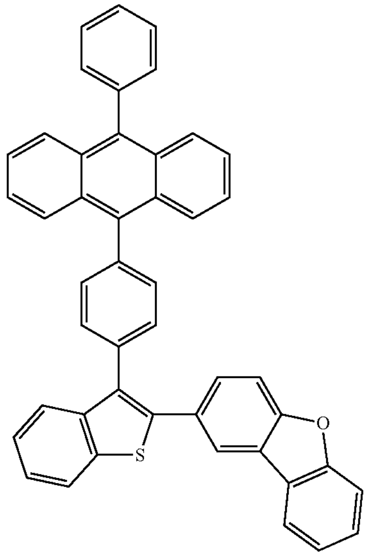
-continued
A-38
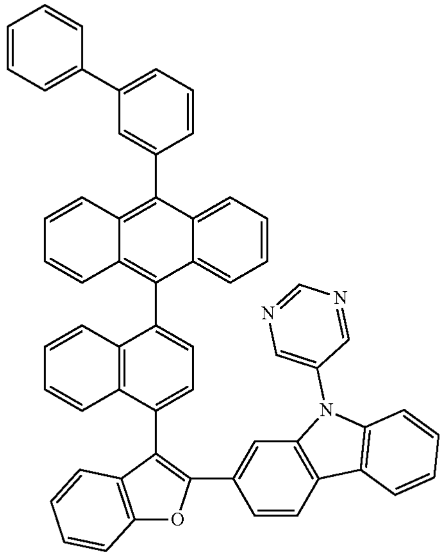
A-39
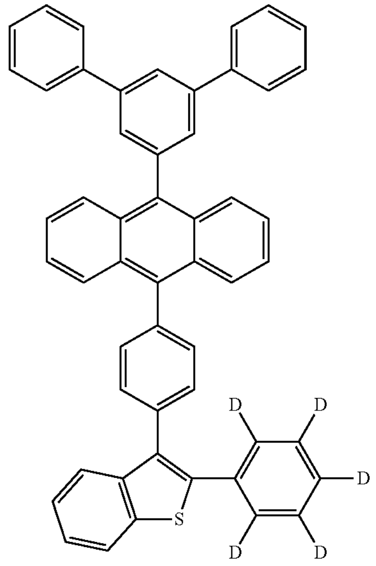
A-40
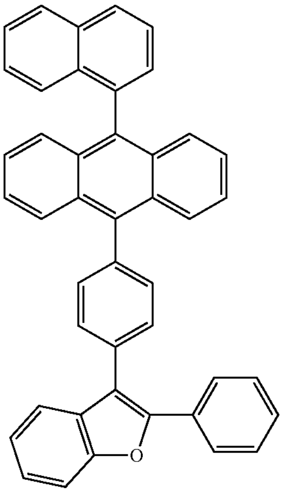

A-41
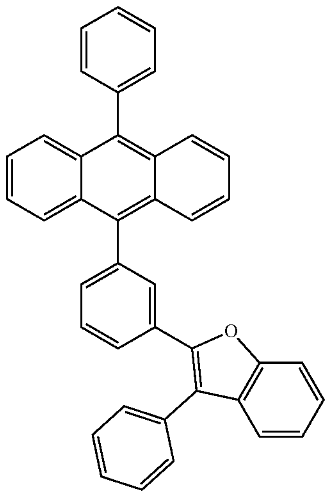
A-42
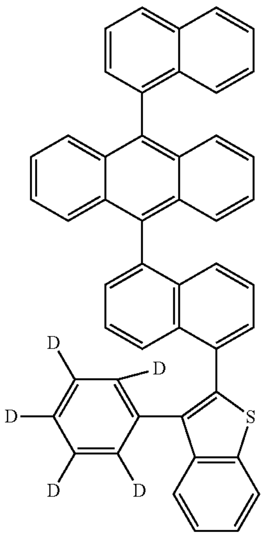
A-43
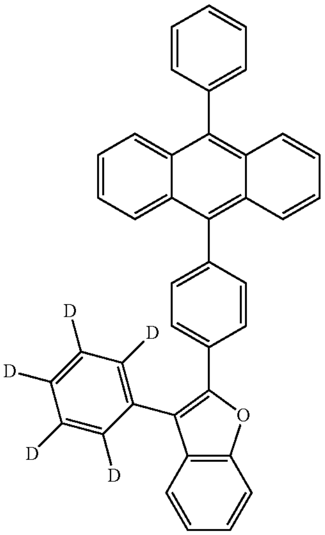
A-44
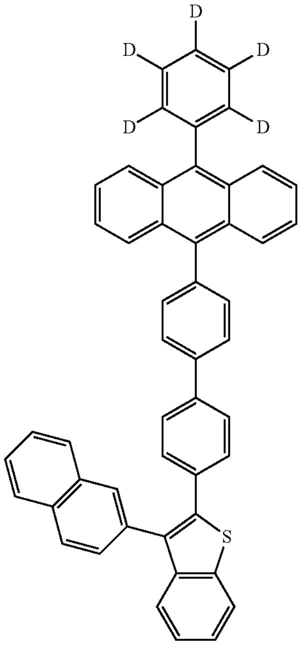
A-45
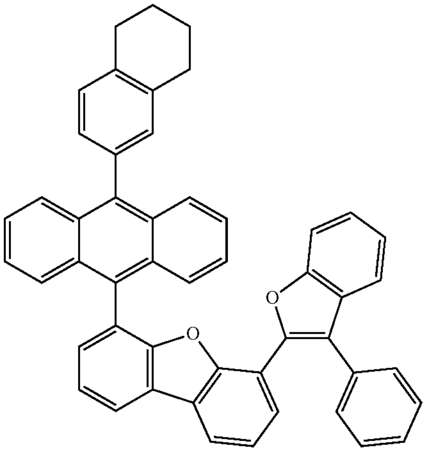
A-46
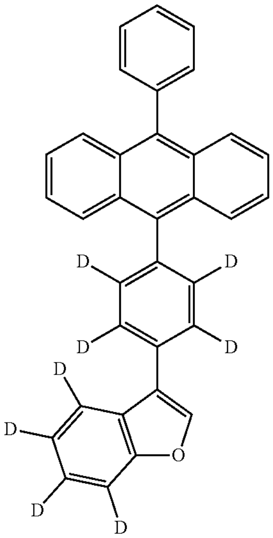

-continued
A-47
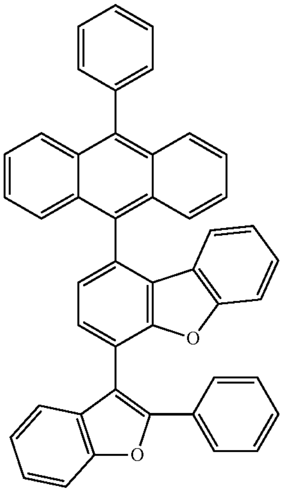
A-48
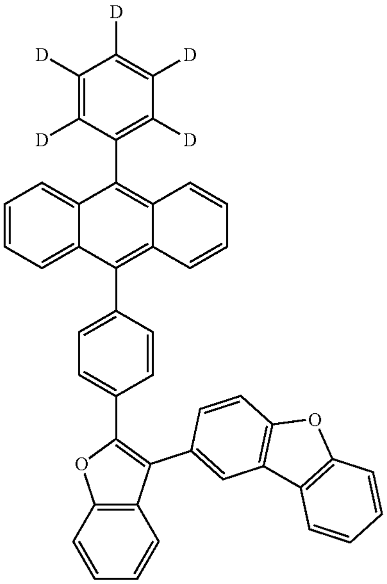
A-49
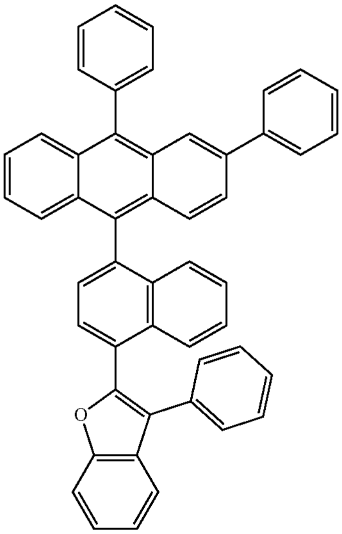
-continued
A-50
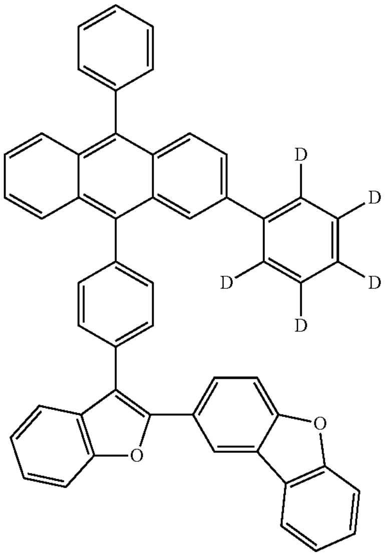
A-51
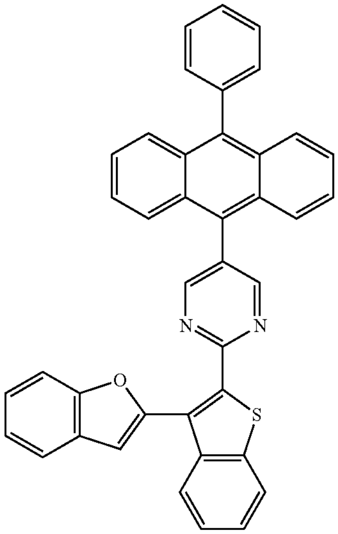

-continued
A-52
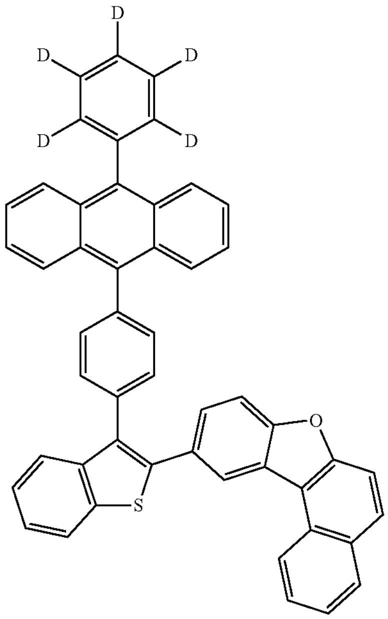
A-53
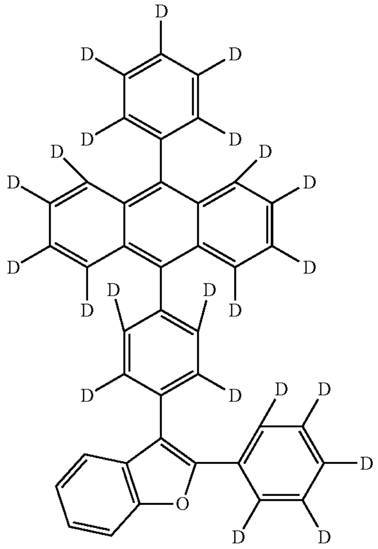
A-54
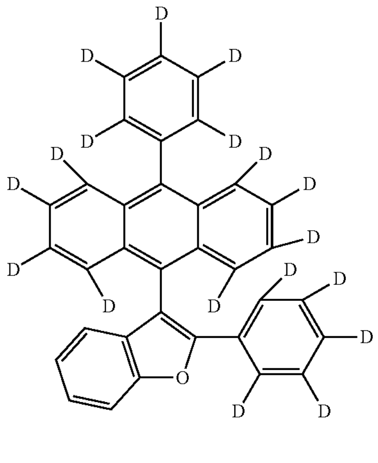
-continued
A-55
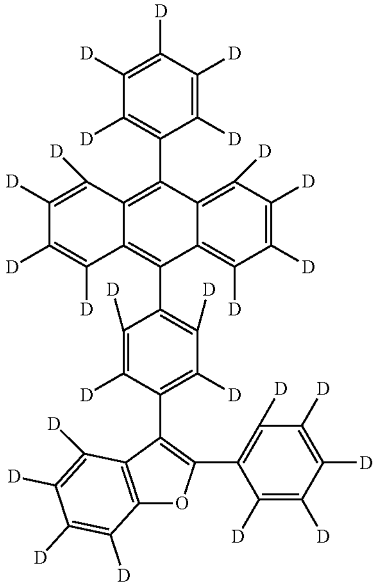
A-56
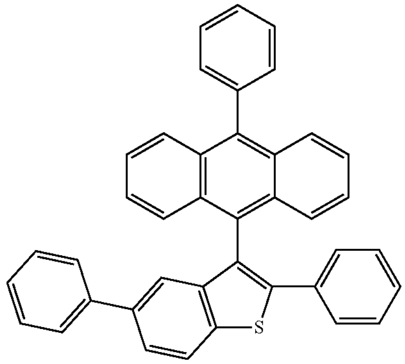
A-57
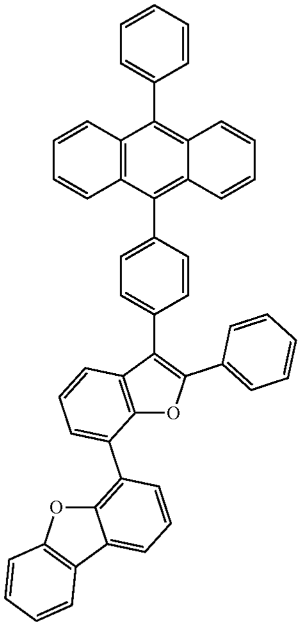

A-58
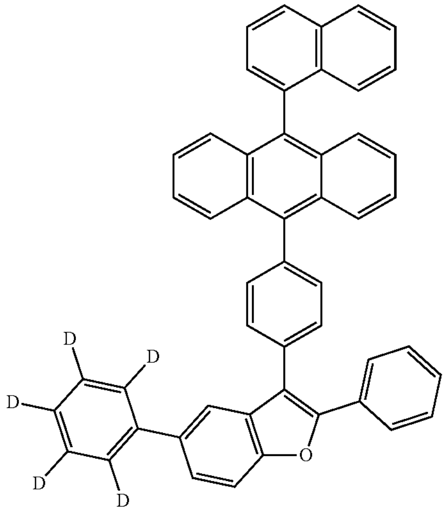
A-59
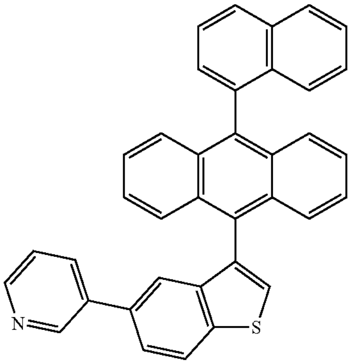
A-60
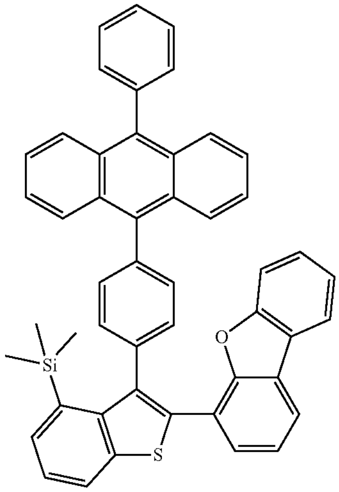
A-61
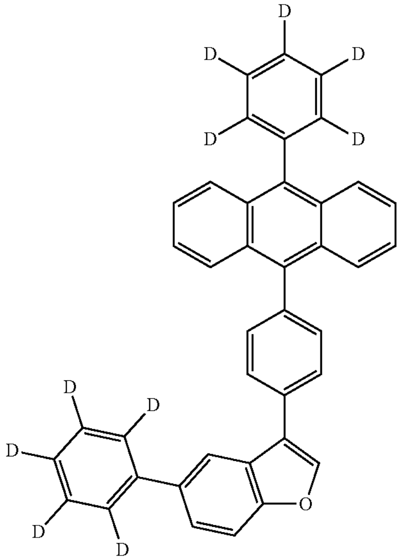
A-62
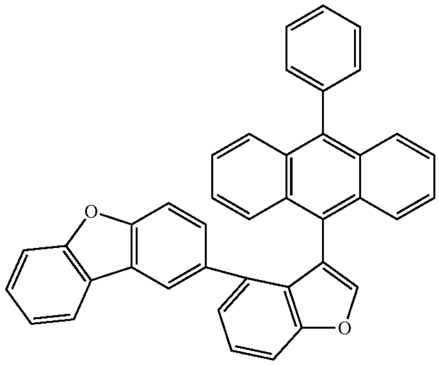
A-63
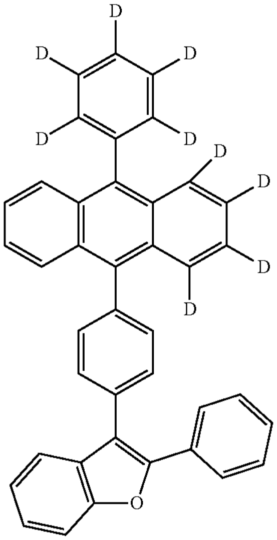

-continued
A-64
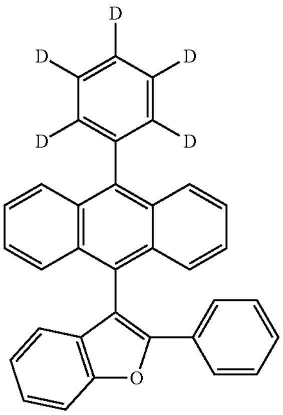
A-65
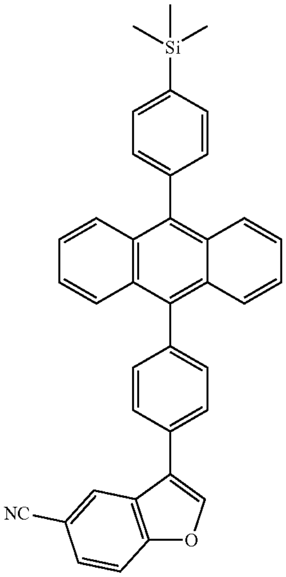
A-66
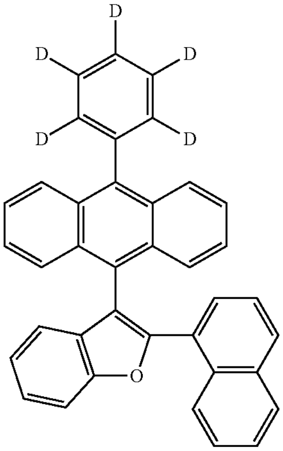
-continued
A-67
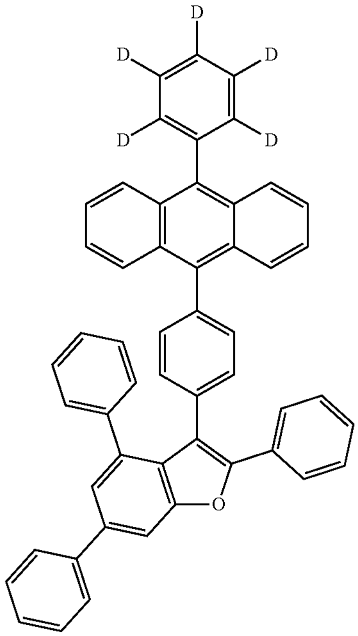
A-68
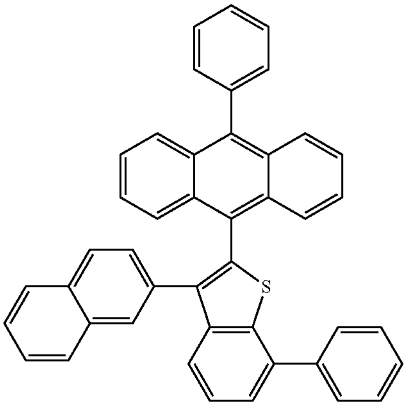
A-69
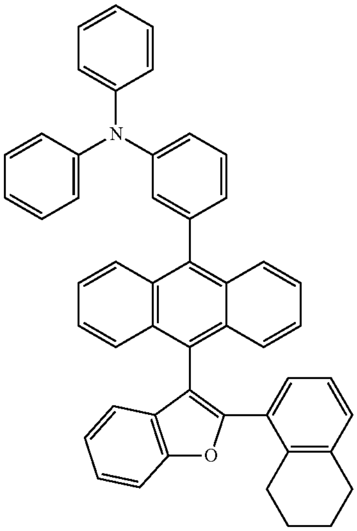

-continued
A-70
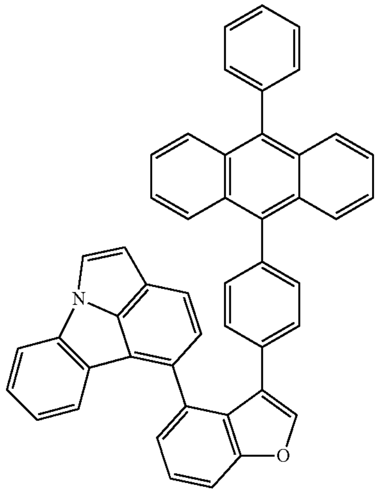
A-71
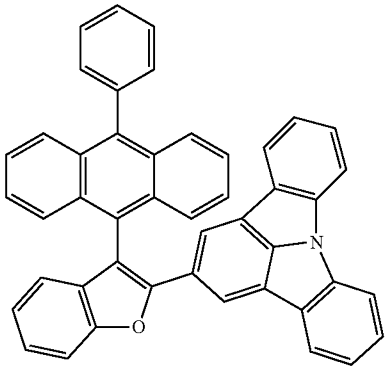
A-72
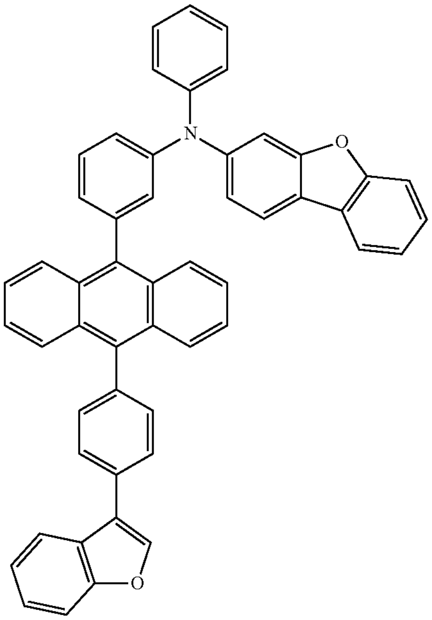
-continued
A-73
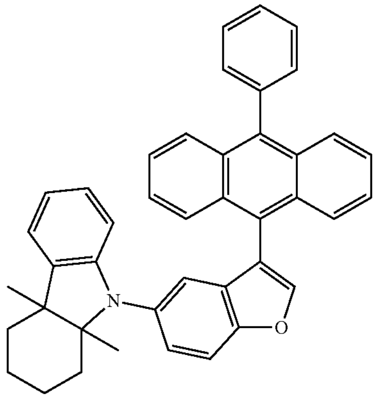
A-74
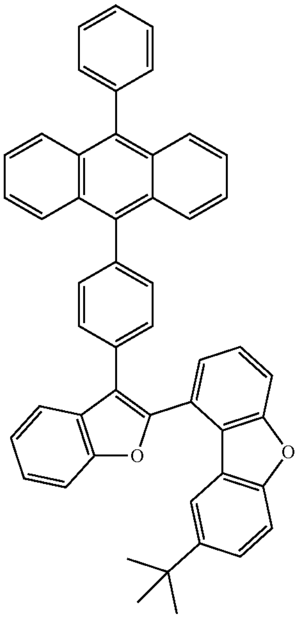
A-75
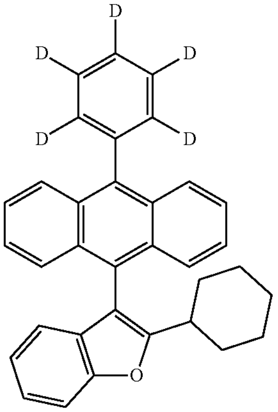

-continued
A-76
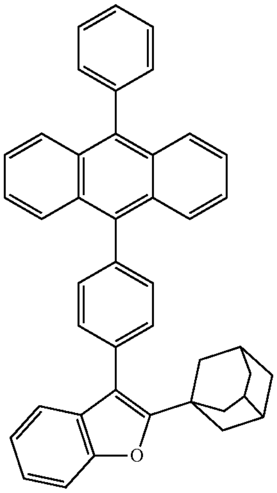
A-77
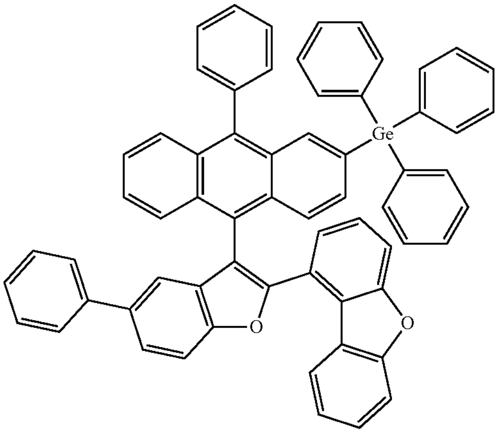
A-78
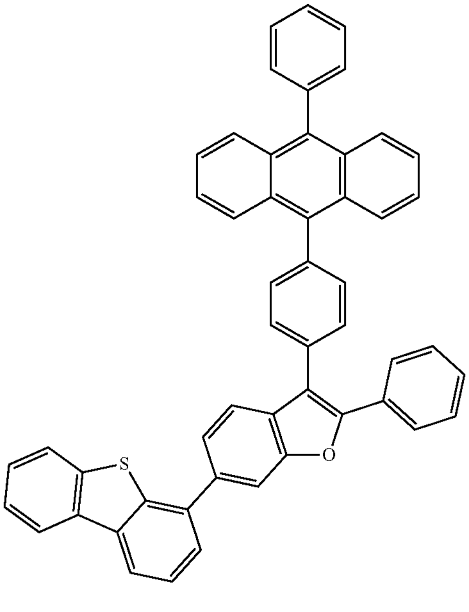
-continued
A-79
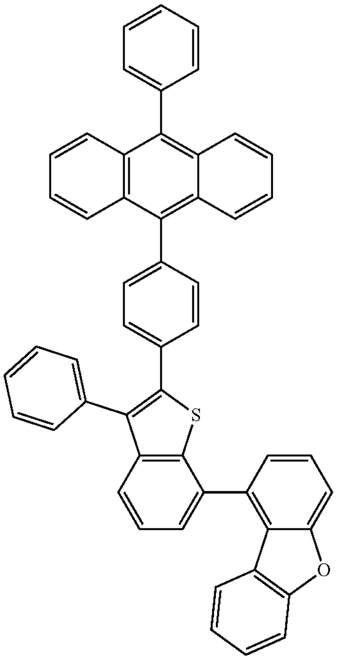
A-80
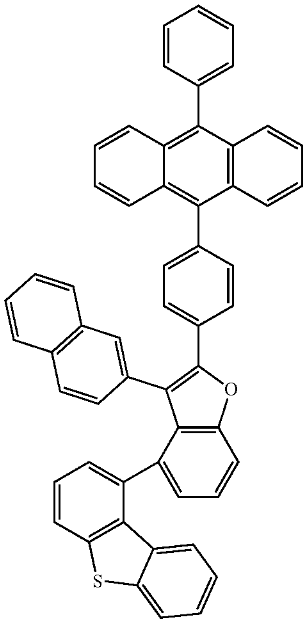

-continued
A-81
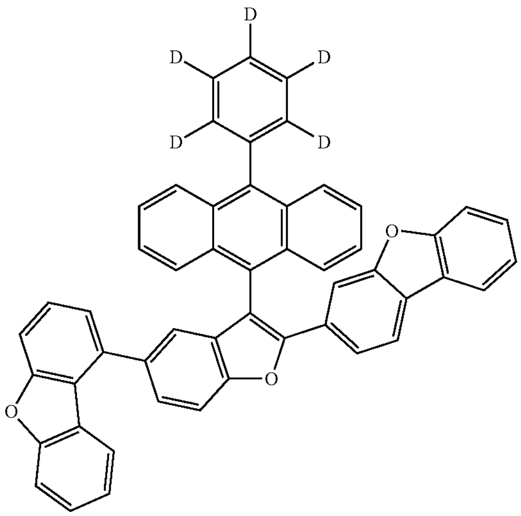
A-82
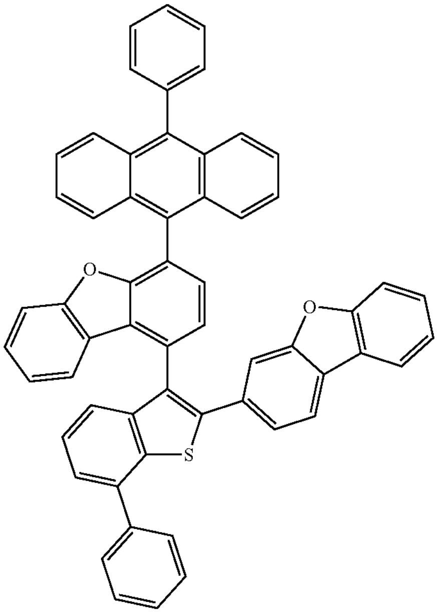
A-83
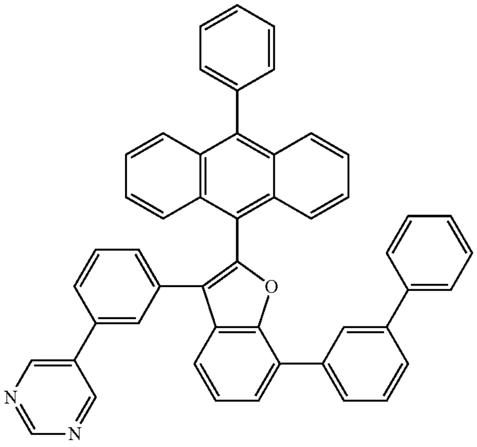
-continued
A-84
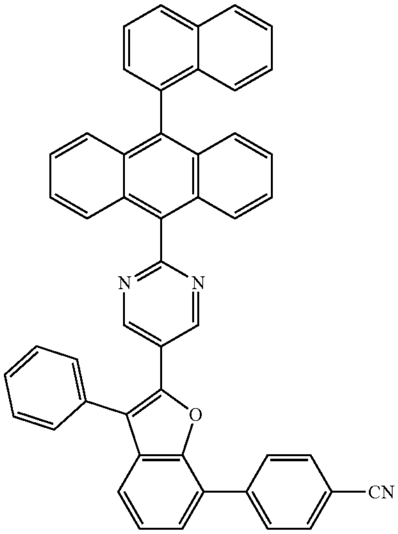
A-85
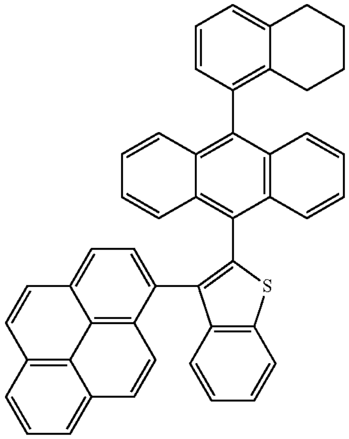
A-86
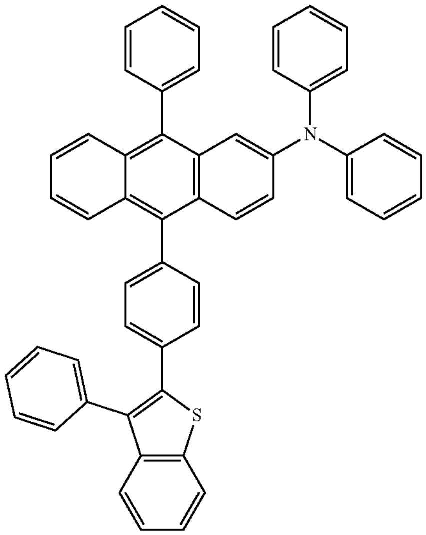

-continued
A-87
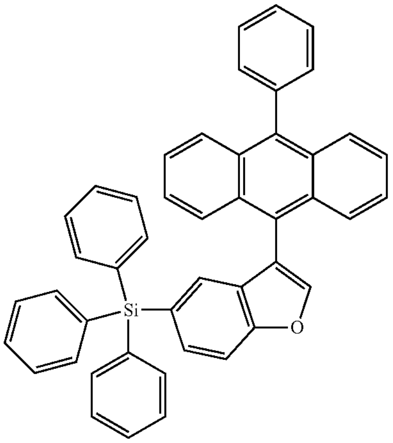
A-88
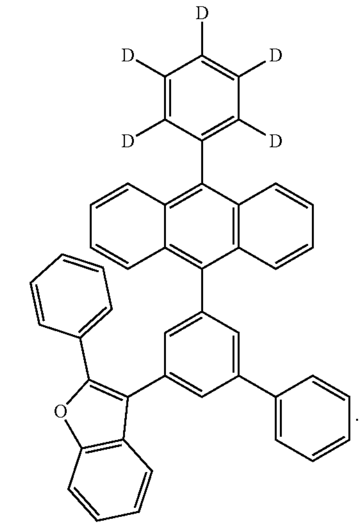
4. The organic light emitting device according to claim 1, wherein the compound represented by Formula D-1 is selected from the following compounds D-101 to D-130:
D-101
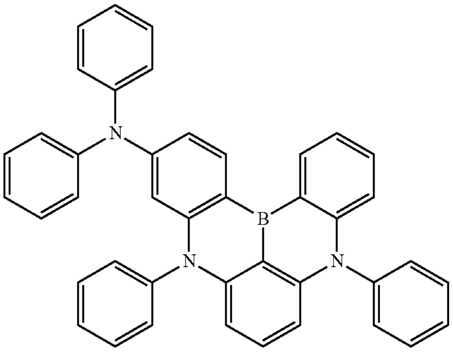
-continued
D-102
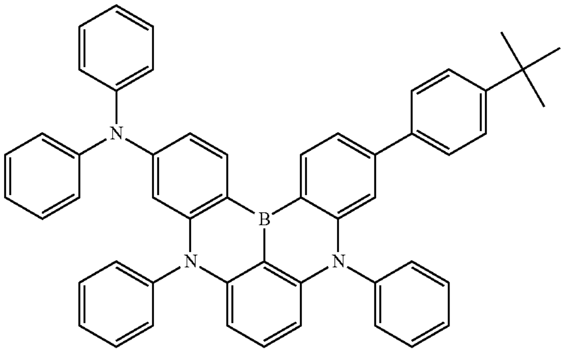
D-103
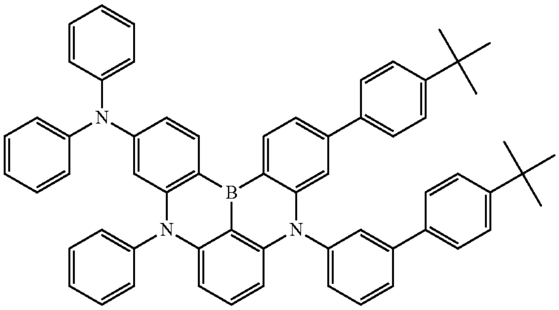
D-104
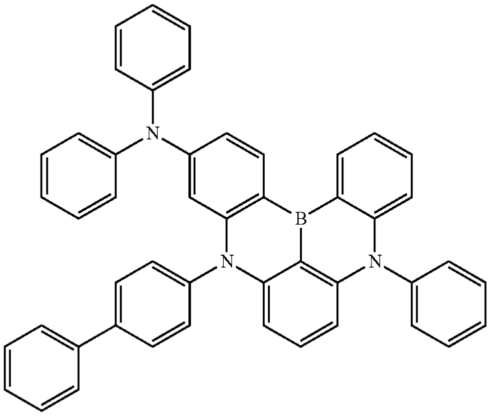
D-105
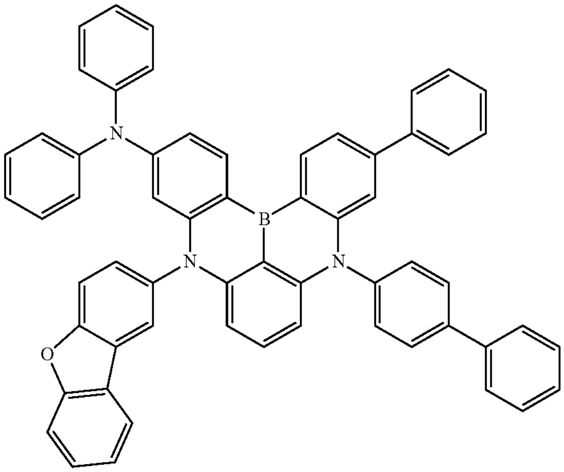

-continued
D-106
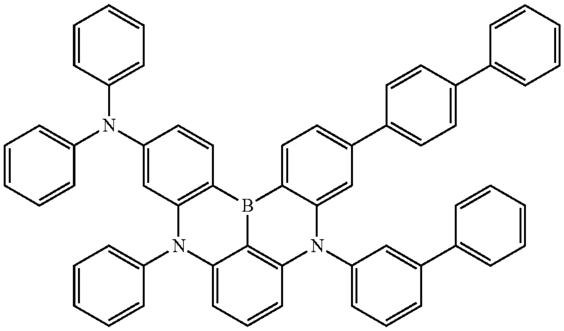
D-107
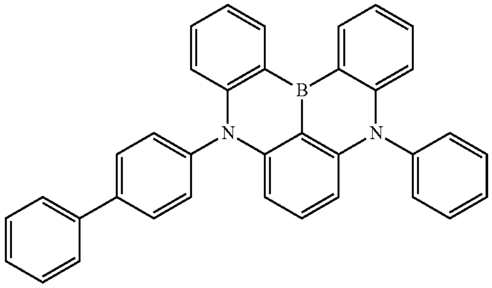
D-108
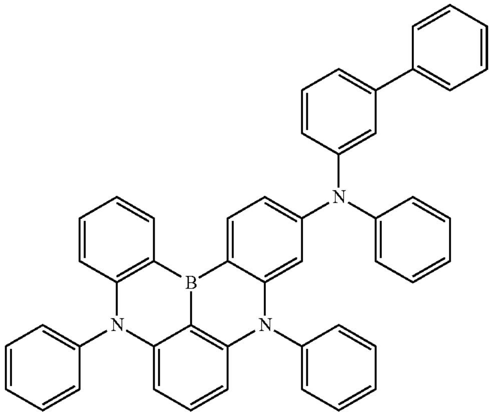
D-109
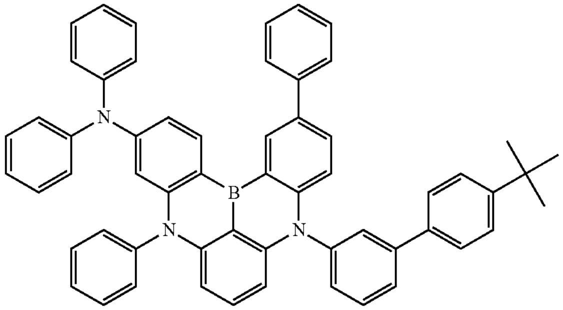
-continued
D-110
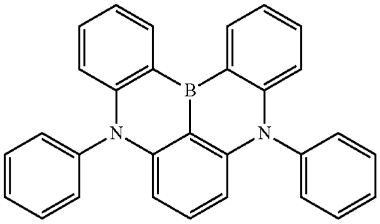
D-111
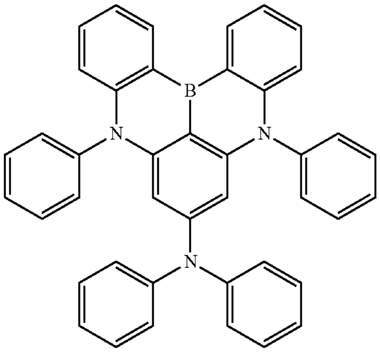
D-112
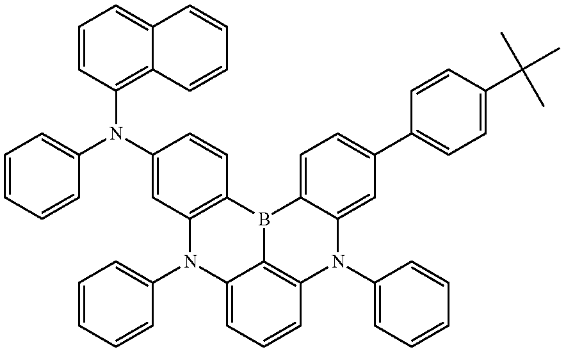
D-113
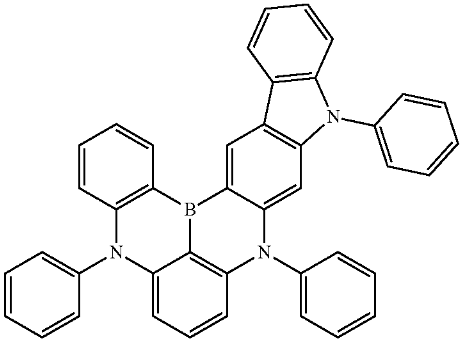

D-114
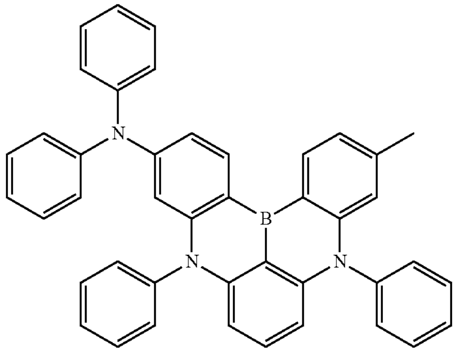
D-115
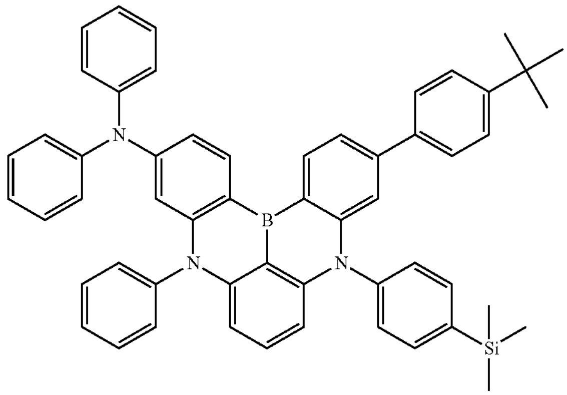
D-116
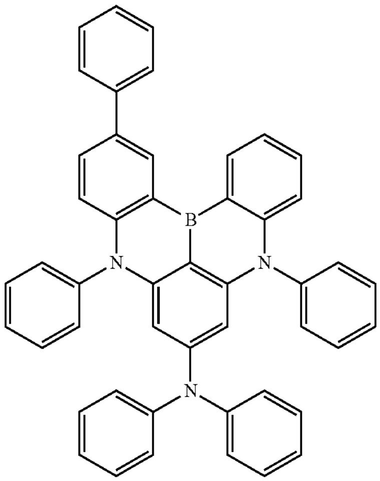
D-117
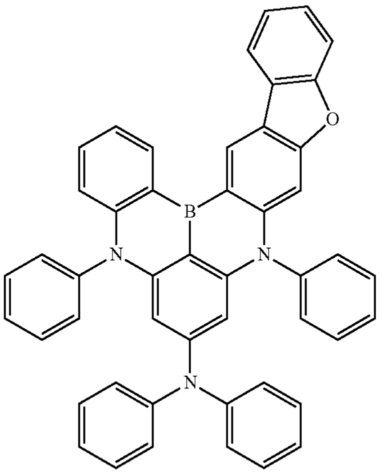
D-118
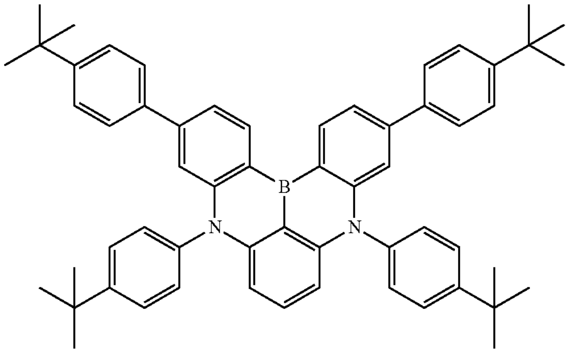
D-119
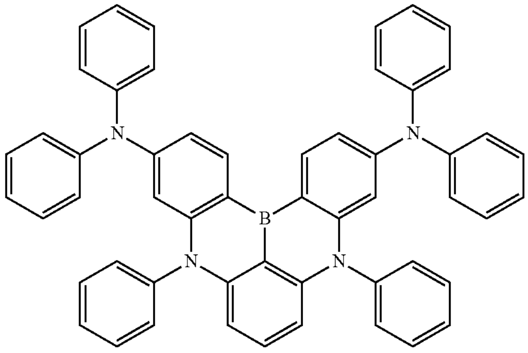

-continued
D-120
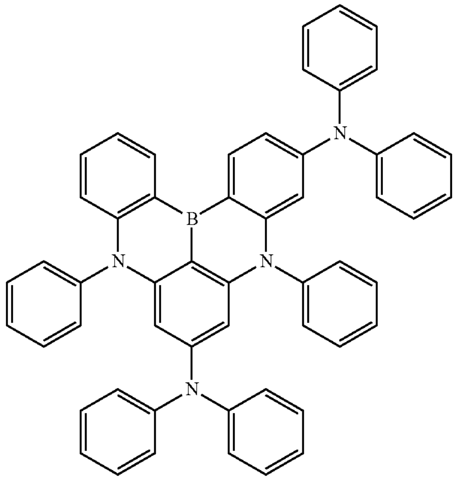
D-121
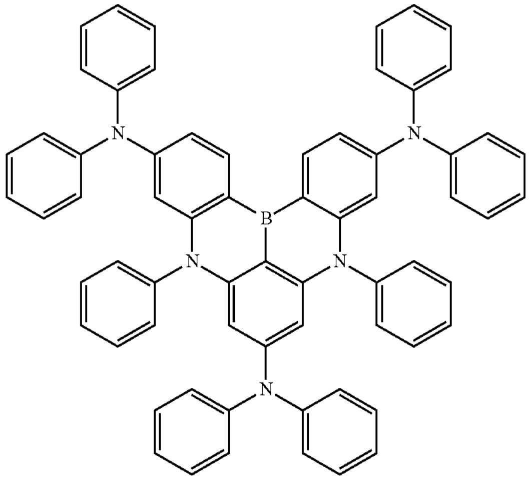
D-122
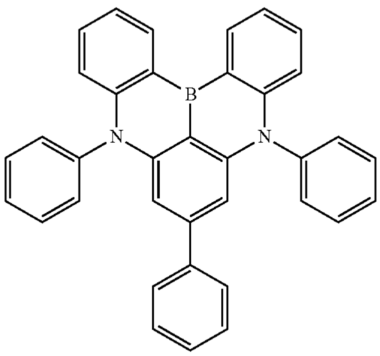
D-123
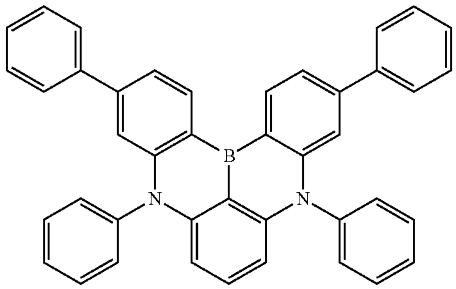
-continued
D-124
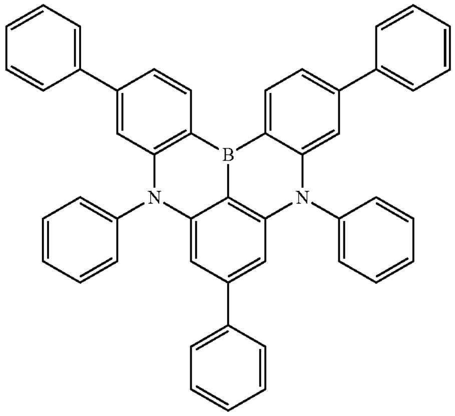
D-125
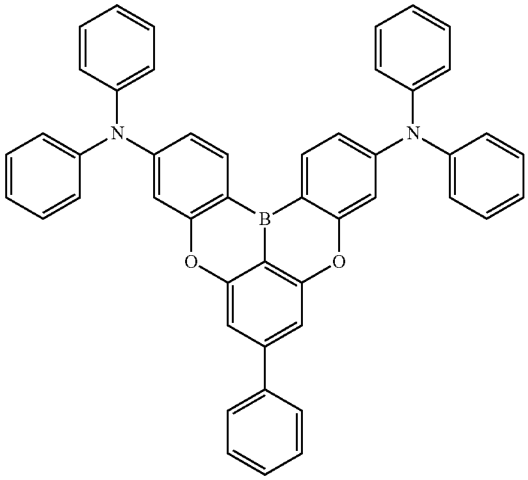
D-126
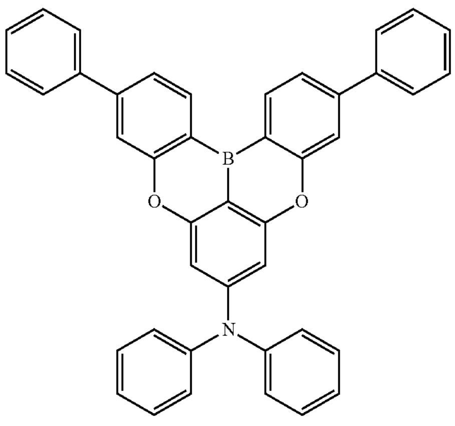

-continued
D-127
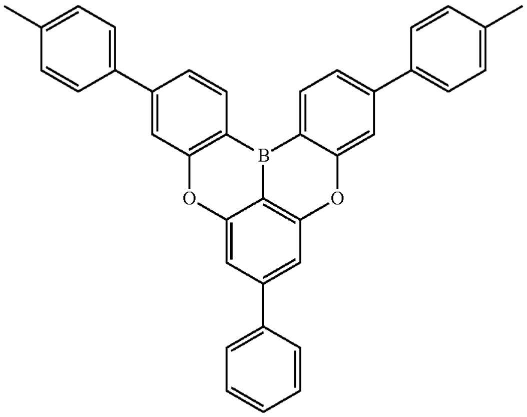
D-128
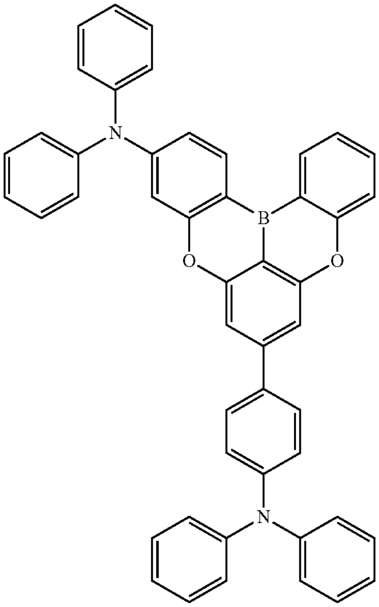
D-129
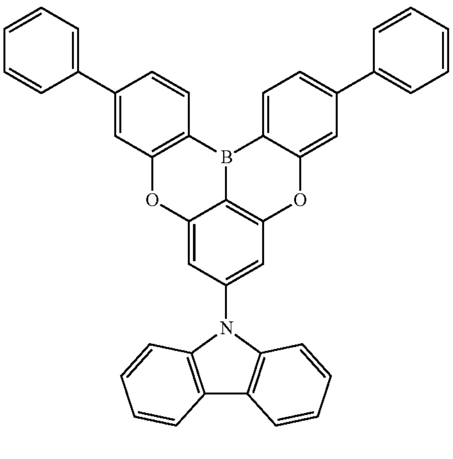
-continued
D-130
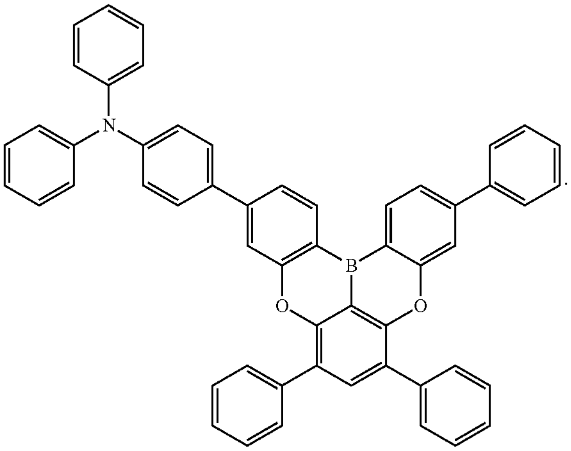
5. The organic light emitting device according to claim 1, wherein the compounds represented by Formulas D-2 and D-3 are selected from the following compounds D-201 to D-332:
D-201
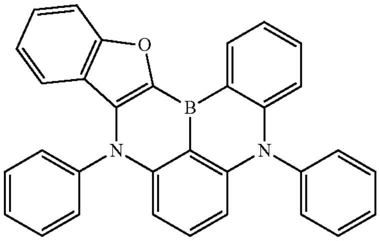
D-202
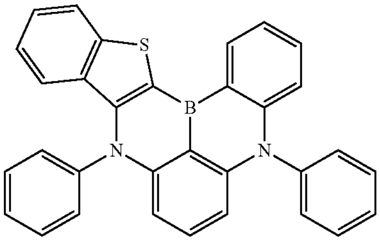
D-203
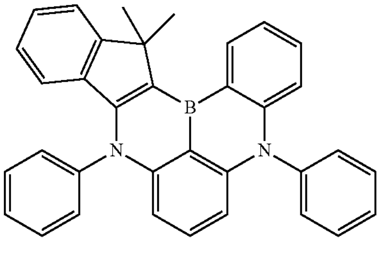

-continued
D-204
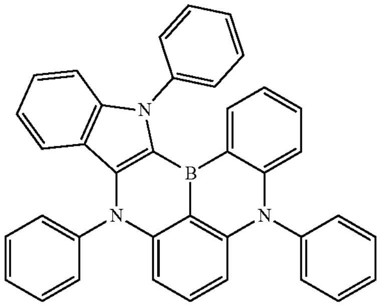
D-205
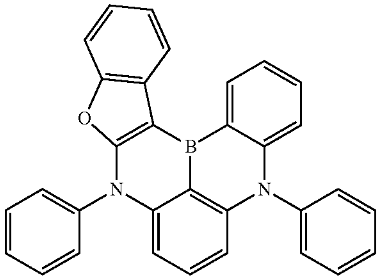
D-206
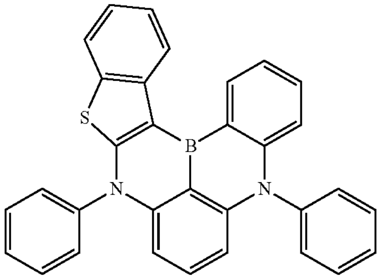
D-207
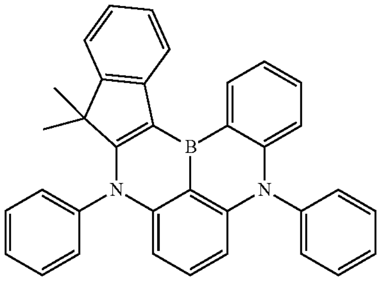
D-208
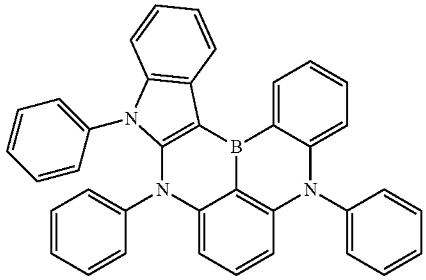
-continued
D-209
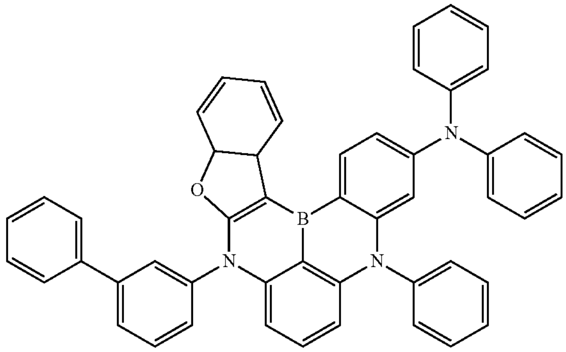
D-210
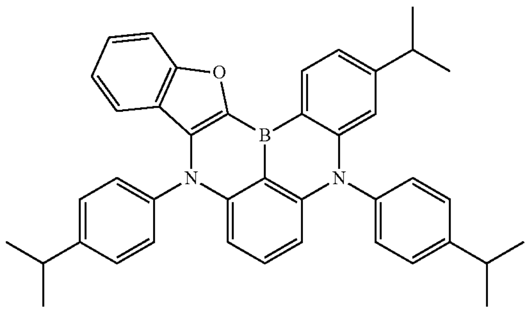
D-211
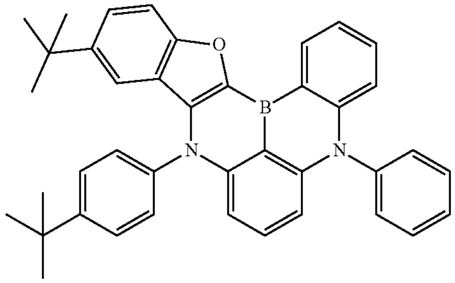
D-212
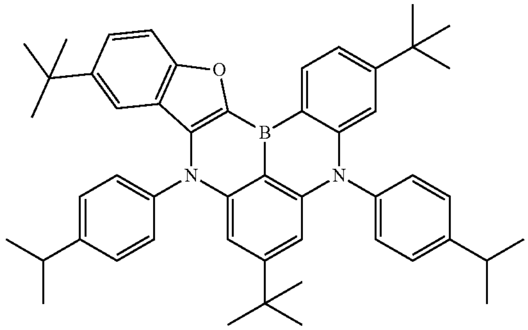

-continued
D-213
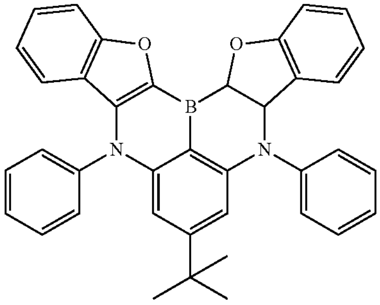
D-214
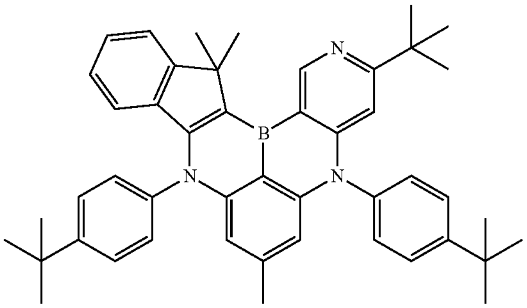
D-215
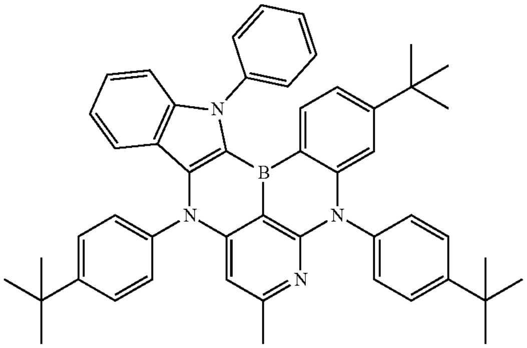
D-216
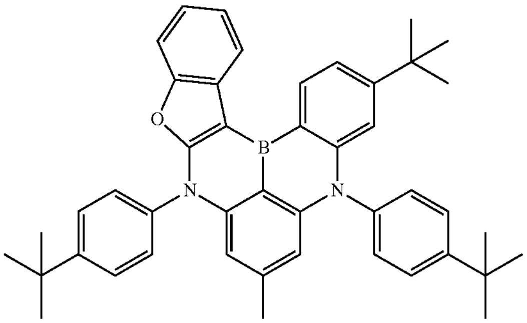
D-217
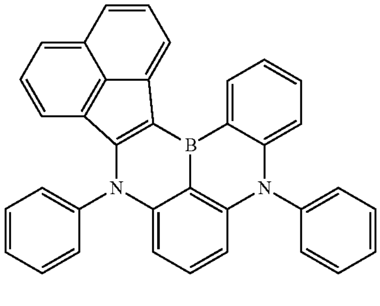
-continued
D-218
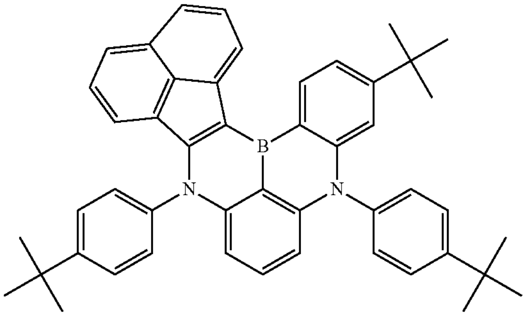
D-219
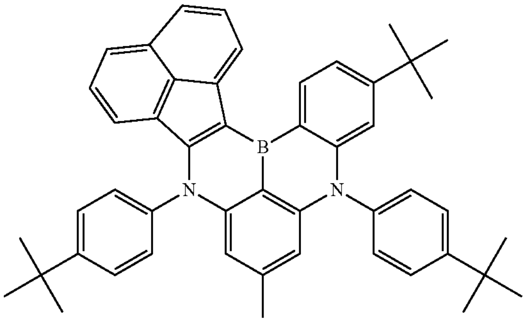
D-220
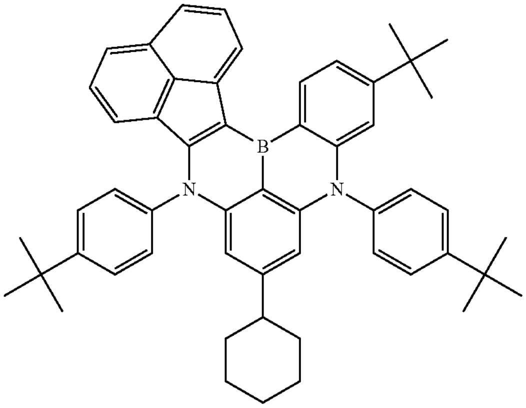
D-221
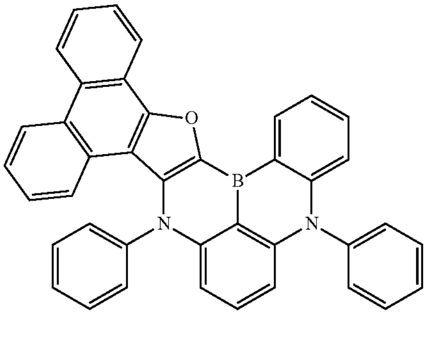

-continued
D-222
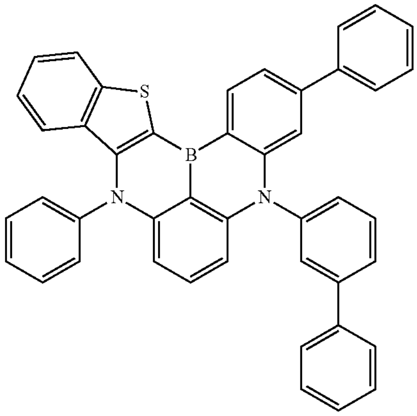
D-223
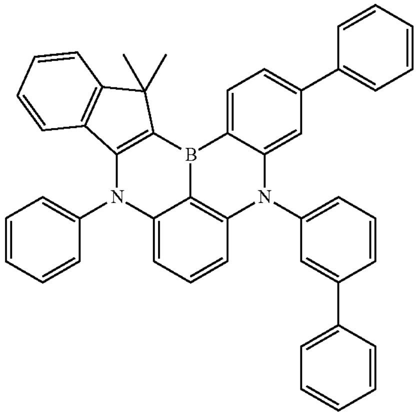
D-224
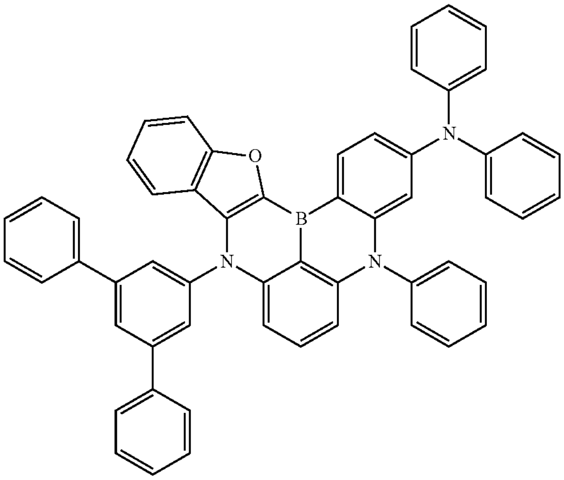
-continued
D-225
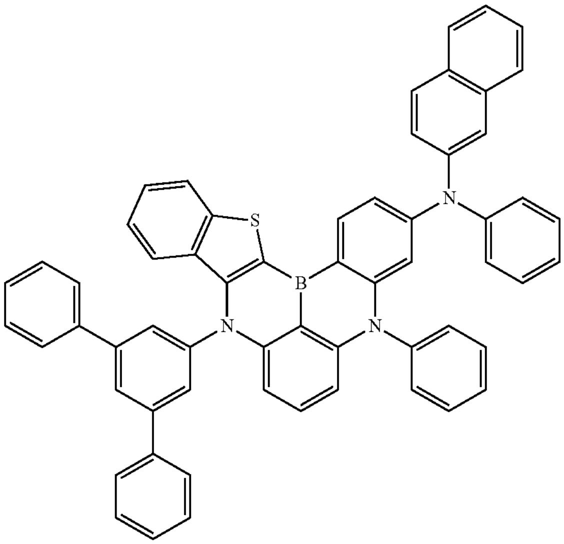
D-226
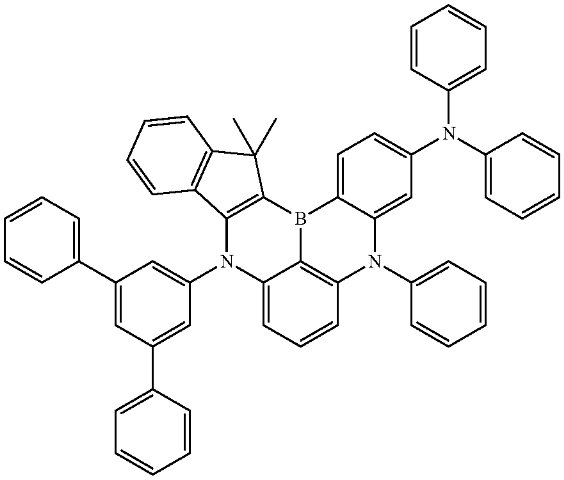
D-227
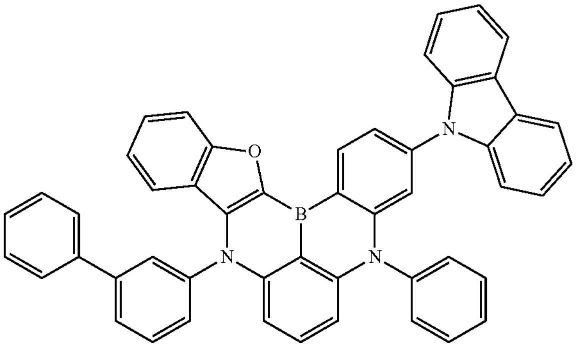

-continued
D-228
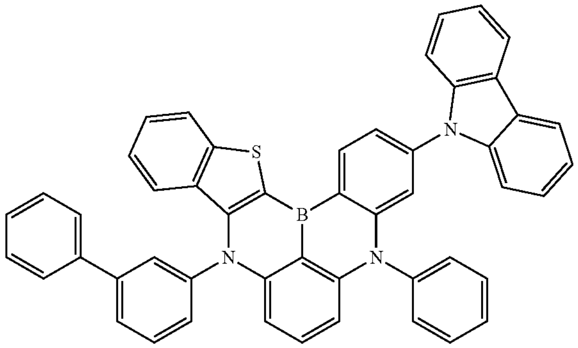
D-229
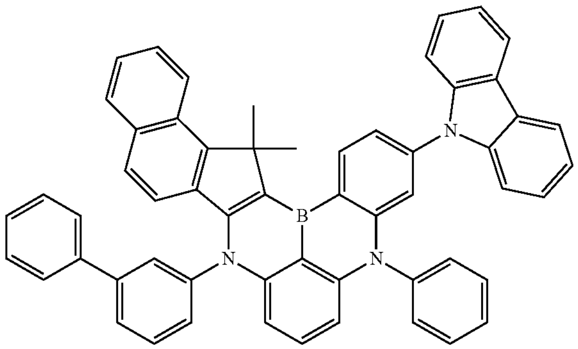
D-230
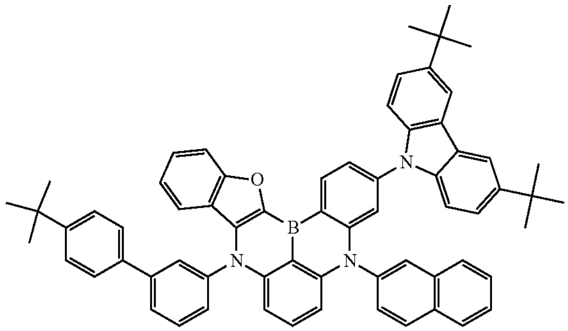
D-231
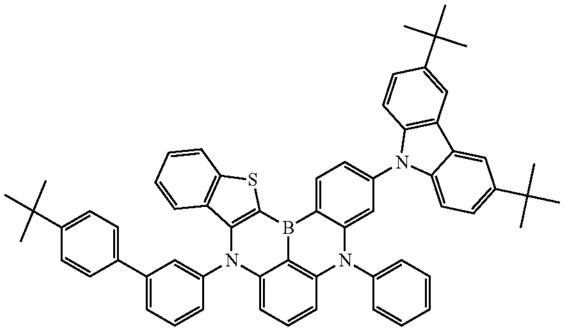
-continued
D-232
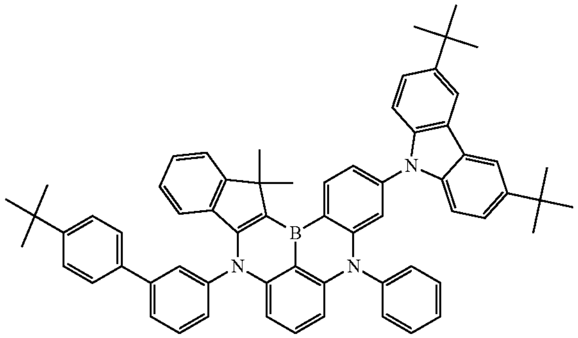
D-233
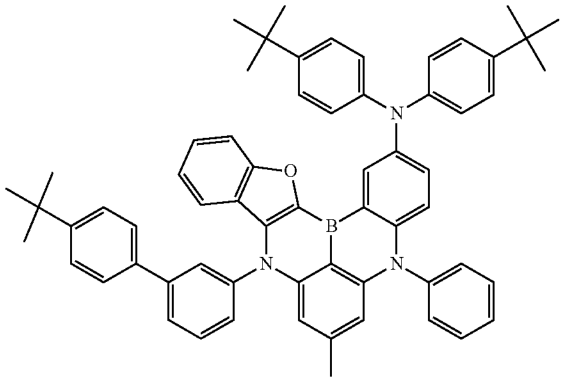
D-234
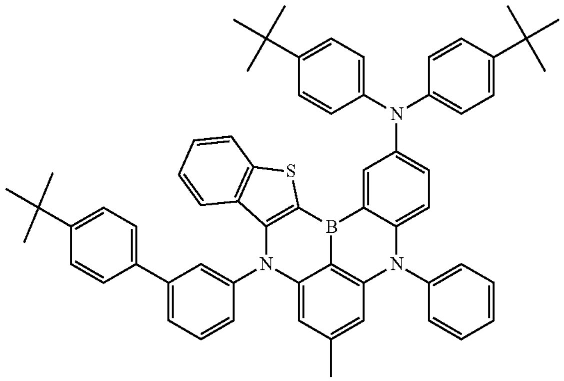
D-235
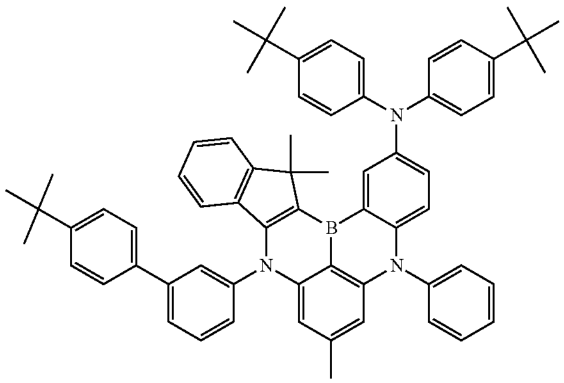

D-236
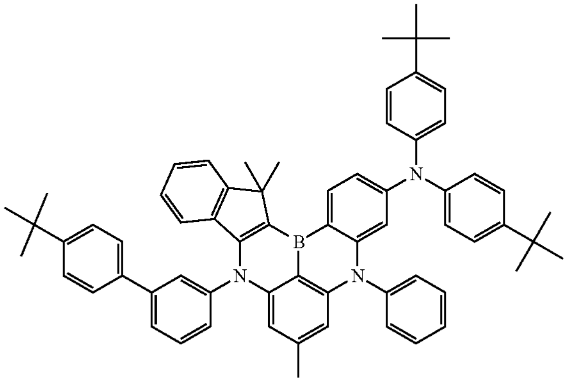
D-237
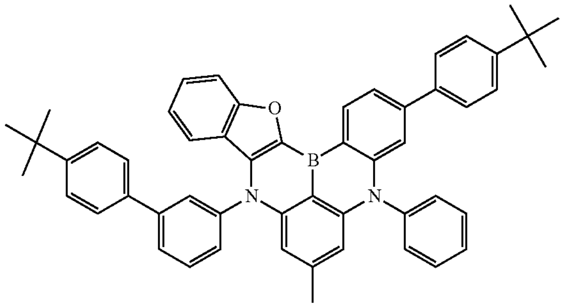
D-238
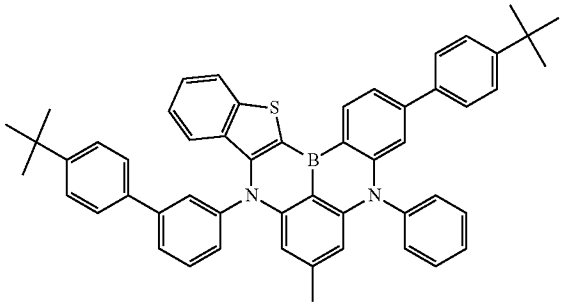
D-239
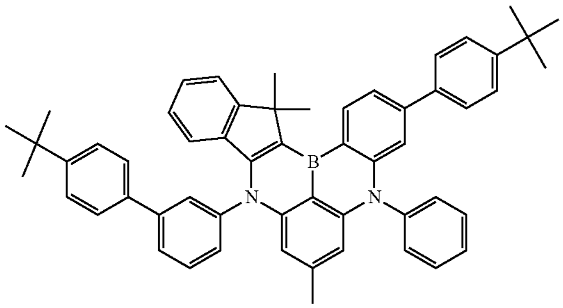
D-240
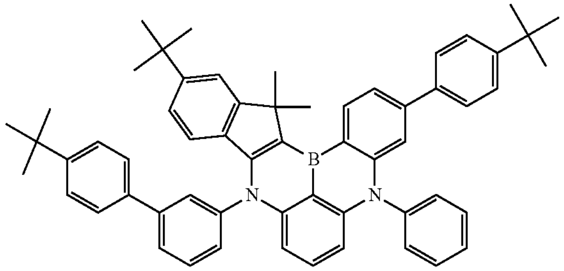
D-241
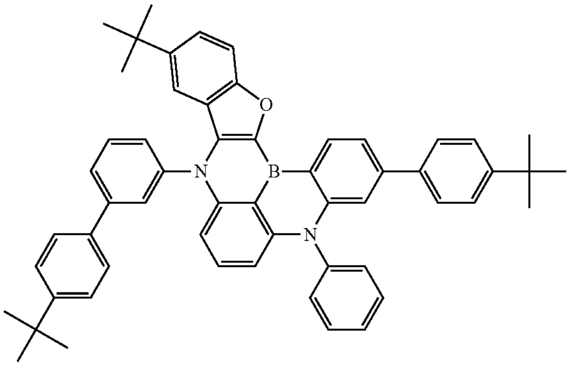
D-242
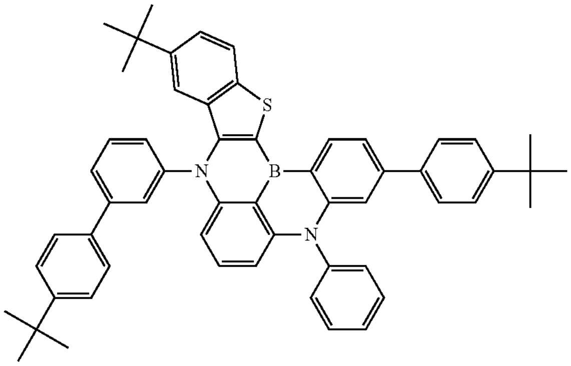
D-243
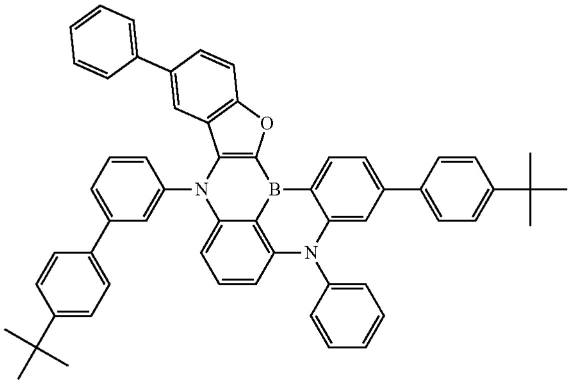

-continued
D-244
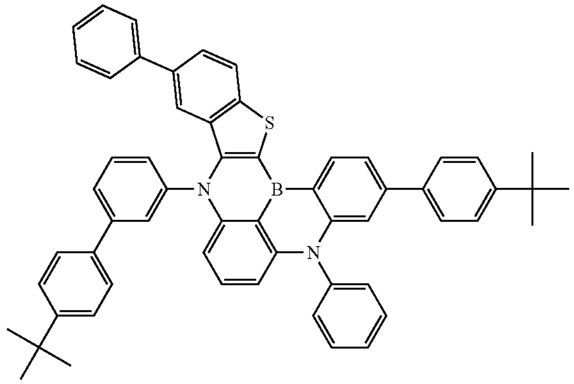
D-245
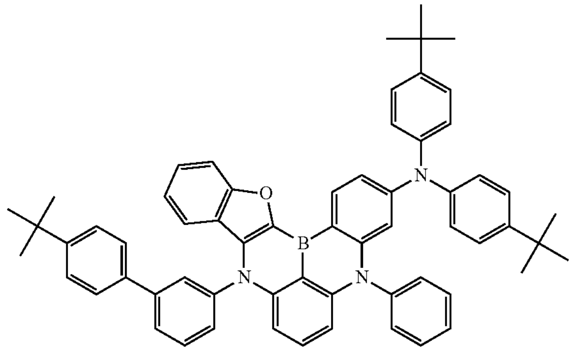
D-246
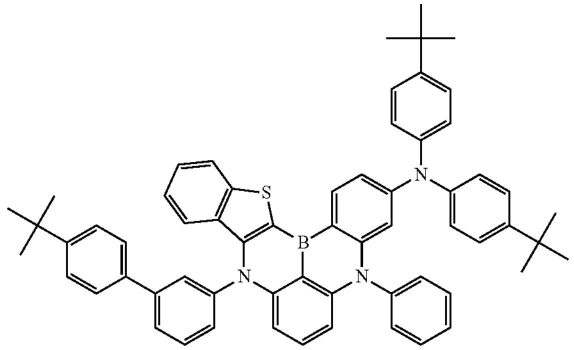
D-247
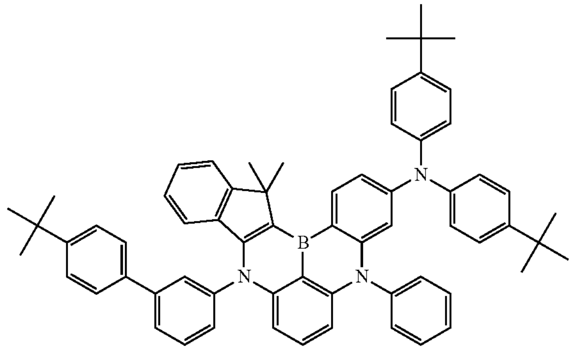
-continued
D-248
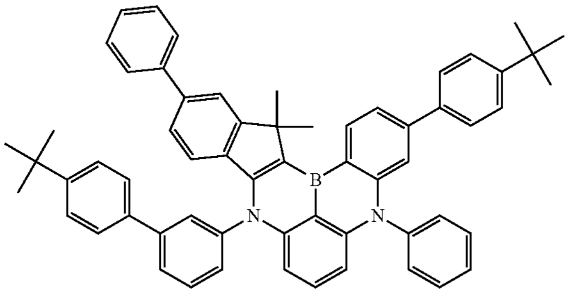
D-249
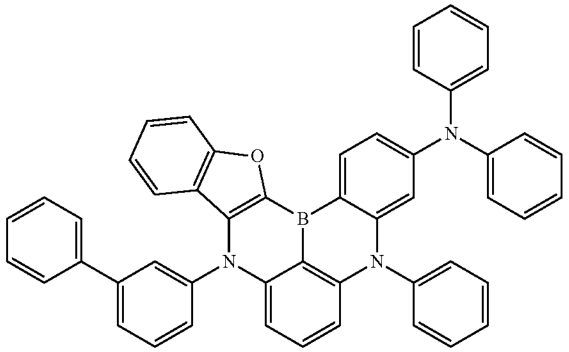
D-250
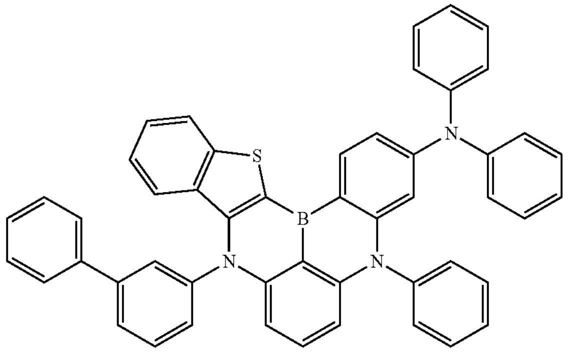
D-251
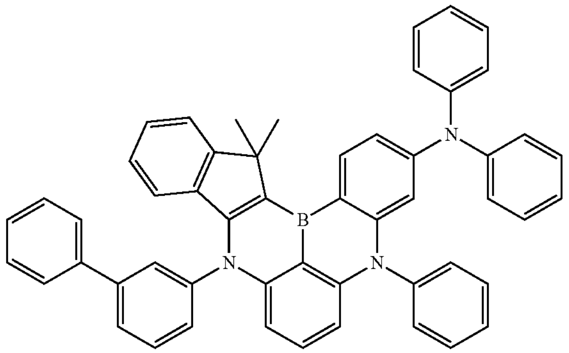

D-252
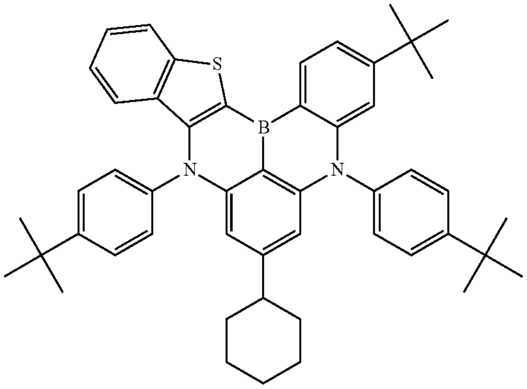
D-253
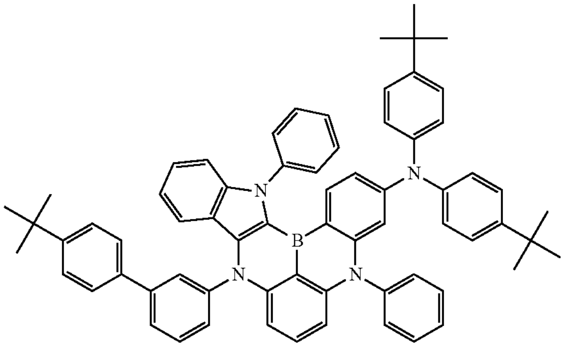
D-254
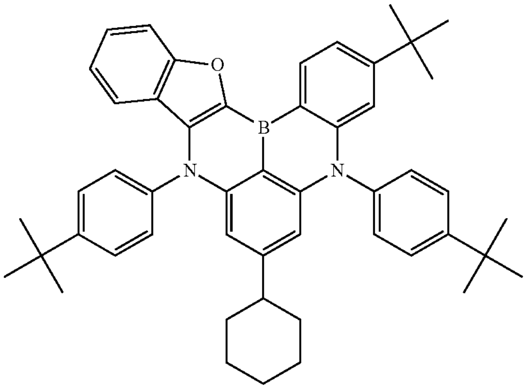
D-255
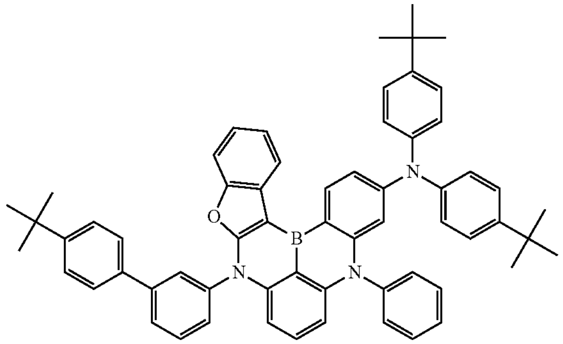
D-256
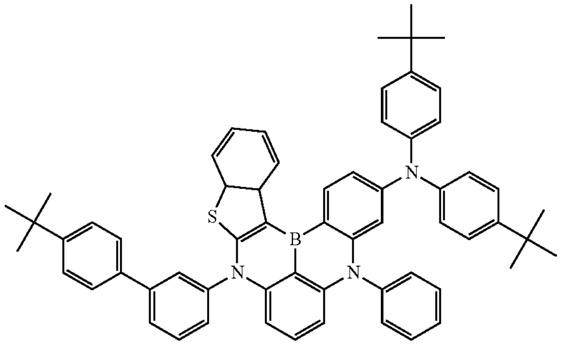
D-257
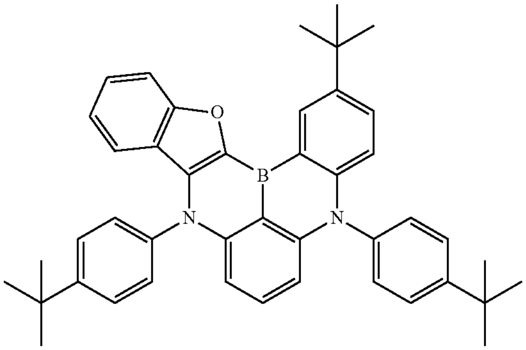
D-258
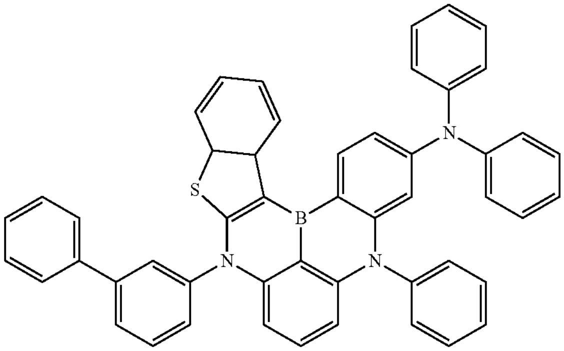
D-259
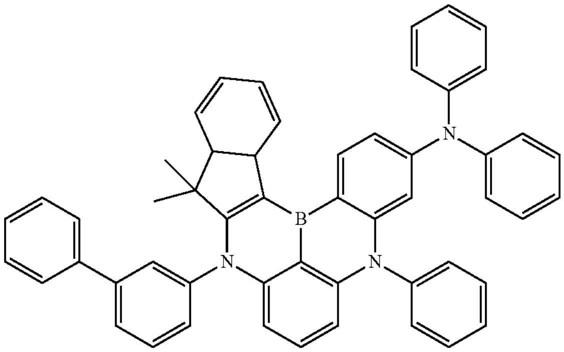

-continued
D-260
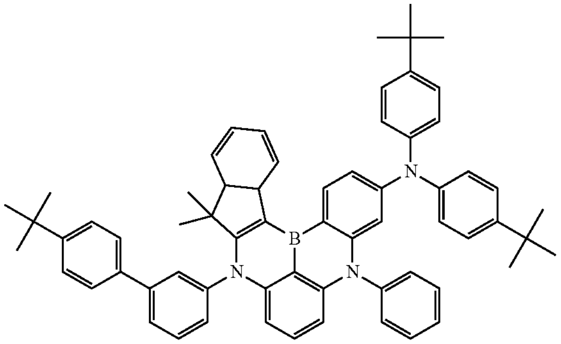
D-261
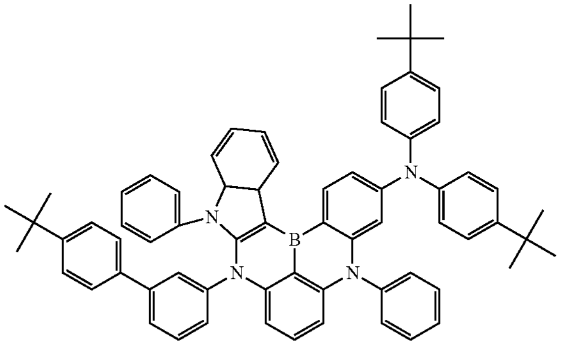
D-262
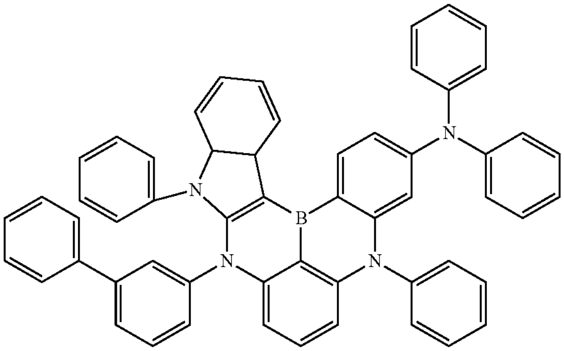
D-263
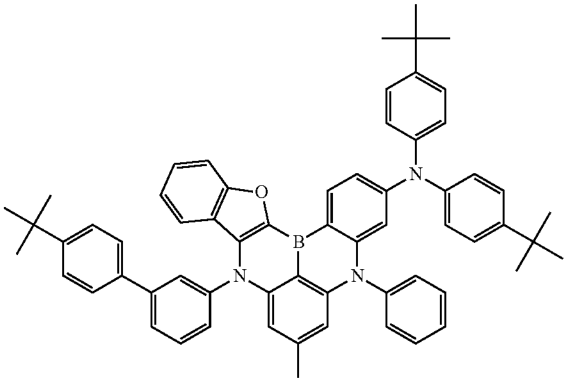
-continued
D-264
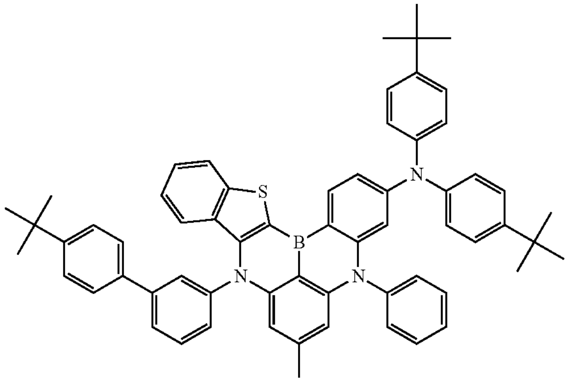
D-265
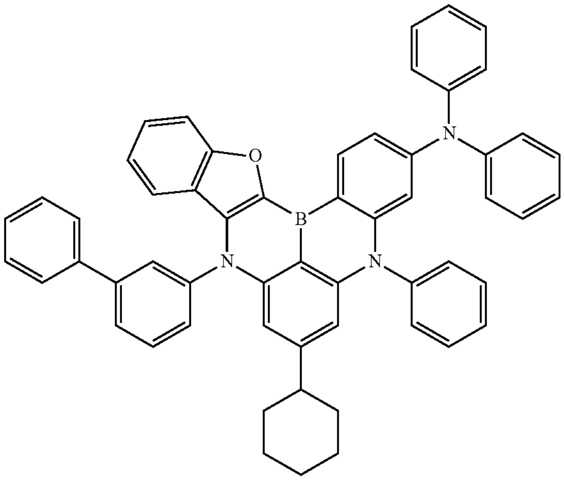
D-266
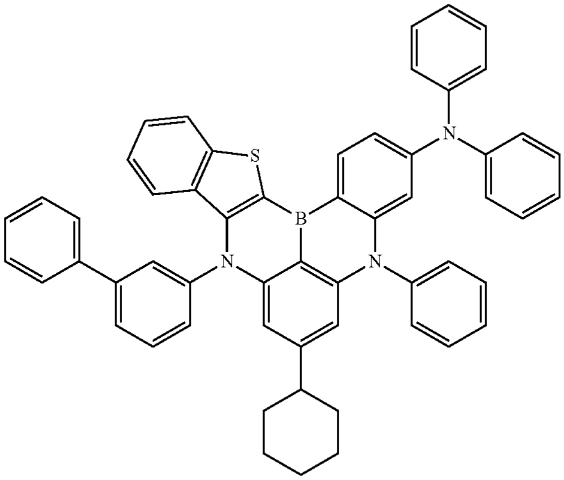

-continued
D-267
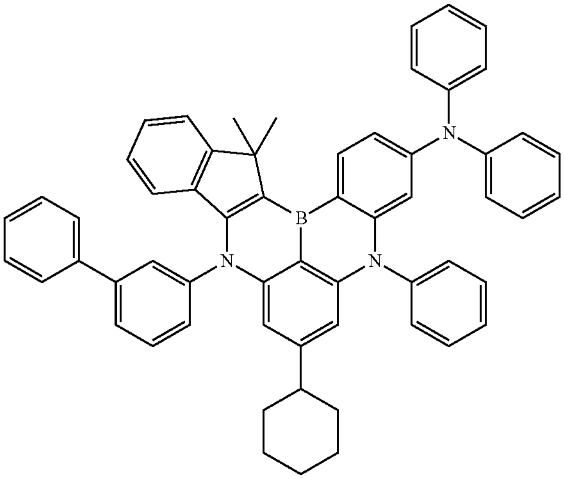
D-268
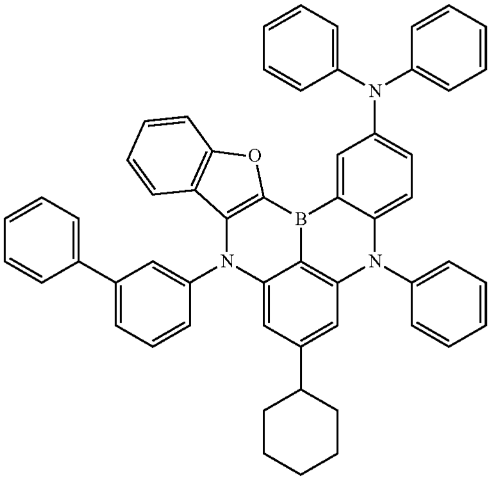
D-269
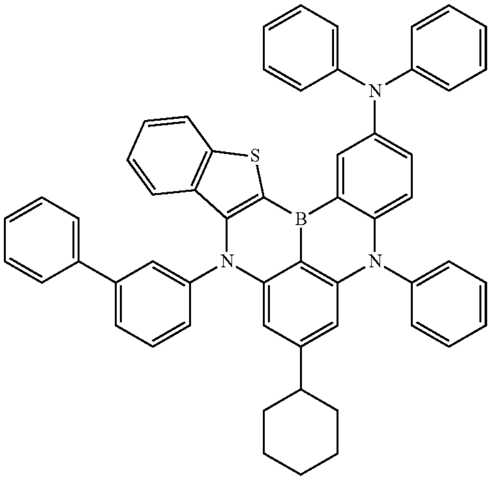
-continued
D-270
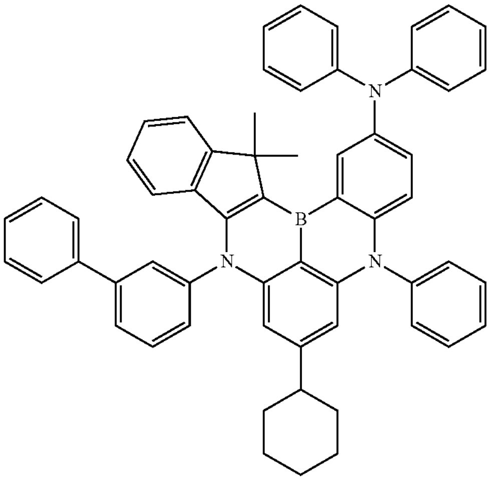
D-271
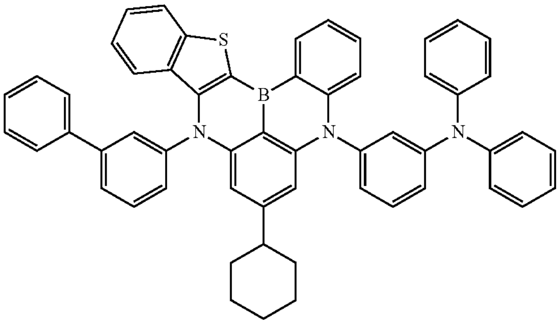
D-272
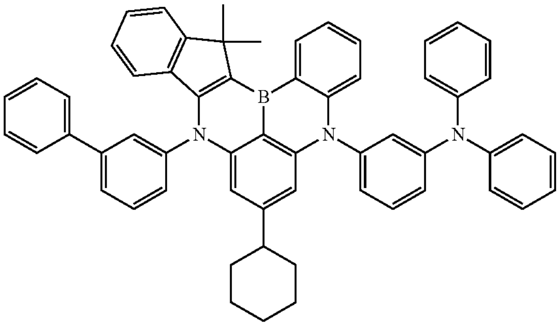
D-273
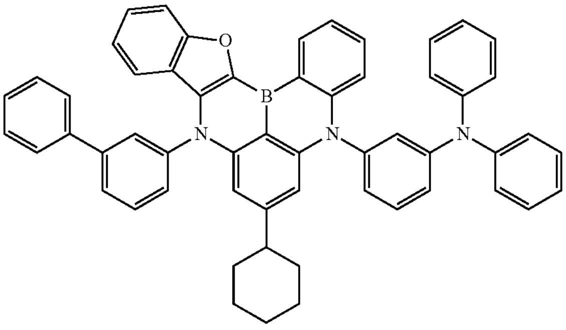

-continued
D-274
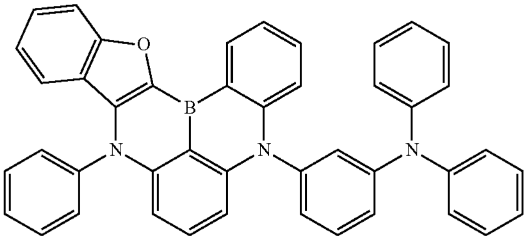
D-275
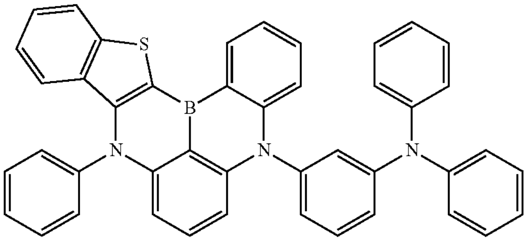
D-276
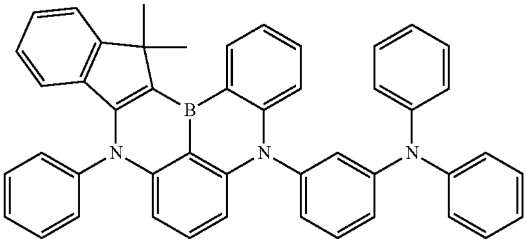
D-277
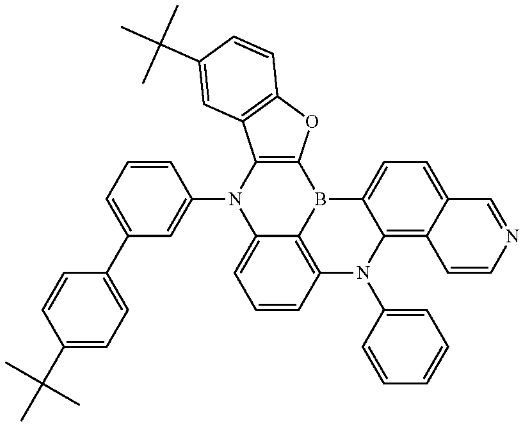
-continued
D-278
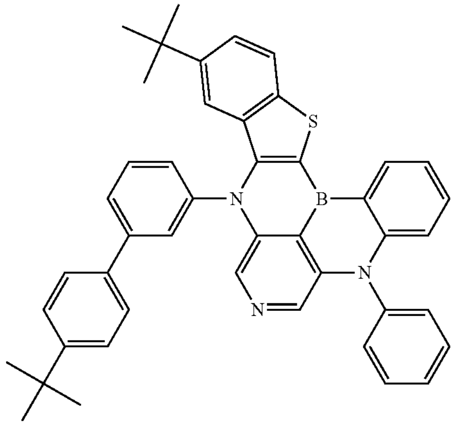
D-279
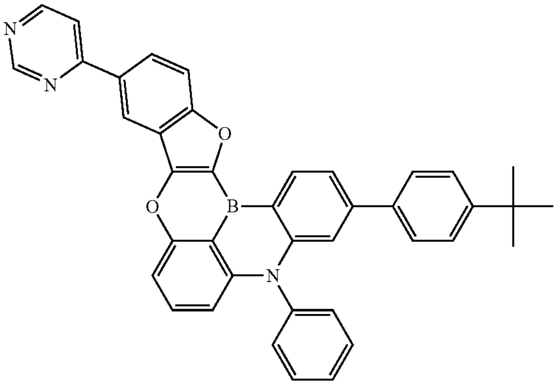
D-280
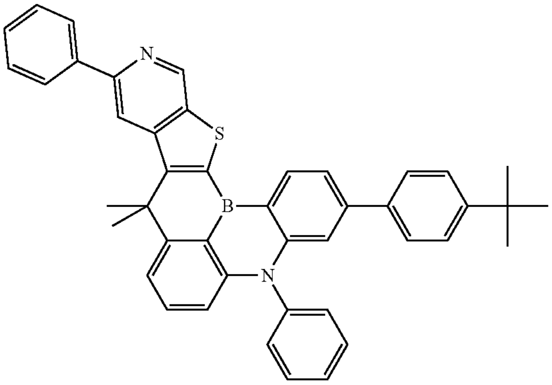
D-281
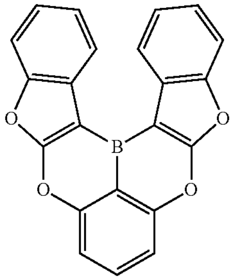

-continued
D-282
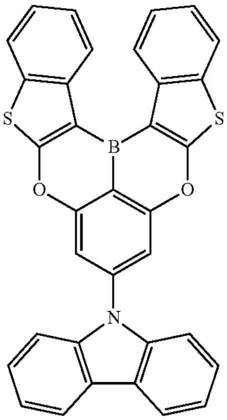
D-283
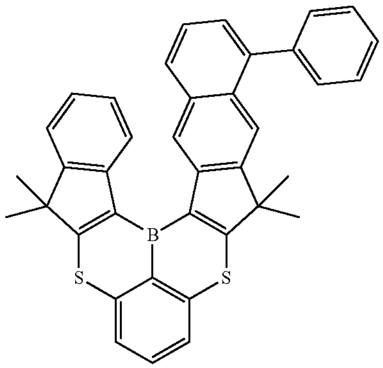
D-284
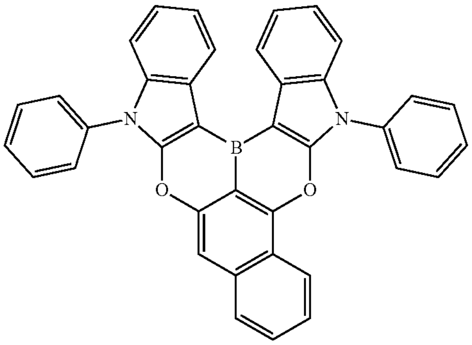
D-285
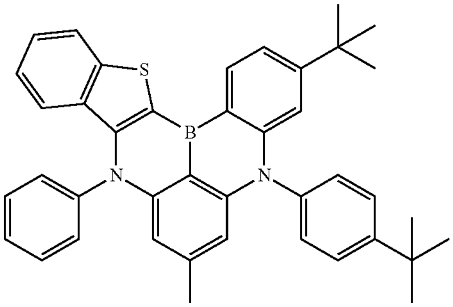
-continued
D-286
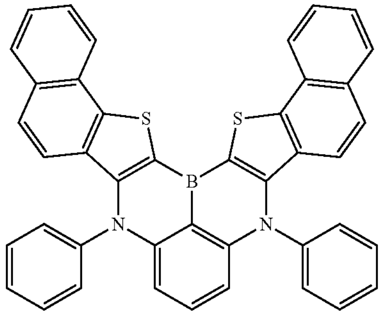
D-287
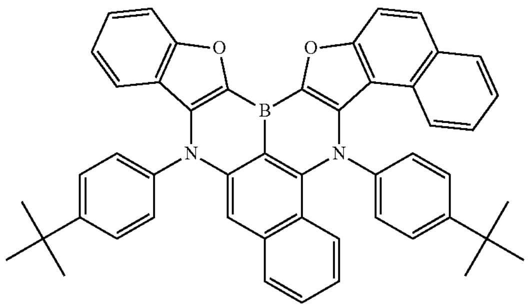
D-288
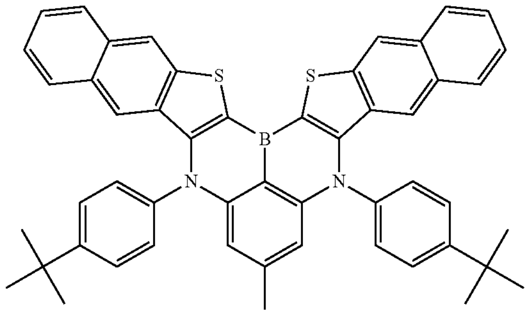
D-289
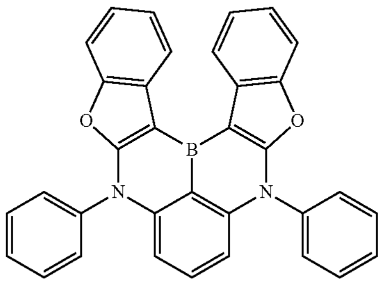
D-290
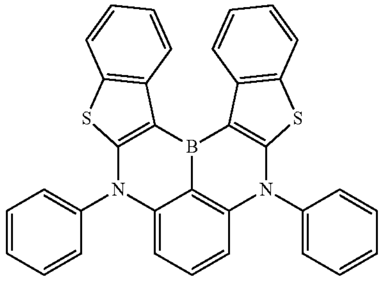

-continued
D-291
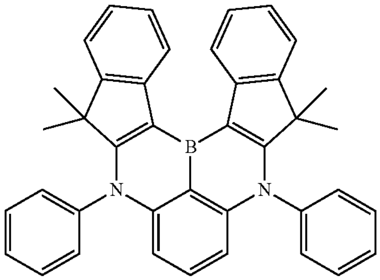
D-292
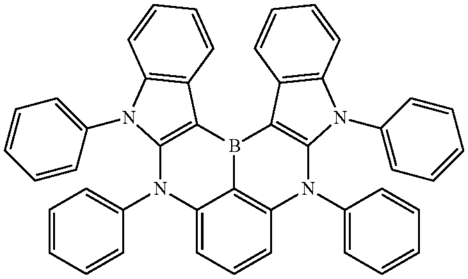
D-293
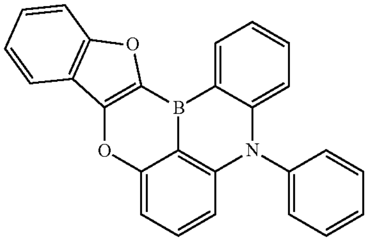
D-294
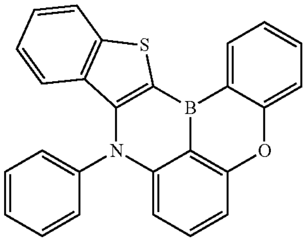
D-295
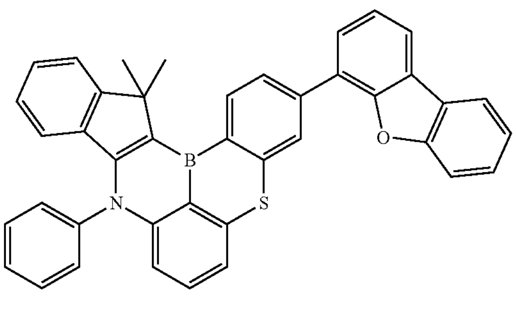
-continued
D-296
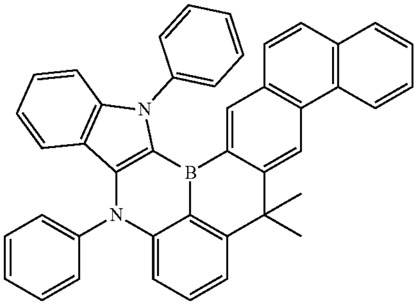
D-297
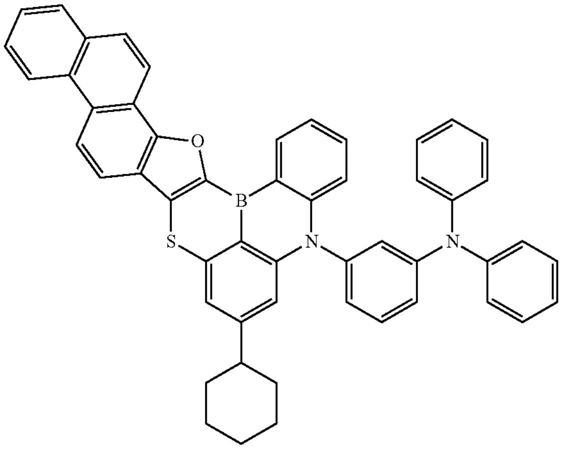
D-298
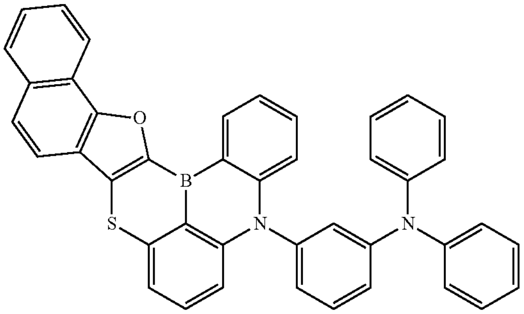
D-299
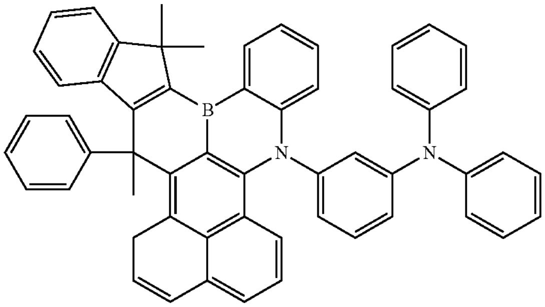

-continued
D-300
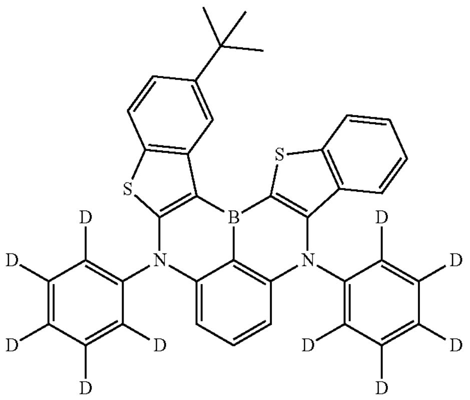
D-301
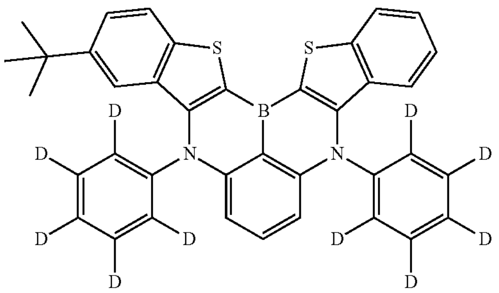
D-302
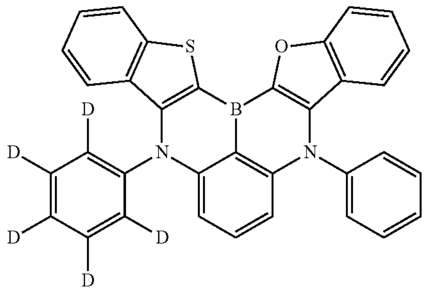
D-303
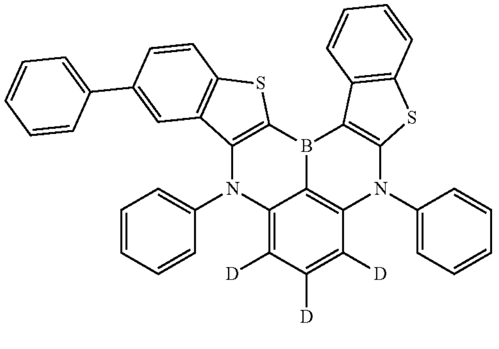
-continued
D-304
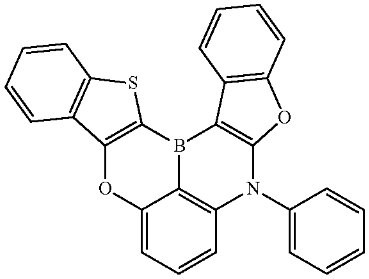
D-305
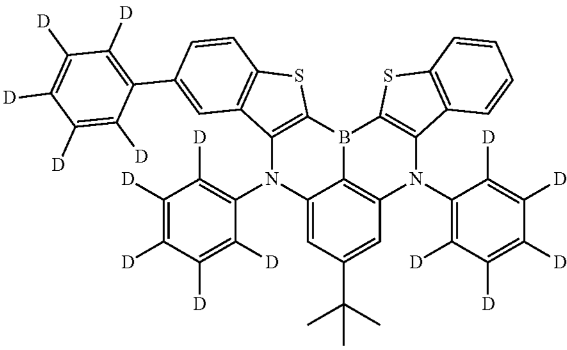
D-306
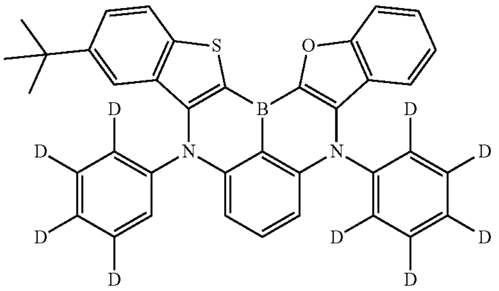
D-307
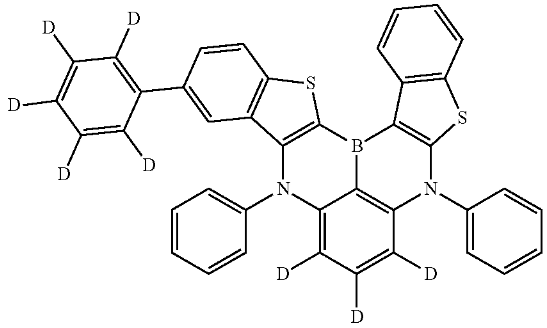
D-308
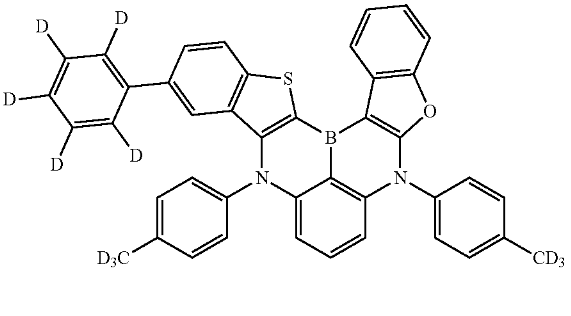

-continued
D-309
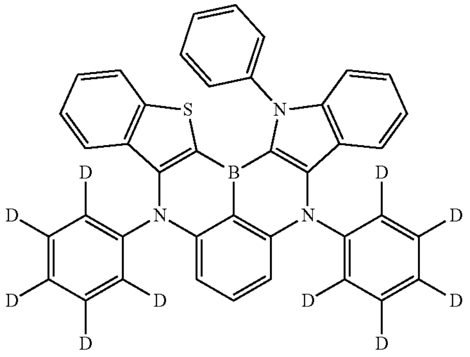
D-310
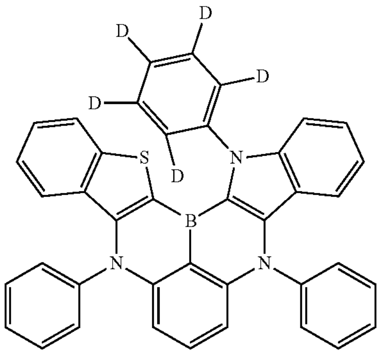
D-311
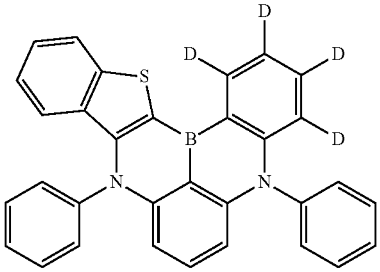
D-312
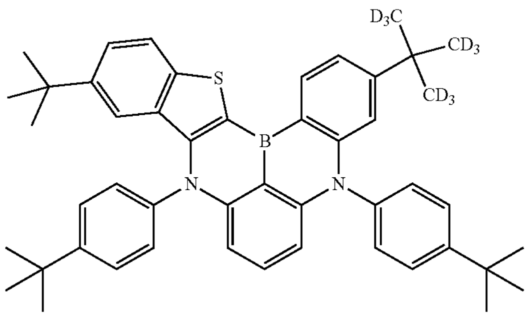
-continued
D-313
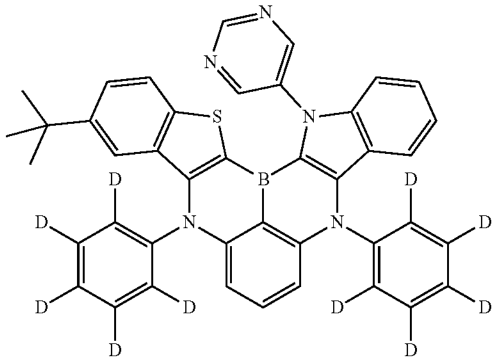
D-314
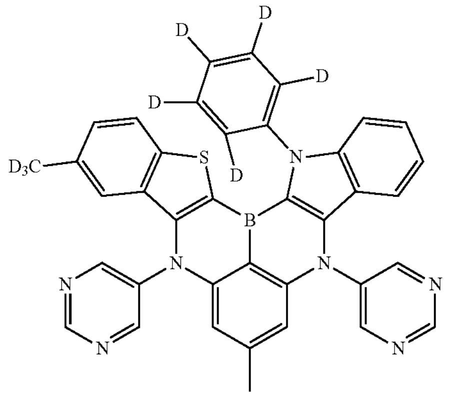
D-315
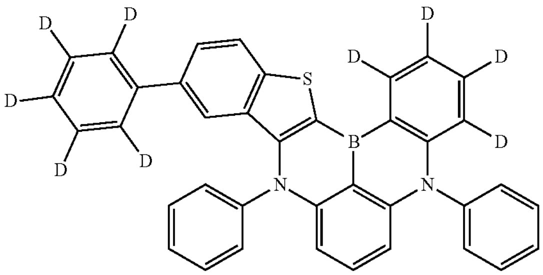
D-316
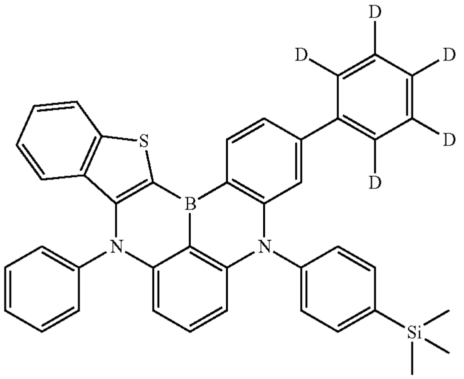

-continued
D-317
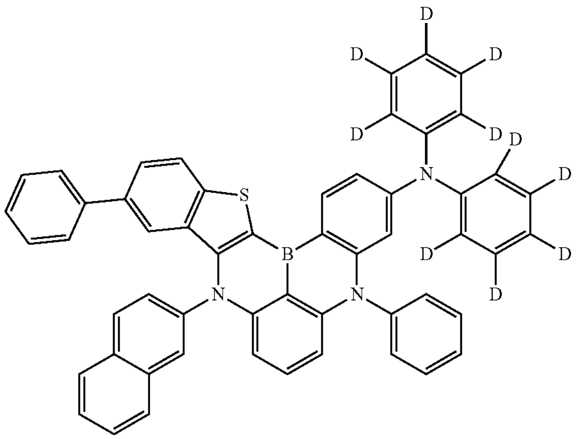
D-318
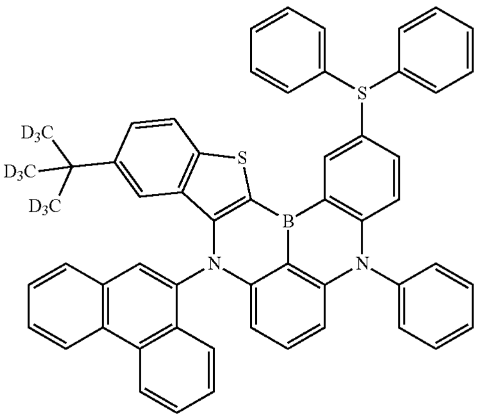
D-319
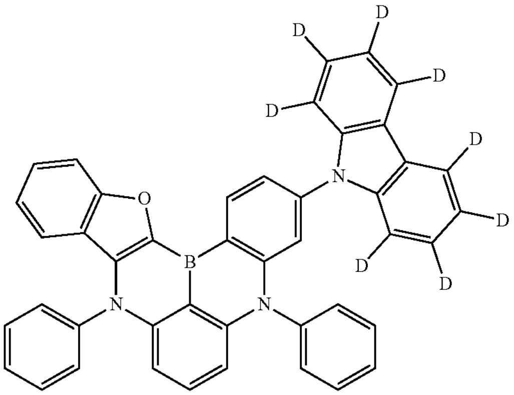
D-320
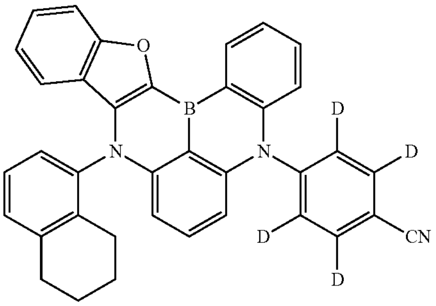
-continued
D-321
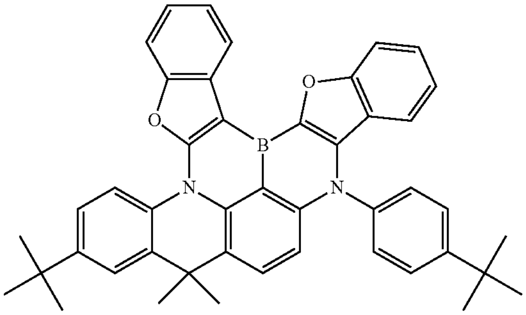
D-322
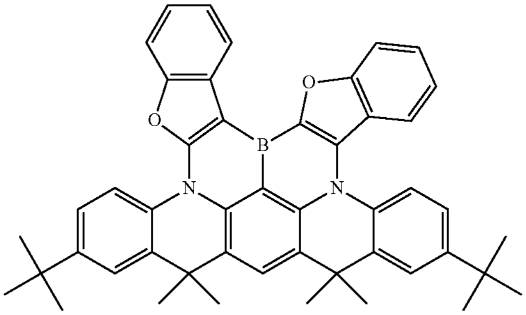
D-323
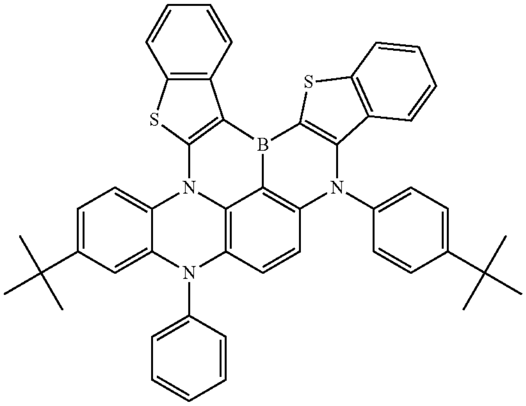
D-324
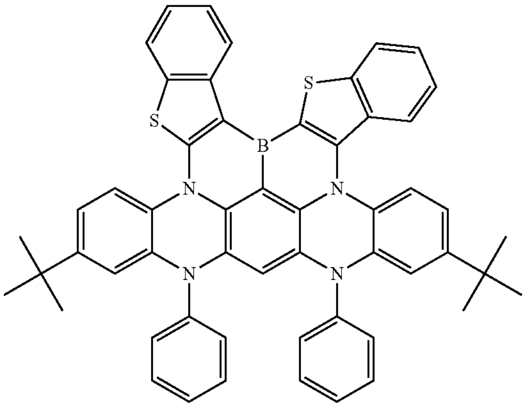

-continued
D-325
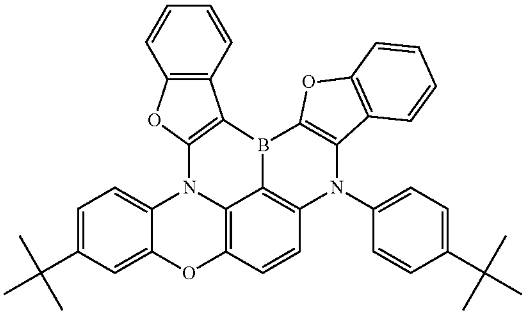
D-326
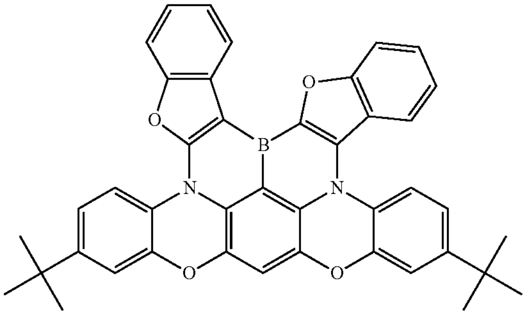
D-327
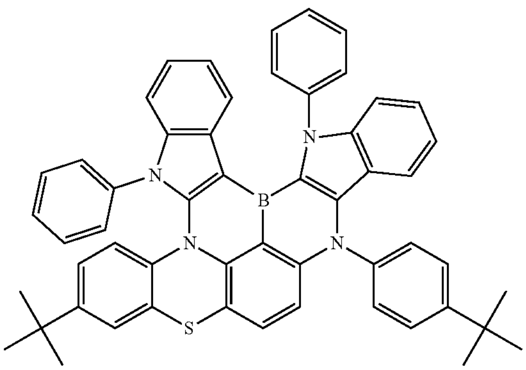
D-328
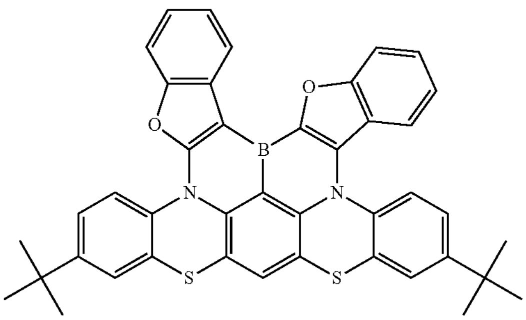
-continued
D-329
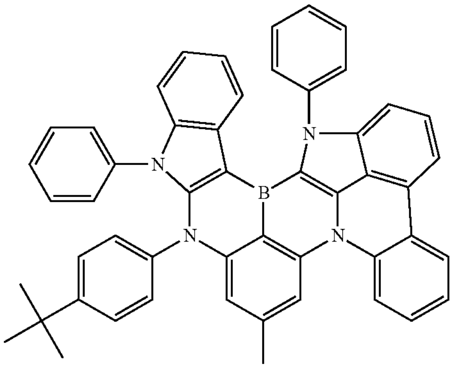
D-330
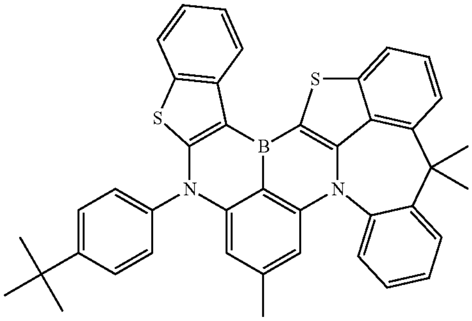
D-331
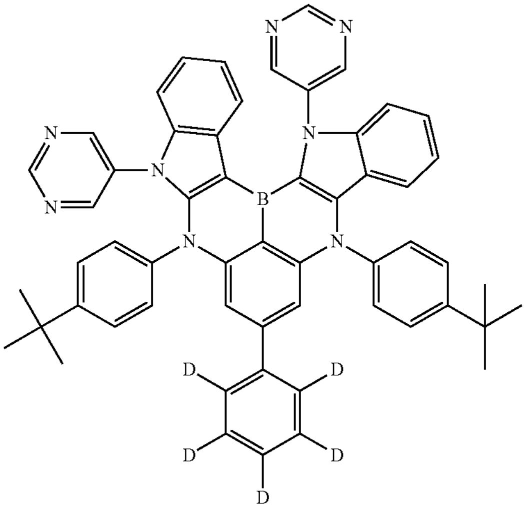
D-332
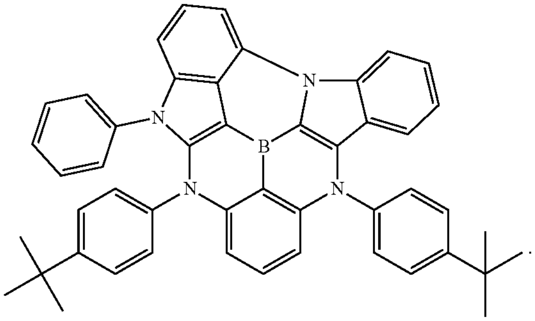
6. The organic light emitting device according to claim 1, wherein compounds represented by Formulas D-4 to D-6 are selected from the following compounds D-401 to D-536:

-continued
D-401
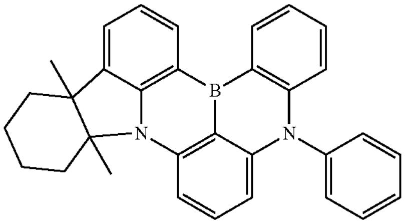
D-402
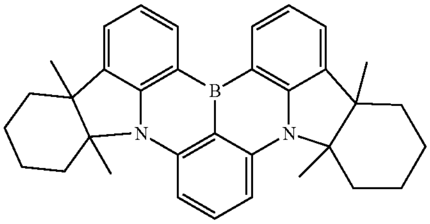
D-403
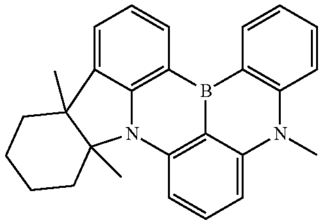
D-404
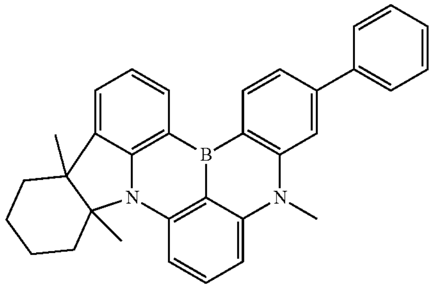
D-405
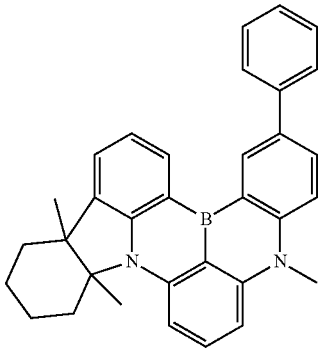
D-406
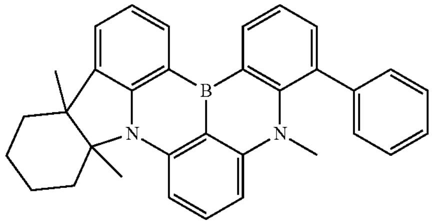
D-407
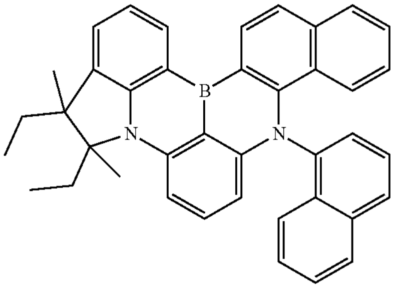
D-408
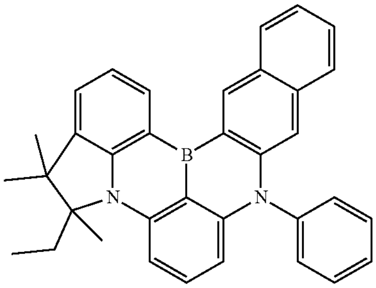
D-409
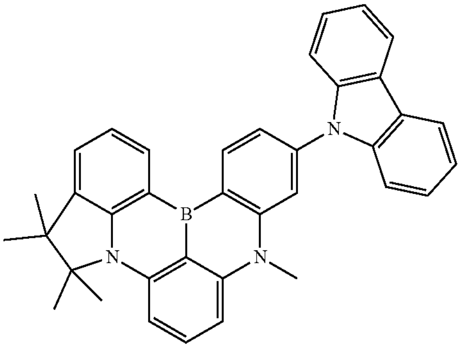
D-410
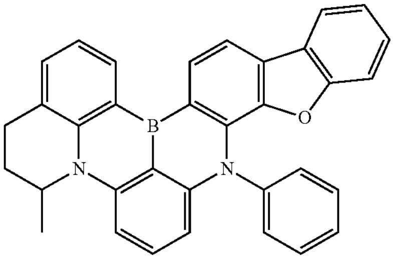
D-411
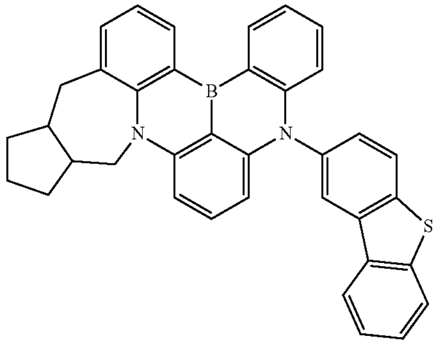

-continued
D-412
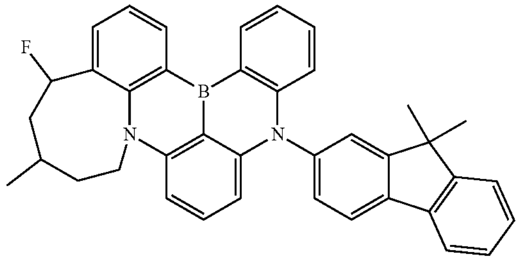
D-413
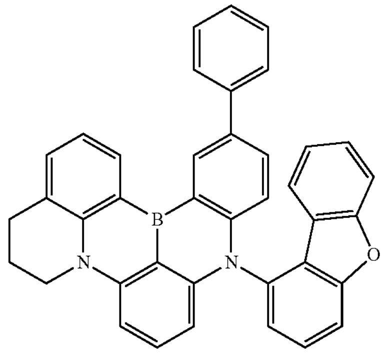
D-414
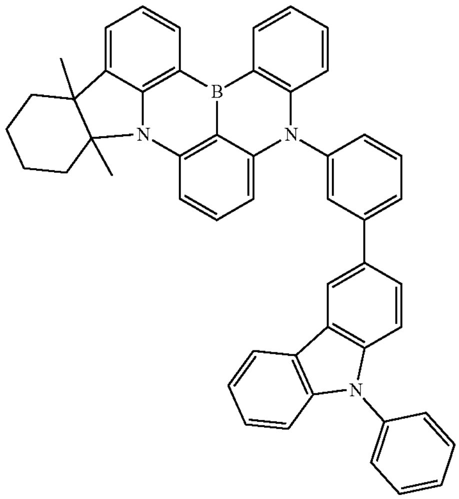
D-415
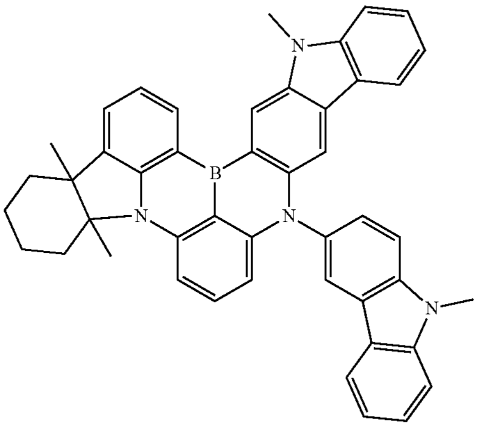
-continued
D-416
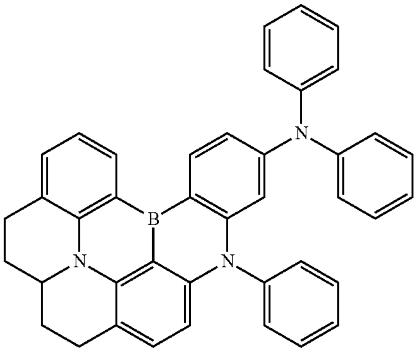
D-417
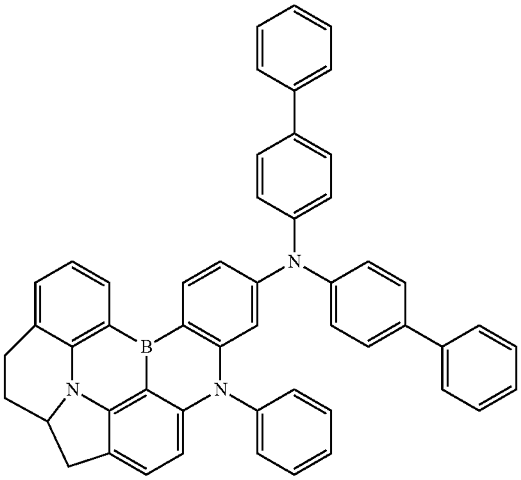
D-418
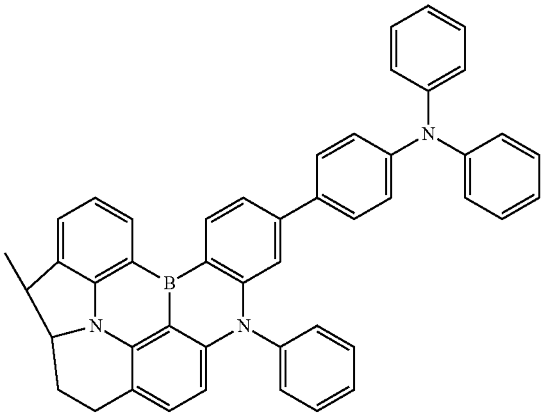

-continued
D-419
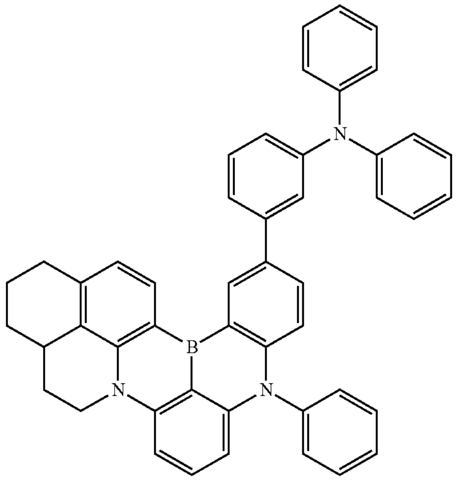
D-420
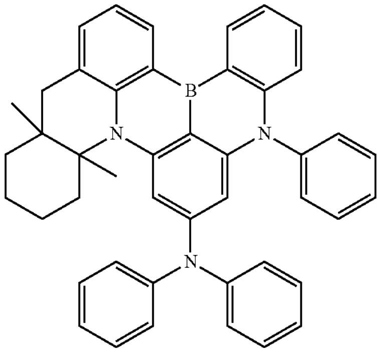
D-421
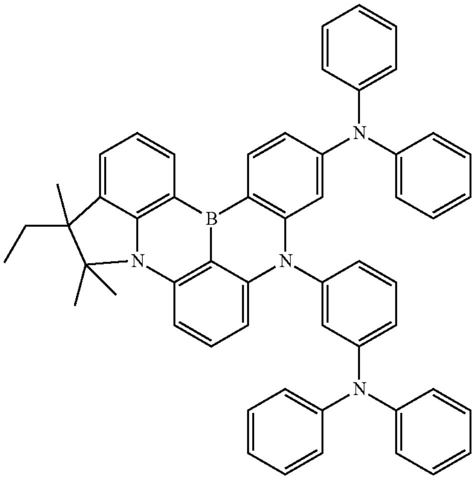
D-422
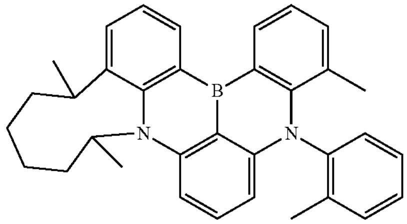
-continued
D-423
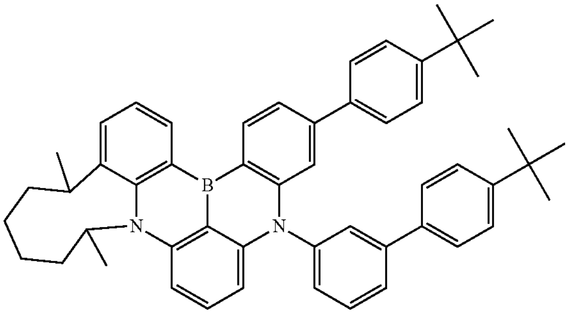
D-424
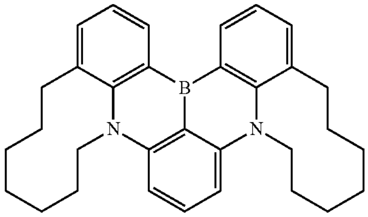
D-425
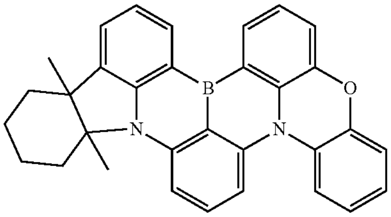
D-426
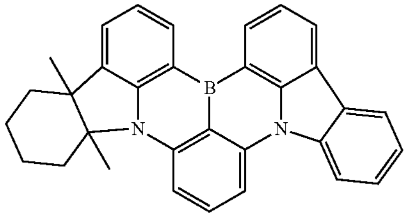
D-427
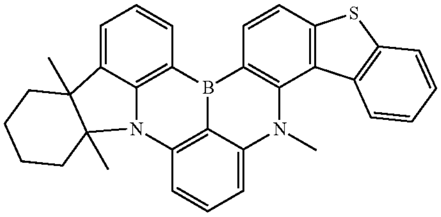
D-428
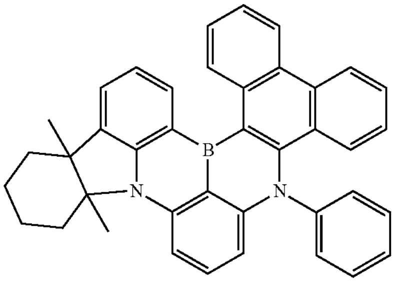

-continued
D-429
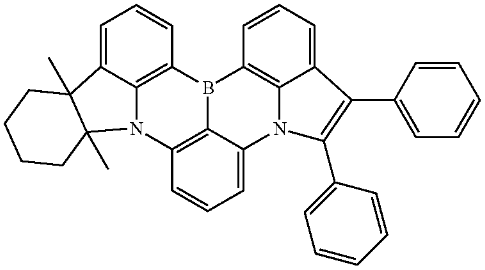
D-430
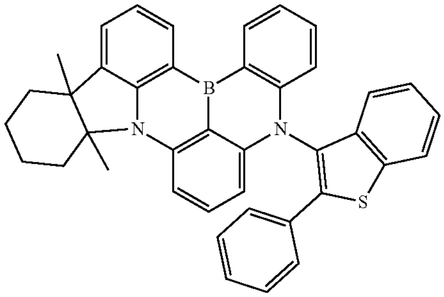
D-431
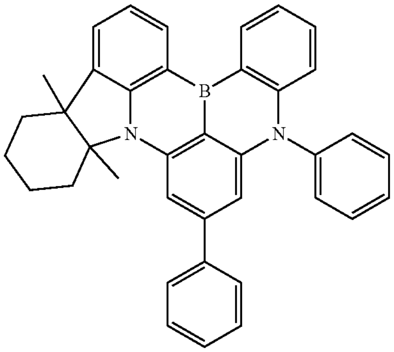
D-432
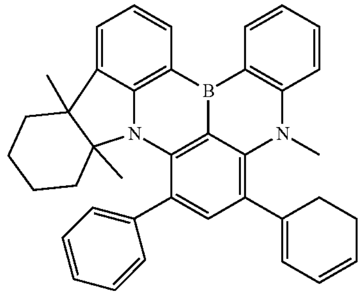
D-433
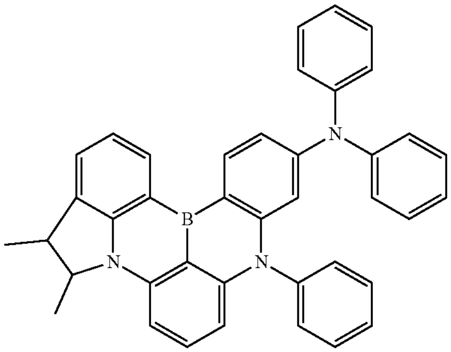
-continued
D-434
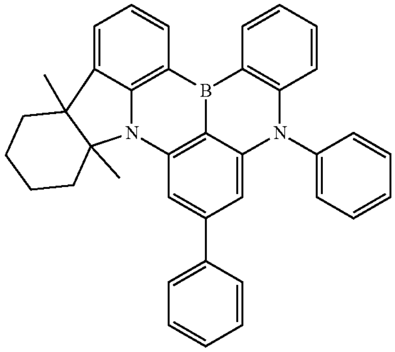
D-435
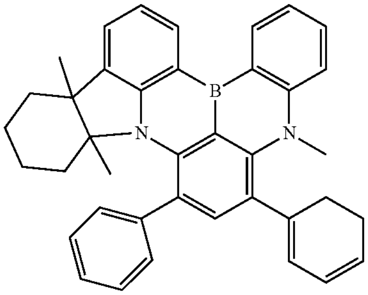
D-436
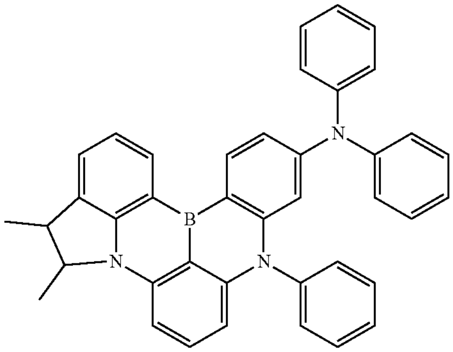
D-437
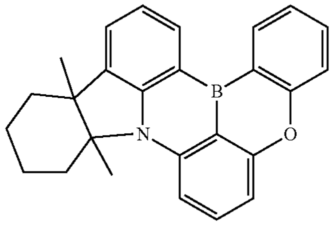
D-438
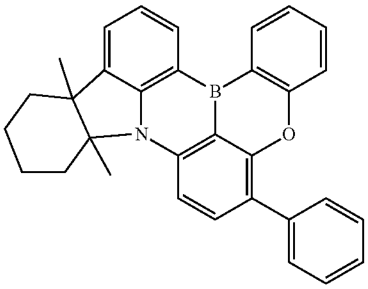

-continued
D-439
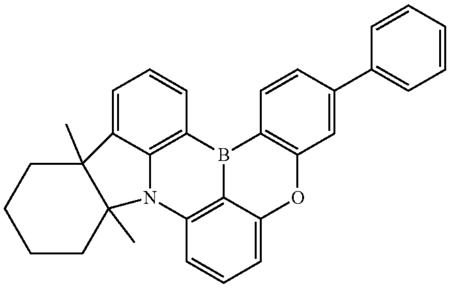
D-440
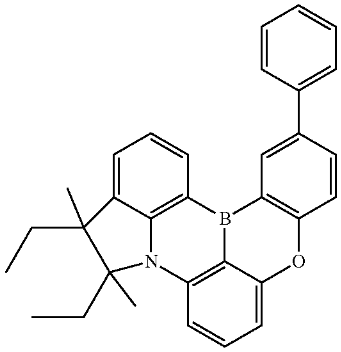
D-441
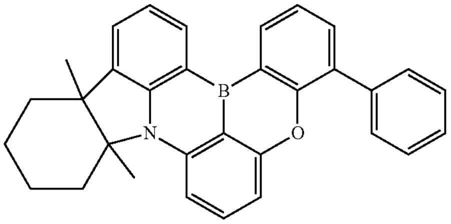
D-442
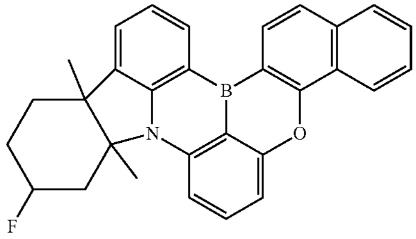
D-443
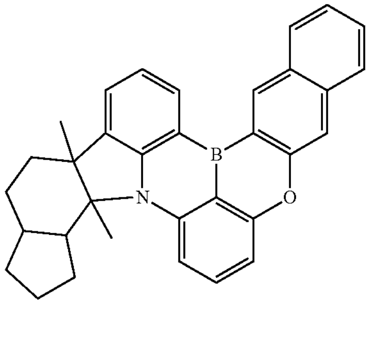
-continued
D-444
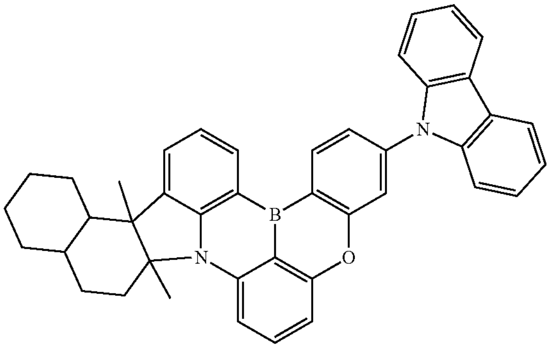
D-445
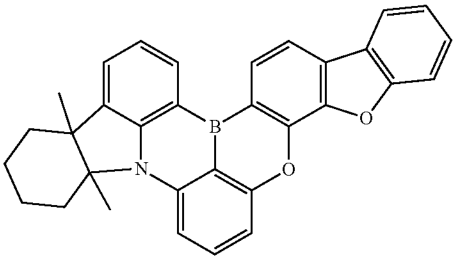
D-446
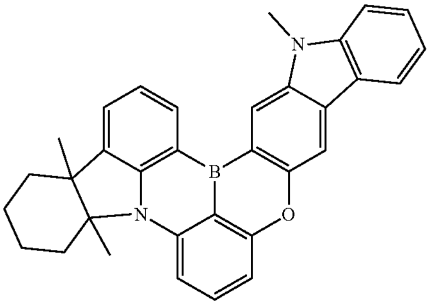
D-447
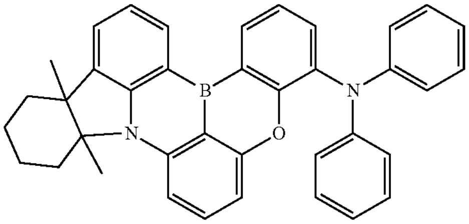
D-448
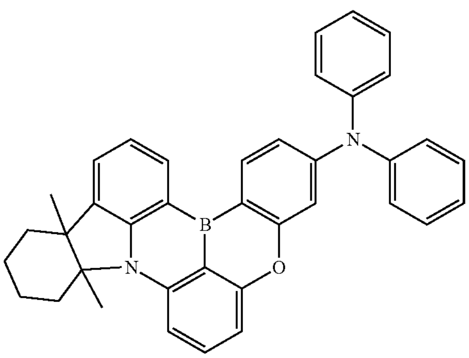

-continued
D-449
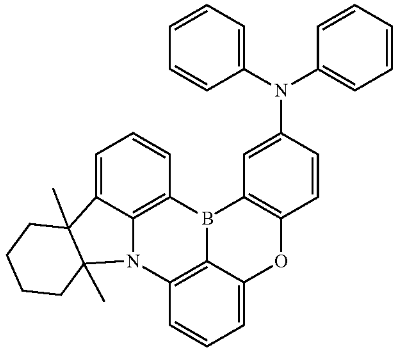
D450
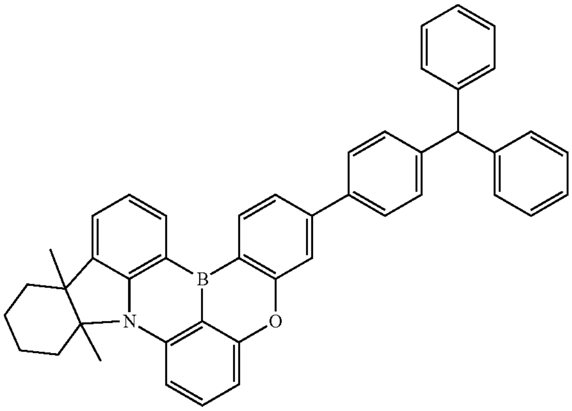
D-451
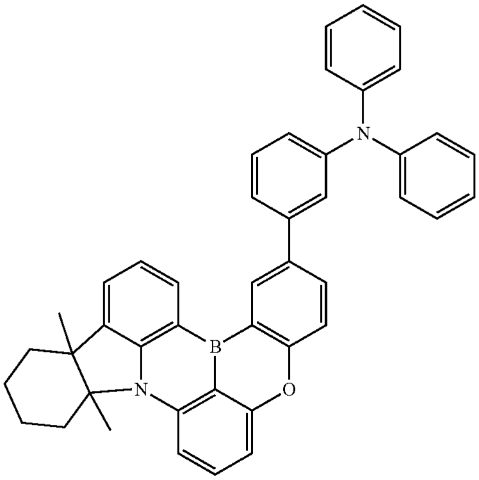
D-452
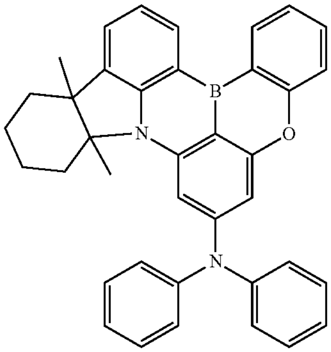
-continued
D-453
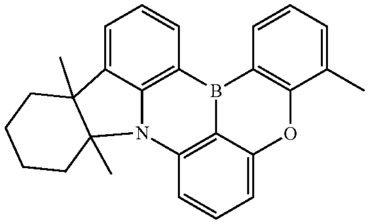
D-454
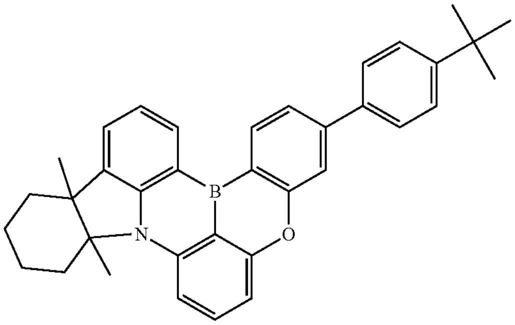
D-455
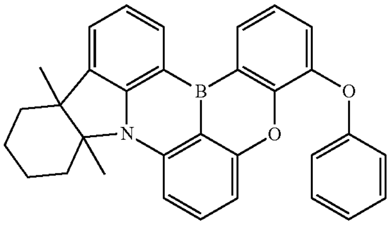
D-456
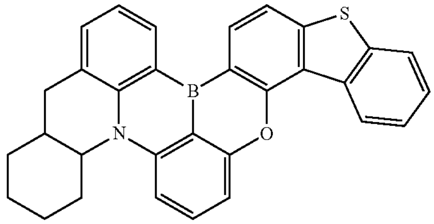
D-457
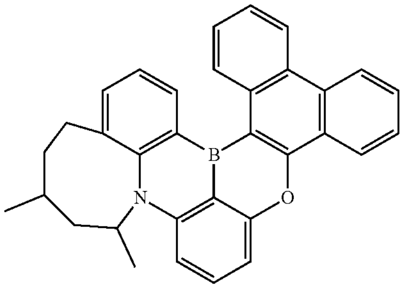

-continued
D-458
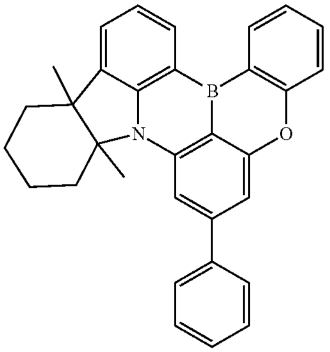
D-459
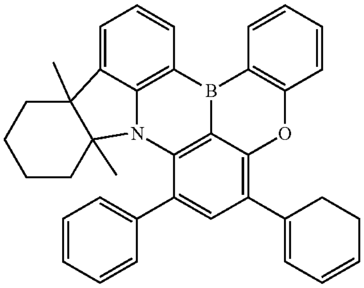
D-460
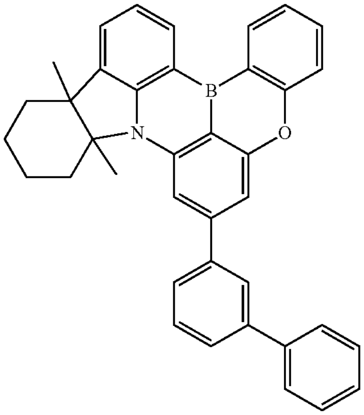
D-461
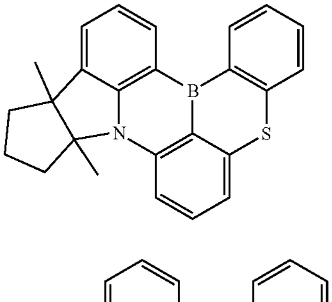
D-462
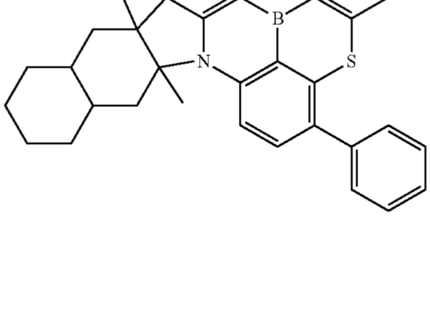
-continued
D-463
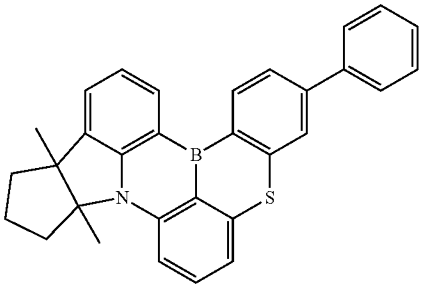
D-464
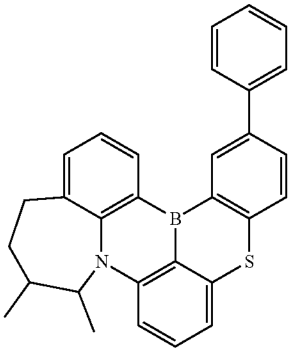
D-465
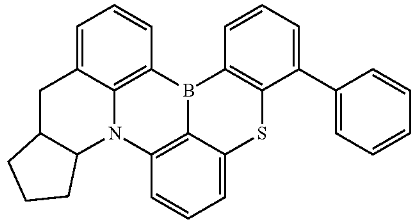
D-466
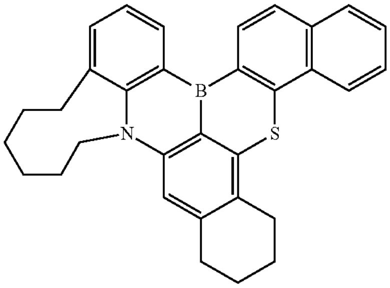
D-467
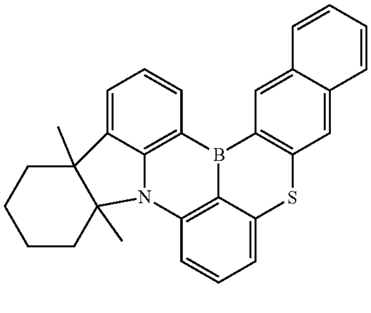

-continued
D-468
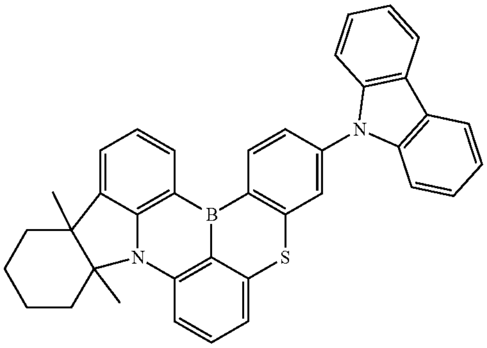
D-469
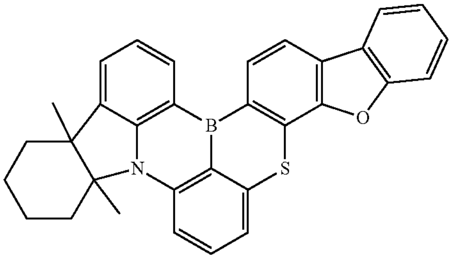
D-470
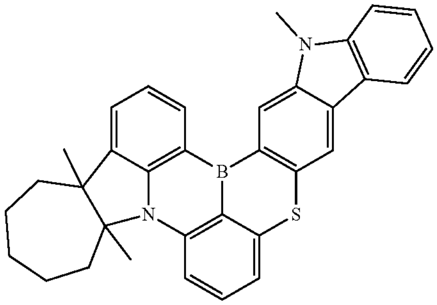
D-471
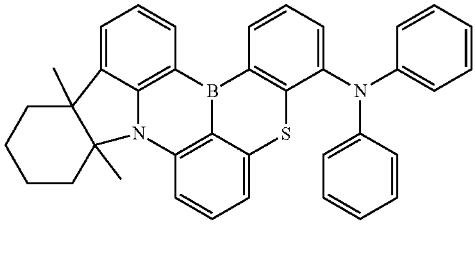
-continued
D-472
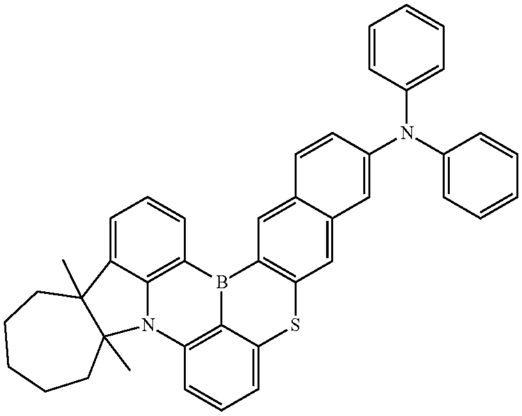
D-473
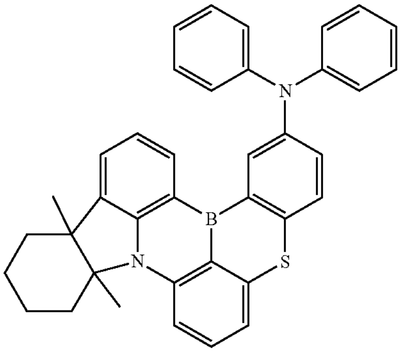
D-474
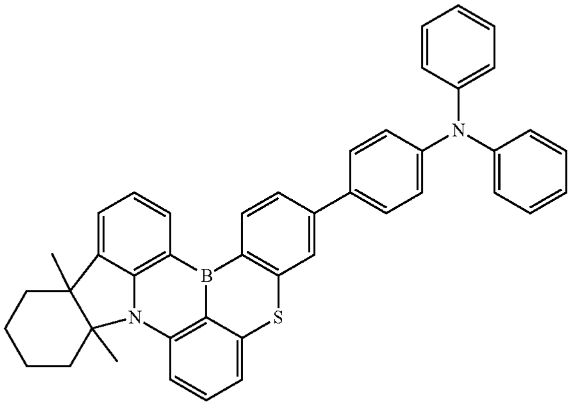

-continued
D-475
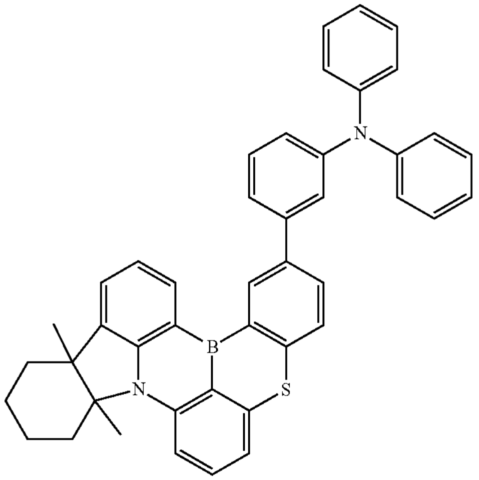
D-476
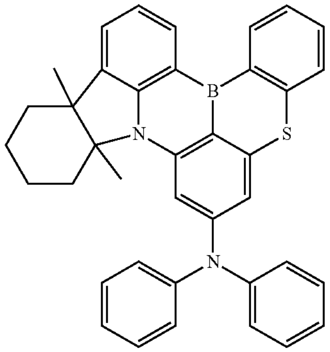
D-477
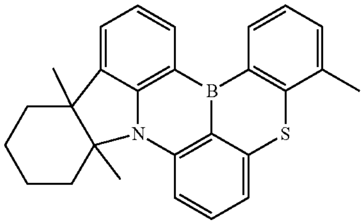
D-478
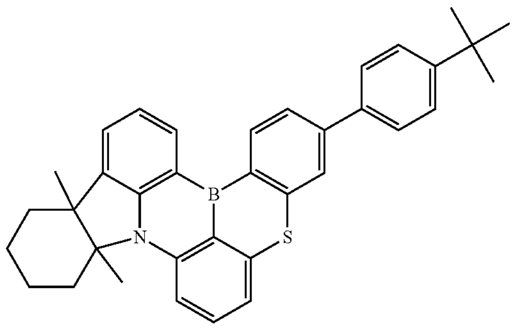
-continued
D-479
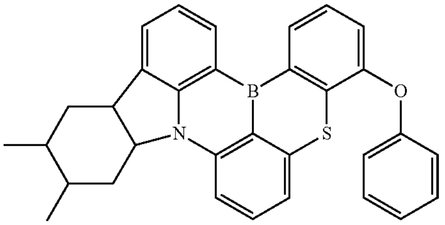
D-480
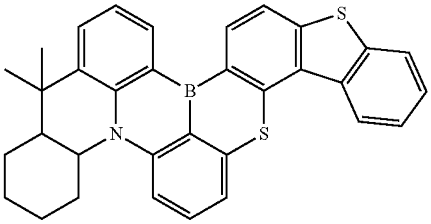
D-481
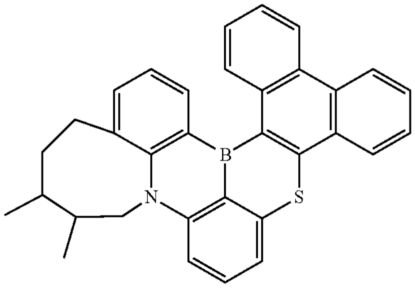
D-482
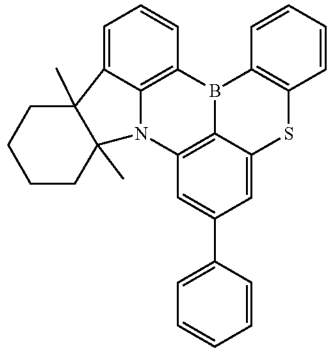
D-483
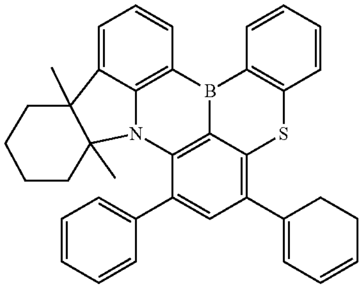

-continued
D-484
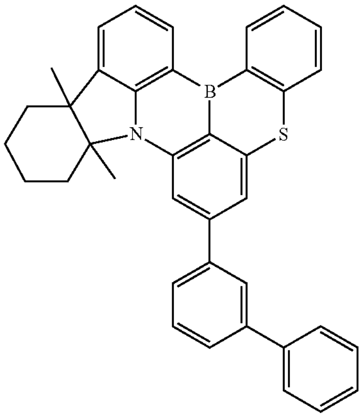
D-485
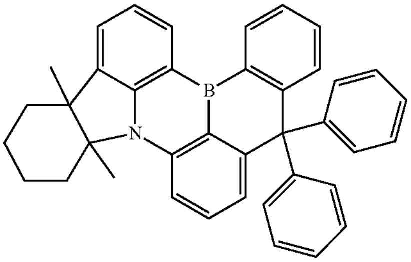
D-486
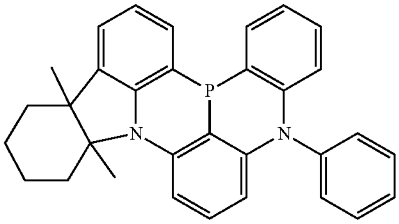
D-487
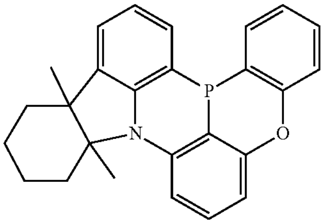
D-488
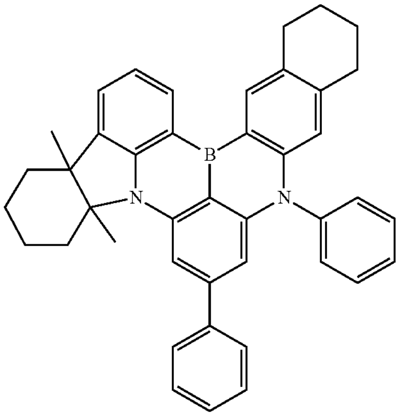
-continued
D-489
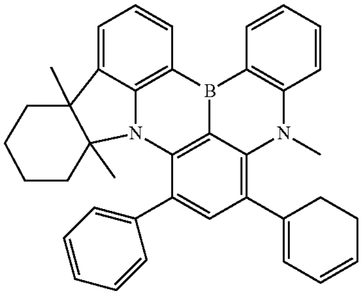
D-490
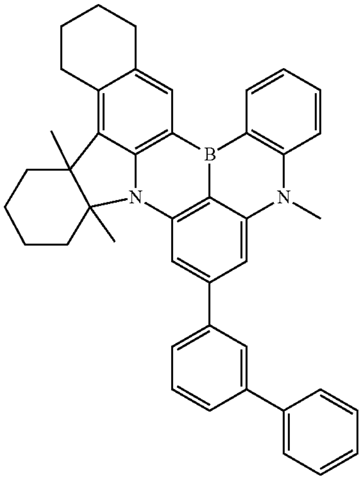
D-491
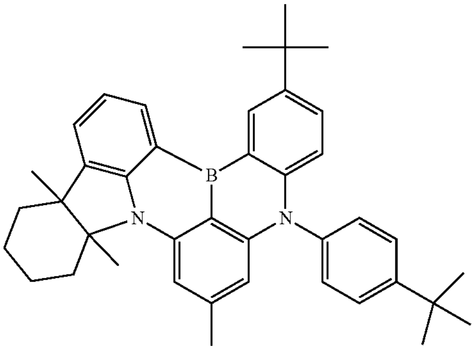
D-492
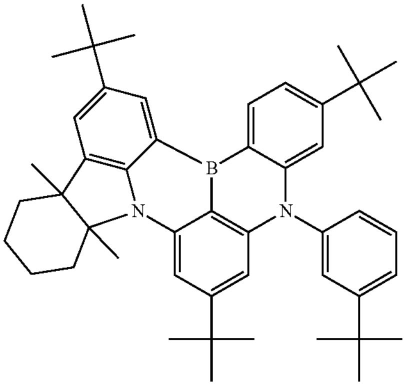

-continued
D-493
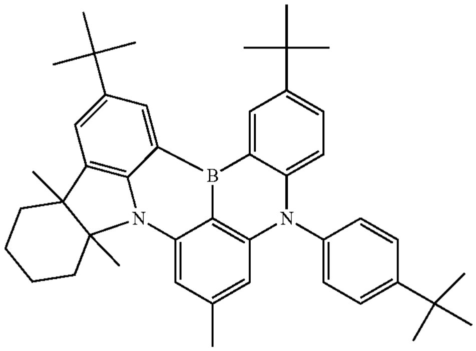
D-494
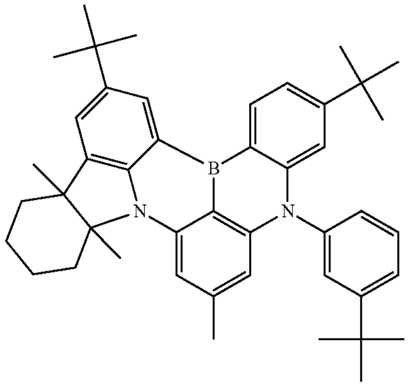
D-495
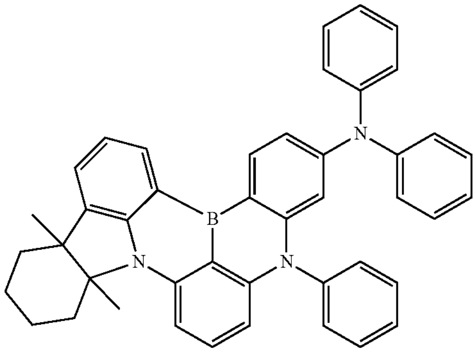
D-496
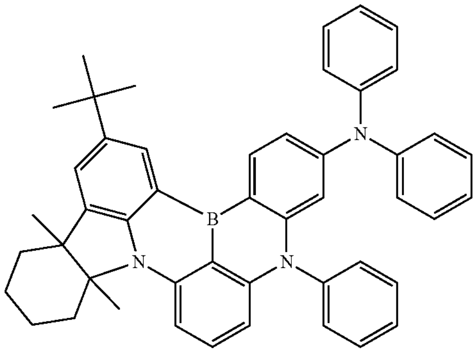
-continued
D-497
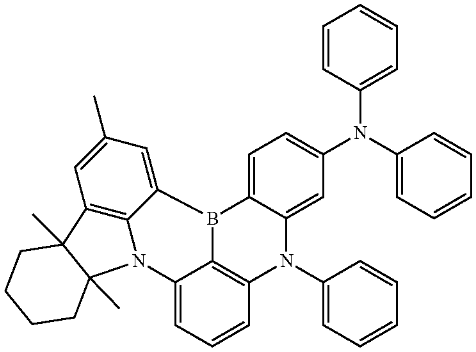
D-498
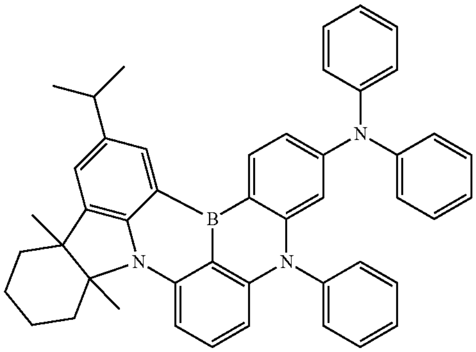
D-499
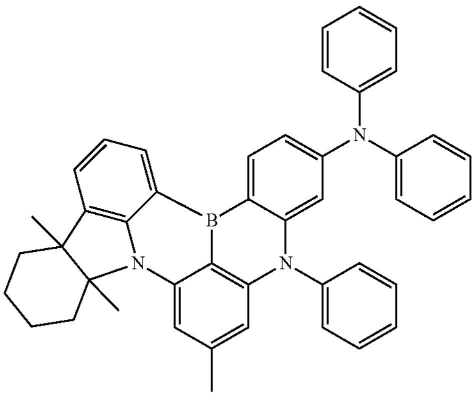
D-500
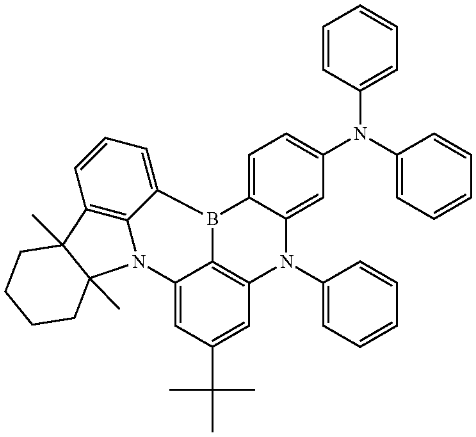

-continued
D-501
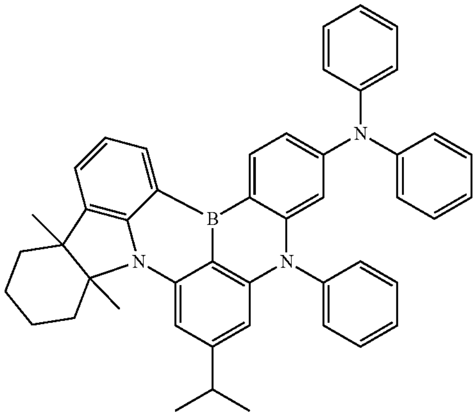
D-502
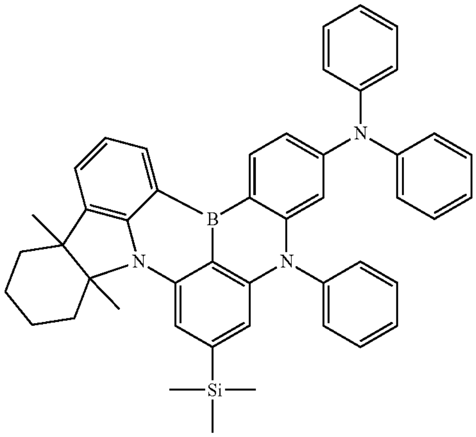
D-503
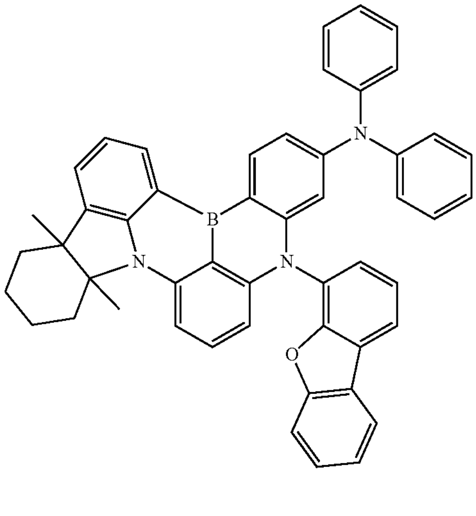
-continued
D-504
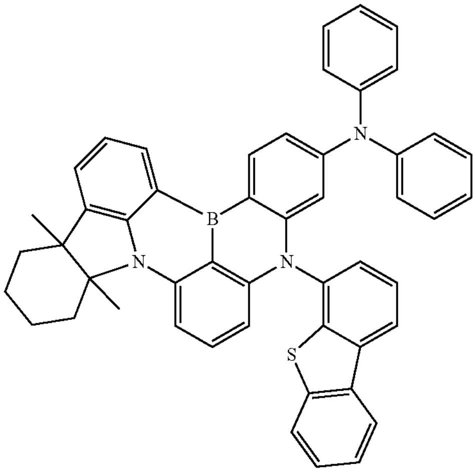
D-505
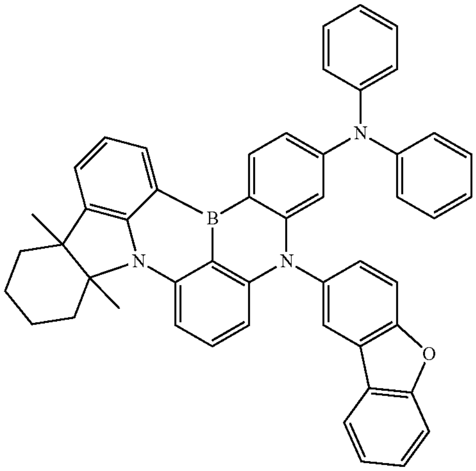
D-506
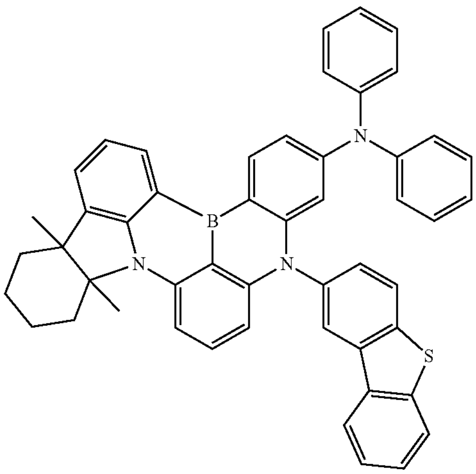

-continued
D-507
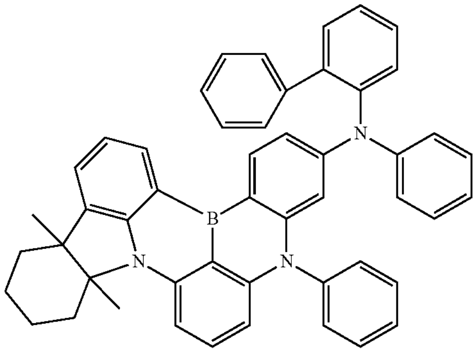
D-508
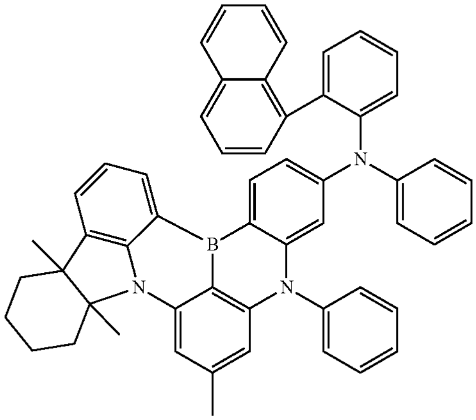
D-509
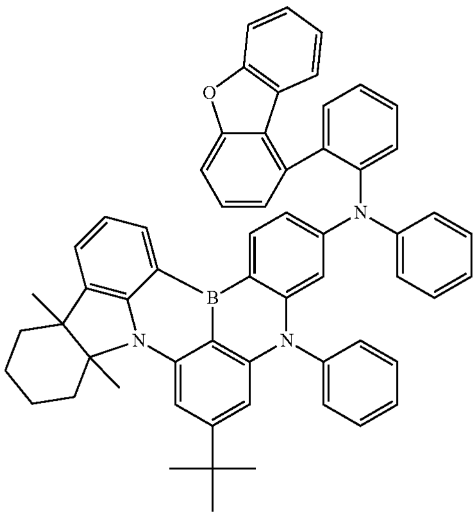
-continued
D-510
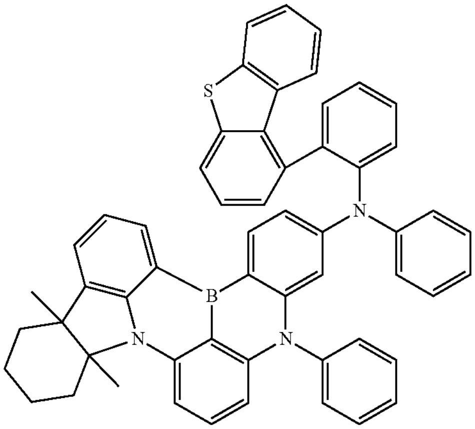
D-511
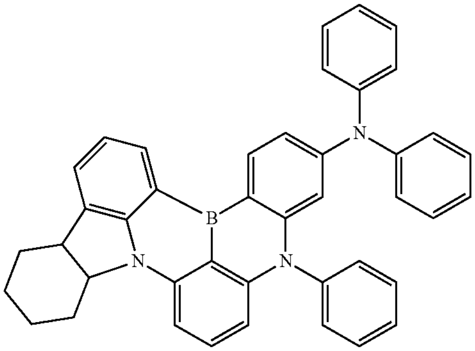
D-512
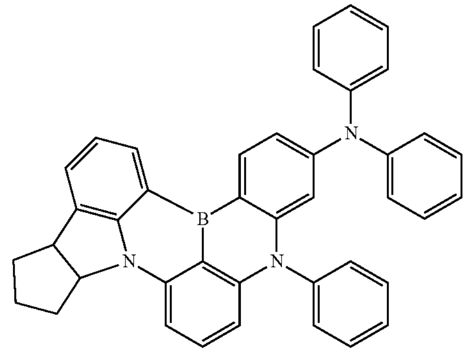
D-513
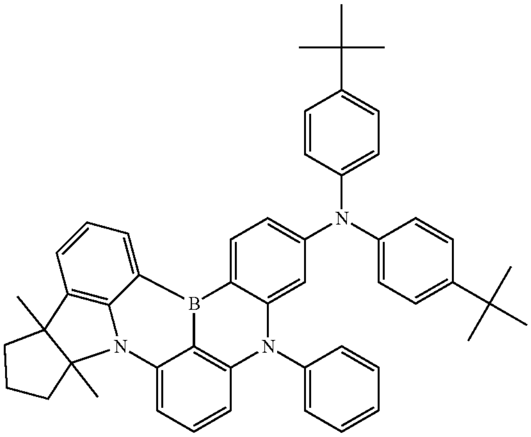

-continued
D-514
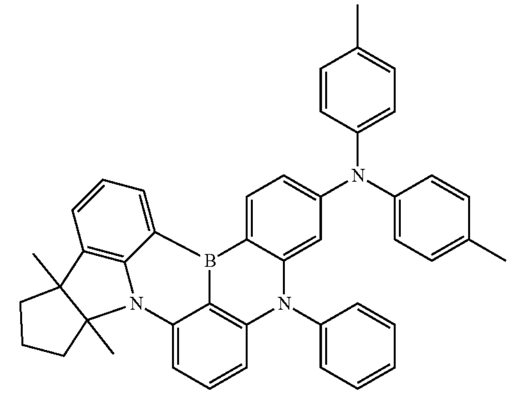
D-515
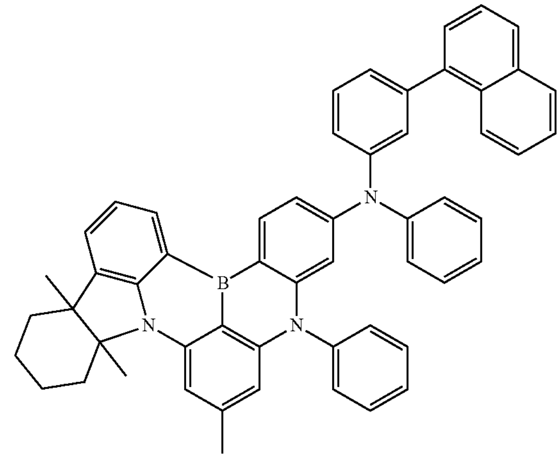
D-516
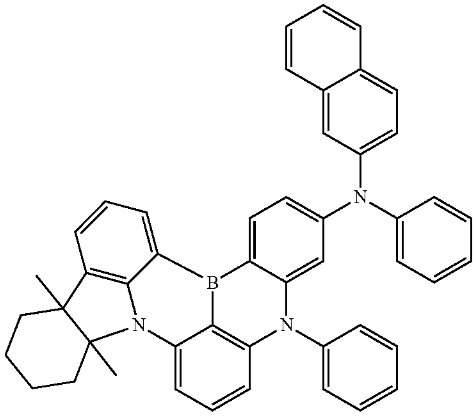
-continued
D-517
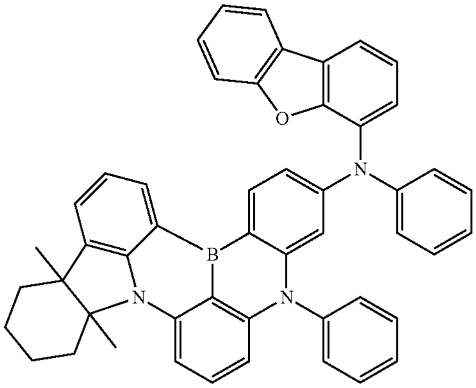
D-518
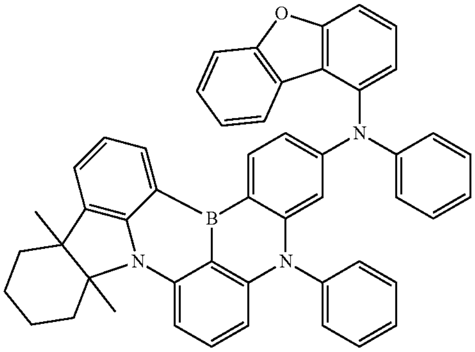
D-519
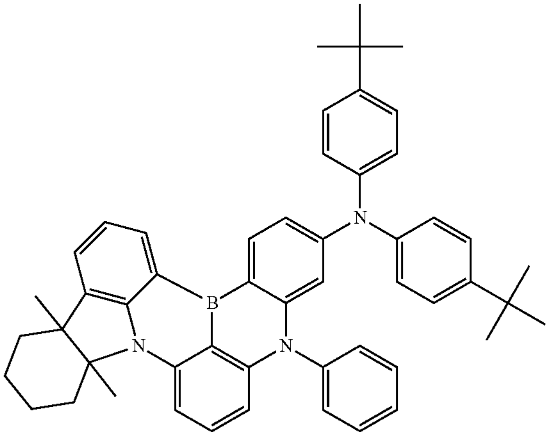

D-520
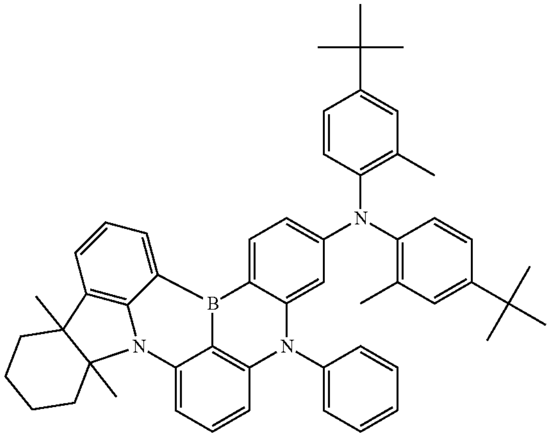
D-521
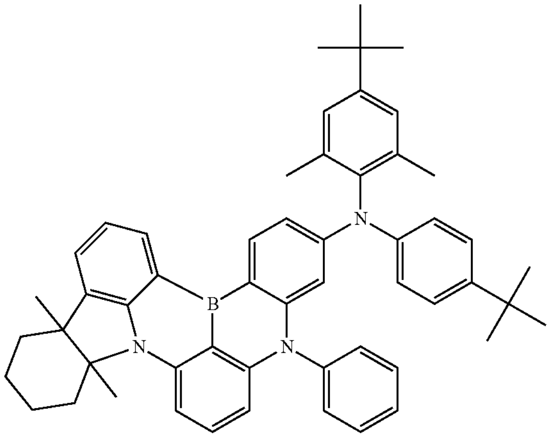
D-522
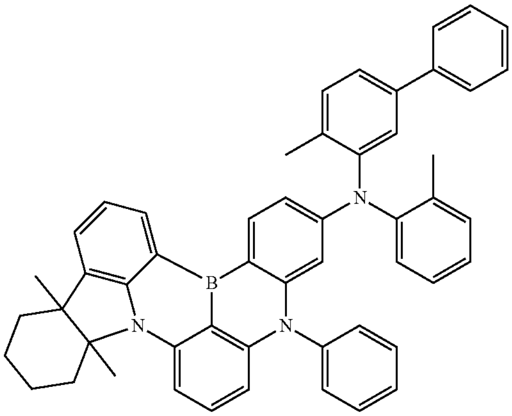
D-523
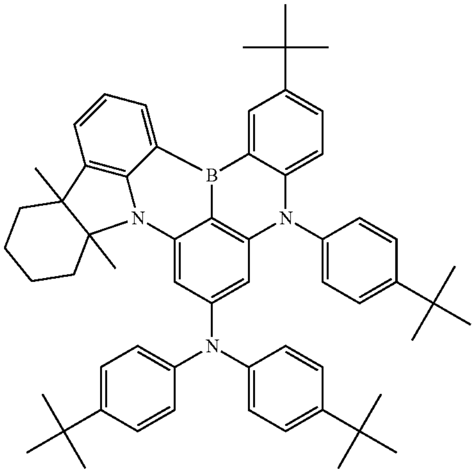
D-524
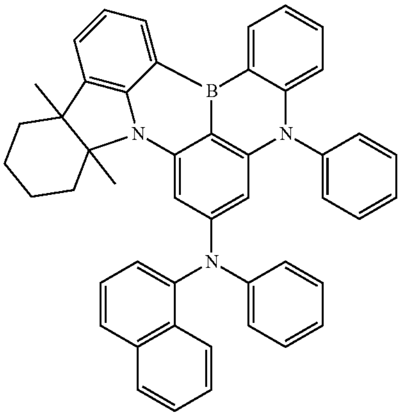
D-525
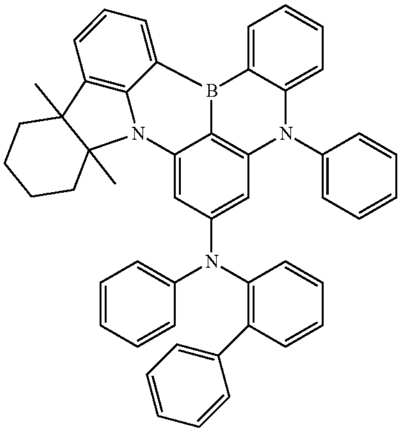

-continued
D-526
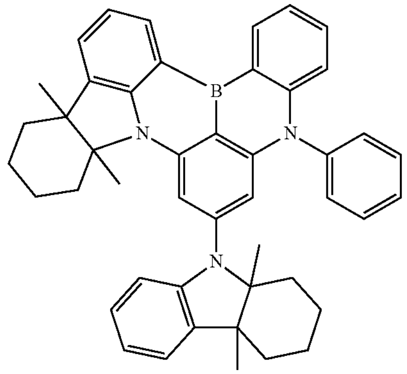
D-527
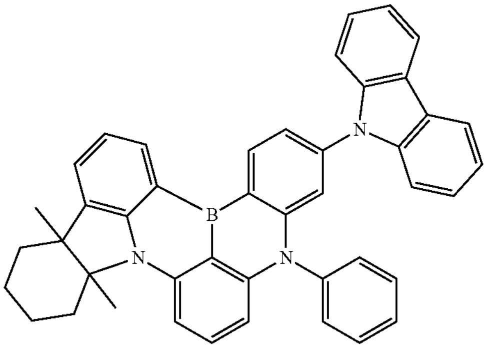
D-528
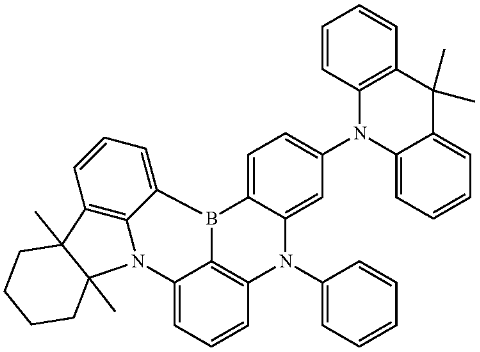
D-529
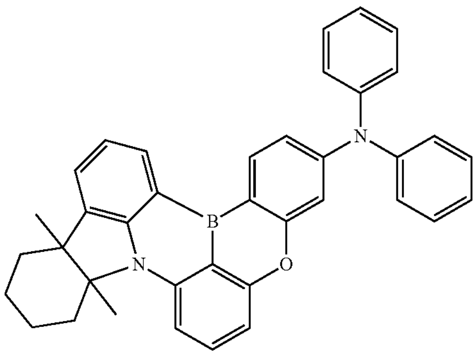
-continued
D-530
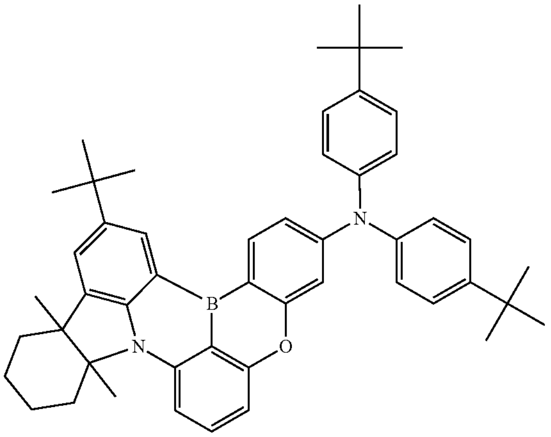
D-531
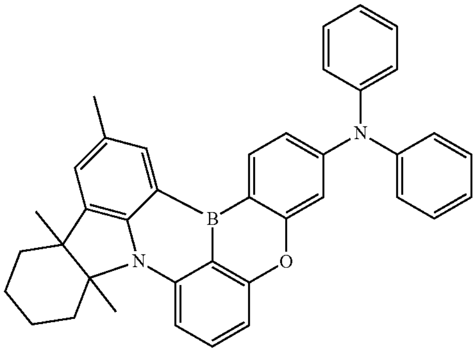
D-532
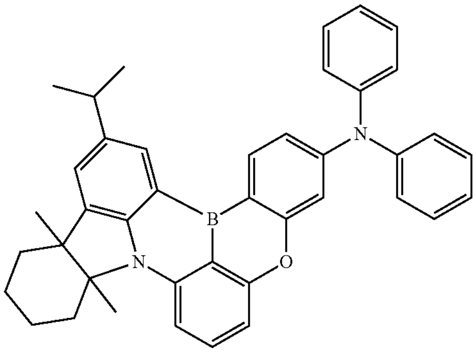
D-533
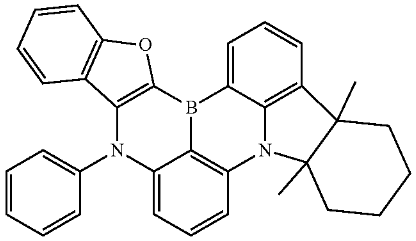

-continued
D-534
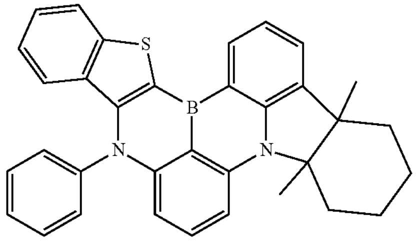
D-535
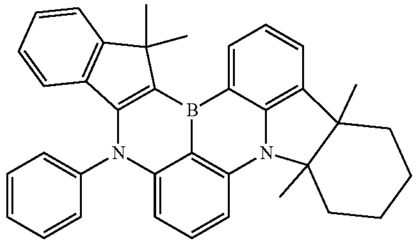
D-536
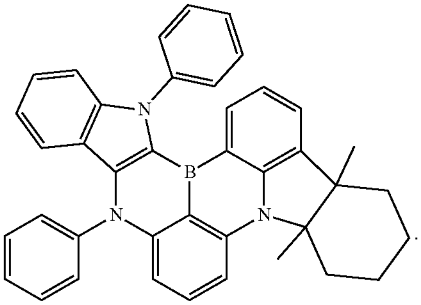
7. The organic light emitting device according to claim 1, wherein the compounds represented by Formulas D-7 and D-8 are selected from the following compounds D-601 to D-727:
D-601
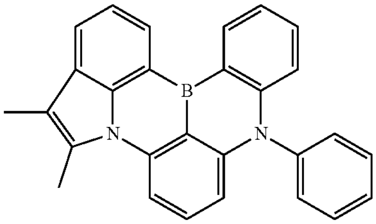
D-602
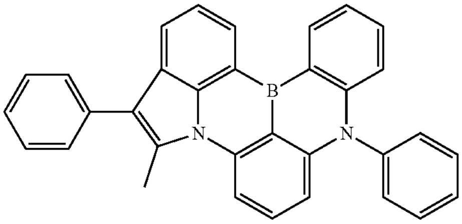
-continued
D-603
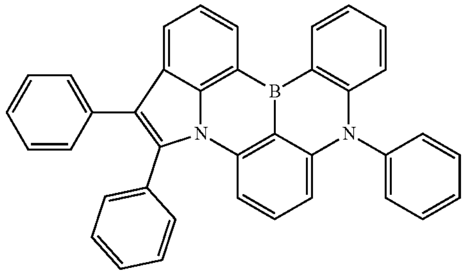
D-604
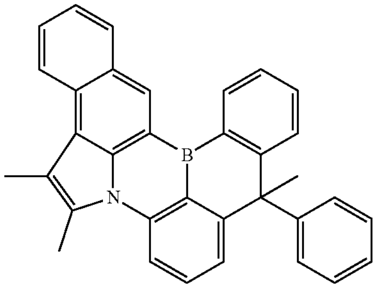
D-605
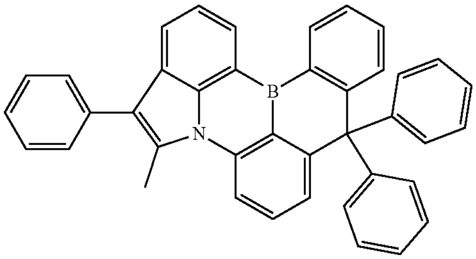
D-606
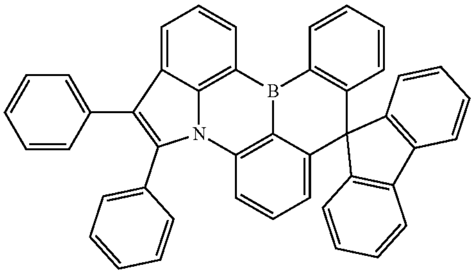
D-607
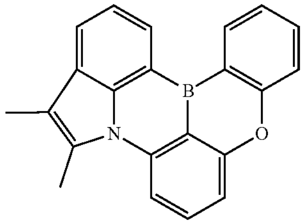
D-608
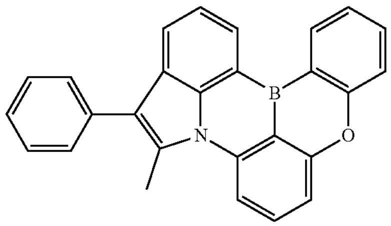

-continued
D-609
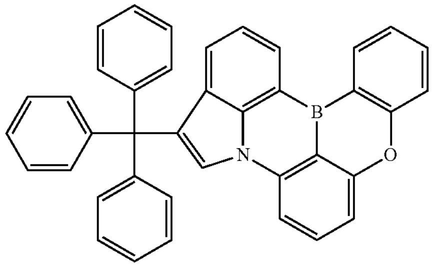
D-610
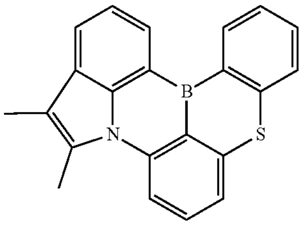
D-611
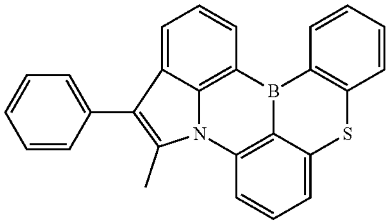
D-612
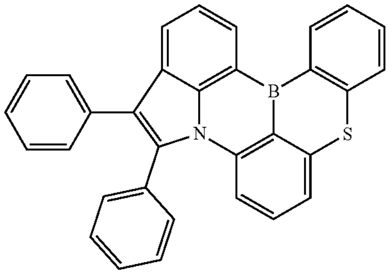
D-613
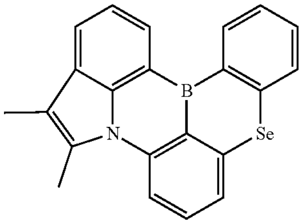
D-614
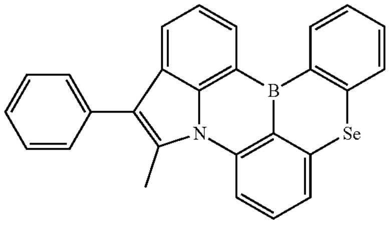
-continued
D-615
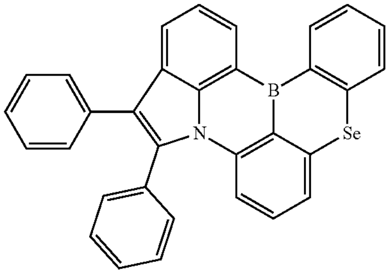
D-616
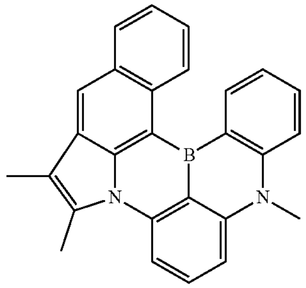
D-617
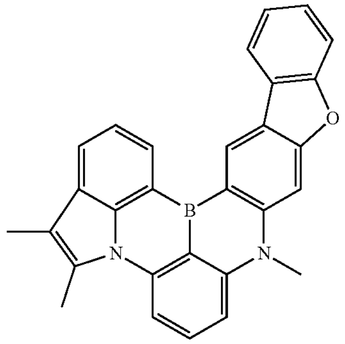
D-618
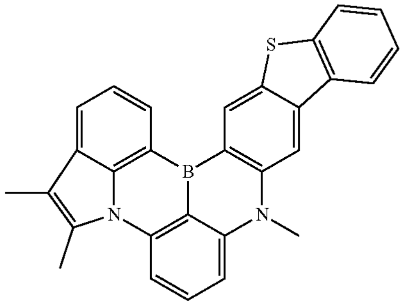
D-619
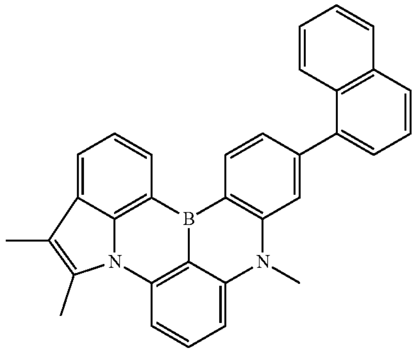

-continued
D-620
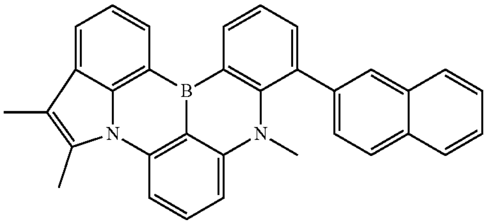
D-621
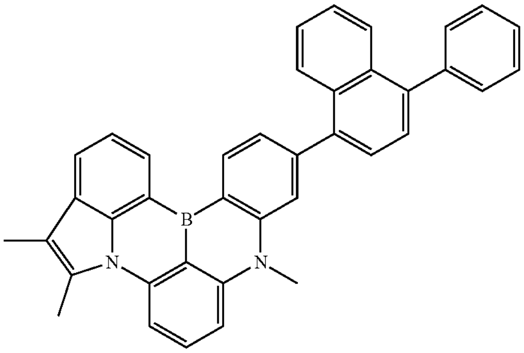
D-622
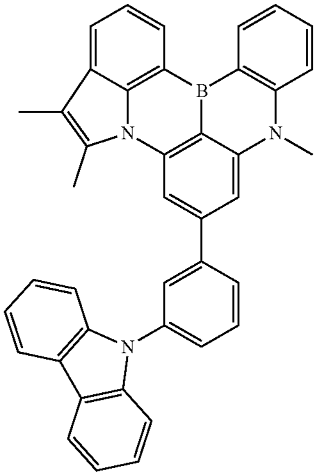
D-623
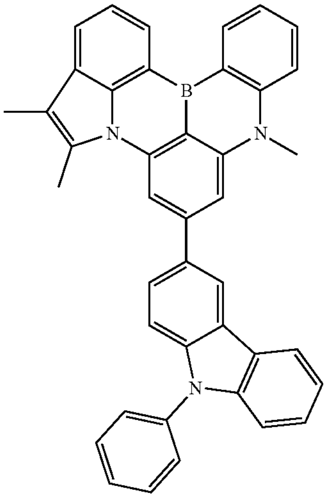
-continued
D-624
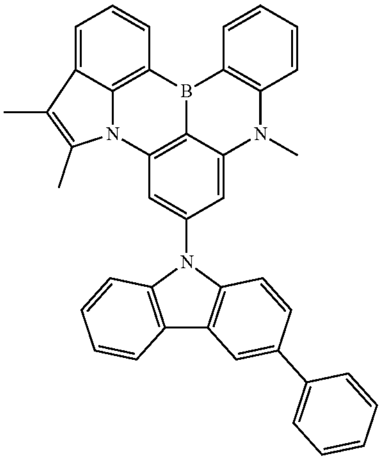
D-625
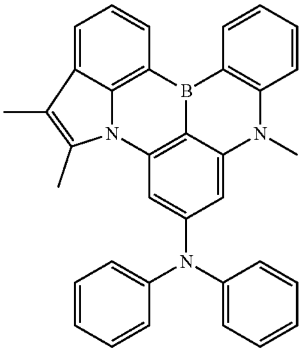
D-626
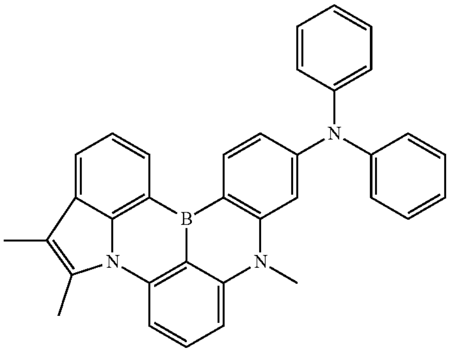
D-627
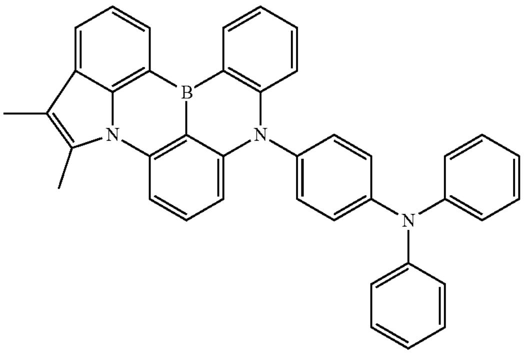

-continued
D-628
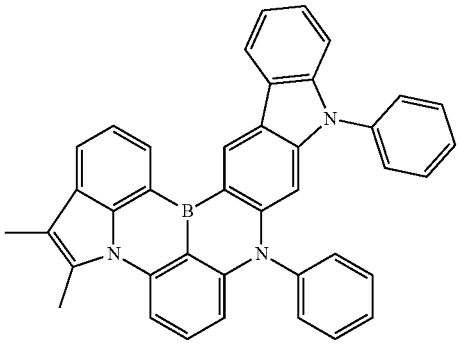
D-629
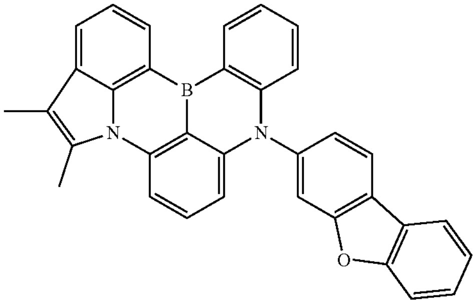
D-630
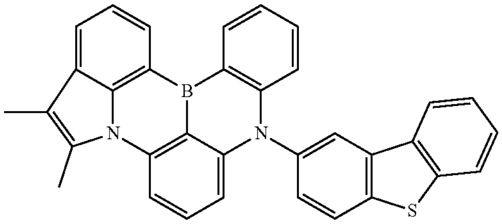
D-631
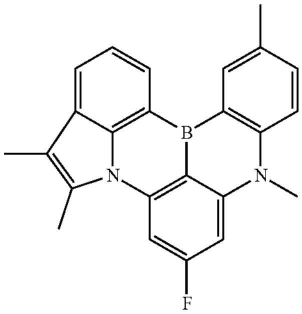
D-632
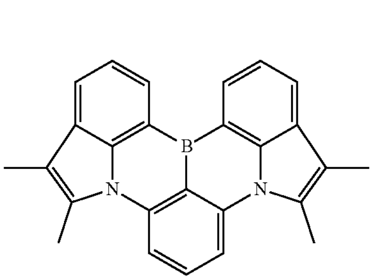
-continued
D-633
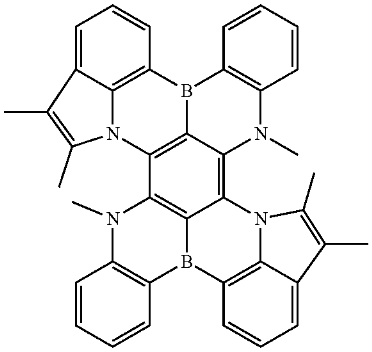
D-634
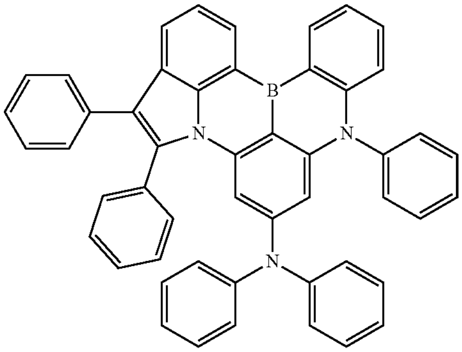
D-635
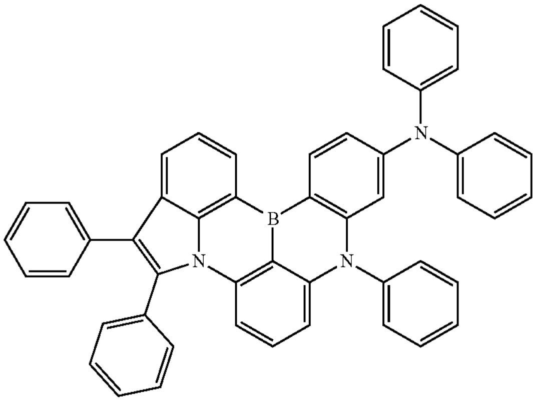
D-636
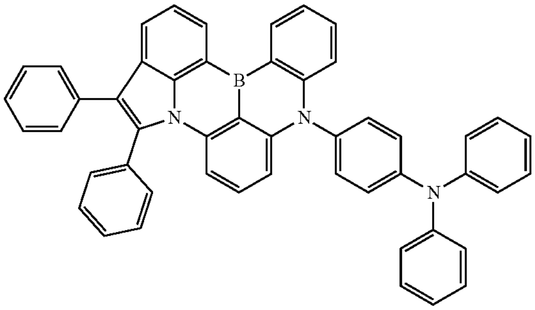

-continued
D-637
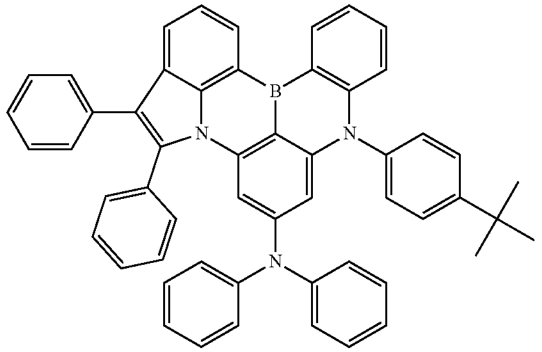
D-638
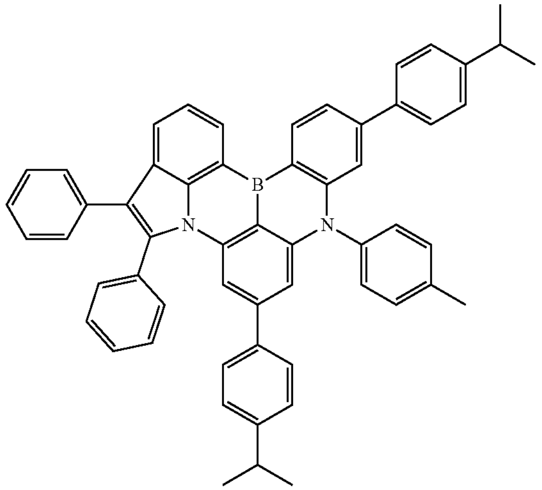
D-639
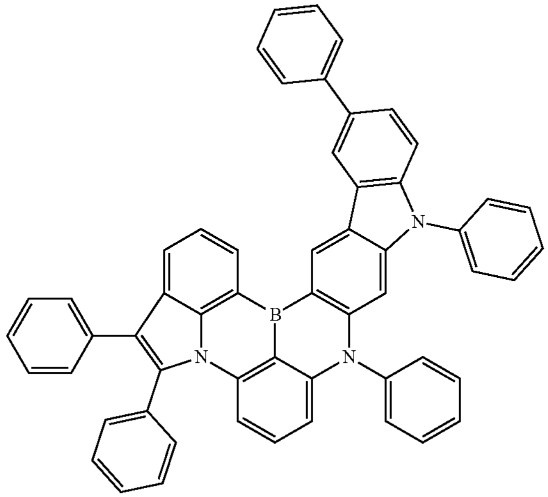
-continued
D-640
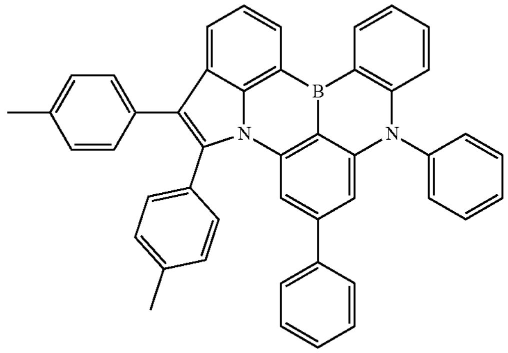
D-641
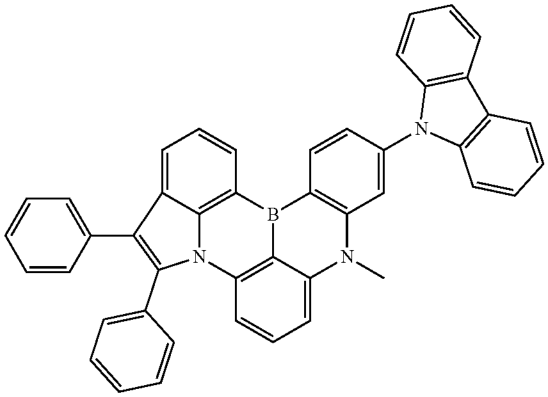
D-642
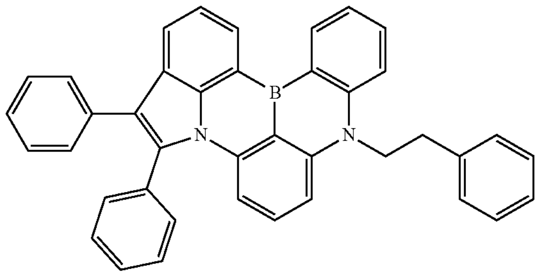
D-643
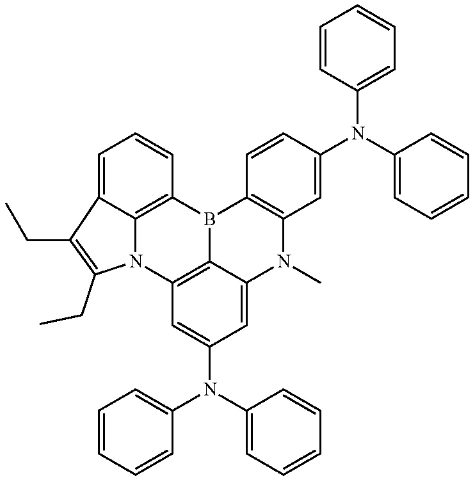

-continued
D-644
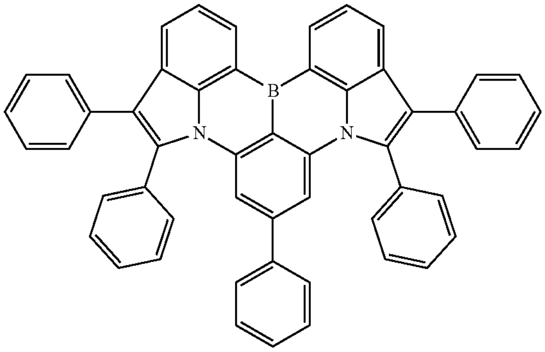
D-645
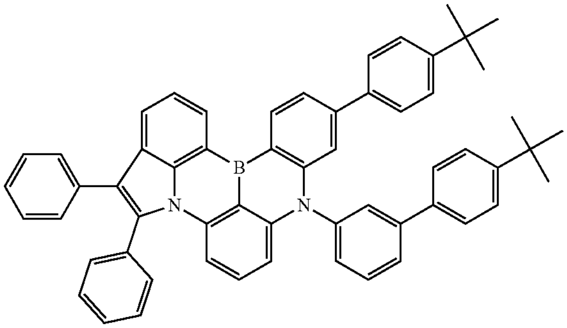
D-646
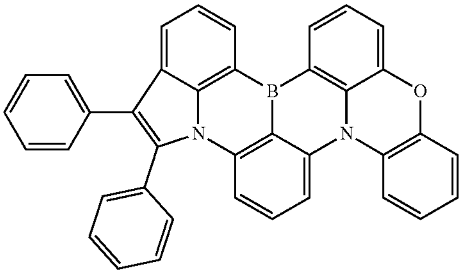
D-647
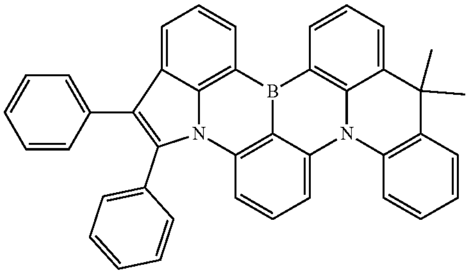
D-648
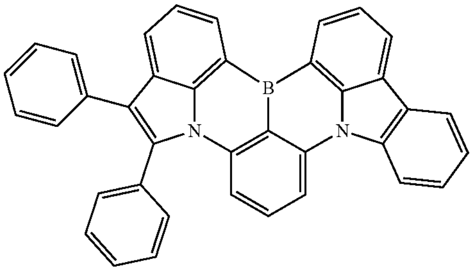
-continued
D-649
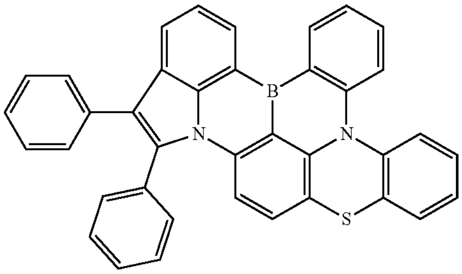
D-650
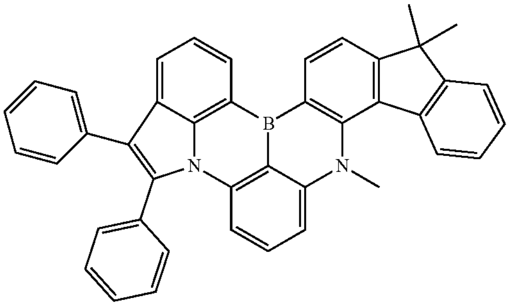
D-651
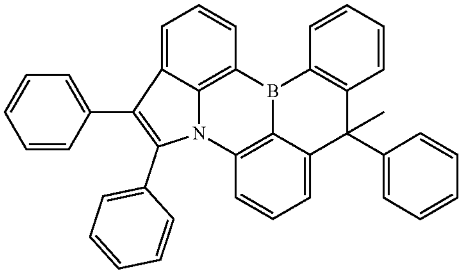
D-652
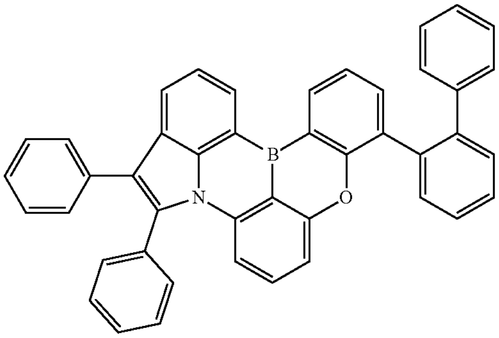

D-653
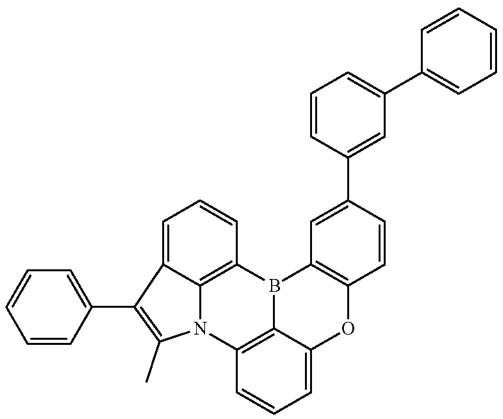
D-654
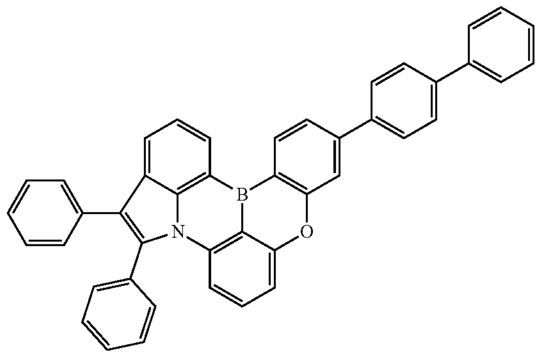
D-655
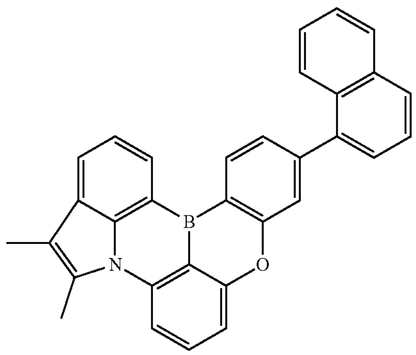
D-656
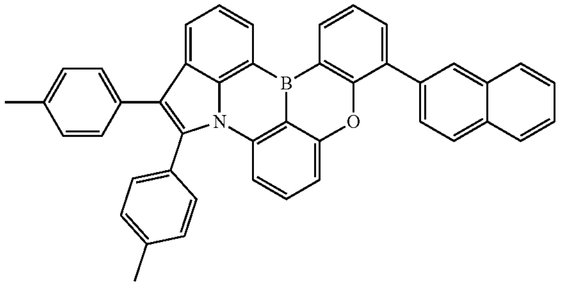
D-657
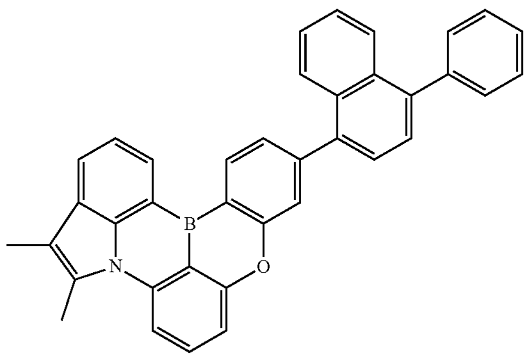
D-658
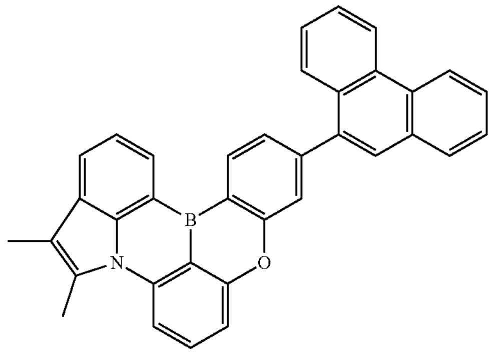
D-659
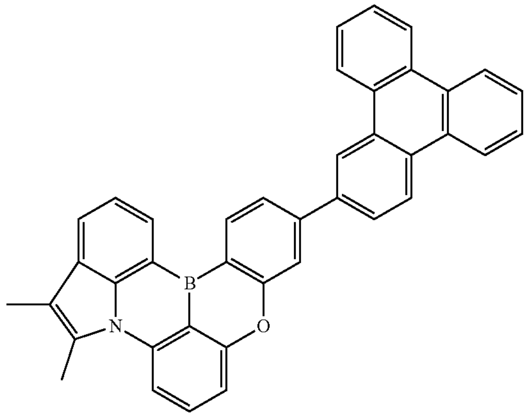
D-660
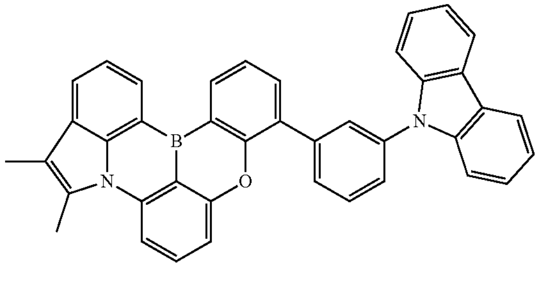

-continued
D-661
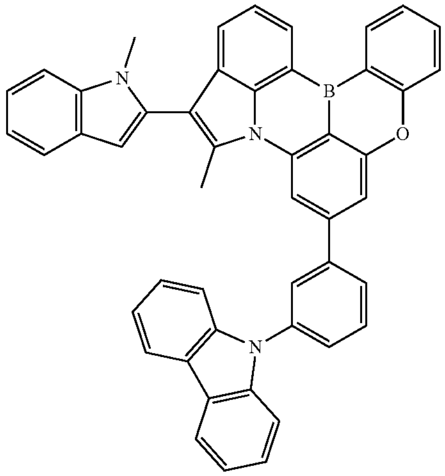
D-662
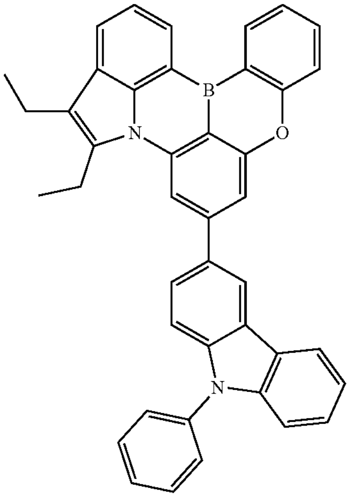
D-663
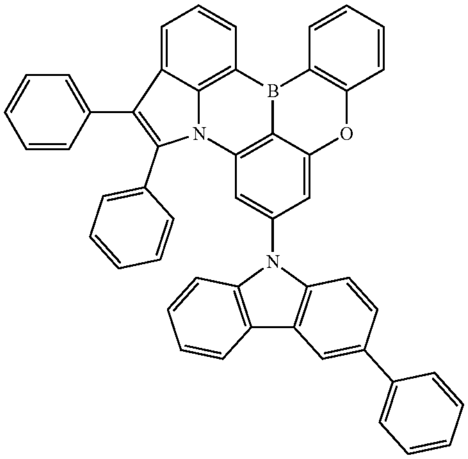
-continued
D-664
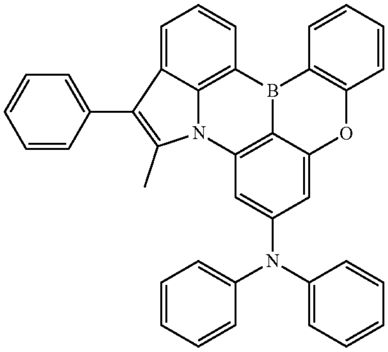
D-665
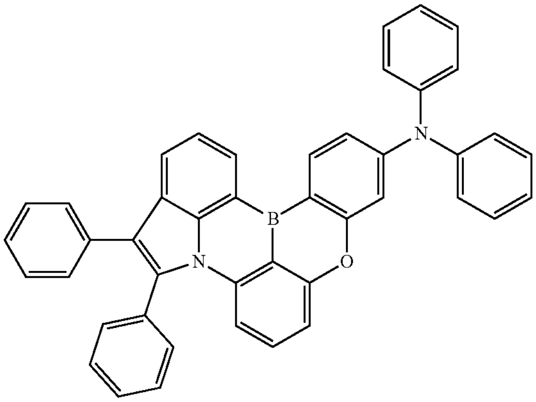
D-666
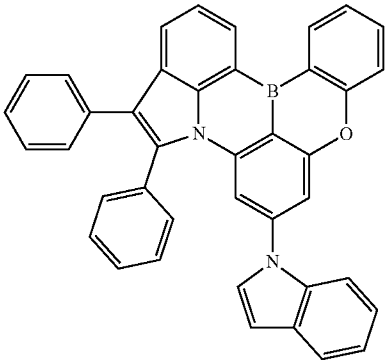
D-667
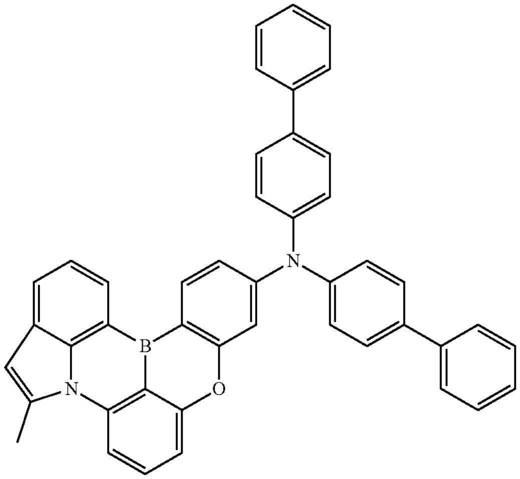

-continued
D-668
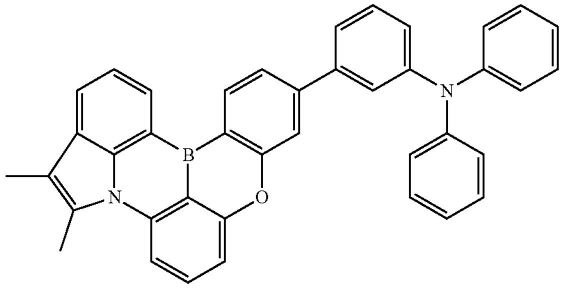
D-669
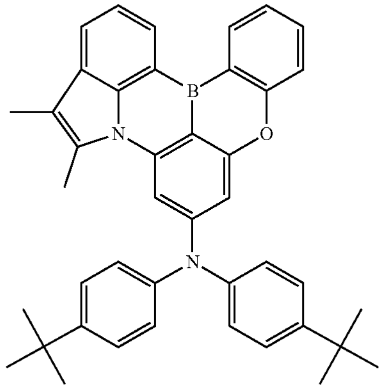
D-670
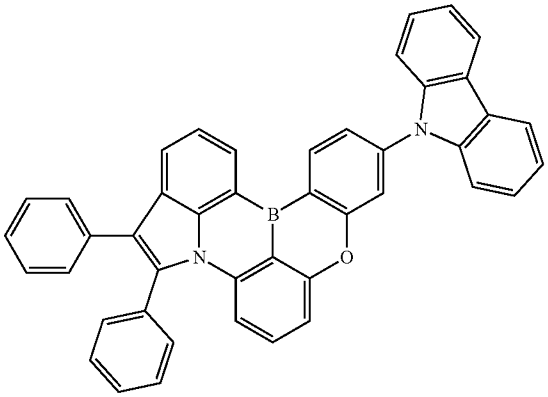
D-671
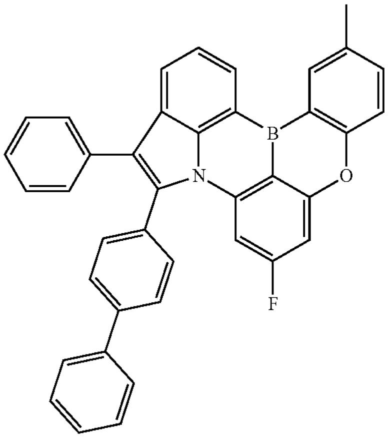
-continued
D-672
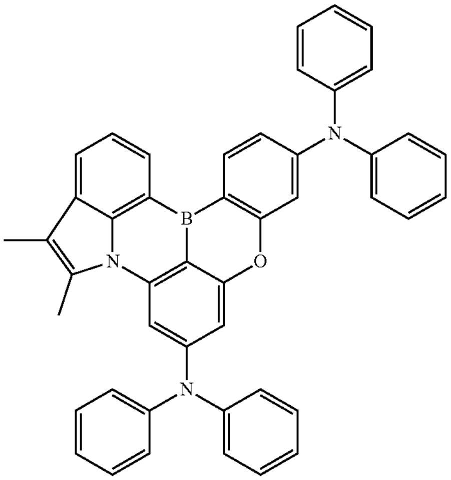
D-673
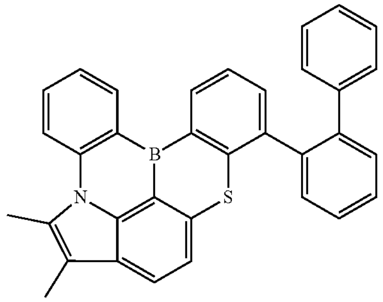
D-674
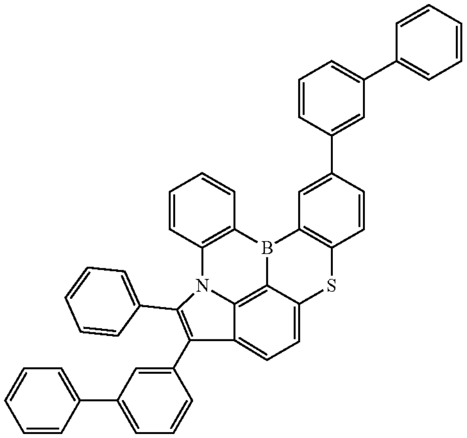
D-675
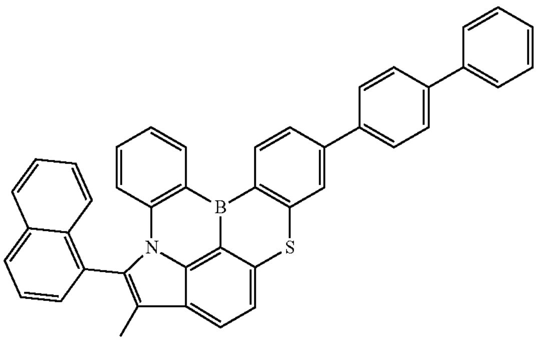

-continued
D-676
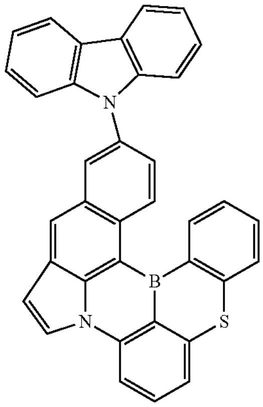
D-677
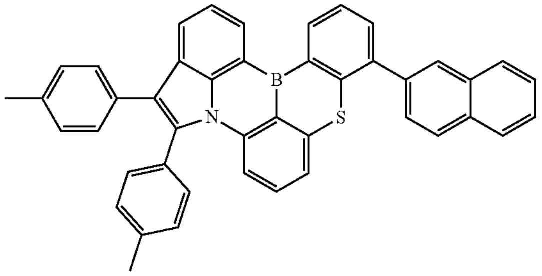
D-678
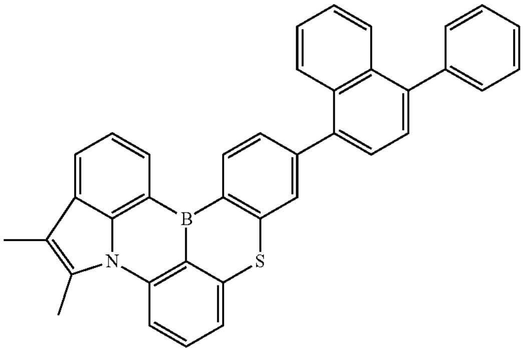
D-679
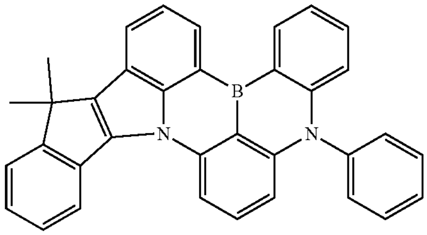
-continued
D-680
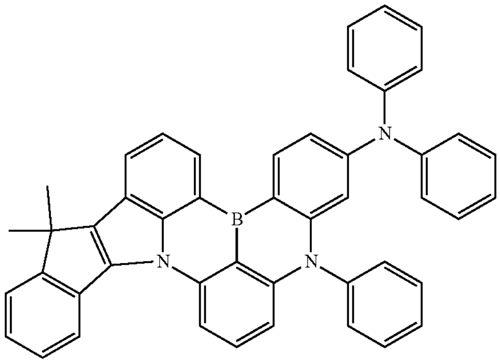
D-681
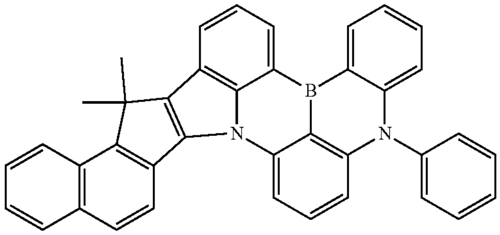
D-682
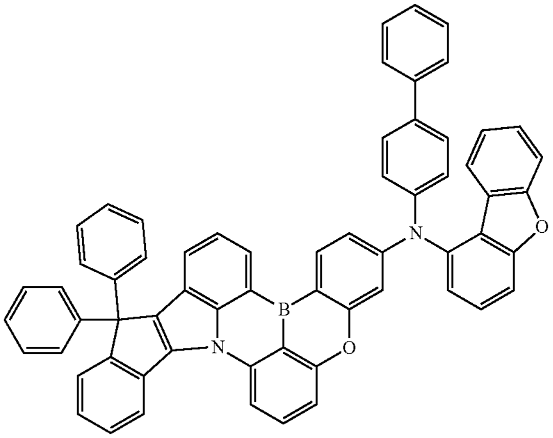
D-683
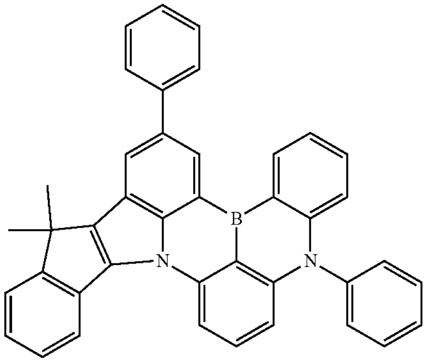

-continued
D-684
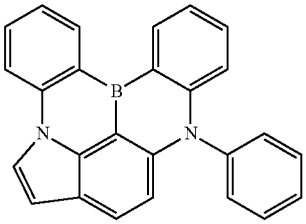
D-685
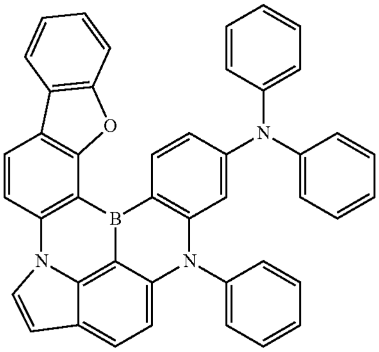
D-686
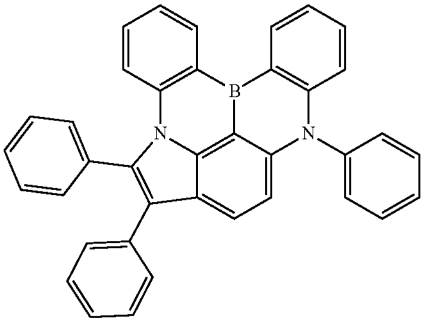
D-687
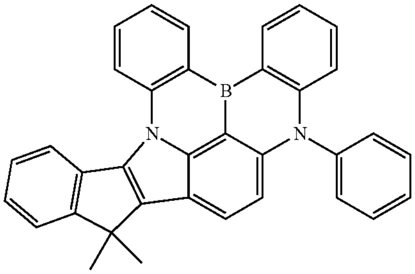
D-688
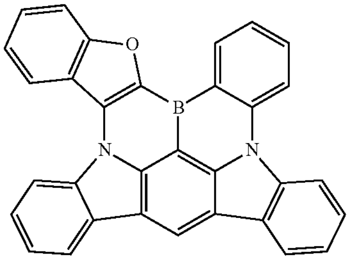
-continued
D-689
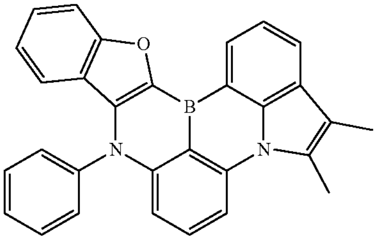
D-690
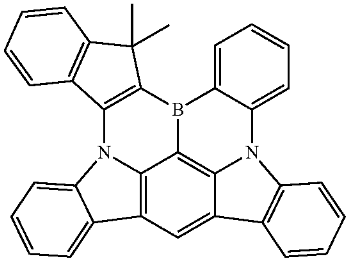
D-691
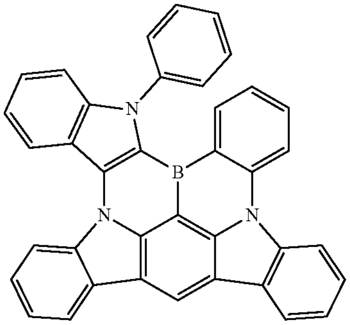
D-692
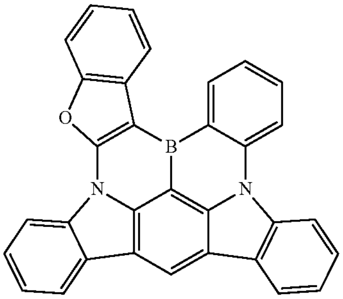
D-693
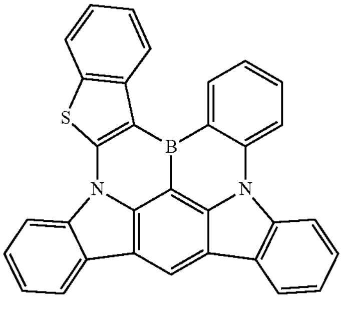

-continued
D-694
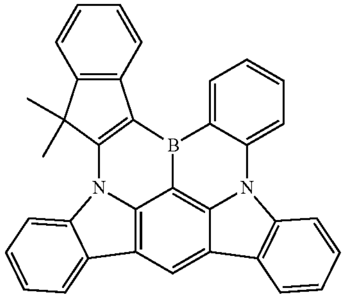
D-695
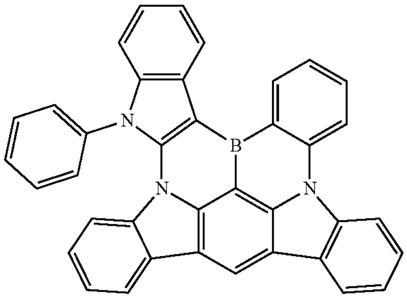
D-696
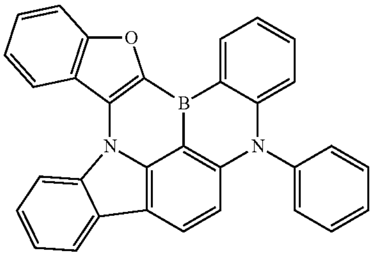
D-697
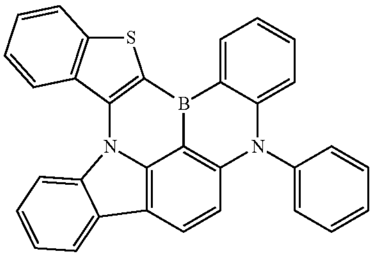
D-698
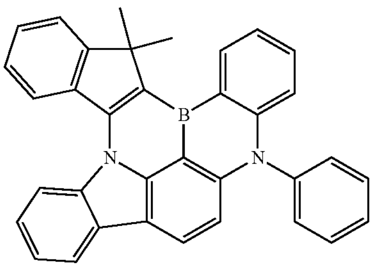
-continued
D-699
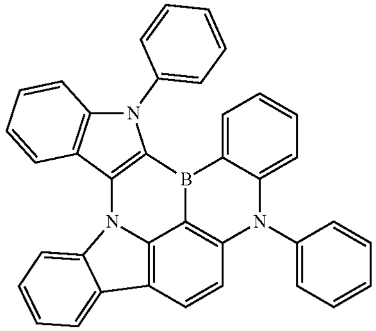
D-700
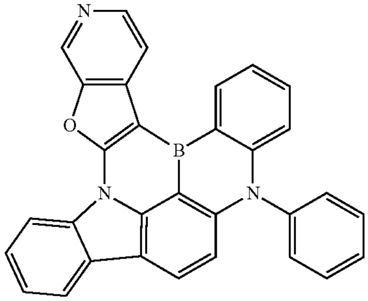
D-701
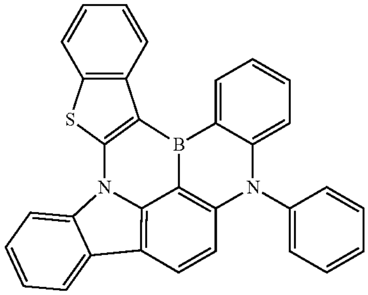
D-702
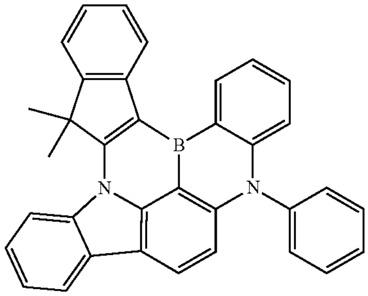
D-703
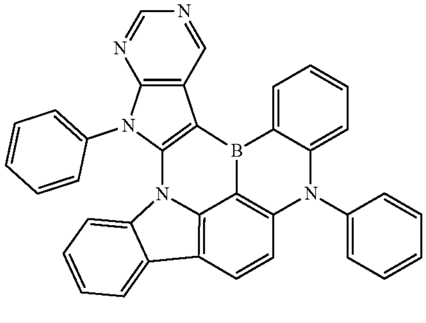

-continued
D-704
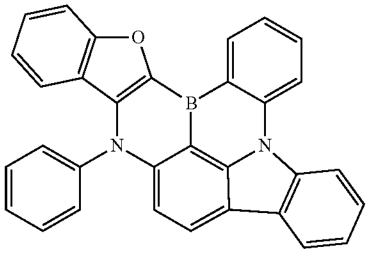
D-705
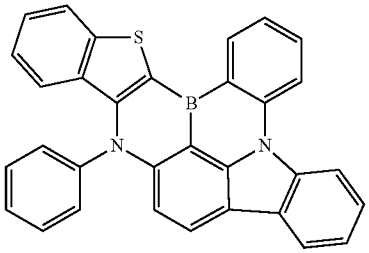
D-706
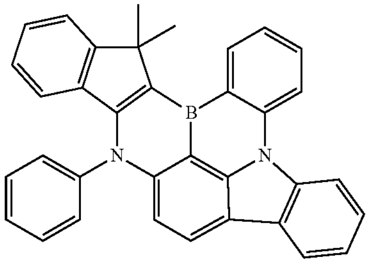
D-707
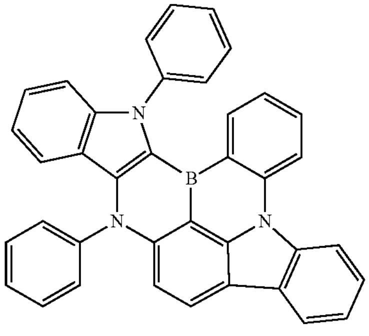
D-708
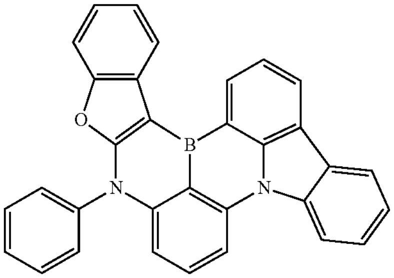
-continued
D-709
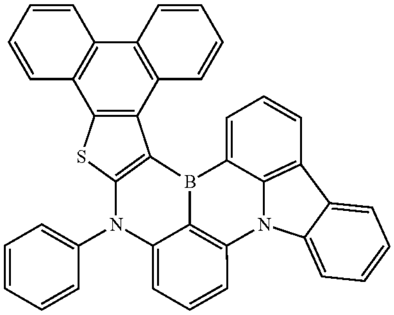
D-710
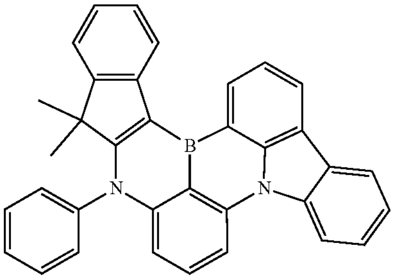
D-711
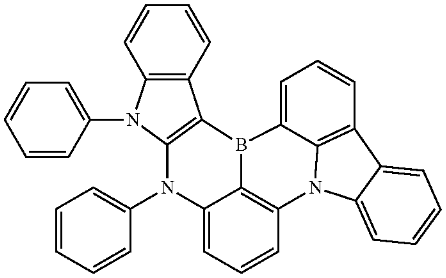
D-712
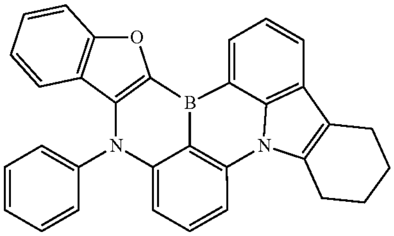
D-713
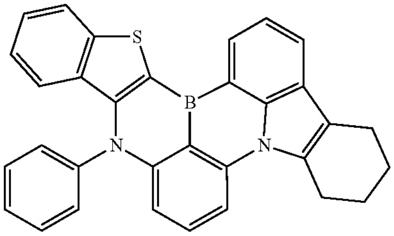
D-714
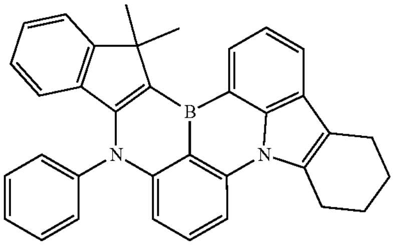

-continued
D-715
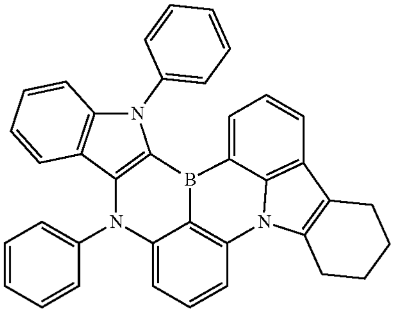
D-716
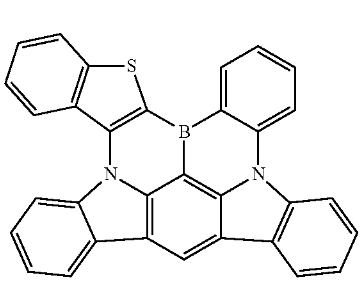
D-717
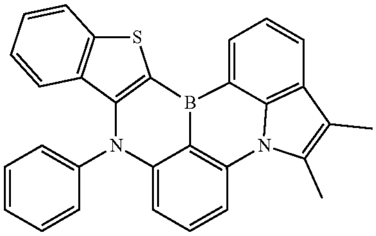
D-718
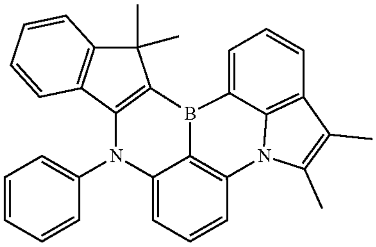
D-719
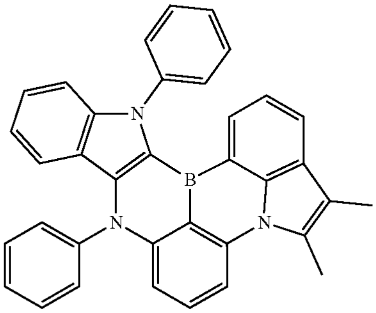
-continued
D-720
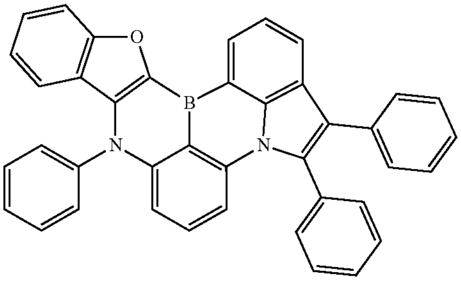
D-721
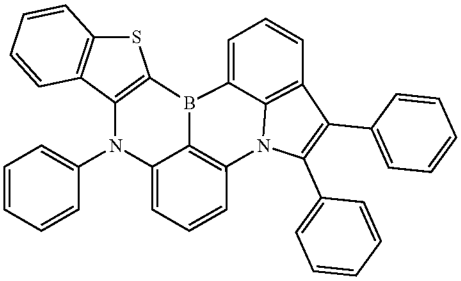
D-722
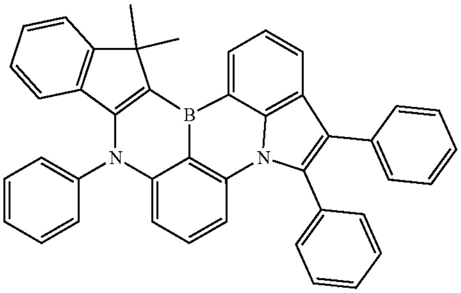
D-723
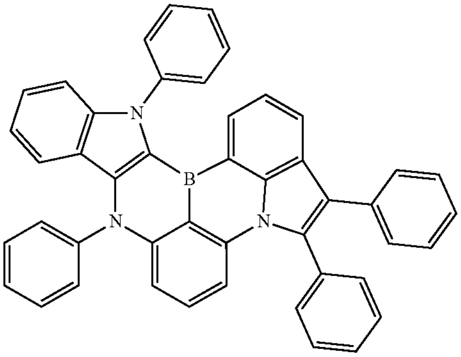
D-724
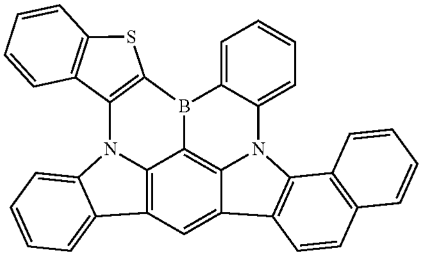

-continued

D-725

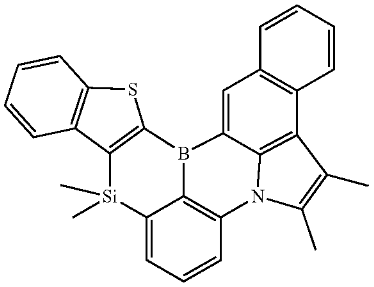

D-726

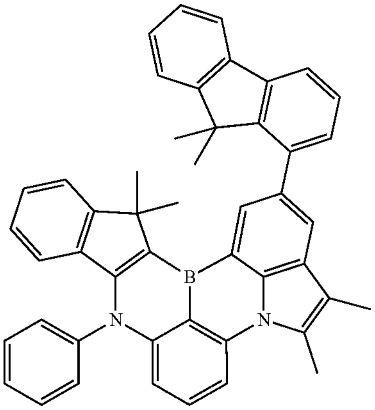

-continued

D-727

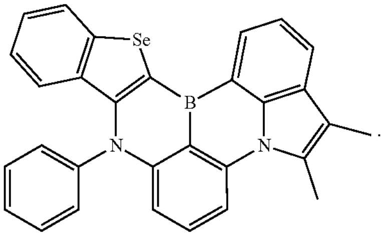

8. The organic light emitting device according to claim 1, further comprising a hole injecting layer, a hole transport layer, a functional layer having functions of both hole injection and hole transport, an electron transport layer, an electron injecting layer, and/or a functional layer having functions of both electron injection and electron transport.

9. The organic light emitting device according to claim 8, wherein one or more of the layers are formed by a deposition or solution process.

10. The organic light emitting device according to claim 1, wherein the organic light emitting device is used in a display or lighting system selected from flat panel displays, flexible displays, monochromatic flat panel lighting systems, white flat panel lighting systems, flexible monochromatic lighting systems, flexible white lighting systems, displays for automotive applications, displays for virtual reality, and displays for augmented reality.

* * * * *